United States Patent
Howard et al.

(10) Patent No.: US 11,524,969 B2
(45) Date of Patent: Dec. 13, 2022

(54) PYRROLOBENZODIAZEPINES AND CONJUGATES THEREOF AS ANTITUMOUR AGENTS

(71) Applicant: MEDIMMUNE LIMITED, Cambridge (GB)

(72) Inventors: Philip Wilson Howard, Cambridge (GB); Niall John Dickinson, Cambridge (GB)

(73) Assignee: MEDIMMUNE LIMITED, Cambridge (GB)

( * ) Notice: Subject to any disclaimer, the term of this patent is extended or adjusted under 35 U.S.C. 154(b) by 151 days.

(21) Appl. No.: 17/046,498

(22) PCT Filed: Apr. 12, 2019

(86) PCT No.: PCT/EP2019/059404
§ 371 (c)(1),
(2) Date: Oct. 9, 2020

(87) PCT Pub. No.: WO2019/197602
PCT Pub. Date: Oct. 17, 2019

(65) Prior Publication Data
US 2021/0079023 A1    Mar. 18, 2021

(30) Foreign Application Priority Data
Apr. 12, 2018  (GB) ................... 1806022

(51) Int. Cl.
| | |
|---|---|
| C07D 487/04 | (2006.01) |
| C07D 519/00 | (2006.01) |
| A61P 35/00 | (2006.01) |
| A61K 31/551 | (2006.01) |
| A61K 47/68 | (2017.01) |
| A61K 45/06 | (2006.01) |

(52) U.S. Cl.
CPC ........ C07D 519/00 (2013.01); A61K 47/6803 (2017.08); A61P 35/00 (2018.01); A61K 45/06 (2013.01)

(58) Field of Classification Search
CPC .... C07D 487/04; C07D 519/00; A61K 47/48; A61K 31/551; A61P 35/00
See application file for complete search history.

(56) References Cited

U.S. PATENT DOCUMENTS

| | | |
|---|---|---|
| 3,361,742 A | 1/1968 | Julius et al. |
| 3,523,941 A | 8/1970 | Leimgruber et al. |
| 3,524,849 A | 8/1970 | Batcho et al. |
| 3,794,644 A | 2/1974 | Karlyone et al. |
| 4,185,016 A | 1/1980 | Takanabe et al. |
| 4,239,683 A | 12/1980 | Takanabe et al. |
| 4,309,437 A | 1/1982 | Ueda et al. |
| 4,353,827 A | 10/1982 | Hunkeler et al. |
| 4,382,032 A | 5/1983 | Hunkeler et al. |
| 4,386,028 A | 5/1983 | Hunkeler et al. |
| 4,405,516 A | 9/1983 | Hunkeler et al. |
| 4,405,517 A | 9/1983 | Hunkeler et al. |
| 4,407,752 A | 10/1983 | Hunkeler et al. |
| 4,427,587 A | 1/1984 | Kaneko et al. |
| 4,427,588 A | 1/1984 | Kaneko et al. |
| 4,701,325 A | 10/1987 | Ueda et al. |
| 4,816,567 A | 3/1989 | Cabilly et al. |
| 4,923,984 A | 5/1990 | Matsumura et al. |
| 5,362,852 A | 11/1994 | Geoghegan |
| 5,418,241 A | 5/1995 | Jegham et al. |
| 5,440,021 A | 8/1995 | Chuntharapai et al. |

(Continued)

FOREIGN PATENT DOCUMENTS

| | | |
|---|---|---|
| CN | 101171257 | 4/2008 |
| EP | 0522868 | 1/1993 |

(Continued)

OTHER PUBLICATIONS

Adair et al., "Antibody-drug conjugates—a perfect synergy," Exp. Opin. Biol. Ther. (2012), pp. 1-16.

(Continued)

*Primary Examiner* — Bruck Kifle
(74) *Attorney, Agent, or Firm* — Casimir Jones SC; Lisa Mueller

(57) ABSTRACT

A compound with the formula I: (I) and salts and solvates thereof, wherein: R" is a group of formula II: (II) where each of n and m are independently selected from 1, 2 and 3.

16 Claims, No Drawings

(56) References Cited

U.S. PATENT DOCUMENTS

| | | |
|---|---|---|
| 5,561,119 A | 10/1996 | Jacquesy et al. |
| 5,583,024 A | 12/1996 | McElroy et al. |
| 5,621,002 A | 4/1997 | Bosslet et al. |
| 5,644,033 A | 7/1997 | Seon |
| 5,674,713 A | 10/1997 | McElroy et al. |
| 5,700,670 A | 12/1997 | Yamagishi et al. |
| 5,773,223 A | 6/1998 | Shyamala et al. |
| 5,792,616 A | 8/1998 | Persico et al. |
| 5,854,399 A | 12/1998 | Salomon et al. |
| 5,869,445 A | 2/1999 | Cheever et al. |
| 5,976,551 A | 11/1999 | Mottez et al. |
| 6,011,146 A | 1/2000 | Mottez et al. |
| 6,153,408 A | 11/2000 | Abastado et al. |
| 6,214,345 B1 | 4/2001 | Firestone et al. |
| 6,218,519 B1 | 4/2001 | Kenten et al. |
| 6,268,488 B1 | 7/2001 | Barbas, III et al. |
| 6,362,331 B1 | 3/2002 | Kamal et al. |
| 6,518,404 B1 | 2/2003 | Li et al. |
| 6,534,482 B1 | 3/2003 | Fikes et al. |
| 6,555,339 B1 | 4/2003 | Liaw et al. |
| 6,562,806 B1 | 5/2003 | Thurston et al. |
| 6,602,677 B1 | 8/2003 | Wood et al. |
| 6,608,192 B1 | 8/2003 | Thurston et al. |
| 6,660,742 B2 | 12/2003 | Lee |
| 6,660,856 B2 | 12/2003 | Wang |
| 6,677,435 B2 | 1/2004 | Barbas, III et al. |
| 6,747,144 B1 | 6/2004 | Thurston et al. |
| 6,759,509 B1 | 7/2004 | King et al. |
| 6,835,807 B1 | 12/2004 | Sasaki et al. |
| 6,884,799 B2 | 4/2005 | Kamal et al. |
| 6,909,006 B1 | 6/2005 | Thurston et al. |
| 7,049,311 B1 | 5/2006 | Thurston et al. |
| 7,067,511 B2 | 6/2006 | Thurston et al. |
| 7,223,837 B2 | 5/2007 | De Groot et al. |
| 7,244,724 B2 | 7/2007 | Liu et al. |
| 7,265,105 B2 | 9/2007 | Thurston et al. |
| 7,375,078 B2 | 5/2008 | Feng |
| 7,407,951 B2 | 8/2008 | Thurston et al. |
| 7,429,658 B2 | 9/2008 | Howard et al. |
| 7,498,298 B2 | 3/2009 | Doronina et al. |
| 7,511,032 B2 | 3/2009 | Liu et al. |
| 7,521,541 B2 | 4/2009 | Eigenbrot et al. |
| 7,528,126 B2 | 5/2009 | Howard et al. |
| 7,557,099 B2 | 7/2009 | Howard et al. |
| 7,612,062 B2 | 11/2009 | Gregson et al. |
| 7,704,924 B2 | 4/2010 | Thurston et al. |
| 7,723,485 B2 | 5/2010 | Junutula et al. |
| 7,741,319 B2 | 6/2010 | Howard et al. |
| 8,034,808 B2 | 11/2011 | Delavault et al. |
| 8,163,736 B2 | 4/2012 | Gauzy et al. |
| 8,321,774 B2 | 11/2012 | Barthal et al. |
| 8,487,092 B2 | 7/2013 | Howard et al. |
| 8,501,934 B2 | 8/2013 | Howard et al. |
| 8,592,576 B2 | 11/2013 | Howard et al. |
| 8,633,185 B2 | 1/2014 | Howard et al. |
| 8,637,664 B2 | 1/2014 | Howard et al. |
| 8,697,688 B2 | 4/2014 | Howard et al. |
| 8,829,184 B2 | 9/2014 | Howard et al. |
| 8,940,733 B2 | 1/2015 | Howard et al. |
| 9,102,704 B2 | 8/2015 | Howard |
| 9,242,013 B2 | 1/2016 | Howard et al. |
| 9,321,774 B2 | 4/2016 | Howard et al. |
| 9,376,440 B2 | 6/2016 | Howard et al. |
| 9,387,259 B2 | 7/2016 | Jeffrey et al. |
| 9,388,187 B2 | 7/2016 | Howard et al. |
| 9,399,073 B2 | 7/2016 | Howard et al. |
| 9,399,641 B2 | 7/2016 | Howard et al. |
| 9,415,117 B2 | 8/2016 | Howard |
| 9,464,141 B2 | 10/2016 | Asundi et al. |
| 9,526,798 B2 | 12/2016 | Jeffrey et al. |
| 9,562,049 B2 | 2/2017 | Howard |
| 9,592,240 B2 | 3/2017 | Howard et al. |
| 9,624,227 B2 | 4/2017 | Howard et al. |
| 9,649,390 B2 | 5/2017 | Howard et al. |
| 9,707,301 B2 | 7/2017 | Jeffrey et al. |
| 9,713,647 B2 | 7/2017 | Jeffrey et al. |
| 9,732,084 B2 | 8/2017 | Howard et al. |
| 9,745,303 B2 | 8/2017 | Howard et al. |
| 9,889,207 B2 | 2/2018 | Howard |
| 9,956,298 B2 | 5/2018 | Howard et al. |
| 2001/0055751 A1 | 12/2001 | Reiter et al. |
| 2002/0034749 A1 | 3/2002 | Billing-Medel et al. |
| 2002/0042366 A1 | 4/2002 | Thompson et al. |
| 2002/0150573 A1 | 10/2002 | Nussenzweig |
| 2002/0193567 A1 | 12/2002 | Jacobs et al. |
| 2003/0060612 A1 | 3/2003 | Goddard et al. |
| 2003/0062401 A1 | 4/2003 | Hasz et al. |
| 2003/0064397 A1 | 4/2003 | Spancake et al. |
| 2003/0065143 A1 | 4/2003 | Eaton et al. |
| 2003/0091580 A1 | 5/2003 | Mitcham et al. |
| 2003/0096743 A1 | 5/2003 | Senter et al. |
| 2003/0096961 A1 | 5/2003 | Baker et al. |
| 2003/0105292 A1 | 6/2003 | Liaw et al. |
| 2003/0109676 A1 | 6/2003 | Li et al. |
| 2003/0118592 A1 | 6/2003 | Ledbetter et al. |
| 2003/0119121 A1 | 6/2003 | Baker et al. |
| 2003/0119122 A1 | 6/2003 | Baker et al. |
| 2003/0119125 A1 | 6/2003 | Baker et al. |
| 2003/0119126 A1 | 6/2003 | Baker et al. |
| 2003/0119128 A1 | 6/2003 | Baker et al. |
| 2003/0119129 A1 | 6/2003 | Baker et al. |
| 2003/0119130 A1 | 6/2003 | Baker et al. |
| 2003/0119131 A1 | 6/2003 | Baker et al. |
| 2003/0124140 A1 | 7/2003 | Bangur et al. |
| 2003/0124579 A1 | 7/2003 | Mack et al. |
| 2003/0129192 A1 | 7/2003 | Chenault et al. |
| 2003/0130189 A1 | 7/2003 | Senter et al. |
| 2003/0134790 A1 | 7/2003 | Langenfeld |
| 2003/0143557 A1 | 7/2003 | Penner |
| 2003/0157089 A1 | 8/2003 | Xu et al. |
| 2003/0165504 A1 | 9/2003 | Retter et al. |
| 2003/0175775 A1 | 9/2003 | Lepoul et al. |
| 2003/0185830 A1 | 10/2003 | Xu et al. |
| 2003/0186372 A1 | 10/2003 | Baker et al. |
| 2003/0186373 A1 | 10/2003 | Baker et al. |
| 2003/0194704 A1 | 10/2003 | Penn et al. |
| 2003/0195196 A1 | 10/2003 | Thurston et al. |
| 2003/0206918 A1 | 11/2003 | Fanger et al. |
| 2003/0219806 A1 | 11/2003 | Glucksmann et al. |
| 2003/0224411 A1 | 12/2003 | Stanton et al. |
| 2003/0224454 A1 | 12/2003 | Ryseck et al. |
| 2003/0228319 A1 | 12/2003 | Frantz et al. |
| 2003/0232056 A1 | 12/2003 | Fanger et al. |
| 2003/0232350 A1 | 12/2003 | Afar et al. |
| 2004/0001827 A1 | 1/2004 | Dennis |
| 2004/0005320 A1 | 1/2004 | Thompson et al. |
| 2004/0005538 A1 | 1/2004 | Chen et al. |
| 2004/0005563 A1 | 1/2004 | Mack et al. |
| 2004/0005598 A1 | 1/2004 | Devaux et al. |
| 2004/0018194 A1 | 1/2004 | Francisco et al. |
| 2004/0018553 A1 | 1/2004 | Billing-Medel et al. |
| 2004/0022727 A1 | 2/2004 | Stanton et al. |
| 2004/0044179 A1 | 3/2004 | Baker et al. |
| 2004/0044180 A1 | 3/2004 | Baker et al. |
| 2004/0052793 A1 | 3/2004 | Carter et al. |
| 2004/0101874 A1 | 5/2004 | Ghosh et al. |
| 2004/0101899 A1 | 5/2004 | Dillon et al. |
| 2004/0121940 A1 | 6/2004 | De Groot et al. |
| 2004/0138269 A1 | 7/2004 | Sun et al. |
| 2004/0197325 A1 | 10/2004 | Law et al. |
| 2004/0198722 A1 | 10/2004 | Thurston et al. |
| 2004/0249130 A1 | 12/2004 | Stanton et al. |
| 2005/0271615 A1 | 12/2005 | Shabat et al. |
| 2006/0116422 A1 | 6/2006 | De Groot et al. |
| 2007/0072846 A1 | 3/2007 | Vishnuvajjala et al. |
| 2007/0092940 A1 | 4/2007 | Eigenbrot et al. |
| 2007/0154906 A1 | 7/2007 | Martin et al. |
| 2007/0185336 A1 | 8/2007 | Rossen et al. |
| 2007/0191349 A1 | 8/2007 | Howard et al. |
| 2007/0232592 A1 | 10/2007 | Delavault et al. |
| 2007/0249591 A1 | 10/2007 | Howard et al. |
| 2008/0090812 A1 | 4/2008 | Pepper et al. |
| 2008/0092940 A1 | 4/2008 | Nakajima |
| 2008/0112961 A1 | 5/2008 | Hagen et al. |

(56) References Cited

U.S. PATENT DOCUMENTS

| | | |
|---|---|---|
| 2008/0206239 A1 | 8/2008 | Jones et al. |
| 2008/0213289 A1 | 9/2008 | Francisco et al. |
| 2008/0214525 A1 | 9/2008 | Howard et al. |
| 2009/0036431 A1 | 2/2009 | Gauzy et al. |
| 2009/0148942 A1 | 6/2009 | McDonagh et al. |
| 2009/0149449 A1 | 6/2009 | Liu et al. |
| 2009/0274713 A1 | 11/2009 | Chari et al. |
| 2009/0304710 A1 | 12/2009 | Park et al. |
| 2010/0028346 A1 | 2/2010 | Lutz et al. |
| 2010/0047257 A1 | 2/2010 | Blanc et al. |
| 2010/0113425 A1 | 5/2010 | Howard et al. |
| 2010/0203007 A1 | 8/2010 | Li et al. |
| 2010/0316656 A1 | 12/2010 | Bouchard et al. |
| 2011/0039969 A1 | 2/2011 | Muratoglu et al. |
| 2011/0070227 A1 | 3/2011 | Novotney-Barry et al. |
| 2011/0091372 A1 | 4/2011 | Ghayur et al. |
| 2011/0160192 A1 | 6/2011 | Howard et al. |
| 2011/0195021 A1 | 8/2011 | Deckert et al. |
| 2011/0195022 A1 | 8/2011 | Deckert et al. |
| 2011/0196148 A1 | 8/2011 | Howard et al. |
| 2011/0201803 A1 | 8/2011 | Howard et al. |
| 2011/0256157 A1 | 10/2011 | Howard et al. |
| 2012/0233172 A1 | 9/2012 | Skillcorn et al. |
| 2012/0238731 A1 | 9/2012 | Fishkin et al. |
| 2013/0028917 A1 | 1/2013 | Howard et al. |
| 2013/0028919 A1 | 1/2013 | Howard et al. |
| 2013/0137659 A1 | 5/2013 | Commercon et al. |
| 2013/0244171 A1 | 9/2013 | Yamasaki et al. |
| 2013/0266595 A1 | 10/2013 | Flygare et al. |
| 2013/0266596 A1 | 10/2013 | Li et al. |
| 2013/0302359 A1 | 11/2013 | Li et al. |
| 2013/0304357 A1 | 11/2013 | Koci et al. |
| 2014/0030279 A1 | 1/2014 | Polakis et al. |
| 2014/0030280 A1 | 1/2014 | Polakis |
| 2014/0066435 A1 | 3/2014 | Howard et al. |
| 2014/0088089 A1 | 3/2014 | Chari |
| 2014/0120118 A1 | 5/2014 | Howard |
| 2014/0121126 A1 | 5/2014 | Bivona et al. |
| 2014/0127239 A1 | 5/2014 | Howard |
| 2014/0155590 A1 | 6/2014 | Commercon et al. |
| 2014/0234346 A1 | 8/2014 | Howard |
| 2014/0274907 A1 | 9/2014 | Howard et al. |
| 2014/0275522 A1 | 9/2014 | Howard et al. |
| 2014/0286970 A1 | 9/2014 | Jeffrey et al. |
| 2014/0294868 A1 | 10/2014 | Howard et al. |
| 2014/0302066 A1 | 10/2014 | Jeffrey et al. |
| 2015/0111880 A1 | 4/2015 | Howard et al. |
| 2015/0126495 A1 | 5/2015 | Howard et al. |
| 2015/0133435 A1 | 5/2015 | Howard et al. |
| 2015/0158869 A1 | 6/2015 | Howard |
| 2015/0183883 A1 | 7/2015 | Asundi |
| 2015/0265722 A1 | 9/2015 | Van Berkel |
| 2015/0273077 A1 | 10/2015 | Van Berkel |
| 2015/0273078 A1 | 10/2015 | Van Berkel |
| 2015/0274737 A1 | 10/2015 | Howard et al. |
| 2015/0283258 A1 | 10/2015 | Van Berkel |
| 2015/0283262 A1 | 10/2015 | Van Berkel |
| 2015/0283263 A1 | 10/2015 | Van Berkel |
| 2015/0297746 A1 | 10/2015 | Van Berkel |
| 2015/0315196 A1 | 11/2015 | Howard et al. |
| 2015/0344482 A1 | 12/2015 | Howard et al. |
| 2016/0015828 A1 | 1/2016 | Torgor |
| 2016/0031887 A1 | 2/2016 | Howard et al. |
| 2016/0075787 A1 | 3/2016 | Zheng et al. |
| 2016/0144052 A1 | 5/2016 | Howard et al. |
| 2016/0074527 A1 | 7/2016 | Flygare et al. |
| 2016/0250344 A1 | 9/2016 | Howard et al. |
| 2016/0250345 A1 | 9/2016 | Howard et al. |
| 2016/0250346 A1 | 9/2016 | Howard et al. |
| 2016/0256561 A1 | 9/2016 | Howard et al. |
| 2016/0263242 A1 | 9/2016 | Howard et al. |
| 2016/0310611 A1 | 10/2016 | Flygare et al. |
| 2017/0239365 A1 | 8/2017 | Howard et al. |
| 2017/0290924 A1 | 10/2017 | Jeffrey et al. |
| 2017/0298137 A1 | 10/2017 | Jeffrey et al. |
| 2017/0340752 A1 | 11/2017 | Howard |
| 2018/0125997 A1 | 5/2018 | Howard et al. |
| 2018/0134717 A1 | 5/2018 | Howard et al. |

FOREIGN PATENT DOCUMENTS

| | | |
|---|---|---|
| EP | 0875569 | 11/1998 |
| EP | 1295944 | 3/2003 |
| EP | 1347046 | 9/2003 |
| EP | 1394274 | 3/2004 |
| EP | 1439393 | 7/2004 |
| EP | 1813614 | 8/2007 |
| EP | 2019104 | 1/2009 |
| EP | 2298817 | 3/2011 |
| EP | 2528625 | 7/2013 |
| EP | 3690038 A1 | 8/2020 |
| FR | 2027356 | 12/1969 |
| FR | 2586683 | 3/1987 |
| GB | 1299198 | 12/1972 |
| GB | 2053894 | 2/1981 |
| JP | 5382792 | 7/1978 |
| JP | 57131791 | 8/1982 |
| JP | 58180487 | 10/1983 |
| JP | 05003790 | 1/1993 |
| JP | 2004113151 | 4/2004 |
| WO | WO 199102536 | 3/1991 |
| WO | WO 199207574 | 5/1992 |
| WO | WO 199217497 | 10/1992 |
| WO | WO 199219620 | 11/1992 |
| WO | WO 199318045 | 9/1993 |
| WO | WO 199410312 | 5/1994 |
| WO | WO 199428931 | 12/1994 |
| WO | WO 199504718 | 2/1995 |
| WO | WO 199630514 | 10/1996 |
| WO | WO 199707198 | 2/1997 |
| WO | WO 199744452 | 11/1997 |
| WO | WO 199813059 | 4/1998 |
| WO | WO 199837193 | 8/1998 |
| WO | WO 199840403 | 9/1998 |
| WO | WO 199851805 | 11/1998 |
| WO | WO 199851824 | 11/1998 |
| WO | WO 199928468 | 6/1999 |
| WO | WO 199946284 | 9/1999 |
| WO | WO 199958658 | 11/1999 |
| WO | WO 200003291 | 1/2000 |
| WO | WO 200012506 | 3/2000 |
| WO | WO 200012507 | 3/2000 |
| WO | WO 200012508 | 3/2000 |
| WO | WO 200012509 | 3/2000 |
| WO | WO 200014228 | 3/2000 |
| WO | WO 200020579 | 4/2000 |
| WO | WO 200022129 | 4/2000 |
| WO | WO 200032752 | 6/2000 |
| WO | WO 200036107 | 6/2000 |
| WO | WO 200040614 | 7/2000 |
| WO | WO 200044899 | 8/2000 |
| WO | WO 200012130 | 9/2000 |
| WO | WO 200053216 | 9/2000 |
| WO | WO 200055351 | 9/2000 |
| WO | WO 200075655 | 12/2000 |
| WO | WO 200100244 | 1/2001 |
| WO | WO 200116104 | 3/2001 |
| WO | WO 200116318 | 3/2001 |
| WO | WO 200138490 | 5/2001 |
| WO | WO 200140269 | 6/2001 |
| WO | WO 200140309 | 6/2001 |
| WO | WO 200141787 | 6/2001 |
| WO | WO 200145746 | 6/2001 |
| WO | WO 200144232 | 6/2001 |
| WO | WO 200146261 | 6/2001 |
| WO | WO 200148204 | 7/2001 |
| WO | WO 200153463 | 7/2001 |
| WO | WO 200157188 | 8/2001 |
| WO | WO 200162794 | 8/2001 |
| WO | WO 200166689 | 9/2001 |
| WO | WO 200172830 | 10/2001 |
| WO | WO 200172962 | 10/2001 |
| WO | WO 200175177 | 10/2001 |
| WO | WO 200177172 | 10/2001 |

(56) References Cited

FOREIGN PATENT DOCUMENTS

| | | |
|---|---|---|
| WO | WO 200188133 | 11/2001 |
| WO | WO 200190304 | 11/2001 |
| WO | WO 200194641 | 12/2001 |
| WO | WO 200198351 | 12/2001 |
| WO | WO 200202587 | 1/2002 |
| WO | WO 200202624 | 1/2002 |
| WO | WO 200202634 | 1/2002 |
| WO | WO 200206317 | 1/2002 |
| WO | WO 200206339 | 1/2002 |
| WO | WO 200210187 | 2/2002 |
| WO | WO 200210382 | 2/2002 |
| WO | WO 200212341 | 2/2002 |
| WO | WO 200213847 | 2/2002 |
| WO | WO 200214503 | 2/2002 |
| WO | WO 200216413 | 2/2002 |
| WO | WO 200222153 | 3/2002 |
| WO | WO 200222636 | 3/2002 |
| WO | WO 200222660 | 3/2002 |
| WO | WO 200222808 | 3/2002 |
| WO | WO 200224909 | 3/2002 |
| WO | WO 200226822 | 4/2002 |
| WO | WO 200230268 | 4/2002 |
| WO | WO 200238766 | 5/2002 |
| WO | WO 200254940 | 7/2002 |
| WO | WO 200259377 | 8/2002 |
| WO | WO 200260317 | 8/2002 |
| WO | WO 200261087 | 8/2002 |
| WO | WO 200264798 | 8/2002 |
| WO | WO 200271928 | 9/2002 |
| WO | WO 200272596 | 9/2002 |
| WO | WO 200278524 | 10/2002 |
| WO | WO 200281646 | 10/2002 |
| WO | WO 200283866 | 10/2002 |
| WO | WO 200286443 | 10/2002 |
| WO | WO 200288170 | 11/2002 |
| WO | WO 200288172 | 11/2002 |
| WO | WO 200289747 | 11/2002 |
| WO | WO 200292836 | 11/2002 |
| WO | WO 200294852 | 11/2002 |
| WO | WO 200298358 | 12/2002 |
| WO | WO 200299074 | 12/2002 |
| WO | WO 200299122 | 12/2002 |
| WO | WO 2002101075 | 12/2002 |
| WO | WO 2002102235 | 12/2002 |
| WO | WO 200216429 | 1/2003 |
| WO | WO 2003000842 | 1/2003 |
| WO | WO 2003002717 | 1/2003 |
| WO | WO 2003003906 | 1/2003 |
| WO | WO 2003003984 | 1/2003 |
| WO | WO 2003004529 | 1/2003 |
| WO | WO 2003004989 | 1/2003 |
| WO | WO 2003008537 | 1/2003 |
| WO | WO 2003009814 | 2/2003 |
| WO | WO 2003014294 | 2/2003 |
| WO | WO 2003016475 | 2/2003 |
| WO | WO 2003016494 | 2/2003 |
| WO | WO 2003018621 | 3/2003 |
| WO | WO 2003022995 | 3/2003 |
| WO | WO 2003023013 | 3/2003 |
| WO | WO 2003024392 | 3/2003 |
| WO | WO 2003025138 | 3/2003 |
| WO | WO 2003025148 | 3/2003 |
| WO | WO 2003025228 | 3/2003 |
| WO | WO 2003026493 | 4/2003 |
| WO | WO 2003026577 | 4/2003 |
| WO | WO 2003029262 | 4/2003 |
| WO | WO 2003029277 | 4/2003 |
| WO | WO 2003029421 | 4/2003 |
| WO | WO 2003034984 | 5/2003 |
| WO | WO 2003035846 | 5/2003 |
| WO | WO 2003042661 | 5/2003 |
| WO | WO 2003043583 | 5/2003 |
| WO | WO 2003045422 | 6/2003 |
| WO | WO 2003048202 | 6/2003 |
| WO | WO 2003054152 | 7/2003 |
| WO | WO 2003055439 | 7/2003 |
| WO | WO 2003055443 | 7/2003 |
| WO | WO 2003060612 | 7/2003 |
| WO | WO 2003062401 | 7/2003 |
| WO | WO 2003072035 | 9/2003 |
| WO | WO 2003072036 | 9/2003 |
| WO | WO 2003077836 | 9/2003 |
| WO | WO 2003081210 | 10/2003 |
| WO | WO 2003083041 | 10/2003 |
| WO | WO 2003083047 | 10/2003 |
| WO | WO 2003083074 | 10/2003 |
| WO | WO 2003087306 | 10/2003 |
| WO | WO 2003087768 | 10/2003 |
| WO | WO 2003088808 | 10/2003 |
| WO | WO 2003089624 | 10/2003 |
| WO | WO 2003089904 | 10/2003 |
| WO | WO 2003093444 | 11/2003 |
| WO | WO 2003097803 | 11/2003 |
| WO | WO 2003101283 | 12/2003 |
| WO | WO 2003101400 | 12/2003 |
| WO | WO 2003104270 | 12/2003 |
| WO | WO 2003104275 | 12/2003 |
| WO | WO 2003104399 | 12/2003 |
| WO | WO 2003105758 | 12/2003 |
| WO | WO 2004000221 | 12/2003 |
| WO | WO 2004000997 | 12/2003 |
| WO | WO 2004001004 | 12/2003 |
| WO | WO 2004005598 | 1/2004 |
| WO | WO 2004009622 | 1/2004 |
| WO | WO 2004011611 | 2/2004 |
| WO | WO 2004015426 | 2/2004 |
| WO | WO 2004016225 | 2/2004 |
| WO | WO 2004020583 | 3/2004 |
| WO | WO 2004020595 | 3/2004 |
| WO | WO 2004022709 | 3/2004 |
| WO | WO 2004022778 | 3/2004 |
| WO | WO 2004027049 | 4/2004 |
| WO | WO 2004031238 | 4/2004 |
| WO | WO 2004032828 | 4/2004 |
| WO | WO 2004032842 | 4/2004 |
| WO | WO 2004040000 | 5/2004 |
| WO | WO 2004042346 | 5/2004 |
| WO | WO 2004043361 | 5/2004 |
| WO | WO 2004043963 | 5/2004 |
| WO | WO 2004044178 | 5/2004 |
| WO | WO 2004045516 | 6/2004 |
| WO | WO 2004045520 | 6/2004 |
| WO | WO 2004045553 | 6/2004 |
| WO | WO 2004046342 | 6/2004 |
| WO | WO 2004047749 | 6/2004 |
| WO | WO 2004048938 | 6/2004 |
| WO | WO 2004053079 | 6/2004 |
| WO | WO 2004058309 | 7/2004 |
| WO | WO 2004063355 | 7/2004 |
| WO | WO 2004063362 | 7/2004 |
| WO | WO 2004063709 | 7/2004 |
| WO | WO 2004065576 | 8/2004 |
| WO | WO 2004065577 | 8/2004 |
| WO | WO 2004074320 | 9/2004 |
| WO | WO 2005023814 | 3/2005 |
| WO | WO 2005040170 | 5/2005 |
| WO | WO 2005042535 | 5/2005 |
| WO | WO 2005079479 | 9/2005 |
| WO | WO 2005082023 | 9/2005 |
| WO | WO 2005085177 | 9/2005 |
| WO | WO 2005085250 | 9/2005 |
| WO | WO 2005085251 | 9/2005 |
| WO | WO 2005085259 | 9/2005 |
| WO | WO 2005085260 | 9/2005 |
| WO | WO 2005105113 | 11/2005 |
| WO | WO 2005110423 | 11/2005 |
| WO | WO 2006065533 A2 | 6/2006 |
| WO | WO 2006111759 | 10/2006 |
| WO | WO 2007039752 | 4/2007 |
| WO | WO 2007044515 | 4/2007 |
| WO | WO 2007085930 | 8/2007 |
| WO | WO 2008010101 | 1/2008 |
| WO | WO 2008022152 | 2/2008 |
| WO | WO 2008047242 | 4/2008 |

(56) References Cited

FOREIGN PATENT DOCUMENTS

| | | |
|---|---|---|
| WO | WO 2008050140 | 5/2008 |
| WO | WO 2008070593 | 6/2008 |
| WO | WO 2009016516 | 2/2009 |
| WO | WO 2009052249 | 4/2009 |
| WO | WO 2009060208 | 5/2009 |
| WO | WO 2009060215 | 5/2009 |
| WO | WO 2009117531 | 9/2009 |
| WO | WO 2010010347 | 1/2010 |
| WO | WO 2010043877 | 4/2010 |
| WO | WO 2010043880 | 4/2010 |
| WO | WO 2010091150 | 8/2010 |
| WO | WO 2010095031 | 8/2010 |
| WO | WO 2011023883 | 3/2011 |
| WO | WO 2011038159 | 3/2011 |
| WO | WO 2011059850 | 5/2011 |
| WO | WO 2011100227 | 8/2011 |
| WO | WO 2011128650 | 10/2011 |
| WO | WO 2011130598 | 10/2011 |
| WO | WO 2011130613 | 10/2011 |
| WO | WO 2011130615 | 10/2011 |
| WO | WO 2011130616 | 10/2011 |
| WO | WO 2011133039 | 10/2011 |
| WO | WO 2012014147 | 2/2012 |
| WO | WO 2012018325 | 2/2012 |
| WO | WO 2012039717 | 3/2012 |
| WO | WO 2012064733 | 5/2012 |
| WO | WO 2012112687 | 8/2012 |
| WO | WO 2012112708 | 8/2012 |
| WO | WO 2012128868 | 9/2012 |
| WO | WO 2013041606 | 3/2013 |
| WO | WO 2013053871 | 4/2013 |
| WO | WO 2013053872 | 4/2013 |
| WO | WO 2013053873 | 4/2013 |
| WO | WO 2013055987 | 4/2013 |
| WO | WO 2013055990 | 4/2013 |
| WO | WO 2013055993 | 4/2013 |
| WO | WO 2013164592 | 11/2013 |
| WO | WO 2013164593 | 11/2013 |
| WO | WO 2013177481 | 11/2013 |
| WO | WO 2014011518 | 1/2014 |
| WO | WO 2014011519 | 1/2014 |
| WO | WO 2014022679 | 2/2014 |
| WO | WO 2014031566 | 2/2014 |
| WO | WO 2014057072 | 4/2014 |
| WO | WO 2014057073 | 4/2014 |
| WO | WO 2014057074 | 4/2014 |
| WO | WO 2014057113 | 4/2014 |
| WO | WO 2014057114 | 4/2014 |
| WO | WO 2014057115 | 4/2014 |
| WO | WO 2014057117 | 4/2014 |
| WO | WO 2014057118 | 4/2014 |
| WO | WO 2014057119 | 4/2014 |
| WO | WO 2014057120 | 4/2014 |
| WO | WO 2014057122 | 4/2014 |
| WO | WO 2014080251 | 5/2014 |
| WO | WO 2014096365 | 6/2014 |
| WO | WO 2014096368 | 6/2014 |
| WO | WO 2014130879 | 8/2014 |
| WO | WO 2014140174 | 9/2014 |
| WO | WO 2014140862 | 9/2014 |
| WO | WO 2014159981 | 10/2014 |
| WO | WO 2014174111 | 10/2014 |
| WO | WO 2015028850 | 3/2015 |
| WO | WO 2015031693 | 3/2015 |
| WO | WO 2015052321 | 4/2015 |
| WO | WO 2015052322 | 4/2015 |
| WO | WO 2015052332 | 4/2015 |
| WO | WO 2015052333 | 4/2015 |
| WO | WO 2015052334 | 4/2015 |
| WO | WO 2015052335 | 4/2015 |
| WO | WO 2015052532 | 4/2015 |
| WO | WO 2015052533 | 4/2015 |
| WO | WO 2015052534 | 4/2015 |
| WO | WO 2015052535 | 4/2015 |
| WO | WO 2015095124 | 6/2015 |
| WO | WO 2015112822 | 7/2015 |
| WO | WO 2015157595 | 10/2015 |
| WO | WO 2015159076 | 10/2015 |
| WO | WO 2016201065 | 12/2015 |
| WO | WO 2016037644 | 3/2016 |
| WO | WO 2016038383 | 3/2016 |
| WO | WO 2016040868 | 3/2016 |
| WO | WO 2016044396 | 3/2016 |
| WO | WO 2016044560 | 3/2016 |
| WO | WO 2016053107 | 4/2016 |
| WO | WO 2016166297 | 10/2016 |
| WO | WO 2016166298 | 10/2016 |
| WO | WO 2016166299 | 10/2016 |
| WO | WO 2016166300 | 10/2016 |
| WO | WO 2016166302 | 10/2016 |
| WO | WO 2016166305 | 10/2016 |
| WO | WO 2016166307 | 10/2016 |
| WO | WO 2017035353 | 3/2017 |
| WO | WO 2017059289 | 4/2017 |
| WO | WO 2017137553 | 8/2017 |
| WO | WO 2017186894 | 11/2017 |
| WO | WO 2017201132 | 11/2017 |
| WO | WO 2018031662 | 2/2018 |
| WO | WO 2018069490 | 4/2018 |
| WO | WO 2018182341 | 10/2018 |
| WO | WO 2018218093 | 11/2018 |
| WO | WO 2020006722 | 1/2020 |

OTHER PUBLICATIONS

Adams et al., "Molecular modelling of a sequence-specific DNA-binding agent based on the pyrrolo[2,1-c][1,4]benzodiazepines," Pharm. Pharmacol. Commun. (1999) 5:555-560.

Aird et al., "ABCB1 genetic polymorphism influences the pharmacology of the new pyrrolobenzodiazepine derivative SJG-136," Pharmacogenomics Journal (2008) 8(4):289-296.

Alley et al., "SJG-136 (NSC 694501), a novel rationally designed DNA minor groove interstrand cross-linking agent with potent and broad spectrum antitumor activity. Part 2: Efficacy evaluations," Cancer Res. (2004) 64:6700-6706.

Alley, M.C., "Efficacy evaluations of SJG-136 (NSC 694501), a novel pyrrolobenzodiazepine dimer with broad spectrum antitumor activity," Proceedings of the American Association for Cancer Research Annual Meeting (Mar. 2002) 43:63.

Alley, S. C., "Contribution of Linker Stability to the Activities of Anticancer Immunoconjugates" Bioconjugate Chem 2008, 19, 759-765.

Althius, T. H. and Hess, H. J., "Synthesis and Identification of the Major Metabolites of Prazosin Formed in Dog and Rat," J. Medicinal Chem. (1977) 20(1):146-148.

Altuvia et al., "Ranking potential binding peptides to MHC molecules by a computational threading approach." J. Mol. Biol., 249, 244-250 (1995).

Amiel J., et al., "Heterozygous endothelin receptor B {EDNRB) mutations in isolated Hirschsprung disease," Hum. Mol. Genet. 5, 355-357, 1996.

Amir et al., "Self-Immolative Dendrimers," (2003) Angew. Chem. Int. Ed. 42:4494-4499.

Amsberry, et al., "The Lactonization of 2'-Hydroxyhydrocinnamic Acid Amides: A Potential Prodrug for Amines," (1990) J. Org. Chem. 55:5867-5877.

Antonow, D. et al., "Structure-activity relationships of monomeric C2-aryl pyrrolo[2,1-c][1,4]benzodiazepine (PBD) antitumor agents." J Med Chem. Apr. 8, 2010;53(7):2927-41.

Antonow, D. et al., "Synthesis of DNA-Interactive Pyrrolo [2,1-c][1,4] benzodiazepines (PBDs)" Chemical Reviews, 2011, 111(4):2815-2864.

Antonow, D. et al.,"Parallel synthesis of a novel C2-aryl pyrrolo[2,1-c][1,4]benzodiazepine (PBD) library," J. Comb. Chem. (2007) 9:437-445.

Arai H., et al., "Molecular cloning of human endothelin receptors and their expression in vascular endothelial cells and smooth muscle cells," Jpn. Circ. J. 56, 1303-1307, 1992.

(56) References Cited

OTHER PUBLICATIONS

Arai H., et al., "The Human Endotbelin-B Receptor Gene. Structural Organization and Chromosomal Assignment," J. Biol. Chem. 268, 3463-3470, 1993.
Arima et al., "Studies on Tomaymycin, a New Antibiotic. I. Isolation and Properties of Tomaymycin," J. Antibiotics (1972) 25:437-444.
Arnould, S., "Impact on the cell cycle and involvement of ATM, ATR, chk1 and chk2 kinases in the cytotoxicity of SJG-136, a new pyrrolobenzodiazepine dimer," Proceedings of the American Association for Cancer Research Annual Meeting (Mar. 2004) 45:1298, Abstract No. 5618.
Arnould, S., "Time-dependent cytotoxicity induced by SJG-136 (NSC 694501): influence of the rate of interstrand cross-link formation on DNA damage signaling," Mol. Canc. Therap. 5(6):1602-1609 (2006).
Attie T., et al., "Mutation of the endothelin-receptor B gene in Waardenburg-Hirschsprung disease," Hum. Mol. Genet. 4, 2407-2409, 1995.
Auricchio A., et al., "Endothelin-B receptor mutations in patients with isolated Hirschsprung disease from a non-inbred population," Hum. Mol. Genet. 5:351-354, 1996.
Axup et al., "Synthesis of site-specific antibody-drug conjugates using unnatural amino acids." Proc Natl Acad Sci U S A. Oct. 2, 2012; 109(40):16101-6.
Bahrenberg et al., "Reduced Expression of PSCA, a Member of the LY-6 Family of Cell Surface Antigens, in Bladder, Esophagus, and Stomach Tumors," Biochem. Biophys. Res. Commun. (2000) 275(3):783-788.
Banker, G.S. et al., "Modern Pharmaceutics", Third edition, Marcel Dekker, New York (1996) 451 and 596.
Barel M., et al., "Evidence for a new transcript of the Epstein-Barr virus/C3d receptor (CR2, CD21) which is due to alternative exon usage," Mol. Immunol. 35, 1025-1031, 1998.
Barella et al., "Sequence variation of a novel heptahelical leucocyte receptor through alternative transcript formation," (1995) Biochem. J. 309:773-779.
Barnett T., et al., "Carcinoembryonic Antigen Family: Characterization of cDNAs Coding for NCA and CEA and Suggestion of Nonrandom Sequence Variation in Their Conserved Loop-Domains," Genomics 3, 59-66, 1988.
Batisse, et al., "A new delivery system for Auristatin in STxB-drug conjugate therapy." European J. Medicinal Chemistry, 2015, 95: 483-491.
Beck et al., "DNA Sequence Analysis of 66 kb of the Human MHC Class II Region Encoding a Cluster of Genes for Antigen Processing," (1992) J. Mol. Biol. 228:433-441.
Beck et al., "Evolutionary Dynamics of Non-coding Sequences Within the Class II Region of the Human MHC," (1996) J. Mol. Biol. 25 255:1-13.
Berge et al., "Pharmaceutical Salts," J. Pharm. Sci. (1977) 66:1-19.
Berry, J. M. et al., "Solid-phase synthesis of DNA-interactive pyrrolo[2,1-c][1,4]benzodiazepines," Tetrahedron Letters (2000) 41:6171-6174.
Berry, J.M. et al., "Synthesis and biological evaluation of an N10-Psec substituted pyrrolo[2,1-c][1,4]benzodiazepine prodrug," Bioorg. Med. Chem. Lett. (2002) 12:1413-1416.
Bien & Balcerska, "Serum Soluble Interleukin 2 receptor in human cancer of adults and children: a review," Biomarkers, 2008, 13(1): 1-26.
Blanc et al., "SAR3419: an anti-CD19-Maytansinoid Immunoconjugate for the treatment of B-cell malignancies," Clin Cancer Res., 2011, 17(20):6448-58.
Blumberg H., et al., "Interleukin 20: Discovery, Receptor Identification, and Role in Epidermal Function," Cell 104, 9-19, 2001.
Bose et al., "New Approaches to Pyrrolo[2,1-c][1,4]benzodiazepines: Synthesis, DNA-binding and cytotoxicity of DC-81," Tetrahedron, 48, 751-758 (1992).
Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.
Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).
Bourgeois C., et al., "Endothelin-1 and ETA Receptor Expression in Vascular Smooth Muscle Cells from Human Placenta: A New ETA Receptor Messenger Ribonucleic Acid Is Generated by Alternative Splicing of Exon 3," J. Clin. Endocrinol. Metab. 82, 3116-3123, 1997.
Brand et al., Prospect for anti-HER2 receptor therapy in breast cancer. Anticancer Res. Jan.-Feb. 2006;26(1B):463-70.
Brinster et al., "Introits increase transcriptional efficiency in transgenic mice," (1988) Proc. Natl. Acad. Sci. USA 85:836-840.
Buchman et al., "Comparison of Intron-Dependent and Intron-Independent Gene Expression," (1988) Mol. Cell. Biol. 8:4395-4405.
Buhrow, S.A., "LC-MS/MS assay and dog pharmacokinetics of the dimeric pyrrolobenzodiazepine SJG-136 (NSC 694501)," J. Chromat. B: Anal. Tech. Biomed. Life Sci. (2006) 840(1):56-62.
Burke, P.J et al., "Anti-CD70 antibody-drug conjugates containing pyrrolobenzodiazepine dimers demonstrate robust antitumor activity," AACR National Meeting, Apr. 2012, Chicago, Illinois, Abstract No. 4631.
Burke, P.J. et al., "Novel immunoconjugates comprised of streptonigrin and 17-amino-geldanamycin attached via a dipeptide-p-aminobenzylamine linker system," Bioorg. Med. Chem. Lett., Apr. 2009, 19(10):2650-2653.
Calcutt, M.W., "Determination of chemically reduced pyrrolobenzodiazepine SJG-136 in human plasma by HPLC-MS/MS: application to an anticancer phase I dose escalation study," J. Mass Spectrom. (2008) 43(1):42-52.
Carl et al., "A Novel Connector Linkage Applicable in Prodrug Design," (1981) J. Med. Chem. 24:479-480.
Carlsson et al., "Protein Thiolation and Reversible Protein-Protein Conjugation," (1978) Biochem. J. 173:723-737.
Carter, P., "Potent antibody therapeutics by design," (2006) Nature Reviews Immunology 6:343-357.
Casset et al., "A peptide mimetic of an anti-CD4 monoclonal antibody by rational design." Biochem Biophys Res Commun. Jul. 18, 2003; 307(1):198-205.
CellTiter-Glo Luminescent Cell Viability Assay, Promega Corp. Technical Bulletin TB288, dated Jan. 13, 2012 (14 pages).
Chakravarty et al., "Plasmin-Activated Prodrugs for Cancer Chemotherapy. 2. Synthesis and Biological Activity of Peptidyl Derivatives of Doxorubicin," (1983) J. Med. Chern. 26:638-644.
Chan, J. and Watt, V.M., "eek and erk, new members of the eph subclass of receptor protein-tyrosine kinases," Oncogene 6 (6), 1057-1061 (1991).
Chang et al., "Molecular cloning of mesothelin, a differentiation antigen present on mesothelium, mesotheliomas, and ovarian cancers," Proc. Natl. Acad. Sci. U.S.A. 93 (1):136-140 (1996).
Chen, Z. et al., "A novel approach to the synthesis of cytotoxic C2-C3 unsaturated pyrrolo[2,1-c][1,4]benzodiazepines (PBDs) with conjugated acrylyl C2-substituents," Biorg. Med. Chem. Lett. (2004) 14:1547-1549.
Cheung, A., "Direct liquid chromatography determination of the reactive imine SJG-136 (NSC 694501)," J. Chromat. B: Anal. Techn. Biomed. Life Sci. (2005) 822(1-2):10-20.
Child et al., "Translational Control by an Upstream Open Reading Frame in the HER-2/neu Transcript," (1999) J. Bioi. Chern. 274: 24335-24341.
Cho et al., "Structure of the extracellular region of HER2 alone and in complex with the Herceptin Fab," Nature 421, 756-760, 2003.
Ciccodicola, A., et al., "Molecular characterization of a gene of the 'EGF family' expressed in undifferentiated human NTERA2 teratocarcinoma cells," EMBO J. 8 (7):1987-1991 (1989).
Cipolla, L., "Pyrrolo[2,1-c][1,4]benzodiazepine as a scaffold for the design and synthesis of anti-tumour drugs," Anti-Cancer Agents in Medicinal Chemistry (Jan. 2009) 9(1):1-31.

(56) References Cited

OTHER PUBLICATIONS

Clackson et al., "Making antibody fragments using phage display libraries," (1991) Nature, 352:624-628.
Clark H.F., et al., "The Secreted Protein Discovery Initiative (SPDI], a Large-Scale Effort to Identify Novel Human Secreted and Transmembrane Proteins: A Bioinformatics Assessment," Genome Res. 13, 2265-2270, 2003.
Clingen, P.H., "The role of nucleotide excision repairand homologous recomination in the sensitivity of mammalian cells to the minor groove crosslinking pyrrolo[2,1-c][1,4]benzodiazepine dimer SJG-136 (NSC694501)," Proceedings of the American Association for Cancer Research Annual Meeting (Jul. 2003) 44:524.
Clingen, P.H., "the XPF-ERCC1 endonuclease and homologous recombination contribute to the repair of minor groove DNA interstrand crosslinks in mammalian cells produced by the pyrrolo[2,1-c][1,4]benzodiazepine dimer SJG-136," Nucl. Acids Res. (2005) 33(10):3283-3291.
Clinical Trial, "Translational research: 4 ways to fix the clinical trial." 2011, http://www.nature.com/news/2011/110928/full/477526a.html.
Clinical Trials Identifier NCT02034227, Safety, Tolerability Study of SG2000 in the Treatment of Advanced Chronic Lymphocytic Leukemia and Acute Myeloid Leukemia [online] NIH U.S. National Library of Medicine 2014 [Retrieved on Nov. 4, 2020], Retrieved from the Internet: <https://www.clinicaltrials.gov/ct2/show/NCT02034227>.
Collins, "Generation and initial analysis of more than 15,000 full-length human and mouse eDNA sequences," Proc. Natl. Acad. Sci. U.S.A. 99 (26):16899-16903 (2002).
Cooper, N. et al., "Synthesis of novel PBDs as anti-tumour agents," Chem. Commun. (2002) 16:1764-1765.
Cooper, N., "Design, Synthesis and Evaluation of Novel C2-Aryl Pyrrolobenzodiazepines as Potential Anticancer Agents," Thesis submitted to School of Pharmacy, University of London, Dated Oct. 5, 2006.
Corey et al., "LuCap35: a new model of prostate cancer progression to androgen independence." The Prostate 2003;55:239-46.
Courtney, S. M. et al., "A new convenient procedure forthe synthesis of pyrrolo[2,1-c][1,4]benzodiazepines", Tetrahedron Letters, vol. 34, No. 33, 5327-28 (1993).
Coussens L., et al., "Tyrosine Kinase Receptor with Extensive Homology to EGF Receptor Shares Chromosomal Location With neu Oncogene," Science (1985) 230(4730):1132-1139.
Cragg et al., "The alternative transcript of CD79b is overexpressed in B-CLL and inhibits signaling for apoptosis," Blood (2002) 100 (9):3068-3076.
Cree et al., "Methotrexate chemosensitivity by ATP luminescence in human leukemia cell lines and in breast cancer primary cultures: comparison of the TCA-100 assay with a clonogenic assay," (1995) AntiCancer Drugs 6:398-404.
Crouch et al., "The use• of ATP bioluminescence as a measure of cell proliferation and cytotoxicity," (1993) J. Immunol. Meth. 160:81-88.
Dall'Acqua, W. F. et al., "Antibody humanization by framework shuffling" Methods, 36, 43-60 (2005).
Dattolo, G. et al., "Polycondensed nitrogen heterocycles. IX. 5,6-dihydro-7H-pyrrolo[1,2- d][1,4]benzodiazepin-6-one," J. Heterocyclic. Chem. (1980) 17:701-703.
Davis et al., "Identification of a family of Fe receptor homo logs with preferential B cell expression," (2001) Proc. Natl. Acad. Sci. USA 98(17):9772-9777.
De Groot et al., "Cascade-Release Dendrimers" Liberate All End Groups upon a Single Triggering Event in the Dendritic Core, (2003) Angew. Chern. Int. Ed. 42:4490-4494.
De Groot et al., "Elongated Multiple Electronic Cascade and Cyclization Spacer Systems in Activatible Anticancer Prodrug for Enhanced Drug Release," (2001) J. Org. Chern. 66:8815-8830.
De Pascalis et al., "Grafting of "abbreviated" complementarity-determining regions containing specificity-determining residues essential for ligand contact to engineer a less immunogenic humanized monoclonal antibody." J Immunol. Sep. 15, 2002;169(6):3076-84.
Dennis et al., (2002) "Albumin Binding As A General Strategy For Improving The Pharmacokinetics Of Proteins" J Biol Chem. 277:35035-35043.
Duke, P., et al., "Characterization of Type I Receptors for Transforming Growth Factor-beta and Activin," Science 264 (5155):101-104 (1994).
Dimasi et al., "Efficient preparation of site specific antibody drug conjugates using cysteine insertion," Mol. Pharmaceutics 14 1501-1516 (2017).
Dimasi et al., "The Design and Characterization of Oligospecific Antibodies for Simultaneous Targeting of Multiple Disease Mediators" Journal of Molecular Biology, 2009, 393,672-692.
Dobner et al., "Differentiation-specific expression of a novel G protein-coupled receptor from Burkitt's lymphoma," (1992) Eur. J. Immunol. 22:2795-2799.
Dong, Q. et al., "Reductive cleavage of TROC groups under neutral conditions with cadmium-lead couple," Tetrahedron Lett. (1995) 36(32):5681-5682.
Dono et al., "Isolation and Characterization of the Cri PTO Autosomal Gene and Its X-linked Related Sequence," Am. J. Hum. Genet. 49:555-565, 1991.
Dornan et al., "Therapeutic potential of an anti-CD79b antibody-drug conjugate, anti-CD79b-vc-MMAE, for the treatment of non-Hodgkin lymphoma," (2009) Blood 114(13):2721-2729.
Doronina et al., "Enhanced Activity of Monomethylauristatin F through Monoclonal Antibody Delivery: Effects of Linker Technology on Efficacy and Toxicity," (2006) Bioconj. Chem. 17:114-124.
Doronina, S.O. et al., "Development of potent monoclonal antibody auristatin conjugates for cancer therapy," Nature Biotech. (2003) 21:778-784.
Dorwald, F.Z., Side Reactions in Organic Synthesis: a Guide to Successful Synthesis Design, Weinheim: Wiley-VCH Verlag GmbH & Co., KGaA (2005) Preface.
Doyle, M., "Response of *Staphylococcus aureus* to subinhibitory concentrations of a sequence-selective, DNA minor groove crosslinking pyrrolobenzodiazepine dimer," J. Antimicrob. Chemo., Aug. 2009, 64(5):949-959.
Dubowchik et al., "Cathepsin B-sensitive dipeptide prodrugs. 1. A model study of structural requirements for efficient release of doxorubicin." Bioorg Med Chem Lett. Dec. 1, 1998; 8(23):3341-6.
Dubowchik et al., "Cathepsin B-sensitive dipeptide prodrugs. 2. Models of anticancer drugs paclitaxel (Taxol), mitomycin C and doxorubicin." Bioorganic & Medicinal Chemistry Letters, 8:3347-3352, (1998).
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem. (2002) 13, 855-869.
Dubowchik et al., "Monomethoxytrityl (MMT) as a Versatile Amino Protecting Group for Complex Prodrugs of Anticancer Compounds Sensitive to Strong Acids, Bases and Nucleophiles," (1997) Tetrahedron Letters. 38:5257-5260.
Dumoutier L., et al., "Cutting Edge: STAT Activation By IL-19, IL-20 and mda-7 Through IL-20 Receptor Complexes of Two Types," J. Immunol. 167, 3545-3549, 2001.
Dupont, C. et al., "Synthesis of rhazinilam analogue acting as an inhibitor of tubulin assembly," Tetrahedron Lett. (2000) 41:5853-5856.
Ehsani A., et al., "Characterization of a New Allele of the Human ERBB2 Gene by Allele-Specific Competition Hybridization," (1993) Genomics 15, 426-429.
Eliel et al., Stereochemistry of Organic Compounds, John Wiley & Sons, Inc., New York (1994).
Elshourbagy N.A., et al., "Molecular Characterization and Regulation of the Human Endothelin Receptors," J. Biol. Chem. 268, 3873-3879, 1993.
Erickson et al., "Antibody-Maytansinoid Conjugates Are Activated in Targeted Cancer Cells by Lysosomal Degradation and Linker-Dependent Intracellular Processing," (2006) Cancer Res. 66(8): 4426-4433.

(56) References Cited

OTHER PUBLICATIONS

Farmer, J.D. et al., "Synthesis and DNA crosslinking ability of a dimeric anthramycin analog," Tetrahedron Letters (1988) 29(40):5105-5108, Abstract only.
Farmer, J.D. et al., "DNA binding properties of a new class of linked anthramycin analogs,", Chemical Abstracts, Abstract No. 239940r, vol. 114, No. 25, 25 899-903 (1991).
Fey, T. et al., "Silica-supported TEMPO catalyst: synthesis and application in the anelli oxidation of alcohols," J. Org. Chem. (2001) 66:8154-8159.
Field, J.A., et al., "Cloning and Functional Characterization of a Sodium-Dependent Phosphate Transporter Expressed in Human Lung and Small Intestine," (1999) Biochem. Biophys. Res. Commun. 258 (3):578-582.
Fields, G. and Noble, R. (1990) "Solid phase peptide synthesis utilizing 9-fluoroenylmethoxycarbonyl amino acids", Int. J. Peptide Protein Res. 35:161-214.
Firsching, A. et al., "Antiproliferative and angiostatic activity of suramin analogues," Cancer Res. (1995) 55:4957-4961.
Flanagan et al., "The ephrins and Eph receptors in neural development," Annu. Rev. Neurosci. 21:309-345 (1998).
Flygare, "Antibody-drug conjugates forthe treatment of cancer," Chem. Biol. & Drug Design (2013) 81(1):113-121.
Flynn et al., "Pre-Clinical Activity of Adct-301, a Novel Pyrrolobenzodiazepine (PBD) Dimer-Containing Antibody Drug Conjugate (ADC) Targeting CD25-Expressing Hematological Malignancies," https://www.researchgate.net/publication/275520174.
Foloppe, M.P. et al., "DNA-binding properties of pyrrolo[2,1-c][1,4]benzodiazephine N10-C11 amidines," Eur. J. Med. Chem., 31, 407-410 (1996).
Fox et al., "cDNA cloning and tissue distribution of five human EPH-like receptor protein-tyrosine kinases," Oncogene 10 (5):897-905 (1995).
Fuchs S., et al., "Functional Characterization of Three Mutations of the Endothelin B Receptor Gene in Patients With Hirschsprung's Disease: Evidence for Selective Loss of Gi Coupling," Mol. Med. 7, 115-124, 2001.
Fujisaku et al., "Genomic Organization and Polymorphisms of the Human C3d/Epstein-Barr Virus Receptor," (1989) J. Biol. Chem. 264 (4):2118-2125.
Fujisawa Pharmaceutical Co. Ltd., "Benzodiazepine derivatives," SciFinder Scholar, 2-3 (2002).
Fujisawa Pharmaceutical Co., Ltd., Abstract No. 139983k, "Benzodiazepine derivatives", Chemical Abstracts, vol. 99, No. 17, 603 (1983).
Fujisawa Pharmaceutical Co., Ltd., Abstract No. 72145x, "Benzodiazepine derivatives", Chemical Abstracts, vol. 98, No. 9, 638 (1983).
Fukuyama, T. et al., "Total Synthesis of (+)-Porothramycin B," Tetrahedron Letters, vol. 34, 16, 2577-2580 (1993).
Gallmeier, E., "Targeted disruption of FANCC and FANCG in human cancer provides a preclinical model for specific therapeutic options," Gastroenterology (2006) 130(7):2145-2154.
Gary S.C., et al., "cDNA cloning chromosomal localization, and expression analysis of human BEHAB/brevican, a brain specific proteoglycan regulated during cortical development and in glioma," Gene 256, 139-147, 2000.
Gaugitsch, H.W., et al., "A novel transiently expressed, integral membrane protein linked to cell activation. Molecular cloning via the rapid degradation signal AUUUA.," (1992) J. Biol. Chem. 267 (16):11267-11273.
Gavezzotti, A., "Are crystal structures predictable?" Acc. Chem. Res. (1994) 27:309-314.
Geiser et al. "Automation of solid-phase peptide synthesis" in Macromolecular Sequencing and Synthesis, Alan R. Liss, Inc., 1988, pp. 199-218.
Genbank accession No. 11038674 (2013).
Genbank accession No. 20 NM_006424 (2013).
Genbank accession No. AAH32229, version No. AAH32229.1 GI:21619004, record update: Mar. 6, 2012.
Genbank accession No. AB040878 (2001).
Genbank accession No. AF116456 (1999).
Genbank accession No. AF179274 (2001).
Genbank accession No. AF229053 (2000).
Genbank accession No. AF343662 (2001).
Genbank accession No. AF343663 (2001).
Genbank accession No. AF343664 (2001).
Genbank accession No. AF343665 (2001).
Genbank accession No. AF361486 (2003).
Genbank accession No. AF369794 (2001).
Genbank accession No. AF397453 (2001).
Genbank accession No. AF455138 (2003).
Genbank accession No. AJ297436 (2008).
Genbank accession No. AK026467 (2006).
Genbank accession No. AK089756 (2010).
Genbank accession No. AK090423 (2006).
Genbank accession No. AK090475 (2006).
Genbank accession No. AL834187 (2008).
Genbank accession No. AX092328 (2001).
Genbank accession No. AY158090 (2003).
Genbank accession No. AY260763 (2003).
Genbank accession No. AY275463 (2003).
Genbank accession No. AY358085 (2003).
Genbank accession No. AY358628 (2003).
Genbank accession No. AY358907 (2003).
Genbank accession No. AY506558 (2004).
Genbank accession No. BC017023 (2006).
Genbank accession No. CAA76847.1 (2001).
Genbank accession No. CAF85723 (2004).
Genbank accession No. CQ782436 (2004).
Genbank accession No. M11730 (1995).
Genbank accession No. M18728 (1995).
Genbank accession No. M26004 (1993).
Genbank accession No. M76125, version No. M76125.1 GI:292869, 1995.
Genbank accession No. NM_000626 (2013).
Genbank accession No. NM_001178098.1 (2012).
Genbank accession No. NM_001203 (2013).
Genbank accession No. NM_003212 (2013).
Genbank accession No. NM_003486 (2013).
Genbank accession No. NM_004442 (2013).
Genbank accession No. NM_005823 (2013).
Genbank accession No. NM_012449 (2013).
Genbank accession No. NM_017636 (2013).
Genbank accession No. NM_030764 (2013).
Genbank accession No. NP 002111.1 (2013).
Genbank accession No. NP_001171569.1 (1992).
Genbank accession No. NP_001194 (2013).
Genbank accession No. NP_001707.1 (2013).
Genbank accession No. NP_001773.1 (2013).
Genbank accession No. NP_001774.10 (2013).
Genbank accession No. NP_002552.2 (2013).
Genbank accession No. NP_003203 (2013).
Genbank accession No. NP_005573.1 (2007).
Genbank accession No. NP_112571.1 (2007).
Geoghegan & Stroh, "Site-Directed Conjugation of Nonpeptide Groups to Peptides and Proteins via Periodate Oxidation of a 2-Amino Alcohol. Application to Modification at N-Terminal Serine," (1992) Bioconjugate Chem. 3:138-146.
Getz et al., "A Comparison between the Sulfhydryl Reductants Tris(2-carboxyethyl)phosphine and Dithiothreitol for Use in Protein Biochemistry," (1999) Anal. Biochem. vol. 273:73-80.
Glynne-Jones et al., "TENB2, a proteogl ycan identified in prostate cancer that is associated with disease progression and androgen independence," (2001) Int J Cancer. Oct. 15; 94(2): 178-184.
Gordon et al., "Somatic hypermutation of the B cell receptor genes B29 (Igβ, CD79b) and mb1 (Igα, CD79a)," PNAS, Apr. 1, 2003, vol. 100, No. 7, 4126-4131.
Greene, T.W. and Wuts, P.G.M., Protective Groups in Organic Synthesis, John Wiley & Sons, 2nd ed Ch 7, 315-345 (1991).
Greene, T.W. et al., Protective Groups in Organic Synthesis, John Wiley & Sons (1999) 3rd Edition, 503-549.

(56) References Cited

OTHER PUBLICATIONS

Greene, T.W. et al., Protective Groups in Organic Synthesis, John Wiley & Sons (1999) 3rd Edition, 23-200.
Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.
Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.
Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.
Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.
Gregson, S.J. et al., "Design, Synthesis and Evaluation of a Novel Pyrrolobenzodiazepine DNA-Interactive Agent with Highly Efficient Cross-Linking Ability and Potent Cytotoxicity", J. Med. Chem., 44: 737-748 (2001).
Gregson, S.J. et al., "Effect of C2-exo Unsaturation on the Cytotoxicity and DNA-Binding Reactivity of Pyrrolo[2,1-c][1,4]benzodiazepines", Bioorganic & Medicinal Chemistry Letters, 10: 1845-1847 (2000).
Gu, Z. et al., "Prostate stem cell antigen (PSCA) expression increases with high gleason score, advanced stage and bone metastasis in prostate cancer," Oncogene 19, 1288-1296, 2000.
Guichard, S.M., "Influence of P-glycoprotein expression on in vitro cytotoxicity and in vivo antitumour activity of the novel pyrrolobenzodiazepine dimer SJG-136," Eur. J. Cancer (2005) 41 (12):1811-1818.
Guiotto, A. et al., "Synthesis of novel C7-aryl substituted pyrrolo[2,1-c][1,4]benzodiazepines (PBDs) via Pro- N10-troc protection and Suzuki coupling," Bioorganic & Medicinal Chemistry Letters, 8, No. 21, 3017-3018 (1998).
Guselnikov et al., "A family of highly diverse human and mouse genes structurally links leukocyte FcR, gp42 and PECAM-1," Immunogenetics 54 (2):87-95 (2002).
Ha et al., "molecular cloning and expression pattern of a human gene homologous to the murine mb-1 gene," (1992) J. Immunol. 148(5):1526-1531.
Hadjivassileva, T., "Antibacterial activity of pyrrolobenzodiazepine dimers, a novel group of DNA-binding compounds," Abstracts of the Interscience Conference on Antimicrobial Agents and Chemotherapy (Oct.-Nov. 2004) 44:202.
Hadjivassileva, T., "Interactions of pyrrolobenzodiazepine dimers and duplex DNA from methicillin-resistant *Staphylococcus aureus*," Int. J. Antimicrob. Agents (2007) 29(6):672-678.
Hadjivassileva, T., "Pyrrolobenzodiazepine dimers: novel sequence-selective, DNA-interactive, cross-linking agents with activity against Gram-positive bacteria," J. Antimicrob. Chemo. (2005) 56(3):513-518.
Haendler B., et al., "Molecular Cloning of Human Endothelin (ET) Receptors ETA and ETB," J. Cardiovasc. Pharmacal. 20, s1-S4, 1992.
Haisma et al., "Comparison of two antracycline-based prodrugs for activation by a monoclonal antibody-β-glucuronidase conjugate in the specific treatment of cancer." Cell biophysics, Humana Press Inc. 1994, 24/25: 185-192.
Hamaguchi, A., "DNA cross-linking and in vivo antitumour activity of the extended pyrrolo[2,1-c][1,4]benzodiazepine dimer SG2057 (DRG-16)," EJC Supplements (Nov. 2006) 4(12):96.
Hamann P. "Monoclonal antibody-drug conjugates," (2005) Expert Opin. Ther. Patents 15(9):1087-1103.

Hamblett et al., "Effects of Drug Loading on the Antitumor Activity of a Monoclonal Antibody Drug Conjugate," (2004) Clin. Cancer Res. 10:7063-7070.
Handbook of Food Additives, 2nd Ed. (eds. M. Ash and I. Ash), Synapse Information Resources, Inc., Endicott, New York, USA (2001).
Handbook of Pharmaceutical Excipients, 2nd edition, 1994, Edited by Ainley Wade and Paul J. Weller.
Hara et al., "DC 102, a new glycosidic pyrrolo(1,4)benzodiazepine antibiotic produced by *Streptomyces* sp.", J. Antibiotics, 41, 702-704 (1988).
Hartley JA: "The development of pyrrolobenzodiazepines as antitumour agents", Expert Opinion on Investigational Drugs, Ashley Publications Ltd., vol. 28, No. 6, Jan. 1, 2011, pp. 733-744.
Hartley, J.A. et al., "Abstract 2856: pyrrolobenzodiazepine (PBD) dimers—potent next generation warheads in antibody drug conjugates (ADCs) targeted at both solid and haematological tumors," Cancer Res. (2013) 78(8)Supp 1:2856.
Hartley, J.A. et al., "SG2285, a novel C2-aryl-substituted pyrrolobenzodiazepine dimer prodrug that cross-links DNA and exerts highly potent antitumor activity," Cancer Res., Sep. 2010, 70(17):6849-6858.
Hartley, J.A. et al., "SJG-136 (NSC 694501), a novel rationally designed DNA minor groove interstrand cross- linking agent with potent and broad spectrum antitumor activity. Part 1: Cellular pharmacology, in vitro and initial in vivo antitumor activity," Cancer Res. (2004) 64:6693-6699.
Hartley, J.A., "In vitro antitumor activity and in vivo DNA interstrand crosslinking by the novel pyrrolobenzodiazepine dimer SJG-136 (NSC 694501)," Proceedings of the American Association for Cancer Research Annual Meeting (Mar. 2002) 43:489.
Hartley, J.A., "SJG-136 (NSC-D694501)—a novel DNA sequence specific minor groove crosslinking agent with significant antitumor activity," Proceedings of the American Association for Cancer Research Annual Meeting (Mar. 2000) 41:425.
Hashimoto et al., "Chromosomal localization, genomic structure, and allelic polymorphism of the human CD79a (Ig-alpha/mb-1) gene," (1994) Immunogenetics 40(4 ):287-295.
Hay et al., "A 2-nitroimidazole carbamate prodrug of 5-amin0-1-(chloromethyl)-3-[(5,6,7-trimethoxyindol-2-yl)carbonyl]-1,2-dihydr0-3h-benz[e]indole (amino-seco-cbi-tmi) for use with adept and gdept," (1999) Bioorg. Med. Chem. Lett. 9:2237-2242.
Herdwijn et al., "Synthesis of trans(+ )6-phenoxyacetamido-1-methylene-3,3-dicarboxymethyl-1-carbapenam," Canadian Journal of Chemistry. 1982, 60, 2903-2907.
Hermanson, G.T., "Heterobifunctional Cross-linkers," (1996) Bioconjugate Techniques; Academic Press: New York, p. 228-286.
Hochhauser, D., "Phase I study of sequence-selective minor groove DNA binding agent SJG-136 in patients with advanced solid tumors," Clin. Cancer Res., Mar. 2009, 15(6):2140-2147.
Hochlowski, J. et al., "Abbeymycin, a new anthramycin-type antibiotic produced by a streptomycete," J. Antibiotics, 40, 145-148 (1987).
Hofstra R.M.W., et al., "A homozygous mutation in the endothelin-3 gene associated with a combined Waardenburg type 2 and Hirschsprung phenotype (Shah-Waardenburg syndrome)" Nat. Genet. 12, 445-447, 1996.
Hofstra R.M.W., et al., "Mutations in Hirschsprung Disease: When Does a Mutation Contribute to the Phenotype," Eur. J. Hum. Genet. 5, 180-185, 1997.
Horie et al., "Identification and Characterization of TMEFF2, a Novel Surviv Factor for Hippocampal and Mesencephalic Neurons," (2000) Genomics 67: 146-152.
Howard, P.W. et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W. et al., "Synthesis of a novel C2/C2'-aryl-substituted pyrrolo[2,1-c][1,4]benzodiazepine dimer prodrug with improved water solubility and reduced DNA reaction rate," Bioorg. Med. Chem., Sep. 2009, In Press, 4 pages now: Sep. 2009, 19:6463-6466.
Howard, P.W. et al., "The design, synthesis and biological evaluation of a set of C2-aryl substituted pyrrolo[2,1- c][1,4]benzodiazepine dimers," EJC Supplements (2006) 4(12):95—Poster Abstract 301.

(56) References Cited

OTHER PUBLICATIONS

Howard, P.W., "Design, synthesis and biological evaluation of novel C2-aryl-substituted pyrrolo[2,1-c][1,4]benzodiazepine monomers," Proceedings of the American Association for Cancer Research Annual Meeting (Apr. 2006) 47:132.
Hubert, R.S., et al., "STEAP: A prostate-specific cell-surface antigen highly expressed in human prostate tumors," (1999) Proc. Natl. Acad. Sci. U.S.A. 96 (25):14523-14528.
Hurley, L. and Needham-Vandevanter, D., "Covalent Binding of Antitumor Antibiotics in the Minor Groove of DNA. Mechanism of Action of CC-1065 and the pyrrolo(1,4)benzodiazepines," Acc. Chem. Res., 19, 230-237 (1986).
Ide et al., "Cloning of human bone morphogenetic protein type IB receptor (BMPRIB) and its expression in prostate cancer in comparison with other BMPRs," Oncogene (1997) 14, 1377-1382.
Iida, H. et al. "Design and synthesis of pyrrolo[2,1-c][1,4]benzodiazepine (PBD)-polyaminoalkyl conjugates by the use of SNA4 reaction 2-nitro-5-fluorobenzoate precursor as key reaction," Heterocycles (2004) 62:693-711.
International Search Report and Written Opinion dated Dec. 21, 2012 for Int. Appl. No. PCT/US2012/059864 (7 pages).
International Search Report and Written Opinion for Application No. PCT/EP2012/070233 dated Jan. 28, 2013 (8 pages).
International Search Report and Written Opinion for Application No. PCT/EP2013/071346 dated Feb. 5, 2014 (11 pages).
International Search Report and Written Opinion for Application No. PCT/EP2013/071352 dated Feb. 5, 2014 (14 pages).
International Search Report and Written Opinion for Application No. PCT/EP2014/054958 dated Jul. 2, 2014 (13 pages).
International Search Report and Written Opinion for Application No. PCT/GB2015/052629 dated Nov. 2, 2015 (12 pages).
International Search Report and Written Opinion for Application No. PCT/US2011/032664 dated Aug. 19, 2011 (13 pages).
International Search Report and Written Opinion for Application No. PCT/US2011/032668 dated May 26, 2011 (12 pages).
International Search Report and Written Opinion for Application No. PCT/US2015/050634 dated Jan. 29, 2016 (14 pages).
International Search Report and Written Opinion for Application No. PCT/EP2018/053163 dated Apr. 4, 2018, 10 pages.
International Search Report and Written Opinion for Application No. PCT/EP2018/053162 dated Apr. 24, 2018 (9 pages).
International Search Report and Written Opinion for Application No. PCT/EP2018/081079 dated Feb. 19, 2019 (12 pages).
International Search Report and Written Opinion dated Jun. 13, 2019, Int. Appl. No. PCT/EP2019/055116, 6 pages.
Iontcho R Vlahov et al., "Preparation of pyrrolobenzodiazepine peptide conjugates for treating cancer diseases." WO2017172930, Oct. 5, 2017 pp. 1-6.
Itoh et al., "Sibanomicin, a new pyrrolo(1,4)benzodiazepine antitumor antibiotic produced by a *Micromonospora* sp." J. Antibiotics, 41, 1281-1284 (1988).
Janjigian, Y.Y., "A phase I trial of SJG-136 (NSC#694501) in advanced solid tumors," Cancer Chemotherapy and Pharmacology, Aug. 2009, 65(5):833-838.
Jeffrey et al., "A Potent Anti-CD70 Antibody-Drug Conjugate Combining a Dimeric Pyrrolobenzodiazepine Drug with Site-Specific Conjugation Technology." Bioconj. Chem. 2013, 24, 1256-1263.
Jeffrey et al., "Development and properties of beta-glucuronide linkers for monoclonal antibody-drug conjugates." Bioconjugate Chemistry, 5, 2006, 17, 831-840. (Abstract).
Jeffrey, S.C. et al., "Development of Pyrrolobenzodiazepine-Based Antibody-Drug Conjugates for Cancer," AACR Annual Meeting 2013, Abstract No. 4321.
Jeffrey, S.C., "Design, synthesis, and in vitro evaluation of dipeptide-based antibody minor groove binder conjugates," J. Med. Chem. (2005) 48(5):1344-1358.
Jespers, L. S., "Guiding the Selection of Human Antibodies from Phage Display Repertoires to a Single Epitope of an Antigen" Nature Biotech., 12, 899-903 (1994).

Jia, L., "Interspecies differences in pharmacokinetics and time-dissociated toxicokinetics of SJG-136," Proceedings of the American Association for Cancer Research Annual Meeting (Mar. 2004) 45:487.
Jia, L., "Use of the comet assay as a surrogate biomarker for the in vivo measurement of DNA damage to lymphocytes," Proceedings of the American Association for Cancer Research Annual Meeting (Mar. 2004) 45:452-453.
Johnson & Goldin, "The clinical impact of screening and other experimental tumor studies." CancerTreat Rev. Mar. 1975; 2(1):1-31.
Jones et al., "Releasable Luciferin—Transporter Conjugates: Tools forthe Real-Time Analysis of Cellular Uptake and Release," J. Am. Chem. Soc., 2006, 128, 6526-6527.
Jonsson et al., "Human class II DNA and DOB genes display low sequence variability," (1989) Immunogenetics 29(6):411-413.
Jordan, V.C., "Tamoxifen: a most unlikely pioneering medicine," Nature Reviews: Drug Discovery (2003) 2:205-213.
Junutula et al., "Rapid identification of reactive cysteine residues for site-specific labeling of antibody-Fabs," (2008) Jourof Immun. Methods 332:41-52.
Junutula, et al., "Site-specific conjugation of a cytotoxic drug to an antibody improves the therapeutic index," 2008b Nature Biotech., 26(8):925-932.
Kamal et a., "Pyrrolo[2,1-c][1,4]benzodiazepine-β-glucuronide prodrugs with a potential for selective therapy of solid tumors by PMT and ADEPT strategies" Bioorganic & Medicinal Chemistry Letters 2008, 18:3769-3773.
Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22): 3955-3958.
Kamal, A. et al., "Design, synthesis and evaluation of new noncross-linking pyrrolobenzodiazepine dimers with efficient DNA binding ability and potent antitumor activity," J. Med. Chem. (2002) 45:4679-4688.
Kamal, A., "Development of pyrrolo[2,1-c][1,4]benzodiazepine beta-galactoside prodrugs for selective therapy of cancer by ADEPT and PMT," Chemmedchem (2008) 3:794-802.
Kamal, A., "Remarkable DNA binding affinity and potential anticancer activity of pyrrolo[2,1-c][1,4]benzodiazepine-naphthalamide conjugates linked through piperazine side-armed alkane spacers," Bioorg. Med. Chem. (2008) 16(15):7218-7224.
Kamal, A., "Remarkable enhancement in the DNA-binding ability of C2-fluoro substituted pyrrolo[2,1-c][1,4]benzodiazepines and their anticancer potential," Bioorg. Med. Chem., Jan. 2009, 17(4):1557-1572.
Kamal, A., "Synthesis of fluorinated analogues of SJG-136 and their DNA-binding potential," Bioorg. Med. Chem. Lett (2004) 14(22):5699-5702.
Kamal, A., et al., "An Efficient Synthesis of Pyrrolo[2,1-c][1,4] Benzodiazepine Antibiotics via Reductive Cyclization," Bioorg. Med. Chem. Ltrs, 7, No. 14, 1825-1828 (1997).
Kamal, A., et al., "Synthesis of Pyrrolo [2,1-c][1,4]-Benzodiazepene Antibiotics: Oxidation of Cyclic Secondary Amine with TPAP", Tetrahedron, v. 53, No. 9, 3223-3230 (1997).
Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.
Kaneko, T. et al., "Bicyclic and tricyclic analogues of anthramycin," J. Med. Chem. (1985) 28:388-392.
Kang, G.-D. et al., "Synthesis of a novel C2-aryl substituted 1,2-unsaturated pyrrolobenzodiazepine," Chem. Commun. (2003) 1680-1689.
Kasahara et al., "Nucleotide sequence of a chimpanzee DOB eDNA clone," (1989) Immunogenetics 30(1):66-68.
King et al., "Facile synthesis of maleimide bifunctional Jinkers," (2002) Tetrahedron Letters 43:1987-1990.
Kingsbury et al., "A Novel Peptide Delivery System Involving Peptidase Activated Prodrugs as Antimicrobial Agents. Synthesis and Biological Activity of Peptidyl Derivatives of 5 Fluorouracil," (1984) J. Med. Chem. 27:1447-1451.

(56) References Cited

OTHER PUBLICATIONS

Kitamura et al., "Synthetic study of (+)-anthramycin using ring-closing enyne metathesis and cross-metathesis," Tetrahedron 2004, 60, 9649-9657.
Kohler et al., "Continuous cultures of fused cells secreting antibody of predefined specificity," (1975) Nature 256:495-497.
Kohn, K., "Anthramycin," Antibiotics III, Springer-Verlag, NY, 3-11 (1975).
Kojima et al., "Molecular Cloning and Expression of Megakaryocyte Potentiating Factor eDNA," The Journal of Biological Chemistry, vol. 270, No. 37, Issue of Sep. 15, p. 21984-21990, 1995.
Konishi, M. et al., "Chicamycin, a new antitumor antibiotic II. Structure determination of chicamycins A and B," J. Antibiotics, 37, 200-206 (1984).
Kovtun et al., "Antibody-Drug Conjugates Designed to Eradicate Tumors with Homogeneous and Heterogeneous Expression of the Target Antigen," (2006) Cancer Res. 66(6):3214-3121.
Kreitman et al., "Phase I Trial of Recombinant Immunotoxin Anti-Tac(Fv)-PE38 (LMB-2) in Patients with Hematologic Malignancies," J. Clin. Oncol., 2000, 18:1622-1636.
Kuhns J.J., et al., "Poor Binding of a HER-2/neu Epitope (GP2) to HLA-A2.1 Is due to a Lack of Interactions with the Center of the Peptide," J. Biol. Chem. 274, 36422-36427, 1999.
Kumar et al., "Antibody drug conjugates," Annual Reports in Medicinal Chemistry 2017, 50 441-480.
Kuminoto, et al., "Mazethramycin, a new member of anthramycin group antibiotics" J Antibiot (Tokyo) Jun. 1980; 33(6):665-7.
Kurebayashi et al., "Isolation and characterization of a new human breast cancer cell line, KPL-4, expressing the Erb B family receptors and interleukin 6," (1999) Brit. Jour. Cancer 79(5-6):707-717.
Lambert, "Drug-conjugated monoclonal antibodies for the treatment of cancer," (2005) Current Opin.In Pharmacal. 5:543-549.
Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).
Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.
Larhammar et al., "Sequence of Gene and eDNA Encoding Murine Major Histocompatibility Complex Class II Gene AP2*," (1985) J. Biol. Chem. 260(26):14111-14119.
Launay et al., "TRPM4 Is a Ca2+-Activated Nonselective Cation Channel Mediating Cell Membrane Depolarization," Cell 109 (3):397-407 (2002).
Law et al., "Lymphocyte Activation Antigen CD70 Expressed by Renal Cell Carcinoma Is a Potential Therapeutic Target for Anti-CD70 Antibody-Drug Conjugates," (2006) Cancer Res. 66(4):2328-2337.
Lazar et al., "A molecular immunology approach to antibody humanization and functional optimization" Molecular Immunology, 2007, 44(8), 1986-1998.
Le et al., "Primary structure and expression of a naturally truncated human P2X ATP receptor subunit from brain and immune system," (1997) FEBS Lett. 418(1-2):195-199.
Leabman; et al., "Effects of altered Fcyγbinding on antibody pharmacokinetics in cynomolgus monkeys." MAbs. Nov.-Dec. 2013; 5(6):896-903.
Leber, J.D. et al., "A revised structure for sibiromycin," J. Am. Chem. Soc., 110, 2992-2993 (1988).
Ledford et al., "Total Synthesis of (+)-Trehazolin: Optically Active Spirocycloheptadienes as Useful Precursors for the Synthesis of Amino Cyclopentitols." J. Am. Chem. Soc. 1995, 117, 47, 11811-11812.
Leimgruber, W. et al., "Isolation and characterization of anthramycin, a new antitumor antibiotic," J. Am. Chem. Soc., 87, 5791-5793 (1965).

Leimgruber, W. et al., "The structure of anthramycin," J. Am. Chem. Soc., 87, 5793-5795 (1965).
Leimgruber, W. et al., "Total synthesis of anthramycin," J. Am. Chem. Soc., 90, 5641-5643 (1968).
Leonard et al., "Phase I/II trial of epratuzumab (humanized anti-CD22 antibody) in indolent non-Hodgkin's lymphoma," J. Clin. Oncology (2003) 21(16):3051-3059.
Leonard et al., "Preclinical and clinical evaluation of epratuzumab (anti-CD22 IgG) in B-cell malignancies," Oncogene (2007) 26:3704-3713.
Leung et al., "Construction and characterization of a humanized, internalizing, B-cell (CD22)-specific, leukemia/lymphoma antibody, LL2," Mol. Immunol. (1995) 32(17-18):1413-1427.
Levenson et al., "MCF-7: The First Hormone-responsive Breast Cancer Cell Line," (1997) Cancer Res. 57(15):3071-3078.
Lewis Phillips et al., "Targeting HER2-Positive Breast Cancer with Trastuzumab-DM1, an Antibody-Cytotoxic Drug Conjugate," Cancer Res, 2008, 68: (22).
Liang et al., "The Gene for a Novel Transmembrane Protein Containing Epidermal Growth Factor and Follistatin Domains Is Frequently Hypermethylated in Human Tumor Cells," (2000) Cancer Res. 60:4907-4912.
Linden et al., "Dose-fractionated radioimmunotherapy in non-Hodgkin's lymphoma using DOTA-conjugated, 90Y-radiolabeled, humanized anti-CD22 monoclonal antibody, epratuzumab," J. Clin. Cancer Res. (2005) 11:5215-5222.
Lonberg, "Fully Human antibodies from transgenic mouse and phage display platforms" Curr. Opinion, 20(4), 450-459 (2008).
Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.
Manfre et al., "Syntheses of Proline Analogues as Potential Mechanism-Based Inhibitors of Proline Dehydrogenase:4-Methylene-L-, (E)- and (Z)-4-(Fluoromethylene)-L-, cis- and trans-5-Ethynyl-(±)-, and cis- and trans-5-Vinyl-L-proline," J. Org. Chem. 1992, 57, 2060-2065.
Marin, D., "Voltammetric studies of the interaction of pyrrolo[2,1-][1,4]benzodiazepine (PBD) monomers and dimers with DNA," J. Electroanal. Chem. (2006) 593(1-2):241-246.
Marks et al., "By-passing Immunization, Human Antibodies from V-gene Libraries Displayed on Phage," (1991) J. Mol. Biol., 222:581-597.
Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.
Masterson et al. "Synthesis and biological evaluation of novel pyrrolo[2,1-c][1,4]benzodiazepine prodrugs for use in antibody-directed enzyme prodrug therapy.", Bioorganic & Medicinal Chemistry Letters, vol. 16., No. 2, Jan. 15, 2006, pp. 252-256.
Mastroberardino et al., "Amino-acid transport by heterodimers of 4F2hc/CD98 and members of a permease family," Nature 395 (6699):288-291 (1998).
Matsumoto, K. et al., "Synthesis of polyaminoalkyl substituted conjugates of pyrrolo[2,1-c][1,4]benzodiazepine (PBD)-polyaminoalkyl involving SNA4 reaction of 2-nitro-5-fluorobenzoate precursors," Heterocycles (2000) 52(3):1015-1020.
McDonagh, "Engineered antibody-drug conjugates with defined sites and stoichiometries of drug attachment," (2006) Protein Eng. Design & Sel. 19(7): 299-307.
Mendoza et al., "Inhibition of Ligand-mediated HER2 Activation in Androgenindependent Prostate Cancer," (2002) Cancer Res. 62:5485-5488.
Miller et al., "Design, Construction, and In Vitro Analyses of Multivalent Antibodies," (2003) Jour. of Immunology 170:4854-4861.
Miller et al., "IRTAs: a new family of immunoglobulinlike receptors differentially expressed in B cells," Blood 99 (8):2662-2669 (2002).
Miura et al., "Molecular cloning of a human RP105 homologue and chromosomal localization of the mouse and human RP105 genes (Ly64 and LY64)." Genomics. Dec. 15, 1996; 38(3):299-304.

(56) References Cited

OTHER PUBLICATIONS

Miura et al., "RPIOS Is Associated With MD-1 and Transmits an Activation Signal in Human B Cells," (1998) Blood 92:2815-2822.
Moore M., et al., "Molecular cloning of the eDNA encoding the Epstein-Barr virus/C3d receptor (complement receptor type 2) of human B lymphocytes," Proc. Natl. Acad. Sci. U.S.A. 84, 9194-9198, 1987.
Mori, M. et al., "Total syntheses of prothracarcin and tomaymycin by use of palladium catalyzed carbonylation," Tetrahedron (1986) 42(14):3793-3806.
Morrison et al., "Chimeric human antibody molecules: Mouse antigen-binding domains with human constant region domains," (1984) Proc. Natl. Acad. Sci. USA, 81:6851-6855.
Mountzouris, J.A et al., "Comparison of a DSB-120 DMS interstrand cross-linked adduct with the corresponding bis-Tomamycin adduct," J. Med. Chem. (1994) 37:3132-3140.
Muller et al., "Cloning and sequencing of the eDNA encoding the human homologue of the murine immunoglobulin-associated protein B29," (1992) Eur. J. Immunol. 22 (6): 1621-1625.
Mungall A.J., et al., "The DNA sequence and analysis of human chromosome 6," Nature 425, 805-811, 2003.
Murphy et al., "Concise, Stereoselective Route to the Four Diastereoisomers of 4-Methylproline." J. Nat. Prod. 2008, 71: 806-809.
Nadler et al., "B4, a human B lymphocyte-associated antigen expressed on normal, mitogen-activated, and malignant B lymphocytes," Journal of Immunology, 1983, 131(1):244-250.
Nagasaka, T. and Koseki, Y, "Stereoselective Synthesis of Tilivalline," Journal of Organic Chemistry, vol. 63, No. 20, 6797-6801 (1998).
Nagasaka, T. et al., "Stereoselective Synthesis of Tilivalline," Tetrahedron Letters, 30:14, 1871-1872 (1989).
Nagase T., et al., "Prediction of the Coding Sequences of Unidentified Human Genes. XVII. The Complete Sequences of 100 New eDNA Clones from Brain Which Code for Large Proteins in vitro," (2000) DNA Res. 7 (2):143-150.
Nakamuta M., et al., "Cloning and sequence analysis of a cDNA encoding human non-selective type of endothelin receptor," Biochem. Biophys. Res. Commun. 177, 34-39, 1991.
Nakayama et al., "Altered Gene Expression upon BCR Cross-Linking in Burkitt's Lymphoma B Cell Line," (2000) Biochem. Biophys. Res. Commun. 277(1):124-127.
Narayanaswamy, M., "A novel HPLC/MS assay to measure DNA interstrand cross-linking efficacy in oligonucleotides of varying sequence," EJC Supplements (Nov. 2006) 4(12):92-93.
Narayanaswamy, M., "An assay combining high-performance liquid chromatography and mass spectrometry to measure DNA interstrand cross-linking efficiency in oligonucleotides of varying sequences," Anal. Biochem. (2008) 374(1):173-181.
Narayanaswamy, M., "Use of HPLC-MS to characterize novel mono and intrastrand cross-linked DNA adducts formed by the sequence-selective DNA-interactive agent SJG-136," Proceedings of the American Association for Cancer Research Annual Meeting (Apr. 2007) 48:760-761.
Narukawa, Y., "General and efficient synthesis of 2-alkylcarbapenems synthesis of dethia carba analogs of clinically useful carbapenems via palladium-catalyzed crosscoupling reaction," Tetrahedron (1997) 53:539-556.
Naruse et al., "The HLA-DOB gene displays limited polymorphism with only one amino acid substitution," (2002) Tissue Antigens 59:512-519.
Neuberger and Williams, "The intron requirement for immunoglobulin gene expression is dependent upon the promoter," (1988) Nucleic Acids Res. 16:6713-6724.
Nicolaou et al., "Calicheamicin θ: A Rationally Designed Molecule with Extremely Potent and Selective DNA Cleaving Properties and Apoptosis Inducing Activity," Angew Chem. Intl. Ed. Engl. (1994) 33:183-186.

Nilius et al., "Voltage Dependence of the Ca2+ -activated Cation Channel TRPM4," The Journal of Biological Chemistry, vol. 278, No. 33, Issue of Aug. 15, p. 30813-30820, 2003.
O'Neil, Chemical Abstract No. 171573p, "The synthesis of Functionalized Pyrrolo-[2,1-c][1,4]-Benzodiazepines", Chemical Abstracts, vol. 126, No. 13, 618 (1997).
O'Neil, I.A., et al., "The Synthesis of Functionalized Pyrrolo-[2,1-c][1,4]-Benzodiazepines," Synlett, 75-78 (1997).
Ogawa Y., et al., "Molecular Cloning of a Non-Isopeptide-Selective Human Endothelin Receptor," Biochem. Biophys. Res. Commun. 178, 248-255, 1991.
Okamoto Y., et al. "Palmitoylation of Human Endothelin B," Biol. Chem. 272, 21589-21596, 1997.
O'Neil, I.A. et al., "DPPE: A Convenient Replacement for Triphenylphosphine in the Staudingerand Mitsunobu Reactions", Tetrahedron Letters, vol. 39, No. 42, 7787-7790 (1998).
Parrish-Novak J., et al., "Interleukins 19, 20, and 24 Signal through Two Distinct Receptor Complexes," J. Biol. Chem. 277, 47517-47523, 2002.
Paul, Fundamental Immunology, 3rd Edition, pp. 292-295.
Payne, G. "Progress in immunoconjugate cancer therapeutics," (2003) Cancer Cell 3:207-212.
Pei et al., "Exploration of Pyrrolobenzodiazepine (PBD)-Dimers Containing Disulfide-Based Prodrugs as Payloads for Antibody-Drug Conjugates." Mol Pharm. Sep. 4, 2018;15(9):3979-3996.
Pepper, C., "Fludarabine-mediated suppression of the excision repair enzyme ERCC1 contributes to the cytotoxic synergy with the DNA minor groove crosslinking agent SJG-136 (NSC 694501) in chronic lymphocytic leukaemia cells," Br. J. Cancer (2007) 97(2):253-259.
Pepper, C.J. et al., "The novel sequence-specific DNA cross-linking agent SJG-136 (NSC 694501) has potent and selective in vitro cytotoxicity in human B-cell chronic lymphocytic leukemia cells with evidence of a p53-independent mechanism of cell kill," Cancer Res. (2004) 64:6750-6755.
Phillips et al., "Targeting HER2-Positive Breast Cancer with Trastuzumab-DM1, an Antibody-Cytotoxic Drug Conjugate," (2008) Cancer Res. 68(22):9280-9290.
Pingault V., et al., "SOX10 mutations in chronic intestinal pseudo-obstruction suggest a complex physiopathological mechanism," (2002) Hum. Genet. 111, 198-206.
Pletnev S., et al., "Characterization of the Recombinant Extracellular Domains of Human Interleukin-20 Receptors and Their Complexe with Interleukin-19 and Interleukin-20," (2003) Biochemistry 42:12617-12624.
Porkaa et al., "Cloning and Characterization of a Novel Six-Transmembrane Protein STEAP2, Expressed in Normal and Malignant Prostate," Lab. Invest. 82 (11):1573-1582 (2002).
Prasad et al.,"Human LAT1, a Subunit of System L Amino Acid Transporter: Molecular Cloning and Transport Function," Biochem. Biophys. Res. Commun. 255 (2), 283-288 (1999).
Preud'Homme et al., "Structure and expression of the mb-1 transcript in human lymphoid cells," (1992) Clin. Exp. Immunol. 90(1):141 -146.
Puffenberger E.G., et al., "A Missense Mutation of the Endothelin-B Receptor Gene in Multigenic Hirschsprung's Disease," Cell 79, 1257-1266, 1994.
Purser, et al., "Fluorine in Medicinal Chemistry." Chem. Soc. Rev., 2008, 37, 320-330.
Puzanov, I., "Phase 1 and pharmacokinetic trial of SJG-136 administered on a daily x5 schedule," EJC Supplements (Nov. 2006) 4(12):93.
Quintas-Cardama, A., "Sequencing of subcloned PCR products facilitates earlier detetction of BCR-ABL1 and other mutants compared to direct sequencing of the ABL1 kinase domain," Leukemia (2008) 22(4):877-878.
Rahman et al. "Antistaphylococcal activity of DNA-interactive pyrrolobenzodiazepine (PBD) dimers and PBD-biaryl conjugates." J Antimicrob Chemother. Jul. 2012; 67(7):1683-96.
Rahman, K.M., "Effect of microwave irradiation on covalent ligand-DNA interactions," Chem. Commun. (Cambridge, UK), Apr. 2009, 20:2875-2877.

(56) References Cited

OTHER PUBLICATIONS

Rahman, K.M., "Rules of DNA adduct formation for pyrrolobenzodiazepine (PBD) dimers," Proceedings of the American Association for Cancer Research Annual Meeting (Apr. 2010) 51:851.
Rahman, K.M., "The pyrrolobenzodiazepine dimer SJG-136 forms sequencedependent intrastrand DNA cross-lins and monoalkylated adducts in addition to interstrand cross-links," J. Am. Chem. Soc., Sep. 2009, 131(38):13756-13766.
Rao et al., "Influence of diet on mammary cancer in transgenic mice bearing an oncogene expressed in mammary tissue," (1997) Breast Cancer Res. and Treatment 45:149-158.
Reid, J.M., "LC-MS/MS assay and rat pharmacokinetics and metabolism of the dimeric pyrrolobenzodiazepine SJG-136," Proceedings of the American Association for Cancer Research Annual Meeting (Mar. 2004) 45:1248.
Reiter R.E., et al., "Prostate stem cell antigen: A cell surface marker overexpressed in prostate cancer," Proc. Natl. Acad. Sci. U.S.A. 95, 1735-1740, 1998.
Remmers et al., "Conformations of complexes between pyrrolo[1,4]benzodiazepines and DNA segments," J Med Chem. Dec. 1986;29(12):2492-2503.
Rich, I.N., "Validation and development of a predictive paradigm for hemotoxicology using a multifunctional bioluminescence colony-forming proliferation assay," Toxicological Sci. (2005) 87(2):427-441.
Rodrigues et al., "Synthesis and beta-lactamase-mediated activation of a cephalosporin-taxol prodrug," (1995) Chemistry Biology 2:223-227.
Roguska et al., "A comparison of two murine monoclonal antibodies humanized by CDR-grafting and variable domain resurfacing," Protein Eng, 1996, 9(10):895-904.
Roguska et al., "Humanization of murine monoclonal antibodies through variable domain resurfacing," PNAS, 1994, 91(3):969-973.
Ross et al., "Prostate Stem Cell Antigen as Therapy Target: Tissue Expression and in Vivo Efficacy of an Immunoconjugate," (2002) Cancer Res. 62:2546-2553.
Rudikoff et al., Single amino acid substitution altering antigen-binding specificity. Proc Natl Acad Sci U S A. Mar. 1982; 79(6):1979-83.
Sagnou, M.J. et al., "Design and Synthesis of Novel Pyrrolobenzodiazepine (PDB) Prodrugs for ADEPT and GDEPT," Bioorganic & Medicinal Chemistry Letters, 10, 2083-2086 (2000).
Sakaguchi et al., "8 lymphocyte lineage-restricted expression of mb-1, a gene with CD3-like structural properties," (1988) EMBO J. 7(11):3457-3464.
Sakamoto A, Yanagisawa M., et al., "Cloning and Functional Expression of Human cDNA For the ETB Endothelin Receptor," Biochem. Biophys. Res. Commun. 178, 656-663, 1991.
Sanderson et al., "In vivo Drug-Linker Stability of an Anti-CD30 Dipeptide-Linked Auristatin Immunoconjugate," (2005) Clin. Cancer Res. 11:843-852.
Scholler et al., "Soluble member(s) of the mesothelin/ megakaryocyte potentiating factor family are detectable in sera from patients with ovarian carcinoma," Proc. Natl. Acad. Sci. USA vol. 96, pp. 11531-11536, Sep. 1999.
Schroder and Lubke, The Peptides, vol. 1. pp 76-136 (1965) Academic Press.
Schweikart, K., "In vitro myelosuppression of SJG-136, a pyrrolobenzodiazepine dimer: comparison to bizelesin," Proceedings of the American Association for Cancer Research Annual Meeting (Mar. 2004) 45:486.
Segawa et al., "Growth-related Renal Type II Na/Pi Cotransporter," The Journal of Biolocjcal Chemistry, vol. 277. No. 22, Issue of May 31, p. 19665-19672, 2002.
Semba K., et al., "A v-erbB-related protooncogene, c-erbB-2, is distinct from the c-erbB-1 /epidermal growth factor-receptor gene and is amplified in a human salivary gland adenocarcinoma," 15 Proc. Natl. Acad. Sci. U.S.A 82, 6497-6501, 1985.

Servenius et al., "Class II Genes of the Human Major Histocompatibility Complex, The DOBeta Gene is a Divergent Member of the Class II P Gene Family," (1987) J. Biol. Chem. 262:8759-8766.
Shamis et al., "Bioactivation of Self-Immolative Dendritic Prodrugs by Catalytic Antibody 38C2," (2004) J . Am. Chem. Soc. 126:1726-1731.
Sharkey et al., "Epratuzumab-SN-38: a new antibody-drug conjugate forthe therapy of hematologic malignancies," Mol. Cancer Ther. (2012) 11(1):224-234.
Sheikh F., et al., "Cutting Edge: IL-26 Signals through a Novel Receptor Complex Composed of IL-20 Receptor 1 and IL-10 Receptor 21," (2004) J.Immunol, 172, 2006-2010.
Shen et al., "Conjugation site modulates the in vivo stability and therapeutic activity of antibody-drug conjugates," (2012) Nature Biotech., 30(2):184-191.
Shimizu, K et al., "Prothracarcin, a Novel Antitumor Antibiotic," J. Antibiotics, 35, 972-978 (1982).
Sinha S.K., et al., "Characterization of the EBV/C3d Receptor on the Human Jurkat T Cell Line: Evidence fora Novel Transcript," (1993) J. Immunol. 150, 5311-5320.
Smellie, M. et al., "Cellular pharmacology of novel C8-linked anthramycin-based sequence-selective DNA minor groove cross-linking agents," Br. J. Cancer (1994) 70:48-53.
Smellie, M. et al., "Sequence selective recognition of duplex DNA through covalent interstrand cross-linking," Biochem. (2003) 42:8232-8239.
Smith, P. K. et al., "Measurement of protein using bicinchoninic acid." Anal Biochem. Oct. 1985; 150(1):76-85.
Souillac, P. et al., "Characterization of delivery systems, differential scanning calorimetry," Encyclopedia of Controlled Drug Delivery (1999) 212-227 (pp. 217-218).
Storm et al., "Effect of Small Changes in Orientation on Reaction Rate," (1972) J. Amer. Chem. Soc. 94:5815-5825.
Strausberg et al., "Generation and initial analysis of more than 15,000 full-length human and mouse eDNA sequences," (2002) Proc. Natl. Acad. Sci USA 99:16899-16903.
Suggitt, M., "The hollow fibre model—facilitating anti-cancer pre-clinical pharmacodynamics and improving animal welfare," Int. J. Oncol. (2006) 29(6):1493-1499.
Suggs, J.W. et al., "Synthesis and structure of anthramycin analogs via hydride reduction of dilactams," Tetrahedron Letters, 26, No. 40, 4871-4874 (1985).
Sun et al., "Enabling ScFvs as Multi-Drug Carriers: A Dendritic Approach," (2003) Bioorganic & Medicinal Chemistry 11:1761-1768.
Sun et al., "Syntheses of Dendritic Linkers Containing Chlorambucil Residues forthe Preparation of Antibody-Multidrug Immunoconjugates," (2002) Bioorganic & Medicinal Chemistry Letters 12:2213-2215.
Sutherland et al., "SGN-CD33A: a novel CD33-targeting antibody-drug conjugate using a pyrrolobenzodiazepine dimer is active in models of drug-resistant AML." Blood 2013, 122:1455-1463.
Sutherland, M.S.K. et al., "SGN-CD33A: a novel CD33-directed antibody-drug conjugate, utilizing pyrrolobenzodiazepine dimers, demonstrates preclinical anti-tumor activity against multi-drug resistant human AML," American Society of Hematology (Dec. 8-12, 2012) Atlanta, Georgia, Abstract No. 3589.
Svensson P.J., et al., "Phenotypic variation in a family with mutations in two Hirschsprung-related genes (RET and endothelin receptor B)," Hum. Genet. 103, 145-148, 1998.
Swiercz J.M., et al., "Plexin-81 /RhoGEF-mediated Rho A activation involves the receptor tyrosine kinase ErbB-2," J. Cell Biol. 165, 869-880, 2004.
Syrigos and Epenetos, "Antibody Directed Enzyme Prodrug Therapy (ADEPT): A Review of the Experimental and Clinical Considerations," (1999) Anticancer Research 19:605-614.
Takeuchi, T. et al., "Neothramycins A and B, New Antitumor Antibiotics," J. Antibiotics, 29, 93-96 (1976).
Talpur et al., "CD25 Expression is Correlated with Histological Grade and Response to Denileukin Diftitox in Cutaneous T-Cell Lymphoma," J. Investigative Dermatology, 2006, 126:575-583.
Tawaragi Y., et al., "Primary Structure of Nonspecific Crossreacting Antigen (NCA), a Member of Carcinoembryonic Antigen (CEA)

(56) References Cited

OTHER PUBLICATIONS

Gene Family, Deduced From cDNA SEQUENCE," Biochem. Biophys. Res. Commun. 150, 89-96, 1988.
Tercel, M. et al., "Unsymmetrical DNA cross-linking agents: combination of the CBI and PBD pharmacophores," J. Med. Chem. (2003) 46:2132-2151.
Thompson J.S., et al., "BAFF-R, a Newly Identified TNF Receptor That Specifically Interacts with BAFF," Science 293 (5537), 2108-2111 (2001).
Thurston, D. E., "Advances in the study of Pyrrolo[2,1-c][1,4] benzodiazepine (PBD) Antitumour Antibiotics", Molecular Aspects of Anticancer Drug-DNA Interaction, Neidle, S. and Waring, M.J., Eds.; Macmillan Press Ltd, 1:54-88 (1993).
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).
Thurston, D.E et al., "Effect of A-ring modifications on the DNA-binding behavior and cytotoxicity of pyrrolo[2,1-c][1,4]benzodiazepines", Journal of Medicinal Chemistry, 42:1951-1964 (1999).
Thurston, D.E. et al., "Synthesis of Sequence-selective C8-linked Pyrrolo [2,1-c][1,4] Benzodiazepine DNA Interstrand Cross-linking Agent," J. Org. Chem., 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting: therapeutic strategies for the 21st century," Brit. J. Cancer (1999) 80(1):65-85.
Tiberghien et al., "Design and Synthesis of Tesirine, a Clinical Antibody-Drug Conjugate Pyrrolobenzodiazepine Dimer Payload." ACS Med Chem Lett. Nov. 10, 2016; 7(11): 983-987.
Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.
Tiberghien, A.C., "Application of the stille coupling reaction to the synthesis of C2-substituted endo-exo unsaturated pyrrolo[2,1-c][1,4]benzodiazepines (PBDs)," Bioorg. Med. Chem. Lett. (2008) 18(6):2073-2077.
Toki et al., "Protease-Mediated Fragmentation of p-Amidobenzyl Ethers: A New Strategy for the Activation of Anticancer Prodrugs," (2002) J. Org. Chem. 67:1866-1872.
Tonnelle et al., "DO Beta a new chain gene in HLA-D with a distinct regulation of expression," (1985) EMBO J. 4(11):2839-2847.
Touchman et al., "The Genomic Region Encompassing the Nephropathic Cystinosis Gene (CTNS): Complete Sequencing of a 200-kb Segment and Discovery of a Novel Gene within the Common Cystinosis-Causing Deletion," (2000) Genome Res. 10:165-173.
Tozuka et al., "Studies on tomaymycin. II. Total synthesis of the antitumor antibiotics, E-and Z-tomaymycins," J. Antibiotics (Tokyo) (1983) 36:276-282.
Trail et al., "Monoclonal antibody drug immunoconjugates for targeted treatment of cancer," (2003) Cancer Immunol. Immunother. 52:328-337.
Tsunakawa, M. et al., "Porothramycin, a new antibiotic of the anthramycin group: Production, isolation, structure and biological activity," J. Antibiotics, 41:1366-1373 (1988).
Tsutsumi M., et al., "Novel endothelin B receptor transcripts with the potential of generating a new receptor," Gene 228, 43-49, 1999.
Uchida et al., "A Novel Epidermal Growth Factor-like Molecule Containing Two Follistatin Modules Stimulates Tyrosine Phosphorylation of erbB-4 in MKN28 Gastric Cancer Cells," (1999) Biochem. Biophys. Res. Commun. 266:593-602.
Umezawa, H. et al., "Mazethramycins," SciFinder Scholar, 2-3 (2002).
Umezawa, H. et al., Chemical Abstract No. 4427a, "Mazethramycins" Chemical Abstracts, vol. 90, No. 1, 428 (1979).
U.S. Appl. No. 62/547,303, filed Aug. 18, 2017.

Van Geel et al., "Chemoenzymatic Conjugation of Toxic Payloads to the Globally Conserved N-Glycan of Native mAbs Provides Homogeneous and Highly Efficacious Antibody-Drug Conjugates," (2015) Bioconjugate Chem. 26: 2233-2242.
Verheij J.B., et al., "ABCD Syndrome Is Caused by a Homozygous Mutation in the EDNRB Gene," Am. J. Med. 15 Genet. 108, 223-225, 2002.
Vippagunta, S.R. et al., "Crystalline solids," Adv. Drug Delivery Rev. (2001) 48:3-26.
Von Hoegen et al., "Identification of a human protein homologous to the mouse Lyb-2 B cell differentiation antigen and sequence of the corresponding cDNA," (1990) J. Immunol. 144(12):4870-4877.
Wakankar, et al., "Physicochemical stability of the antibody-drug conjugate Trastuzumab-DM1: changes due to modification and conjugation processes." Bioconjugate Chemistry, 2010, 21, 1588-1595.
Wang, J.H., "Determination of antitumor agent AJG-136 in human serum by HPLC with tandem mass spectrometric detection (HPLC-MS/MS)," Abstracts of Papers American Chemical Society (Mar. 13, 2005) 229(1):U119.
Webster et al., "Mammary tumorigenesis and metastasis in transgenic mice," (1994) Semin. Cancer Biol. 5:69-76.
Weidner-Wells, M.A. et al., "Photochemical approach to the synthesis of the pyrrolo[1,4]benzodiazepine antibiotics," J. Org. Chem. (1989) 54:5746-5758.
Weis J.J., et al., "Identification of a partial eDNA clone for the C3d/Epstein-Barr virus receptor of human B lymphocytes: Homology with the receptor for fragments C3b and C4b of the third and fourth components of complement," Proc. Natl. Acad. Sci. U.S.A. 83, 5639-5643, 1986.
Weis J.J., et al., "Structure of the human b lymphocyte receptor for c3d and the epstein-barr virus and relatedness to other members of the family of C3/C4 binding proteins," J. Exp. Med. 167, 1047-1066, 1988.
Wells, G. et al., "Design, synthesis and biophysical and biological evaluation of a series of pyrrolobenzodiazepine-poly(N-methylpyrrole) conjugates," J. Med. Chem. (2006) 49:5442-5461.
Wikipedia, "How many types of cancer are there?", 2012, 3 pages; http://wiki.answers.com/Q/How-many-different-types_of_cancer_are_there.
Wikipedia, "Management of Cancer," 2012, 1 page; http://en.wikipedia.org/wiki/Management of cancer.
Wilkinson "Eph Receptors and Ephrins: Regulators of Guidance and Assembly," Int. Rev. Cytol. 196:177-244 (2000).
Wilkinson, G.P., "Pharmacokinetics and intracellular pharmacological characteristics of the novel pyrrolobenzodiazepine (PBD) dimer SJG-136," Proceedings of the American Association for Cancer Research Annual Meeting (Jul. 2003) 44:320.
Wilkinson, G.P., "Pharmacokinetics, metabolism and glutathione reactivity of SJG-136," Br. J. Cancer (2003) 88(Supp. 1):S29.
Wilkinson, G.P., "Preliminary pharmacokinetic and bioanalytical studies of SJG-136 (NSC 694501), a sequence-selective pyrrolobenzodiazepine dimer DNA-cross-linking agent," Investigational New Drugs (2004) 22(3):231-240.
Wilson et al., "eDNA Cloning of the B Cell Membrane Protein CD22: A Mediator of B-B Cell Interactions," (1991) J. Exp. Med. 173:137-146.
Wilson, S.C. et al., "Design and Synthesis of a Novel Epoxide-Containing Pyrrolo[2,1-c][1,4]benzodiazepine (PBD) via a New Cyclization Procedure," Tetrahedron Letters, 36, No. 35, 6333-6336 (1995).
Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", J. Med. Chem. 42: 4028-4041 (1999).
Wolff, M.E., Burger's Medicinal Chemistry, 4th Edition, Part I, Wiley: New York (1979) 336-337.
Wolff, M.E., Burger's Medicinal Chemistry, 5th Edition, Part I, John Wiley & Sons (1995) 975-977.
Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.

(56) References Cited

OTHER PUBLICATIONS

Wu et al., "Arming antibodies: prospects and challenges for immunoconjugates," (2005) Nature Biotech. 23(9):1137-1145.

Wuts, P & Greene, T, Greene's Protective Groups in Organic Synthesis, Fourth Edition (Wiley-Interscience), 2007.

Xie et al., "In vivo behaviour of antibody-drug conjugates for the targeted treatment of cancer," (2006) Expert. Opin Biol. Ther. 6(3):281-291.

Xie, G. et al., "Bisindolylmaleimides linked to DNA minor groove binding lexitropsins: synthesis, inhibitory activity against topoisomeraseI, and biological evaluation," J. Med. Chem. (1996) 39:1049-1055.

Xu et al., "Molecular Cloning, Functional Characterization, Tissue Distribution, and Chromosomal Localization of a Human, Small Intestinal Sodium-Phosphate (Na + -Pi) Transporter (SLC34A2)," Genomics 62 (2):281-284 (1999).

Xu, M.J., et al., "Molecular Cloning and Characterization of SPAP1, an Inhibitory Receptor," (2001) Biochem. Biophys. Res. Commun. 280 (3):768-775.

Xu, X.Z., et al., "Regulation of melastatin, a TRP-related protein, through interaction with a cytoplasmic isoform," Proc. Natl. Acad. Sci. U.S.A. 98 (19):10692-10697 (2001).

Yamaguchi, N., et al., "A Novel Cytokine Exhibiting Megakaryocyte Potentiating Activity From a Human Pancreatic Tumor Cell Line HPC-Y5," Biol. Chem. 269 (2), 805-808 (1994).

Yamamoto T., et al., "Similarity of protein encoded by the human c-erb-B-2 gene to epidermal growth factor receptor," Nature 319, 230-234, 1986.

Yang et al., "Murine Six-Transmembrane Epithelial Antigen of the Prostate, Prostate Stem Cell Antigen, and Prostate-specific Membrane Antigen: Prostate-specific Cell-Surface Antigens Highly Expressed in Prostate Cancer of Transgenic Adenocarcinoma Mouse Prostate Mice," Cancer Research, 61, 5857-5860. Aug. 1, 2001.

Yin & Lloyd, "Molecular Cloning of the CA125 Ovarian Cancer Antigen," J. Biol. Chem. 276 (29):27371-27375 (2001).

Younes et al., "Phase I multidose-escalation study of the anti-CD19 maytansinoid immunoconjugate SAR3419 administered by intravenous infusion every 3 weeks to patients with relapsed/refractory B-cell lymphoma," J Clin Oncol., 2012, 30(22):2776-82.

Yu et al., "Human mb-1 gene: complete edna sequence and its expression in b cells bearing membrane Ig of various isotypes," (1992) J. Immunol. 148(2) 633-637.

Zammarchi et al., "Pre-Clinical Development of Adct-402, a Novel Pyrrolobenzodiazepine (PBD)-Based Antibody Drug Conjugate (ADC) Targeting CD19-Expressing B-Cell Malignancies," Blood, 2015, 126:1564, Abstract.

Zammarchi et al., Abstract 51: Characterization of the mechanism of action, pharmacodynamics and preclinical safety of ADCT-402, a pyrrolobenzodiazepine (PBD) dimer-containing antibody-drug conjugate (ADC) targeting CD19-expressing hematological malignancies, Proceedings: American Association for Cancer Research, Apr. 2017; Washington DC.

Zammarchi et al., Abstract 52: Mechanistic and benchmarking studies of ADCT-502, a pyrrolobenzodiazepine (PBD) dimer-containing antibody-drug conjugate (ADC) targeting HER2-expressing solid tumors, Proceedings: American Association for Cancer Research, Apr. 2017; Washington DC.

Zhao et al., "Novel Antibody Therapeutics Targeting Mesothelin In Solid Tumors," (2016) Clin. Cancer Drugs 3: 76-86.

PYRROLOBENZODIAZEPINES AND CONJUGATES THEREOF AS ANTITUMOUR AGENTS

CROSS-REFERENCE TO RELATED APPLICATIONS

This application is a national phase application under 35 U.S.C. § 371 of International Patent Application No. PCT/EP2019/059404, filed Apr. 12, 2019, which claims the benefit of Great Britain Application No. 1806022.8, filed Apr. 12, 2018, each of which is herein incorporated by reference.

The present invention relates to pyrrolobenzodiazepines (PBDs), and their inclusion in targeted conjugates. The PBDs of the present invention are dimer where the group linking the two PBD moieties comprises a benzene or pyridine ring substituted by a carboxy or ester group.

BACKGROUND TO THE INVENTION

Pyrrolobenzodiazepines

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994)). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102)(Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

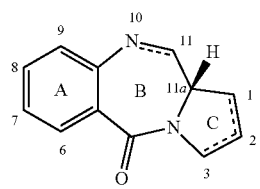

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

A particularly advantageous pyrrolobenzodiazepine compound is described by Gregson et al. (*Chem. Commun.* 1999, 797-798) as compound 1, and by Gregson et al. (*J. Med. Chem.* 2001, 44, 1161-1174) as compound 4a. This compound, also known as SG2000, is shown below:

SG2000

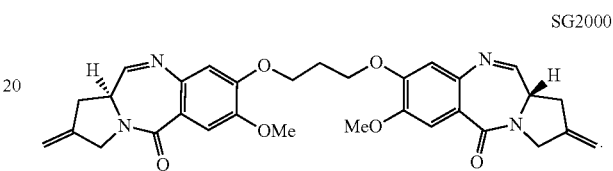

WO 2007/085930 describes the preparation of dimer PBD compounds having linker groups for connection to a cell binding agent, such as an antibody. The linker is present in the bridge linking the monomer PBD units of the dimer.

Dimer PBD compounds having linker groups for connection to a cell binding agent, such as an antibody, are described in WO 2011/130598. The linker in these compounds is attached to one of the available N10 positions, and are generally cleaved by action of an enzyme on the linker group. More recently, the warhead:

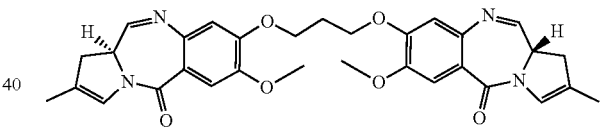

has been used in drug linkers and antibody-drug conjugates. WO 2014/057074 discloses:

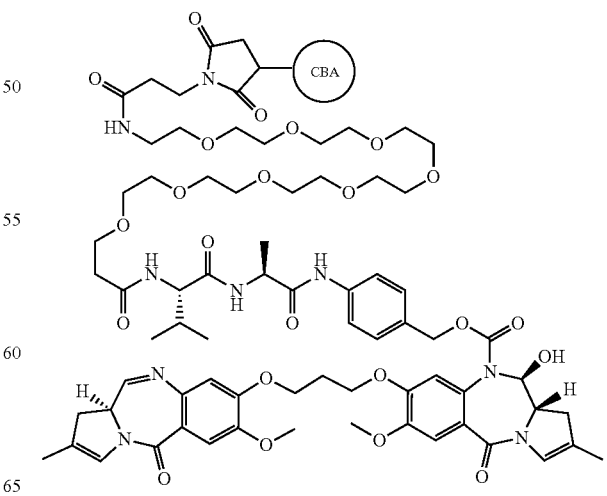

WO2015/052322 discloses:

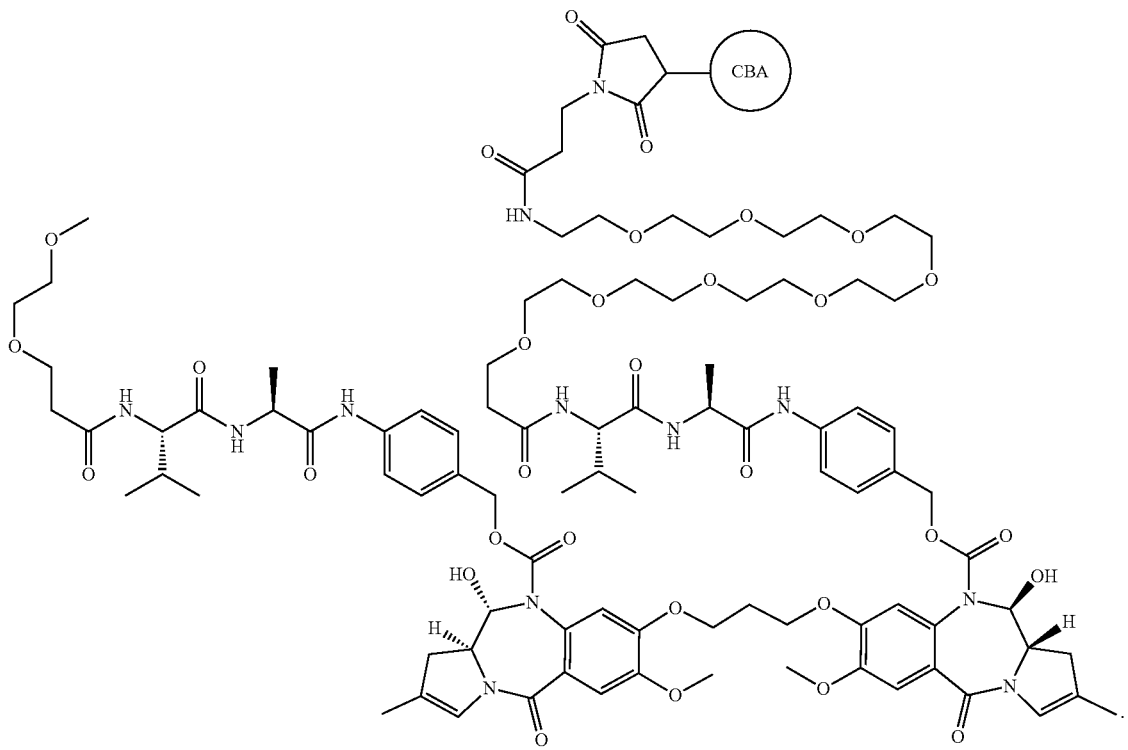 [SMILES: COCCOCCC(=O)N[C@H](C(=O)N[C@@H](C)C(=O)Nc1ccc(COC(=O)N2c3cc(OCCCOc4cc5c(cc4OC)C(=O)N4C=C(C)C[C@H]4[C@H](O)N5C(=O)OCc4ccc(NC(=O)[C@H](C)NC(=O)[C@@H](NC(=O)CCOCCOCCOCCOCCOCCOCCOCCOCCNC(=O)CCN5C(=O)CC(C)C5=O)C(C)C)cc4)c(OC)cc3C(=O)N3C=C(C)C[C@H]3[C@@H]2O)cc1)C(C)C]

A number of disclosures, such as US2014/155590, WO2014/159981, WO2014/140862, and WO 2016/038383 disclose PBD dimers linked from an aromatic group in the tether, such as compound 33 in WO2014/159981

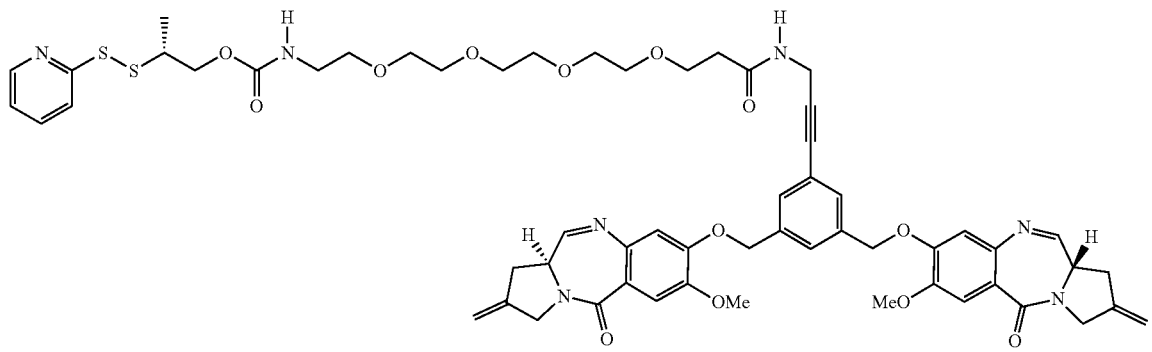 [SMILES: C=C1C[C@H]2C=Nc3cc(OCc4cc(C#CCNC(=O)CCOCCOCCOCCOCCNC(=O)OC[C@@H](C)SSc5ccccn5)cc(COc5cc6c(cc5OC)C(=O)N5CC(=C)C[C@H]5C=N6)c4)c(OC)cc3C(=O)N2C1]

as well as intermediates in their synthesis.

DISCLOSURE OF THE INVENTION

The present invention provides PBD dimers where the group linking the two PBD moieties comprises a benzene or pyridine ring substituted by a carboxy or ester group, as drug linkers, and conjugates made from these drug linkers, as well as the released drugs.

The presence of the carboxy group or ester group should reduce the activity of the drug linker and warhead compared to the analogous drug linkers and warheads being unsubstituted. However, the conjugate with an ester group shows good activity in vitro and in vivo of a level which is comparable to the analogous unsubstituted conjugates. Without wishing to be bound by theory, it is thought that the carboxy group may limit the ability of the warhead to enter the cell when not conjugated.

A first aspect of the present invention comprises a compound with the formula I:

I

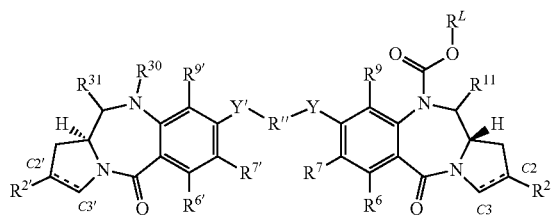

and salts and solvates thereof, wherein:
R" is a group of formula II:

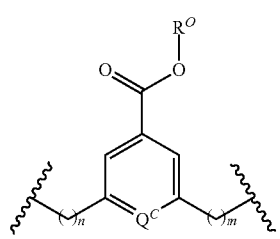

where each of n and m are independently selected from 1, 2 and 3;
$R^O$ is selected from the group consisting of H, methyl, ethyl, iso-propyl and benzyl;
$Q^C$ is selected from N and CH;
Y and Y' are selected from O, S, or NH;
when there is a double bond present between C2 and C3, $R^2$ is selected from the group consisting of:
(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;
(ib) $C_{1-5}$ saturated aliphatic alkyl;
(ic) $C_{3-6}$ saturated cycloalkyl;

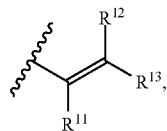

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

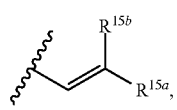

wherein one of $R^{15a}$ and $R^{15b}$ is H and the other is selected from: phenyl, which phenyl is optionally substituted by a group selected from halo, methyl, methoxy; pyridyl; and thiophenyl; and

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;
when there is a single bond present between C2 and C3, $R^2$ is H or

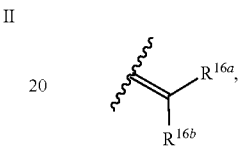

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;
when there is a double bond present between C2' and C3', $R^{2'}$ is selected from the group consisting of:
(iia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;
(iib) $C_{1-5}$ saturated aliphatic alkyl;
(iic) $C_{3-6}$ saturated cycloalkyl;

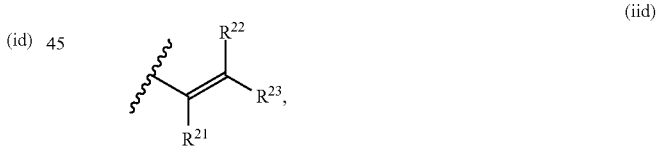

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{2'}$ group is no more than 5;

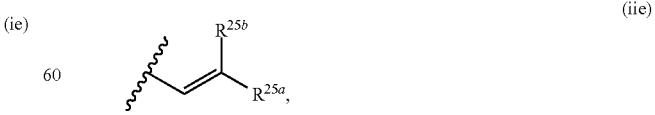

wherein one of $R^{25a}$ and $R^{25b}$ is H and the other is selected from: phenyl, which phenyl is optionally substituted by a group selected from halo, methyl, methoxy; pyridyl; and thiophenyl; and (iif)

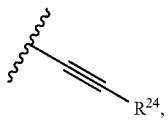

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2' and C3', $R^{2'}$ is H or

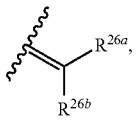

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;

$R^6$ and $R^9$ are independently selected from H, R, OH, OR, SH, SR, $NH_2$, NHR, NRR', nitro, $Me_3Sn$ and halo;

where R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, $NH_2$, NHR, NHRR', nitro, $Me_3Sn$ and halo;

$R^{6'}$, $R^{7'}$, $R^{9'}$ are selected from the same groups as $R^6$, $R^7$ and $R^9$ respectively;

$R^{11a}$ is selected from OH, $OR^A$, where $R^A$ is $C_{1-4}$ alkyl, and $SO_zM$, where z is 2 or 3 and M is a monovalent pharmaceutically acceptable cation;

and either (a) $R^{30}$ is H, and $R^{31}$ is OH, $OR^A$, where $R^A$ is $C_{1-4}$alkyl;

(b) $R^{30}$ and $R^{31}$ form a nitrogen-carbon double bond between the nitrogen and carbon atoms to which they are bound; or (c) $R^{30}$ is H and $R^{31}$ is $SO_zM$, where z is 2 or 3 and M is a monovalent pharmaceutically acceptable cation, wherein if $R^{11a}$ and $R^{31}$ are $SO_zM$, M may represent a divalent pharmaceutically acceptable cation $R^L$ is a linker for connection to a cell binding agent, which is selected from:

(iiia)

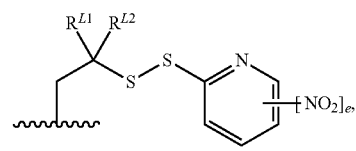

wherein
Q is:

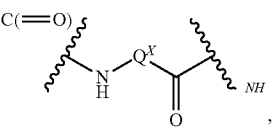

where $Q^X$ is such that Q is an amino-acid residue, a dipeptide residue or a tripeptide residue;

X is:

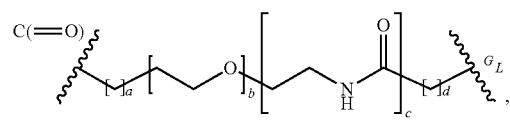

where a=0 to 5, b=0 to 16, c=0 or 1, d=0 to 5;
$G^L$ is a linker for connecting to a Ligand Unit; and (iiib)

IIIb

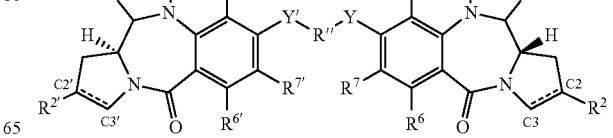

where $R^{L1}$ and $R^{L2}$ are independently selected from H and methyl, or together with the carbon atom to which they are bound form a cyclopropylene or cyclobutylene group; and e is 0 or 1.

A second aspect of the present invention provides a method of making a compound of the first aspect of the invention, comprising at least one of the method steps set out below.

In a third aspect, the present invention relates to Conjugates comprising dimers of PBDs linked to a Ligand unit/targeting agent, wherein the PBD dimer is a derivative of formula I, or a pharmaceutically acceptable salt or solvate thereof.

In some embodiments, the Conjugates having the following formula IV:

$$L\text{-}(D^L)_p \qquad (IV)$$

or a pharmaceutically acceptable salt or solvate thereof, wherein L is a Ligand unit (i.e., a targeting agent), $D^L$ is a Drug Linker unit that is a PBD dimer of formula III:

III wherein $R^2$, $R^6$, $R^7$, $R^9$, $R^{11a}$, Y, R", Y'. $R^{2'}$, $R^{6'}$, $R^{7'}$, $R^{9'}$, $R^{30}$ and $R^{31}$ are as defined in the first aspect of the invention;

$R^{LL}$ is a linker for connection to a cell binding agent, which is selected from:

(iiia)

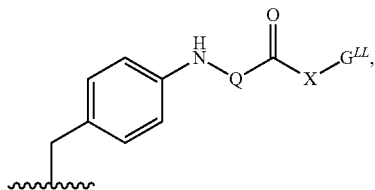
IIIa' where Q and X are as defined in the first aspect and $G^{LL}$ is a linker connected to a Ligand Unit; and (iiib)

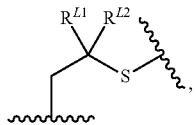
IIIb' where $R^L$ and $R^{L2}$ are as defined in the first aspect;

wherein p is an integer of from 1 to 20.

Accordingly, the Conjugates comprise a Ligand unit covalently linked to at least one Drug unit by a Linker unit. The Ligand unit, described more fully below, is a targeting agent that binds to a target moiety. The Ligand unit can, for example, specifically bind to a cell component (a Cell Binding Agent) or to other target molecules of interest. Accordingly, the present invention also provides methods for the treatment of, for example, various cancers and autoimmune disease. These methods encompass the use of the Conjugates wherein the Ligand unit is a targeting agent that specifically binds to a target molecule. The Ligand unit can be, for example, a protein, polypeptide or peptide, such as an antibody, an antigen-binding fragment of an antibody, or other binding agent, such as an Fc fusion protein.

The drug loading is represented by p, the number of drug molecules per Ligand unit (e.g., an antibody). Drug loading may range from 1 to 20 Drug units (D) per Ligand unit (e.g., Ab or mAb). For compositions, p represents the average drug loading of the Conjugates in the composition, and p ranges from 1 to 20.

A fourth aspect of the present invention provides the use of a conjugate of the third aspect of the invention in the manufacture of a medicament for treating a proliferative disease. The fourth aspect also provides a conjugate of the third aspect of the invention for use in the treatment of a proliferative disease.

One of ordinary skill in the art is readily able to determine whether or not a candidate compound treats a proliferative condition for any particular cell type. For example, assays which may conveniently be used to assess the activity offered by a particular compound are described in the examples below.

A further aspect of the invention provides compounds with the formula REL:

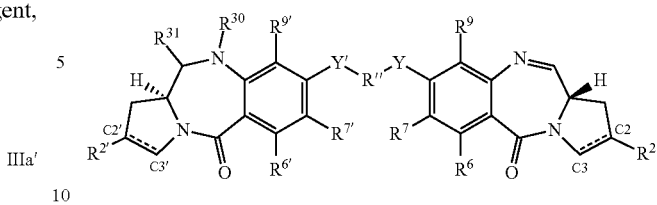
REL and salts and solvates thereof, where all the substituents are as defined above.

Definitions

Pharmaceutically Acceptable Cations

Examples of pharmaceutically acceptable monovalent and divalent cations are discussed in Berge, et al., *J. Pharm. Sci.*, 66, 1-19 (1977), which is incorporated herein by reference.

The pharmaceutically acceptable cation may be inorganic or organic.

Examples of pharmaceutically acceptable monovalent inorganic cations include, but are not limited to, alkali metal ions such as $Na^+$ and $K^+$. Examples of pharmaceutically acceptable divalent inorganic cations include, but are not limited to, alkaline earth cations such as $Ca^{2+}$ and $Mg^{2+}$. Examples of pharmaceutically acceptable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Substituents

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). The term "$C_{1-n}$ alkyl" as used herein, pertains to a monovalent moiety obtained by removing a hydrogen atom from a carbon atom of a hydrocarbon compound having from 1 to n carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —C($CH_3$)=$CH_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —$CH_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

Saturated Monocyclic Hydrocarbon Compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

Unsaturated Monocyclic Hydrocarbon Compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and Saturated Polycyclic Hydrocarbon Compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$); $S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine (C6);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. The term "$C_{5-7}$ aryl", as used herein, pertains to a monovalent moiety obtained by removing a hydrogen atom from an aromatic ring atom of an aromatic compound, which moiety has from 5 to 7 ring atoms and the term "$C_{5-10}$ aryl", as used herein, pertains to a monovalent moiety obtained by removing a hydrogen atom from an aromatic ring atom of an aromatic compound, which moiety has from 5 to 10 ring atoms. Preferably, each ring has from 5 to 7 ring atoms.

In this context, the prefixes (e.g. $C_{3-20}$, $C_{5-7}$, $C_{5-6}$, $C_{5-10}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

N$_2$: imidazole (1,3-diazole) (C$_5$), pyrazole (1,2-diazole) (C$_5$), pyridazine (1,2-diazine) (C$_6$), pyrimidine (1,3-diazine) (C$_6$) (e.g., cytosine, thymine, uracil), pyrazine (1,4-diazine) (C$_6$);

N$_3$: triazole (C$_5$), triazine (C$_6$); and,

N$_4$: tetrazole (C$_5$).

Examples of heteroaryl which comprise fused rings, include, but are not limited to:

C$_9$ (with 2 fused rings) derived from benzofuran (O$_1$), isobenzofuran (O$_1$), indole (N$_1$), isoindole (N$_1$), indolizine (N$_1$), indoline (N$_1$), isoindoline (N$_1$), purine (N$_4$) (e.g., adenine, guanine), benzimidazole (N$_2$), indazole (N$_2$), benzoxazole (N$_1$O$_1$), benzisoxazole (N$_1$O$_1$), benzodioxole (O$_2$), benzofurazan (N$_2$O$_1$), benzotriazole (N$_3$), benzothiofuran (S), benzothiazole (N$_1$S$_1$), benzothiadiazole (N$_2$S);

C$_{10}$ (with 2 fused rings) derived from chromene (O$_1$), isochromene (O$_1$), chroman (O$_1$), isochroman (O$_1$), benzodioxan (O$_2$), quinoline (N$_1$), isoquinoline (N$_1$), quinolizine (N$_1$), benzoxazine (N$_1$O$_1$), benzodiazine (N$_2$), pyridopyridine (N$_2$), quinoxaline (N$_2$), quinazoline (N$_2$), cinnoline (N$_2$), phthalazine (N$_2$), naphthyridine (N$_2$), pteridine (N$_4$);

C$_{11}$ (with 2 fused rings) derived from benzodiazepine (N$_2$);

C$_{13}$ (with 3 fused rings) derived from carbazole (N$_1$), dibenzofuran (O$_1$), dibenzothiophene (S$_1$), carboline (N$_2$), perimidine (N$_2$), pyridoindole (N$_2$); and, C$_{14}$ (with 3 fused rings) derived from acridine (N$_1$), xanthene (O$_1$), thioxanthene (S$_1$), oxanthrene (O$_2$), phenoxathiin (OS$_1$), phenazine (N$_2$), phenoxazine (N$_1$O$_1$), phenothiazine (N$_1$S$_1$), thianthrene (S$_2$), phenanthridine (N$_1$), phenanthroline (N$_2$), phenazine (N$_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a C$_{1-7}$ alkyl group (also referred to as a C$_{1-7}$ alkoxy group, discussed below), a C$_{3-20}$ heterocyclyl group (also referred to as a C$_{3-20}$ heterocyclyloxy group), or a C$_{5-20}$ aryl group (also referred to as a C$_{5-20}$ aryloxy group), preferably a C$_{1-7}$ alkyl group.

Alkoxy: —OR, wherein R is an alkyl group, for example, a C$_{1-7}$ alkyl group. Examples of C$_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a C$_{1-7}$ alkyl group, a C$_{3-20}$ heterocyclyl group, or a C$_{5-20}$ aryl group, preferably a C$_{1-7}$ alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a C$_{1-7}$ alkyl group, a C$_{3-20}$ heterocyclyl group, or a C$_{5-20}$ aryl group, preferably a C$_{1-7}$ alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a C$_{1-7}$ alkyl group, a C$_{3-20}$ heterocyclyl group, or a C$_{5-20}$ aryl group, preferably a C$_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a C$_{1-7}$ alkyl group, a C$_{3-20}$ heterocyclyl group, or a C$_{5-20}$ aryl group, preferably a C$_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, C$_{1-7}$alkyl group, a C$_{3-20}$ heterocyclyl group, or a C$_{5-20}$ aryl group, preferably hydrogen or a C$_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a C$_{1-7}$ alkyl group (also referred to as C$_{1-7}$ alkylacyl or C$_{1-7}$ alkanoyl), a C$_{3-20}$ heterocyclyl group (also referred to as C$_{3-20}$ heterocyclylacyl), or a C$_{5-20}$ aryl group (also referred to as C$_{5-20}$ arylacyl), preferably a C$_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a C$_{1-7}$ alkyl group, a C$_{3-20}$ heterocyclyl group, or a C$_{5-20}$ aryl group, preferably a C$_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a C$_{1-7}$ alkyl group, a C$_{3-20}$ heterocyclyl group, or a C$_{5-20}$ aryl group, preferably a C$_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a C$_{1-7}$ alkyl group, a C$_{3-20}$ heterocyclyl group, or a C$_{5-20}$ aryl group, preferably a C$_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a C$_{1-7}$ alkyl group (also referred to as C$_{1-7}$ alkylamino or di-C$_{1-7}$ alkylamino), a C$_{3-20}$ heterocyclyl group, or a C$_{5-20}$ aryl group, preferably H or a C$_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR), or tertiary (—NHR$^1$R$^2$), and in cationic form, may be quaternary (—⁺NR¹R²R³). Examples of amino groups include, but are not limited to, —NH₂, —NHCH₃, —NHC(CH₃)₂, —N(CH₃)₂, —N(CH₂CH₃)₂, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR¹R², wherein R¹ and R² are independently amino substituents, as defined for amino groups. Examples of amido groups include, but are not limited to, —C(=O)NH₂, —C(=O)NHCH₃, —C(=O)N(CH₃)₂, —C(=O)NHCH₂CH₃, and —C(=O)N(CH₂CH₃)₂, as well as amido groups in which R¹ and R², together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR¹R², wherein R¹ and R² are independently amino substituents, as defined for amino groups. Examples of amido groups include, but are not limited to, —C(=S)NH₂, —C(=S)NHCH₃, —C(=S)N(CH₃)₂, and —C(=S)NHCH₂CH₃.

Acylamido (acylamino): —NR¹C(=O)R², wherein R¹ is an amide substituent, for example, hydrogen, a C₁₋₇ alkyl group, a C₃₋₂₀ heterocyclyl group, or a C₅₋₂₀ aryl group, preferably hydrogen or a C₁₋₇ alkyl group, and R² is an acyl substituent, for example, a C₁₋₇ alkyl group, a C₃₋₂₀ heterocyclyl group, or a C₅₋₂₀ aryl group, preferably hydrogen or a C₁₋₇ alkyl group. Examples of acylamide groups include, but are not limited to, —NHC(=O)CH₃, —NHC(=O)CH₂CH₃, and —NHC(=O)Ph. R¹ and R² may together form a cyclic structure, as in, for example, succinimidyl, maleimidyl, and phthalimidyl:

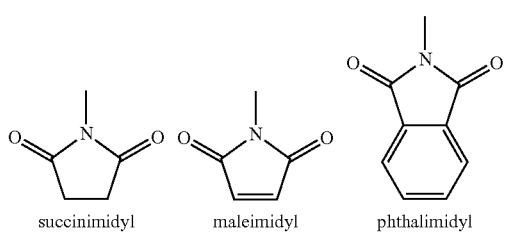

succinimidyl    maleimidyl    phthalimidyl

Aminocarbonyloxy: —OC(=O)NR¹R², wherein R¹ and R² are independently amino substituents, as defined for amino groups. Examples of aminocarbonyloxy groups include, but are not limited to, —OC(=O)NH₂, —OC(=O)NHMe, —OC(=O)NMe₂, and —OC(=O)NEt₂.

Ureido: —N(R¹)CONR²R³ wherein R² and R³ are independently amino substituents, as defined for amino groups, and R¹ is a ureido substituent, for example, hydrogen, a C₁₋₇ alkyl group, a C₃₋₂₀ heterocyclyl group, or a C₅₋₂₀ aryl group, preferably hydrogen or a C₁₋₇ alkyl group. Examples of ureido groups include, but are not limited to, —NHCONH₂, —NHCONHMe, —NHCONHEt, —NHCONMe₂, —NHCONEt₂, —NMeCONH₂, —NMeCONHMe, —NMeCONHEt, —NMeCONMe₂, and —NMeCONEt₂.

Guanidino: —NH—C(=NH)NH₂.

Tetrazolyl: a five membered aromatic ring having four nitrogen atoms and one carbon atom,

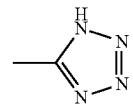

Imino: =NR, wherein R is an imino substituent, for example, for example, hydrogen, a C₁₋₇ alkyl group, a C₃₋₂₀ heterocyclyl group, or a C₅₋₂₀ aryl group, preferably H or a C₁₋₇alkyl group. Examples of imino groups include, but are not limited to, =NH, =NMe, and =NEt.

Amidine (amidino): —C(=NR)NR₂, wherein each R is an amidine substituent, for example, hydrogen, a C₁₋₇ alkyl group, a C₃₋₂₀ heterocyclyl group, or a C₅₋₂₀ aryl group, preferably H or a C₁₋₇alkyl group. Examples of amidine groups include, but are not limited to, —C(=NH)NH₂, —C(=NH)NMe₂, and —C(=NMe)NMe₂.

Nitro: —NO₂.
Nitroso: —NO.
Azido: —N₃.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.

Thioether (sulfide): —SR, wherein R is a thioether substituent, for example, a C₁₋₇ alkyl group (also referred to as a C₁₋₇alkylthio group), a C₃₋₂₀ heterocyclyl group, or a C₅₋₂₀ aryl group, preferably a C₁₋₇ alkyl group. Examples of C₁₋₇ alkylthio groups include, but are not limited to, —SCH₃ and —SCH₂CH₃.

Disulfide: —SS—R, wherein R is a disulfide substituent, for example, a C₁₋₇ alkyl group, a C₃₋₂₀ heterocyclyl group, or a C₅₋₂₀ aryl group, preferably a C₁₋₇ alkyl group (also referred to herein as C₁₋₇ alkyl disulfide). Examples of C₁₋₇ alkyl disulfide groups include, but are not limited to, —SSCH₃ and —SSCH₂CH₃.

Sulfine (sulfinyl, sulfoxide): —S(=O)R, wherein R is a sulfine substituent, for example, a C₁₋₇ alkyl group, a C₃₋₂₀ heterocyclyl group, or a C₅₋₂₀ aryl group, preferably a C₁₋₇ alkyl group. Examples of sulfine groups include, but are not limited to, —S(=O)CH₃ and —S(=O)CH₂CH₃.

Sulfone (sulfonyl): —S(=O)₂R, wherein R is a sulfone substituent, for example, a C₁₋₇ alkyl group, a C₃₋₂₀ heterocyclyl group, or a C₅₋₂₀ aryl group, preferably a C₁₋₇ alkyl group, including, for example, a fluorinated or perfluorinated C₁₋₇ alkyl group. Examples of sulfone groups include, but are not limited to, —S(=O)₂CH₃ (methanesulfonyl, mesyl), —S(=O)₂CF₃ (triflyl), —S(=O)₂CH₂CH₃ (esyl), —S(=O)₂C₄F₉ (nonaflyl), —S(=O)₂CH₂CF₃ (tresyl), —S(=O)₂CH₂CH₂NH₂ (tauryl), —S(=O)₂Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO₂H.
Sulfonic acid (sulfo): —S(=O)₂OH, —SO₃H.

Sulfinate (sulfinic acid ester): —S(=O)OR; wherein R is a sulfinate substituent, for example, a C₁₋₇ alkyl group, a C₃₋₂₀ heterocyclyl group, or a C₅₋₂₀ aryl group, preferably a C₁₋₇ alkyl group. Examples of sulfinate groups include, but are not limited to, —S(=O)OCH₃ (methoxysulfinyl; methyl sulfinate) and —S(=O)OCH₂CH₃ (ethoxysulfinyl; ethyl sulfinate).

Sulfonate (sulfonic acid ester): —S(=O)$_2$OR, wherein R is a sulfonate substituent, for example, a C$_{1-7}$ alkyl group, a C$_{3-20}$ heterocyclyl group, or a C$_{5-20}$ aryl group, preferably a C$_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a C$_{1-7}$ alkyl group, a C$_{3-20}$ heterocyclyl group, or a C$_{5-20}$ aryl group, preferably a C$_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NRS(=O)$_2$OH, wherein R$^1$ is an amino substituent, as defined for amino groups.

Examples of sulfamino groups include, but are not limited to, —NHS(=O)$_2$OH and —N(CH$_3$)S(=O)$_2$OH.

Sulfonamino: —NRS(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR'S(=O)R, wherein R$^1$ is an amino substituent, as defined for amino groups, and R is a sulfinamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a C$_{1-7}$ alkyl group, a C$_{3-20}$ heterocyclyl group, or a C$_{5-20}$ aryl group, preferably a C$_{1-7}$ alkyl group or a C$_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^{22}$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^{22}$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Alkylene

C$_{3-12}$ alkylene: The term "C$_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the subclasses alkenylene, alkynylene, cycloalkylene, etc., discussed below.

Examples of linear saturated C$_{3-12}$ alkylene groups include, but are not limited to, —(CH$_2$)$_n$— where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH$_2$—CH$_2$CH$_2$CH$_2$— (heptylene).

Examples of branched saturated C$_{3-12}$ alkylene groups include, but are not limited to, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated C$_{3-12}$ alkylene groups (C$_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH$_2$—CH$_2$—, —CH=CH—CH$_2$—CH=CH—, —CH=CH—, —CH=CH—CH$_2$—CH$_2$—CH=CH—, and —CH$_2$—C≡C≡CH$_2$—.

Examples of branched partially unsaturated C$_{3\text{-}12}$ alkylene groups (C$_{3\text{-}12}$ alkenylene and alkynylene groups) include, but are not limited to, —C(CH$_3$)=CH—, —C(CH$_3$)=CH—CH$_2$—, —CH=CH—CH(CH$_3$)— and —C≡C≡CH(CH$_3$)—.

Examples of alicyclic saturated C$_{3\text{-}12}$ alkylene groups (C$_{3\text{-}12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated C$_{3\text{-}12}$ alkylene groups (C$_{3\text{-}12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Bis-oxy-C$_{13}$ alkylene: The term "Bis-oxy-C$_{13}$ alkylene", as used herein, pertains to a bidentate moiety of formula —O—(CH$_2$)$_q$—O—, where q is from 1 to 3, i.e. —OCH$_2$CH$_2$CH$_2$O—, —OCH$_2$CH$_2$O—, —OCH$_2$O—.

Carbamate nitrogen protecting group: the term "carbamate nitrogen protecting group" pertains to a moiety which masks the nitrogen in the imine bond, and these are well known in the art. These groups have the following structure:

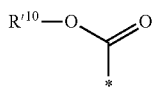

wherein R$^{\prime 10}$ is R as defined above. A large number of suitable groups are described on pages 503 to 549 of Greene, T. W. and Wuts, G. M., Protective Groups in Organic Synthesis, 3$^{rd}$ Edition, John Wiley & Sons, Inc., 1999, which is incorporated herein by reference.

Hemi-aminal nitrogen protecting group: the term "hemi-aminal nitrogen protecting group" pertains to a group having the following structure:

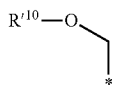

wherein R$^{\prime 10}$ is R as defined above. A large number of suitable groups are described on pages 633 to 647 as amide protecting groups of Greene, T. W. and Wuts, G. M., Protective Groups in Organic Synthesis, 3$^{rd}$ Edition, John Wiley & Sons, Inc., 1999, which is incorporated herein by reference.

The groups Carbamate nitrogen protecting group and Hemi-aminal nitrogen protecting group may be jointly termed a "nitrogen protecting group for synthesis".

Includes Other Forms

Unless otherwise specified, included in the above are the well known ionic, salt, solvate, and protected forms of these substituents. For example, a reference to carboxylic acid (—COOH) also includes the anionic (carboxylate) form (—COO—), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O—), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., J. Pharm. Sci., 66, 1-19 (1977).

For example, if the compound is anionic, or has a functional group which may be anionic (e.g. —COOH may be —COO—), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$^{2+}$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

The invention includes compounds where a solvent adds across the imine bond of the PBD moiety, which is illustrated below where the solvent is water or an alcohol (R$^A$OH, where R$^A$ is C$_{1\text{-}4}$ alkyl):

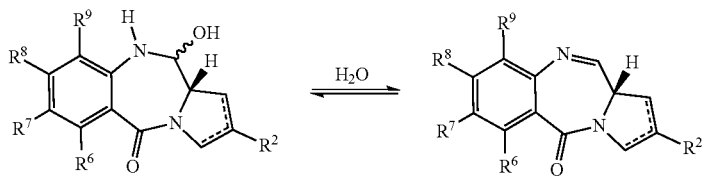
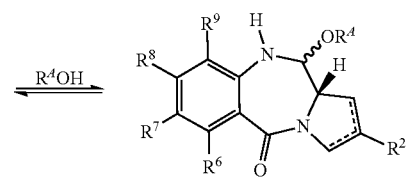

These forms can be called the carbinolamine and carbinolamine ether forms of the PBD (as described in the section relating to $R^{10}$ above). The balance of these equilibria depends on the conditions in which the compounds are found, as well as the nature of the moiety itself.

These particular compounds may be isolated in solid form, for example, by lyophilisation.

Isomers

Certain compounds of the invention may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

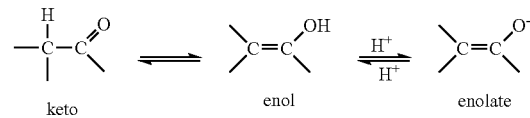

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Ligand Unit

The Ligand Unit may be of any kind, and include a protein, polypeptide, peptide and a non-peptidic agent that specifically binds to a target molecule. In some embodiments, the Ligand unit may be a protein, polypeptide or peptide. In some embodiments, the Ligand unit may be a cyclic polypeptide. These Ligand units can include antibodies or a fragment of an antibody that contains at least one target molecule-binding site, lymphokines, hormones, growth factors, or any other cell binding molecule or substance that can specifically bind to a target.

The terms "specifically binds" and "specific binding" refer to the binding of an antibody or other protein, polypeptide or peptide to a predetermined molecule (e.g., an antigen). Typically, the antibody or other molecule binds with an affinity of at least about $1 \times 10^7$ M$^{-1}$, and binds to the predetermined molecule with an affinity that is at least two-fold greater than its affinity for binding to a non-specific molecule (e.g., BSA, casein) other than the predetermined molecule or a closely-related molecule.

Examples of Ligand units include those agents described for use in WO 2007/085930, which is incorporated herein.

In some embodiments, the Ligand unit is a Cell Binding Agent that binds to an extracellular target on a cell. Such a Cell Binding Agent can be a protein, polypeptide, peptide or a non-peptidic agent. In some embodiments, the Cell Binding Agent may be a protein, polypeptide or peptide. In some embodiments, the Cell Binding Agent may be a cyclic polypeptide. The Cell Binding Agent also may be antibody or an antigen-binding fragment of an antibody. Thus, in one embodiment, the present invention provides an antibody-drug conjugate (ADC).

Cell Binding Agent

A cell binding agent may be of any kind, and include peptides and non-peptides. These can include antibodies or a fragment of an antibody that contains at least one binding site, lymphokines, hormones, hormone mimetics, vitamins, growth factors, nutrient-transport molecules, or any other cell binding molecule or substance.

Peptides

In one embodiment, the cell binding agent is a linear or cyclic peptide comprising 4-30, preferably 6-20, contiguous amino acid residues. In this embodiment, it is preferred that one cell binding agent is linked to one monomer or dimer pyrrolobenzodiazepine compound.

In one embodiment the cell binding agent comprises a peptide that binds integrin $\alpha_v\beta_6$. The peptide may be selective for $\alpha_v\beta_6$ over XYS.

In one embodiment the cell binding agent comprises the A20FMDV-Cys polypeptide. The A20FMDV-Cys has the sequence: NAVPNLRGDLQVLAQKVARTC. Alternatively, a variant of the A20FMDV-Cys sequence may be used wherein one, two, three, four, five, six, seven, eight, nine or ten amino acid residues are substituted with another amino acid residue. Furthermore, the polypeptide may have the sequence NAVXXXXXXXXXXXXXXXXRTC.

Antibodies

The term "antibody" herein is used in the broadest sense and specifically covers monoclonal antibodies, polyclonal antibodies, dimers, multimers, multispecific antibodies (e.g., bispecific antibodies), multivalent antibodies and antibody fragments, so long as they exhibit the desired biological activity (Miller et al (2003) *Jour. of Immunology* 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology*, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass of immunoglobulin molecule. The immunoglobulins can be derived from any species, including human, murine, or rabbit origin.

"Antibody fragments" comprise a portion of a full-length antibody, generally the antigen binding or variable region thereof. Examples of antibody fragments include Fab, Fab', F(ab')$_2$, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597 or from transgenic mice carrying a fully human immunoglobulin system (Lonberg (2008) Curr. Opinion 20(4):450-459).

The monoclonal antibodies herein specifically include chimeric antibodies, humanized antibodies and human antibodies.

Examples of cell binding agents include those agents described for use in WO 2007/085930, which is incorporated herein.

Tumour-associate antigens and cognate antibodies for use in embodiments of the present invention are listed below, and are described in more detail on pages 14 to 86 of WO 2017/186894, which is incorporated herein.

(1) BMPR1B (bone morphogenetic protein receptor-type IB)
(2) E16 (LAT1, SLC7A5)
(3) STEAP1 (six transmembrane epithelial antigen of prostate)
(4) 0772P (CA125, MUC16)
(5) MPF (MPF, MSLN, SMR, megakaryocyte potentiating factor, mesothelin)
(6) Napi3b (NAPI-3B, NPTIIb, SLC34A2, solute carrier family 34 (sodium phosphate), member 2, type II sodium-dependent phosphate transporter 3b)
(7) Sema 5b (FLJ10372, KIAA1445, Mm.42015, SEMA5B, SEMAG, Semaphorin 5b Hlog, 25 sema domain, seven thrombospondin repeats (type 1 and type 1-like), transmembrane domain (TM) and short cytoplasmic domain, (semaphorin) 5B)
(8) PSCA hlg (2700050C12Rik, C530008O16Rik, RIKEN cDNA 2700050C12, RIKEN cDNA 2700050C12 gene)
(9) ETBR (Endothelin type B receptor)
(10) MSG783 (RNF124, hypothetical protein FLJ20315)
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein)
(12) TrpM4 (BR22450, FLJ20041, TRPM4, TRPM4B, transient receptor potential cation 5 channel, subfamily M, member 4)
(13) CRIPTO (CR, CR1, CRGF, CRIPTO, TDGF1, teratocarcinoma-derived growth factor)
(14) CD21 (CR2 (Complement receptor 2) or C3DR (C3d/Epstein Barr virus receptor) or Hs.73792)
(15) CD79b (CD79B, CD79p, IGb (immunoglobulin-associated beta), B29)
(16) FcRH2 (IFGP4, IRTA4, SPAP1A (SH2 domain containing phosphatase anchor protein 1a), SPAP1B, SPAP1C)
(17) HER2 (ErbB2)
(18) NCA (CEACAM6)
(19) MDP (DPEP1)
(20) IL20R-alpha (IL20Ra, ZCYTOR7)
(21) Brevican (BCAN, BEHAB)
(22) EphB2R (DRT, ERK, Hek5, EPHT3, Tyro5)
(23) ASLG659 (B7h)
(24) PSCA (Prostate stem cell antigen precursor)
(25) GEDA
(26) BAFF-R (B cell-activating factor receptor, BLyS receptor 3, BR3)
(27) CD22 (B-cell receptor CD22-B isoform, BL-CAM, Lyb-8, Lyb8, SIGLEC-2, FLJ22814)
(27a) CD22 (CD22 molecule)
(28) CD79a (CD79A, CD79alpha), immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2).
(29) CXCR5 (Burkitt's lymphoma receptor 1, a G protein-coupled receptor that is activated by the CXCL13 chemokine, functions in lymphocyte migration and humoral defense, plays a 10 role in HIV-2 infection and perhaps development of AIDS, lymphoma, myeloma, and leukemia); 372 aa, pI: 8.54 MW: 41959 TM: 7 [P] Gene Chromosome: 11q23.3,
(30) HLA-DOB (Beta subunit of MHC class II molecule (Ia antigen) that binds peptides and 20 presents them to CD4+T lymphocytes); 273 aa, pI: 6.56, MW: 30820.TM: 1 [P] Gene Chromosome: 6p21.3)
(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3).
(32) CD72 (B-cell differentiation antigen CD72, Lyb-2); 359 aa, pI: 8.66, MW: 40225, TM: 1 5 [P] Gene Chromosome: 9p13.3).
(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12).
(34) FcRH1 (Fc receptor-like protein 1, a putative receptor for the immunoglobulin Fc domain that contains C2 type Ig-like and ITAM domains, may have a role in B-lymphocyte 20 differentiation); 429 aa, pI: 5.28, MW: 46925 TM: 1 [P] Gene Chromosome: 1q21-1q22)
(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pl: 6.88, MW: 106468, TM: 1 [P] Gene Chromosome: 1q21)

(36) TENB2 (TMEFF2, tomoregulin, TPEF, HPP1, TR, putative transmembrane 35 proteoglycan, related to the EGF/heregulin family of growth factors and follistatin); 374 aa)

(37) PSMA—FOLH1 (Folate hydrolase (prostate-specific membrane antigen) 1)

(38) SST (Somatostatin Receptor; note that there are 5 subtypes)
  (38.1) SSTR2 (Somatostatin receptor 2)
  (38.2) SSTR5 (Somatostatin receptor 5)
  (38.3) SSTR1
  (38.4) SSTR3
  (38.5) SSTR4
AvB6—Both Subunits (39+40)
  (39) ITGAV (Integrin, alpha V)
  (40) ITGB6 (Integrin, beta 6)
  (41) CEACAM5 (Carcinoembryonic antigen-related cell adhesion molecule 5)
  (42) MET (met proto-oncogene; hepatocyte growth factor receptor)
  (43) MUC1 (Mucin 1, cell surface associated)
  (44) CA9 (Carbonic anhydrase IX)
  (45) EGFRvlll (Epidermal growth factor receptor (EGFR), transcript variant 3,
  (46) CD33 (CD33 molecule)
  (47) CD19 (CD19 molecule)
  (48) IL2RA (Interleukin 2 receptor, alpha); NCBI Reference Sequence: NM_000417.2);
  (49) AXL (AXL receptor tyrosine kinase)
  (50) CD30—TNFRSF8 (Tumor necrosis factor receptor superfamily, member 8)
  (51) BCMA (B-cell maturation antigen)—TNFRSF17 (Tumor necrosis factor receptor superfamily, member 17)
  (52) CT Ags—CTA (Cancer Testis Antigens)
  (53) CD174 (Lewis Y)—FUT3 (fucosyltransferase 3 (galactoside 3(4)-L-fucosyltransferase, Lewis blood group)
  (54) CLEC14A (C-type lectin domain family 14, member A; Genbank accession no. NM175060)
  (55) GRP78—HSPA5 (heat shock 70 kDa protein 5 (glucose-regulated protein, 78 kDa)
  (56) CD70 (CD70 molecule) L08096
  (57) Stem Cell specific antigens. For example:
  5T4 (see entry (63) below)
  CD25 (see entry (48) above)
  CD32
  LGR5/GPR49
  Prominin/CD133
  (58) ASG-5
  (59) ENPP3 (Ectonucleotide pyrophosphatase/phosphodiesterase 3)
  (60) PRR4 (Proline rich 4 (lacrimal))
  (61) GCC—GUCY2C (guanylate cyclase 2C (heat stable enterotoxin receptor)
  (62) Liv-1—SLC39A6 (Solute carrier family 39 (zinc transporter), member 6)
  (63) 5T4, Trophoblast glycoprotein, TPBG—TPBG (trophoblast glycoprotein)
  (64) CD56—NCMA1 (Neural cell adhesion molecule 1)
  (65) CanAg (Tumor associated antigen CA242)
  (66) FOLR1 (Folate Receptor 1)
  (67) GPNMB (Glycoprotein (transmembrane) nmb)
  (68) TIM-1—HAVCR1 (Hepatitis A virus cellular receptor 1)
  (69) RG-1/Prostate tumor target Mindin—Mindin/RG-1
  (70) B7-H4—VTCN1 (V-set domain containing T cell activation inhibitor 1
  (71) PTK7 (PTK7 protein tyrosine kinase 7)
  (72) CD37 (CD37 molecule)
  (73) CD138—SDC1 (syndecan 1)
  (74) CD74 (CD74 molecule, major histocompatibility complex, class II invariant chain)
  (75) Claudins—CLs (Claudins)
  (76) EGFR (Epidermal growth factor receptor)
  (77) Her3 (ErbB3)—ERBB3 (v-erb-b2 erythroblastic leukemia viral oncogene homolog 3 (avian))
  (78) RON—MST1R (macrophage stimulating 1 receptor (c-met-related tyrosine kinase))
  (79) EPHA2 (EPH receptor A2)
  (80) CD20—MS4A1 (membrane-spanning 4-domains, subfamily A, member 1)
  (81) Tenascin C—TNC (Tenascin C)
  (82) FAP (Fibroblast activation protein, alpha)
  (83) DKK-1 (Dickkopf 1 homolog (*Xenopus laevis*)
  (84) CD52 (CD52 molecule)
  (85) CS1—SLAMF7 (SLAM family member 7)
  (86) Endoglin—ENG (Endoglin)
  (87) Annexin A1—ANXA1 (Annexin A1)
  (88) V-CAM (CD106)—VCAM1 (Vascular cell adhesion molecule 1)

The cell binding agent may be labelled, for example to aid detection or purification of the agent either prior to incorporation as a conjugate, or as part of the conjugate. The label may be a biotin label. In another embodiment, the cell binding agent may be labelled with a radioisotope.

Connection of Linker Unit to Ligand Unit

The Ligand unit may be connected to the Linker unit through a disulfide bond.

In one embodiment, the connection between the Ligand unit and the Drug Linker is formed between a thiol group of a cysteine residue of the Ligand unit and a maleimide group of the Drug Linker unit.

The cysteine residues of the Ligand unit may be available for reaction with the functional group of the Linker unit to form a connection. In other embodiments, for example where the Ligand unit is an antibody, the thiol groups of the antibody may participate in interchain disulfide bonds. These interchain bonds may be converted to free thiol groups by e.g. treatment of the antibody with DTT prior to reaction with the functional group of the Linker unit.

In some embodiments, the cysteine residue is an introduced into the heavy or light chain of an antibody. Positions for cysteine insertion by substitution in antibody heavy or light chains include those described in Published U.S. Application No. 2007-0092940 and International Patent Publication WO2008070593, which are incorporated herein.

Methods of Treatment

The compounds of the present invention may be used in a method of therapy. Also provided is a method of treatment, comprising administering to a subject in need of treatment a therapeutically-effective amount of a conjugate of formula II. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A conjugate may be administered alone or in combination with other treatments, either simultaneously or sequentially dependent upon the condition to be treated. Examples of treatments and therapies include, but are not limited to, chemotherapy (the administration of active agents, including, e.g. drugs; surgery; and radiation therapy.

Pharmaceutical compositions according to the present invention, and for use in accordance with the present invention, may comprise, in addition to the active ingredient, i.e. a conjugate of formula I, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The Conjugates can be used to treat proliferative disease and autoimmune disease. The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreatic cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Other cancers of interest include, but are not limited to, haematological; malignancies such as leukemias and lymphomas, such as non-Hodgkin lymphoma, and subtypes such as DLBCL, marginal zone, mantle zone, and follicular, Hodgkin lymphoma, AML, and other cancers of B or T cell origin. Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Examples of autoimmune disease include the following: rheumatoid arthritis, autoimmune demyelinative diseases (e.g., multiple sclerosis, allergic encephalomyelitis), psoriatic arthritis, endocrine ophthalmopathy, uveoretinitis, systemic lupus erythematosus, myasthenia gravis, Graves' disease, glomerulonephritis, autoimmune hepatological disorder, inflammatory bowel disease (e.g., Crohn's disease), anaphylaxis, allergic reaction, Sjögren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, and autoimmune gonadal failure.

In some embodiments, the autoimmune disease is a disorder of B lymphocytes (e.g., systemic lupus erythematosus, Goodpasture's syndrome, rheumatoid arthritis, and type I diabetes), Th1-lymphocytes (e.g., rheumatoid arthritis, multiple sclerosis, psoriasis, Sjögren's syndrome, Hashimoto's thyroiditis, Graves' disease, primary biliary cirrhosis, Wegener's granulomatosis, tuberculosis, or graft versus host disease), or Th2-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of Th1-lymphocytes or Th2-lymphocytes. In some embodiments, the autoimmunie disorder is a T cell-mediated immunological disorder.

Methods of Treatment

The conjugates of the present invention may be used in a method of therapy. Also provided is a method of treatment, comprising administering to a subject in need of treatment a therapeutically-effective amount of a conjugate compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound of the invention may be administered alone or in combination with other treatments, either simultaneously or sequentially dependent upon the condition to be treated. Examples of treatments and therapies include, but are not limited to, chemotherapy (the administration of active agents, including, e.g. drugs, such as chemotherapeutics); surgery; and radiation therapy.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®. Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0]nona-2,7,9-triene-9-carboxamide, CAS No. 85622-93-1, TEMODAR®, TEMODAL, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (P3K inhibitor, Semafore Pharmaceuticals), BEZ-235 (P3K inhibitor, Novartis), XL-147 (PI3K inhibitor, Exelixis), PTK787/ZK 222584 (Novartis), fulvestrant (FASLODEX, AstraZeneca), leucovorin (folinic acid), rapamycin (sirolimus, RAPAMUNE®, Wyeth), lapatinib (TYKERB, GSK572016, Glaxo Smith Kline), lonafarnib (SARASAR™, SCH 66336, Schering Plough), sorafenib (NEXAVAR®, BAY43-9006, Bayer Labs), gefitinib (IRESSA, AstraZeneca), irinotecan (CAMPTOSAR, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA, Telik), thiotepa and cyclosphosphamide (CYTOXAN®, NEOSAR); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gammal, calicheamicin omegal1 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE@(megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the conjugates of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Pharmaceutical compositions according to the present invention, and for use in accordance with the present invention, may comprise, in addition to the active ingredient, i.e. a conjugate compound, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Formulations

While it is possible for the conjugate compound to be used (e.g., administered) alone, it is often preferable to present it as a composition or formulation.

In one embodiment, the composition is a pharmaceutical composition (e.g., formulation, preparation, medicament) comprising a conjugate compound, as described herein, and a pharmaceutically acceptable carrier, diluent, or excipient.

In one embodiment, the composition is a pharmaceutical composition comprising at least one conjugate compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives,* 2nd Edition (eds. M. Ash and I. Ash), 2001 (Synapse Information Resources, Inc., Endicott, N.Y., USA), *Remington's Pharmaceutical Sciences,* 20th edition, pub. Lippincott, Williams & Wilkins, 2000; and *Handbook of Pharmaceutical Excipients,* 2nd edition, 1994.

Another aspect of the present invention pertains to methods of making a pharmaceutical composition comprising admixing at least one [$^{11}$C]-radiolabelled conjugate or conjugate-like compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the conjugate compound, and compositions comprising the conjugate compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the conjugate compound is administered to a human patient according to the following dosage regime: about 50 or about 75 mg, 3 or 4 times daily.

In one embodiment, the conjugate compound is administered to a human patient according to the following dosage regime: about 100 or about 125 mg, 2 times daily.

The dosage amounts described above may apply to the conjugate (including the PBD moiety and the linker to the antibody) or to the effective amount of PBD compound provided, for example the amount of compound that is releasable after cleavage of the linker.

For the prevention or treatment of disease, the appropriate dosage of an ADC of the invention will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of an ADC. Other dosage regimens may be useful. The progress of this therapy is easily monitored by conventional techniques and assays.

Drug Loading

The drug loading (p) is the average number of PBD drugs per cell binding agent, e.g. antibody. Where the compounds of the invention are bound to cysteines, drug loading may range from 1 to 8 drugs (D) per cell binding agent, i.e. where 1, 2, 3, 4, 5, 6, 7, and 8 drug moieties are covalently attached to the cell binding agent. Compositions of conjugates include collections of cell binding agents, e.g. antibodies, conjugated with a range of drugs, from 1 to 8. Where the compounds of the invention are bound to lysines, drug loading may range from 1 to 80 drugs (D) per cell binding agent, although an upper limit of 40, 20, 10 or 8 may be preferred. Compositions of conjugates include collections of cell binding agents, e.g. antibodies, conjugated with a range of drugs, from 1 to 80, 1 to 40, 1 to 20, 1 to 10 or 1 to 8.

The average number of drugs per antibody in preparations of ADC from conjugation reactions may be characterized by conventional means such as UV, reverse phase HPLC, HIC, mass spectroscopy, ELISA assay, and electrophoresis. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis. Such techniques are also applicable to other types of conjugates.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p >5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the Drug Linker. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety.

Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio) of an ADC may be controlled in several different manners, including: (i) limiting the molar excess of Drug Linker relative to antibody, (ii) limiting the conjugation reaction time or temperature, and (iii) partial or limiting reductive conditions for cysteine thiol modification.

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by engineering one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. Nos. 7,521,541; 7,723,485; WO2009/052249). The engineered cysteine thiols may react with linker reagents or the drug-linker reagents of the present invention which have thiol-reactive, electrophilic groups such as maleimide or alpha-halo amides to form ADC with cysteine engineered antibodies and the PBD drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved with near homogeneity of the conjugation product ADC.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

Thus the antibody-drug conjugate compositions of the invention include mixtures of antibody-drug conjugate compounds where the antibody has one or more PBD drug moieties and where the drug moieties may be attached to the antibody at various amino acid residues.

In one embodiment, the average number of dimer pyrrolobenzodiazepine groups per cell binding agent is in the range 1 to 20. In some embodiments the range is selected from 1 to 8, 2 to 8, 2 to 6, 2 to4, and 4 to 8.

In some embodiments, there is one dimer pyrrolobenzodiazepine group per cell binding agent.

General Synthetic Routes

The synthesis of PBD compounds is extensively discussed in the following references, which discussions are incorporated herein by reference:
a) WO 00/12508 (pages 14 to 30);
b) WO 2005/023814 (pages 3 to 10);
c) WO 2004/043963 (pages 28 to 29); and
d) WO 2005/085251 (pages 30 to 39).

Synthesis Route

Compounds of the present invention of formula I may be synthesised from compounds of formula IP:

IP

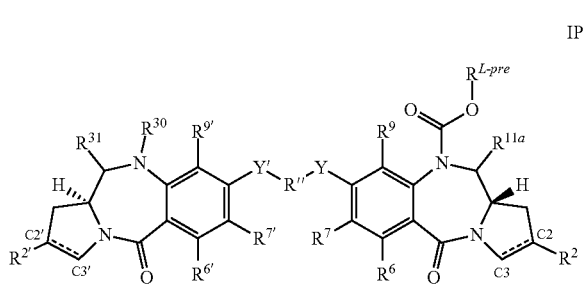

where $R^{L-pre}$ represents a precursor to the group $R^L$. Where $R^O$ is H, the carboxy group may be protected during synthesis (for example a tert-butyl ester), which can be removed in a final step.

For example, when $R^L$ is a group:

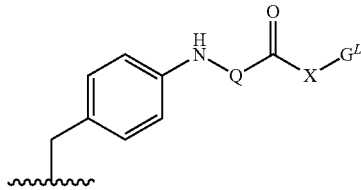

IIIa $R^{L-pre}$ may be:

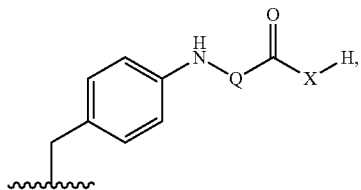

or a protected version thereof. The addition of $G^L$ may be achieved by conventional means. $R^{30}$ and $R^{31}$ may also be a nitrogen protecting group and $OProt^O$ respectively, when $Prot^O$ represents an oxygen protecting group for synthesis, which are removed as appropriate.

Alternatively, compounds of formula IP may be synthesised by coupling compounds of formulae 2 and 3:

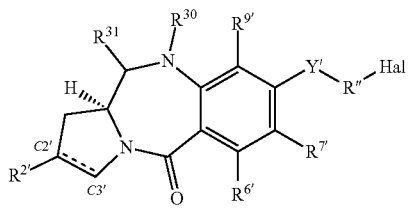

Formula 2

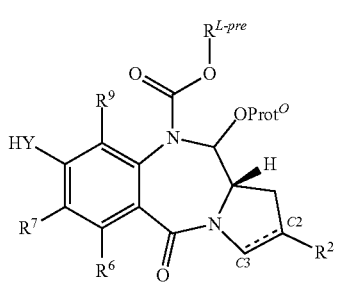

Formula 3 where Hal is selected from I, Cl, and Br, and $Prot^O$ represents an oxygen protecting group for synthesis, following by removal of the $Prot^O$ group under standard conditions.

The coupling can be achieved, for example, in refluxing acetone with a base, such as $K_2CO_3$.

Compounds of formula 2 can be synthesised from compounds of formula 4:

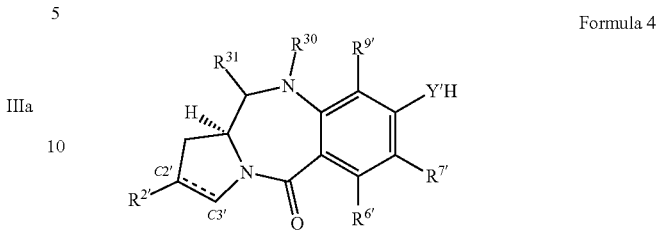

Formula 4

By coupling a compound of Formula 5:

Hal-R''-Q    Formula 5 where Q is selected from I, Cl, and Br, the reaction can be achieved, for example, in refluxing acetone with a base, such as $K_2CO_3$. An excess of the compound of Formula 5 is required to achieve the desired product.

The compound of formula 4 may be synthesised from a compound of Formula 6:

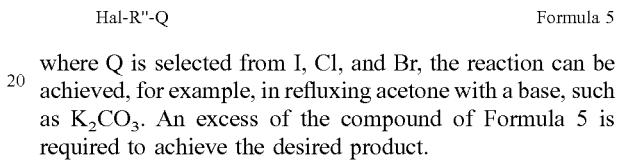

Formula 6 where $Prot^{Y'}$ is a protecting group for Y' that is orthogonal to the other protecting groups in the compound. The synthesis is achieved by deprotection of Y', under standard conditions.

Compounds of formula 3 can be synthesised from compounds of formula 7:

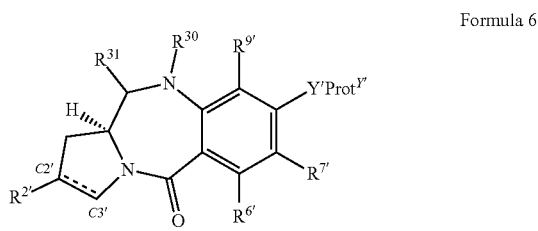

Formula 7 where $Prot^Y$ is a protecting group for Y that is orthogonal to the other protecting groups in the compound. The synthesis is achieved by deprotection of Y, under standard conditions.

Compounds of formula 7 can be synthesised from compounds of formula 8:

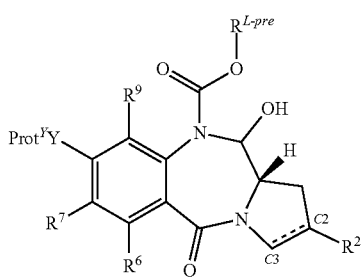

Formula 8 by protecting the OH group with Prot$^O$, under standard conditions.

Compounds of formula 8 can be synthesised from compounds of formula 9:

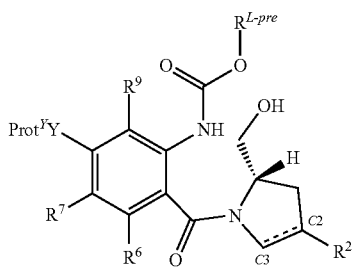

Formula 9 by oxidation. The oxidation may be carried out, for example, with Dess-Martin periodinane (or alternatively TPAP/NMO, TFAA/DMSO, SO$_3$.Pyridine complex/DMSO, PDC, PCC, BAIB/TEMPO or under Swern conditions).

Compounds of formula 9 can be synthesised from compounds of formula 10:

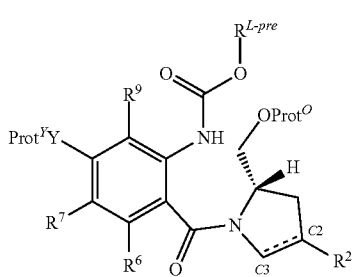

Formula 10 by deprotection of the OH group under standard conditions.

Compounds of Formula 10 can also be used to make compounds of Formula 11:

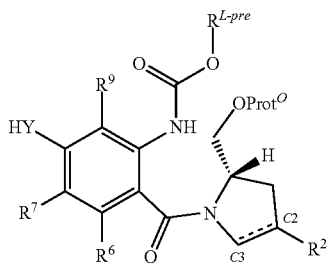

Formula 11 which may be coupled to a compound of Formula 2, following by cyclisation.

The coupling of the two PBD (or pre-PBD) moieities to the group comprising R" may be carried out in either order.

Synthesis of Drug Conjugates

Conjugates can be prepared as previously described. Antibodies can be conjugated to the Drug Linker compound as described in Doronina et al., Nature Biotechnology, 2003, 21, 778-784). Briefly, antibodies (4-5 mg/mL) in PBS containing 50 mM sodium borate at pH 7.4 are reduced with tris(carboxyethyl)phosphine hydrochloride (TCEP) at 37° C. The progress of the reaction, which reduces interchain disulfides, is monitored by reaction with 5,5'-dithiobis(2-nitrobenzoic acid) and allowed to proceed until the desired level of thiols/mAb is achieved. The reduced antibody is then cooled to 0° C. and alkylated with 1.5 equivalents of maleimide drug-linker per antibody thiol. After 1 hour, the reaction is quenched by the addition of 5 equivalents of N-acetyl cysteine. Quenched drug-linker is removed by gel filtration over a PD-10 column. The ADC is then sterile-filtered through a 0.22 μm syringe filter. Protein concentration can be determined by spectral analysis at 280 nm and 329 nm, respectively, with correction for the contribution of drug absorbance at 280 nm. Size exclusion chromatography can be used to determine the extent of antibody aggregation, and RP-HPLC can be used to determine the levels of remaining NAC-quenched drug-linker.

Further Preferences

The following preferences may apply to all aspects of the invention as described above, or may relate to a single aspect. The preferences may be combined together in any combination.

$R^{6'}$, $R^{7'}$, $R^{9'}$, and Y' are selected from the same groups as $R^6$, $R^7$, $R^9$ and Y respectively. In some embodiments, $R^{6'}$, $R^{7'}$, $R^{9'}$, and Y' are the same as R, $R^7$, $R^9$ and Y respectively.

In some embodiments, $R^{2'}$ is the same as $R^2$.

Dimer Link

Y and Y' are preferably O.

In some embodiments, n is 1. In other embodiments, n is 2. In other embodiments, n is 3.

In some embodiments, m is 1. In other embodiments, m is 2. In other embodiments, m is 3.

In certain embodiments, n and m are the same. In some of these embodiments, n and m are 1. In other of these embodiments, n and m are 2. In other of these embodiments, n and m are 3.

In some embodiments, Q is N. In other embodiments, Q is CH.

In some embodiments, $R^O$ is H. In other embodiments, $R^O$ is methyl. In other embodiments, $R^O$ is ethyl. In other embodiments, $R^O$ is iso-propyl. In other embodiments, $R^O$ is benzyl.

In particular embodiments, R" is of formula Ia:

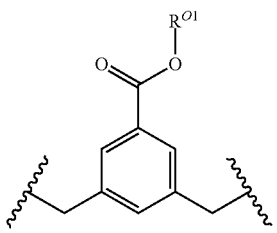

IIa where $R^{O1}$ is selected from the group consisting of H and methyl.

$R^6$ to $R^9$

In some embodiments, $R^9$ is H.

In some embodiments, $R^6$ is selected from H, OH, OR, SH, $NH_2$, nitro and halo, and may be selected from H or halo. In some of these embodiments $R^6$ is H.

In some embodiments, $R^7$ is selected from H, OH, OR, SH, SR, $NH_2$, NHR, NRR', and halo.

In some of these embodiments $R^7$ is selected from H, OH and OR, where R is selected from optionally substituted $C_{1-7}$ alkyl, $C_{3-10}$ heterocyclyl and $C_{5-10}$ aryl groups. R may be more preferably a $C_{1-4}$ alkyl group, which may or may not be substituted. A substituent of interest is a $C_{5-6}$ aryl group (e.g. phenyl). Particularly preferred substituents at the 7-positions are OMe and $OCH_2Ph$. Other substituents of particular interest are dimethylamino (i.e. —$NMe_2$); —$(OC_2H_4)_q$OMe, where q is from 0 to 2; nitrogen-containing C heterocyclyls, including morpholino, piperidinyl and N-methyl-piperazinyl.

These embodiments and preferences apply to $R^{9'}$, $R^{6'}$ and $R^{7'}$ respectively.

$R^2$

When there is a double bond present between C2 and C3, $R^2$ is selected from:

(a) $C_{5-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene;

(b) $C_{1-5}$ saturated aliphatic alkyl;

(c) $C_{3-6}$ saturated cycloalkyl;

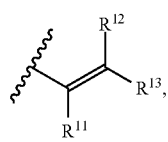
(d)

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

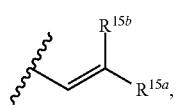
(e)

wherein one of $R^{15a}$ and $R^{15b}$ is H and the other is selected from: phenyl, which phenyl is optionally substituted by a group selected from halo methyl, methoxy; pyridyl; and thiophenyl; and

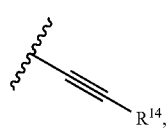
(f)

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl.

When $R^2$ is a $C_{5-10}$ aryl group, it may be a $C_{5-7}$ aryl group. A $C_{5-7}$ aryl group may be a phenyl group or a $C_{5-7}$ heteroaryl group, for example furanyl, thiophenyl and pyridyl. In some embodiments, $R^2$ is preferably phenyl. In other embodiments, $R^2$ is preferably thiophenyl, for example, thiophen-2-yl and thiophen-3-yl.

When $R^2$ is a $C_{5-10}$ aryl group, it may be a $C_{8-10}$ aryl, for example a quinolinyl or isoquinolinyl group. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. Of these quinolin-3-yl and quinolin-6-yl may be preferred. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. Of these isoquinolin-3-yl and isoquinolin-6-yl may be preferred.

When $R^2$ is a $C_{5-10}$ aryl group, it may bear any number of substituent groups. It preferably bears from 1 to 3 substituent groups, with 1 and 2 being more preferred, and singly substituted groups being most preferred. The substituents may be any position.

Where $R^2$ is $C_{5-7}$ aryl group, a single substituent is preferably on a ring atom that is not adjacent the bond to the remainder of the compound, i.e. it is preferably β or γ to the bond to the remainder of the compound. Therefore, where the $C_{5-7}$ aryl group is phenyl, the substituent is preferably in the meta- or para-positions, and more preferably is in the para-position.

Where $R^2$ is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

$R^2$ substituents, when $R^2$ is a $C_{5-10}$ aryl group

If a substituent on $R^2$ when $R^2$ is a $C_{5-10}$ aryl group is halo, it is preferably F or Cl, more preferably Cl.

If a substituent on $R^2$ when $R^2$ is a $C_{5-10}$ aryl group is ether, it may in some embodiments be an alkoxy group, for example, a $C_{1-7}$ alkoxy group (e.g. methoxy, ethoxy) or it may in some embodiments be a $C_{5-7}$ aryloxy group (e.g phenoxy, pyridyloxy, furanyloxy). The alkoxy group may itself be further substituted, for example by an amino group (e.g. dimethylamino).

If a substituent on $R^2$ when $R^2$ is a $C_{5-10}$ aryl group is $C_{1-7}$ alkyl, it may preferably be a $C_{1-4}$ alkyl group (e.g. methyl, ethyl, propryl, butyl).

If a substituent on $R^2$ when $R^2$ is a $C_{5-10}$ aryl group is $C_{3-7}$ heterocyclyl, it may in some embodiments be C nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups. If the C nitrogen containing heterocyclyl group is piperazinyl, the said further substituent may be on the second nitrogen ring atom.

If a substituent on $R^2$ when $R^2$ is a $C_{5-10}$ aryl group is bis-oxy-$C_{1-3}$ alkylene, this is preferably bis-oxy-methylene or bis-oxy-ethylene.

If a substituent on $R^2$ when $R^2$ is a $C_{5-10}$ aryl group is ester, this is preferably methyl ester or ethyl ester.

Particularly preferred substituents when $R^2$ is a $C_{5-10}$ aryl group include methoxy, ethoxy, fluoro, chloro, cyano, bis-oxy-methylene, methyl-piperazinyl, morpholino and methyl-thiophenyl. Other particularly preferred substituents for $R^2$ are dimethylaminopropyloxy and carboxy.

Particularly preferred substituted $R^2$ groups when $R^2$ is a $C_{5-10}$ aryl group include, but are not limited to, 4-methoxyphenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthiophenyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl. Another possible substituted $R^{12}$ group is 4-nitrophenyl. $R^{12}$ groups of particular interest include 4-(4-methylpiperazin-1-yl)phenyl and 3,4-bisoxymethylene-phenyl.

When $R^2$ is $C_{1-5}$ saturated aliphatic alkyl, it may be methyl, ethyl, propyl, butyl or pentyl. In some embodiments, it may be methyl, ethyl or propyl (n-pentyl or isopropyl). In some of these embodiments, it may be methyl. In other embodiments, it may be butyl or pentyl, which may be linear or branched.

When $R^2$ is $C_{3-6}$ saturated cycloalkyl, it may be cyclopropyl, cyclobutyl, cyclopentyl or cyclohexyl. In some embodiments, it may be cyclopropyl.

When $R^2$ is

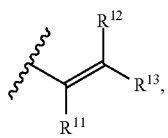

each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5. In some embodiments, the total number of carbon atoms in the $R^2$ group is no more than 4 or no more than 3.

In some embodiments, one of $R^{11}$, $R^{12}$ and $R^{13}$ is H, with the other two groups being selected from H, $C_{1-3}$ saturated alkyl, $C_{2-3}$ alkenyl, $C_{2-3}$ alkynyl and cyclopropyl.

In other embodiments, two of $R^{11}$, $R^{12}$ and $R^{13}$ are H, with the other group being selected from H, $C_{1-3}$ saturated alkyl, $C_{2-3}$ alkenyl, $C_{2-3}$ alkynyl and cyclopropyl.

In some embodiments, the groups that are not H are selected from methyl and ethyl. In some of these embodiments, the groups that re not H are methyl.

In some embodiments, $R^{11}$ is H.
In some embodiments, $R^{12}$ is H.
In some embodiments, $R^{13}$ is H.
In some embodiments, $R^{11}$ and $R^{12}$ are H.
In some embodiments, $R^{11}$ and $R^{13}$ are H.
In some embodiments, $R^{12}$ and $R^{13}$ are H.

An $R^2$ group of particular interest is:

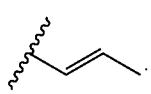 [SMILES: */C=C/C]

When $R^2$ is

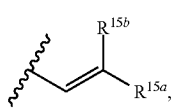

one of $R^{15a}$ and $R^{15b}$ is H and the other is selected from: phenyl, which phenyl is optionally substituted by a group selected from halo, methyl, methoxy; pyridyl; and thiophenyl. In some embodiments, the group which is not H is optionally substituted phenyl. If the phenyl optional substituent is halo, it is preferably fluoro. In some embodiment, the phenyl group is unsubstituted.

When $R^2$ is

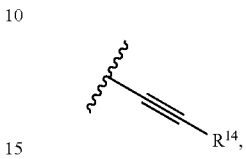

$R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl. If the phenyl optional substituent is halo, it is preferably fluoro. In some embodiment, the phenyl group is unsubstituted.

In some embodiments, $R^{14}$ is selected from H, methyl, ethyl, ethenyl and ethynyl. In some of these embodiments, $R^{14}$ is selected from H and methyl.

When there is a single bond present between C2 and C3, $R^2$ is H or

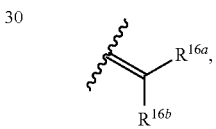

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester.

In some embodiments, $R^2$ is H.
In some embodiments, $R^2$ is

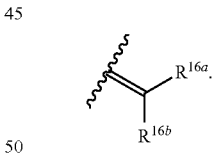

In some embodiments, it is preferred that $R^{16a}$ and $R^{16b}$ are both H.

In other embodiments, it is preferred that $R^{16a}$ and $R^{16b}$ are both methyl.

In further embodiments, it is preferred that one of $R^{16a}$ and $R^{16b}$ is H, and the other is selected from $C_{1-4}$ saturated alkyl, $C_{2-3}$ alkenyl, which alkyl and alkenyl groups are optionally substituted. In these further embodiment, it may be further preferred that the group which is not H is selected from methyl and ethyl.

$R^{2'}$

The above preferences for $R^2$ apply equally to $R^{2'}$ $R^{11a}$

In some embodiments, $R^{11}$ is OH.

In some embodiments, $R^{11a}$ is $OR^A$. In some of these embodiments, $R^A$ is methyl.

In some embodiments, $R^{11a}$ is selected from OH, $OR^A$, where $R^A$ is $C_{1-4}$ alkyl, and $SO_zM$, where z is 2 or 3 and M is a monovalent pharmaceutically acceptable cation.

$R^{30}$ and $R^{31}$

In some embodiments, $R^{30}$ is H, and $R^{31}$ is OH. In other embodiments, $R^{30}$ is H, and $R^{31}$ is $OR^A$. In some of these embodiments, $R^A$ is methyl.

In other embodiment, $R^{30}$ and $R^{31}$ form a nitrogen-carbon double bond between the nitrogen and carbon atoms to which they are bound.

In other embodiments, $R^{30}$ is H and $R^{31}$ is $SO_zM$, where z is 2 or 3 and M is a monovalent pharmaceutically acceptable cation.

M and z

It is preferred that M is a monovalent pharmaceutically acceptable cation, and is more preferably $Na^+$.

is preferably 3.

Linker ($R^L$)

In some embodiments, $R^L$ is of formula IIIa.

In some embodiments, $R^{LL}$ is of formula IIIa'.

$G^L$ $G^L$ may be selected from

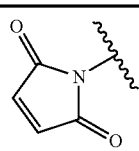
(G$^{L1-1}$)

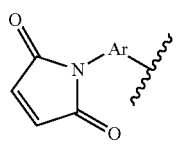
(G$^{L1-2}$)

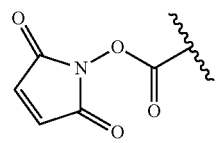 [SMILES: *C(=O)ON1C(=O)C=CC1=O]
(G$^{L2}$)

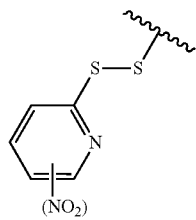
(G$^{L3-1}$)

where the NO$_2$ group is optional

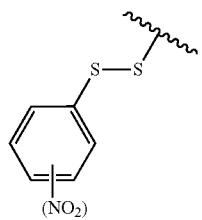
(G$^{L3-2}$)

where the NO$_2$ group is optional

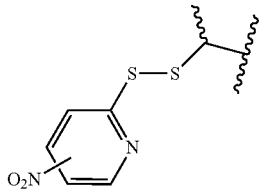
(G$^{L3-3}$)

where the NO$_2$ group is optional

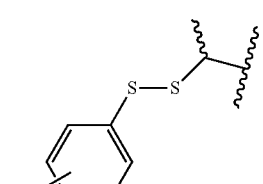
(G$^{L3-4}$)

where the NO$_2$ group is optional

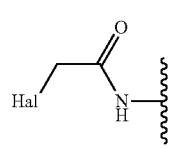
(G$^{L4}$)

Where Hal = I, Br, Cl

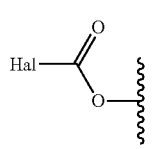
(G$^{L5}$)

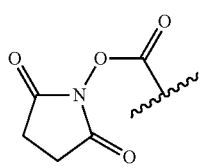 [SMILES: *C(=O)ON1C(=O)CCC1=O]
(G$^{L6}$)

(G$^{L7}$)

(G$^{L8}$)

(G$^{L9}$)

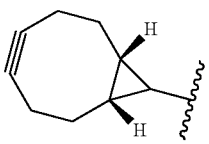 [SMILES: *C1[C@H]2CCC#CCC[C@@H]12]
(G$^{L10}$)

-continued
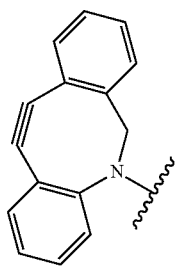 [SMILES: *N1Cc2ccccc2C#Cc2ccccc21]
(G$^{L11}$)
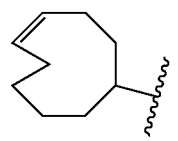 [SMILES: *C1CC/C=C\CCCC1]
(G$^{L12}$)
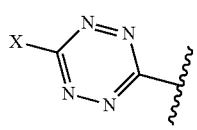
(G$^{L13}$)
where Ar represents a $C_{5-6}$ arylene group, e.g. phenylene, and X represents $C_{1-4}$ alkyl.
In some embodiments, $G^L$ is selected from $G^{L1-1}$ and $G^{L1-2}$. In some of these embodiments, $G^L$ is $GL^{1-1}$.
$G^{LL}$
$G^{LL}$ may be selected from:
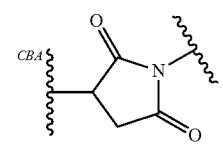
(G$^{LL1-1}$)
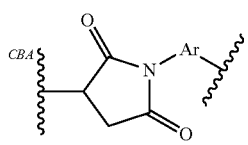
(G$^{LL1-2}$)
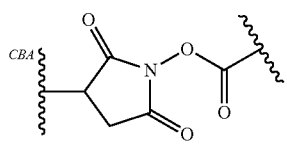 [SMILES: *C(=O)ON1C(=O)CC(*)C1=O]
(G$^{LL2}$)
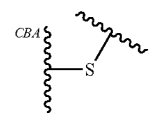
(G$^{LL3-1}$)
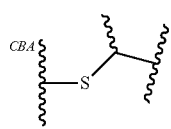
(G$^{LL3-2}$)
-continued
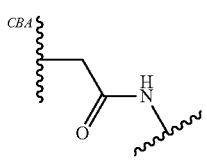
(G$^{LL-4}$)
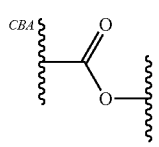 [SMILES: *OC(*)=O]
(G$^{LL5}$)
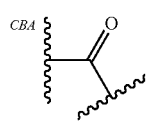 [SMILES: *C(*)=O]
(G$^{LL6}$)
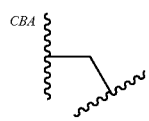
(G$^{LL7}$)
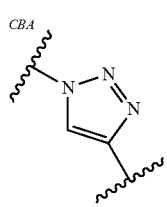
(G$^{LL8-1}$)
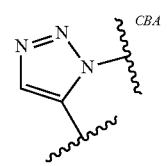
(G$^{LL8-2}$)
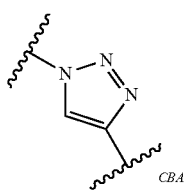
(G$^{LL9-1}$)
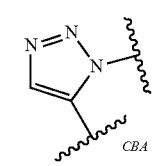
(G$^{LL9-2}$)
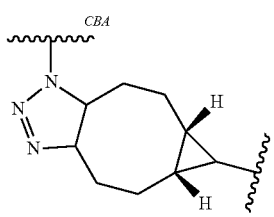 [SMILES: *C1[C@H]2CCC3C(CC[C@@H]12)N=NN3*]
G$^{L10}$ -continued

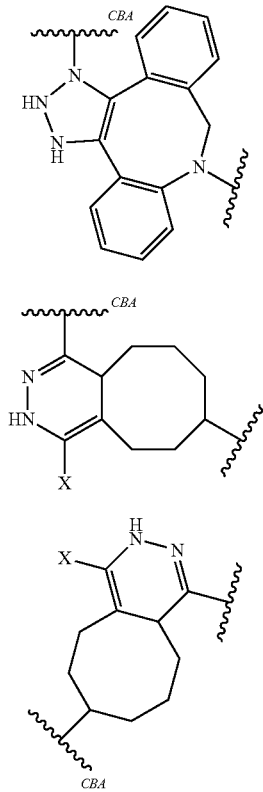

where Ar represents a $C_{5-6}$ arylene group, e.g. phenylene and X represents $C_{1-4}$ alkyl.

In some embodiments, $G^{LL}$ is selected from $G^{LL1-1}$ and $G^{LL1-2}$. In some of these embodiments, $G^{LL}$ is $G^{LL1-1}$.

X

X is:

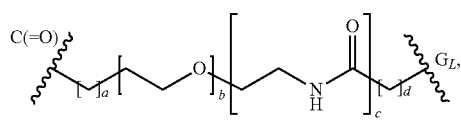

where a=0 to 5, b=0 to 16, c=0 or 1, d=0 to 5.

a may be 0, 1, 2, 3, 4 or 5. In some embodiments, a is 0 to 3. In some of these embodiments, a is 0 or 1. In further embodiments, a is 0.

b may be 0, 1, 2, 3, 4, 5, 6, 7, 8, 9, 10, 11, 12, 13, 14, 15 or 16. In some embodiments, b is 0 to 12. In some of these embodiments, b is 0 to 8, and may be 0, 2, 4 or 8.

c may be 0 or 1.

d may be 0, 1, 2, 3, 4 or 5. In some embodiments, d is 0 to 3. In some of these embodiments, d is 1 or 2. In further embodiments, d is 2.

In some embodiments of X, a is 0, c is 1 and d is 2, and b may be from 0 to 8. In some of these embodiments, b is 0, 4 or 8.

Q

In one embodiment, Q is an amino acid residue. The amino acid may a natural amino acids or a non-natural amino acid.

In one embodiment, Q is selected from: Phe, Lys, Val, Ala, Cit, Leu, Ie, Arg, and Trp, where Cit is citrulline.

In one embodiment, Q comprises a dipeptide residue. The amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, Q is selected from:
$^{CO}$-Phe-Lys-$^{NH}$,
$^{CO}$-Val-Ala-$^{NH}$,
$^{CO}$-Val-Lys-$^{NH}$,
$^{CO}$-Ala-Lys-$^{NH}$,
$^{CO}$-Val-Cit-$^{NH}$,
$^{CO}$-Phe-Cit-$^{NH}$,
$^{CO}$-Leu-Cit-$^{NH}$,
$^{CO}$-Ile-Cit-$^{NH}$,
$^{CO}$-Phe-Arg-$^{NH}$, and
$^{CO}$-Trp-Cit-$^{NH}$;
where Cit is citrulline.

Preferably, Q is selected from:
$^{CO}$-Phe-Lys-$^{NH}$,
$^{CO}$-Val-Ala-$^{NH}$, P1 $^{CO}$-Val-Lys-$^{NH}$,
$^{CO}$-Ala-Lys-$^{NH}$,
$^{CO}$-Val-Cit-$^{NH}$, Most preferably, Q is selected from $^{CO}$-Phe-Lys-$^{NH}$, $^{CO}$-Val-Cit-$^{NH}$ and $^{CO}$-Val-Ala-$^{NH}$.

Other dipeptide combinations of interest include:
$^{CO}$-Gly-Gly-$^{NH}$,
$^{CO}$-Pro-Pro-$^{NH}$, and
$^{CO}$-Val-Glu-$^{NH}$, Other dipeptide combinations may be used, including those described by Dubowchik et al., Bioconjugate Chemistry, 2002, 13, 855-869, which is incorporated herein by reference.

In some embodiments, $Q^X$ is a tripeptide residue. The amino acids in the tripeptide may be any combination of natural amino acids and non-natural amino acids. In some embodiments, the tripeptide comprises natural amino acids. Where the linker is a cathepsin labile linker, the tripeptide is the site of action for cathepsin-mediated cleavage. The tripeptide then is a recognition site for cathepsin.

In one embodiment, the amino acid side chain is chemically protected, where appropriate.

The side chain protecting group may be a group as discussed below. Protected amino acid sequences are cleavable by enzymes. For example, a dipeptide sequence comprising a Boc side chain-protected Lys residue is cleavable by cathepsin.

Protecting groups for the side chains of amino acids are well known in the art and are described in the Novabiochem Catalog, and as described above.

In some embodiments, $R^L$ is of formula IIIb.

In some embodiments, $R^{LL}$ is is formula IIIb'.

$R^L$ and $R^{L2}$ are independently selected from H and methyl, or together with the carbon atom to which they are bound form a cyclopropylene or cyclobutylene group.

In some embodiments, both $R^L$ and $R^{L2}$ are H.

In some embodiments, $R^L$ is H and $R^{L2}$ is methyl.

In some embodiments, both $R^L$ and $R^{L2}$ are methyl.

In some embodiments, $R^L$ and $R^{L2}$ together with the carbon atom to which they are bound form a cyclopropylene group.

In some embodiments, $R^L$ and $R^{L2}$ together with the carbon atom to which they are bound form a cyclobutylene group.

In the group IIIb, in some embodiments, e is 0. In other embodiments, e is 1 and the nitro group may be in any available position of the ring. In some of these embodiments, it is in the ortho position. In others of these embodiments, it is in the para position.

In one particular embodiment, the first aspect of the invention comprises a compound of In some embodiments of the first aspect of the present invention are of formula Ia, Ib or Ic:

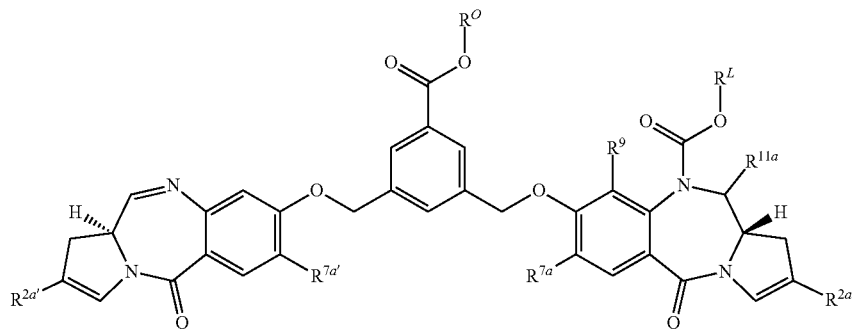

Ia

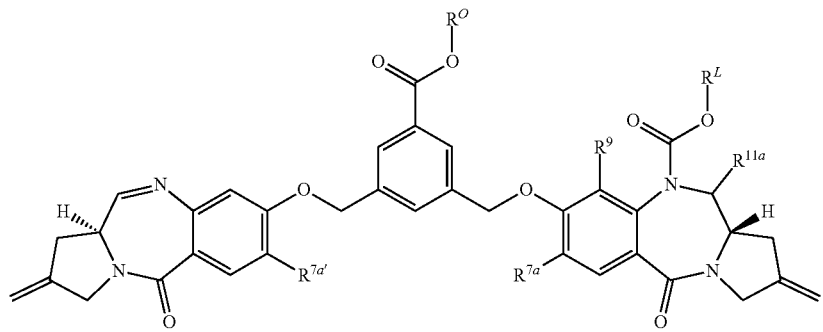

Ib

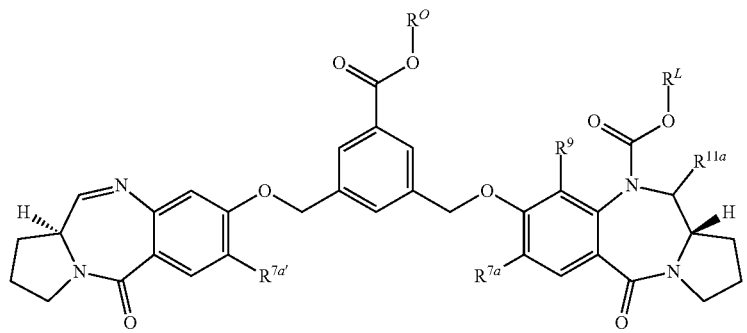

Ic where $R^{2a}$ and $R^{2a'}$ are the same and are selected from:

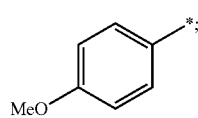

(a)

(b)

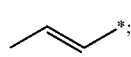

(c)

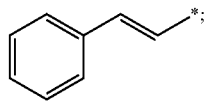

(d)

(e)

(f)

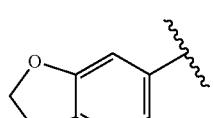

; and (g)

-continued (h)
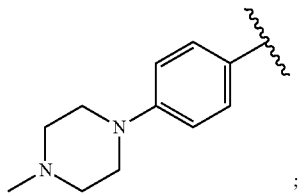
$R^{7a}$ and $R^{7a'}$ are the same and are selected from methoxy and benzyloxy;
$R^O$, $R^{L1}$ and $R^{11a}$ are as defined above.
In some embodiments of the third aspect of the present invention, the drug linkers ($D^L$) are of formula IIIa, IIIb or IIIc:
IIIa
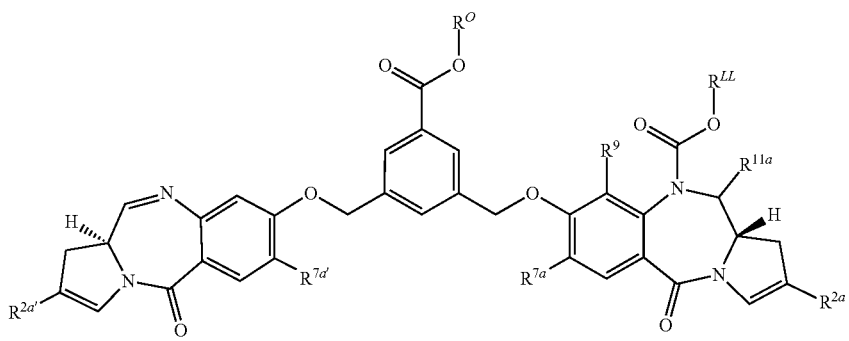
IIIb
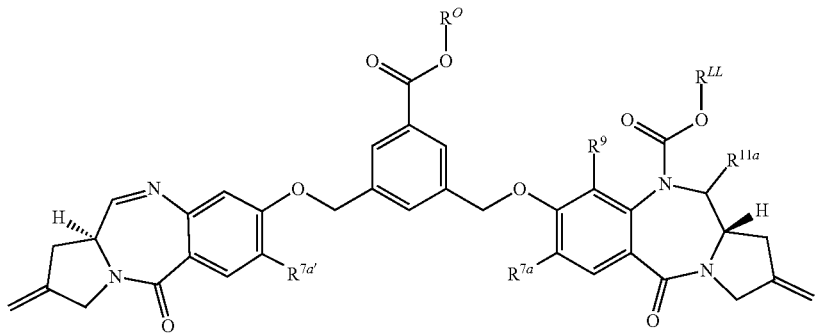
IIIc
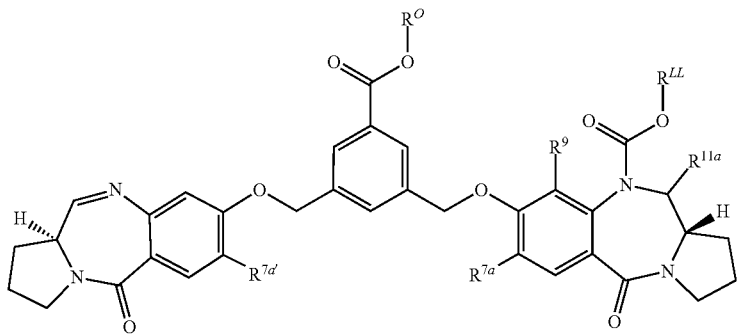
where $R^{2a}$ and $R^{2a'}$ are the same and are selected from:
(a)
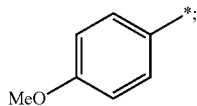
(b)
(c)
(d)
(e)
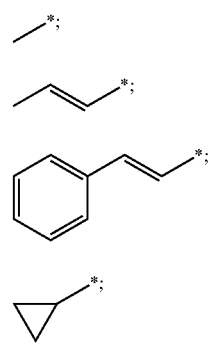
(f)

(g) 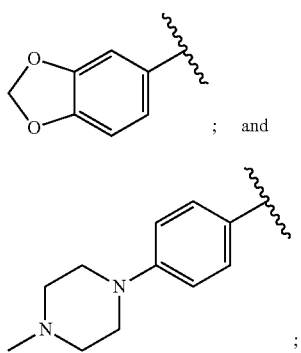 ; and (h) 
[structure showing 4-(4-methylpiperazin-1-yl)phenyl group]
;

$R^{7a}$ and $R^{7a'}$ are the same and are selected from methoxy and benzyloxy;

$R^O$, $R^{La}$ and $R^{11a}$ are as defined above.

EXAMPLES

General Information

Flash chromatography was performed using a Biotage Isolera 1™ using gradient elution with hexane/EtOAc or $CH_2Cl_2$/MeOH mixtures as indicated until all UV active components eluted from the column. The gradient was manually held whenever substantial elution of UV active material was observed. Fractions were checked for purity using thin-layer chromatography (TLC) using Merck Kieselgel 60 F254 silica gel, with fluorescent indicator on aluminium plates. Visualisation of TLC was achieved with UV light or iodine vapour unless otherwise stated. Extraction and chromatography solvents were bought and used without further purification from VWR U.K. All fine chemicals were purchased from Sigma-Aldrich or VWR.

The analytical LC/MS conditions (for reaction monitoring and purity determination) were as follows: Positive mode electrospray mass spectrometry was performed using a Shimadzu Nexera®/Prominence® LCMS-2020. Mobile phases used were solvent A ($H_2O$ with 0.1% formic acid) and solvent B ($CH_3CN$ with 0.1% formic acid).

LCMS-A: Gradient for 3-minute run: Initial composition 5% B held over 25 seconds, then increased from 5% B to 100% B over a 1 minute 35 seconds' period. The composition was held for 50 seconds at 100% B, then returned to 5% B in 5 seconds and held there for 5 seconds. The total duration of the gradient run was 3.0 minutes at a flow rate of 0.8 mL/min. Column: Waters Acquity UPLC® BEH Shield RP18 1.7 µm 2.1×50 mm at 50° C. fitted with Waters Acquity UPLC® BEH Shield RP18 VanGuard Pre-column, 130A, 1.7 µm, 2.1 mm×5 mm LCMS-B: Gradient for 15-minute run: Initial composition 5% B held over 1 minute, then increased from 5% B to 100% B over a 9 minute period. The composition was held for 2 minutes at 100% B, then returned to 5% B in 10 seconds and held there for 2 minutes 50 seconds. The total duration of the gradient run was 15.0 minutes at a flow rate of 0.6 mL/minute. Detection was monitored at 254 nm, 223 nm and 214 nm. ACE Excel 2 C18-AR, 2µ, 3.0×100 mm fitted with Waters Acquity UPLC® BEH Shield RP18 VanGuard Pre-column, 130A, 1.7 µm, 2.1 mm×5 mm.

Intermediates

| | Structure | Reference |
|---|---|---|
| I1 | [structure: HO-CH2-C6H4-NH-C(=O)-CH(CH3)-NH-C(=O)-CH(iPr)-NHAlloc] | WO2011/130598; Compound 8 |
| I2 | [structure: THPO-, Boc-N, pyrrolo-benzodiazepine with OH and OMe] | WO2014/159981; Compound 1 |
| I3 | [structure: THPO-, Alloc-N, pyrrolo-benzodiazepine with OH and OMe] | WO2013/053872; Compound 26 |

| Structure | Reference |
|---|---|
| I4 | WO2013/053872; Compound 32 |
| I5 | See below |

Synthesis of tert-butyl(11S,11aS)-11-((tert-butyldimethylsilyl)oxy)-8-hydroxy-7-methoxy-2-methylene-5-oxo-2,3,11,11a-tetrahydro-1H-benzo[e]pyrrolo[1,2-a][1,4]diazepine-10(5H)-carboxylate(I5)

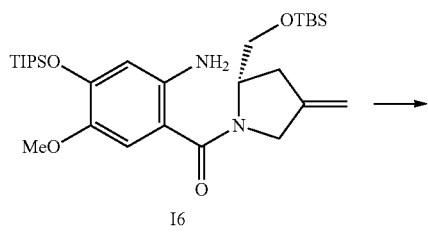

I6

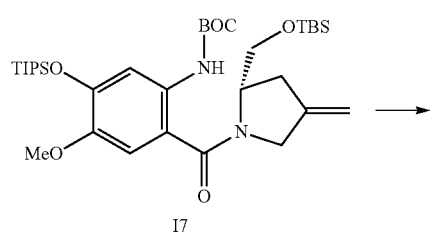

I7

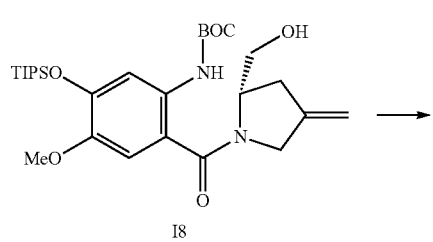

I8

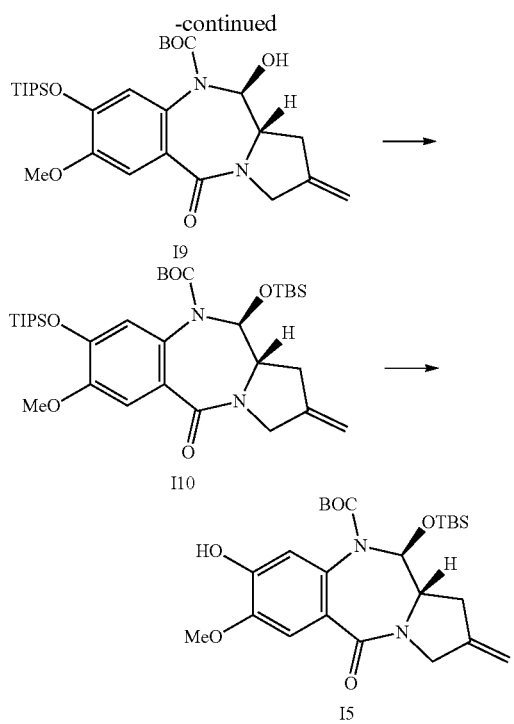

I6 is Compound 152 of WO 2018/182341

(i) tert-Butyl (S)-(2-(2-(((tert-butyldimethylsilyl)oxy)methyl)-4-methylenepyrrolidine-1-carbonyl)-4-methoxy-5-((triisopropylsilyl)oxy)phenyl)carbamate (I7)

I6 (400 g, 1 eq.), CH$_2$Cl$_2$ (4 L) and Boc$_2$O (206.7 g, 1.3 eq.) were added to a reactor and stirred for 20 h at 70° C. The mixture was cooled to rt and concentrated in vacuo to afford 17 (450 g, 95%) which was used without further purification.

(ii) tert-Butyl (S)-(2-(2-(hydroxymethyl)-4-methylenepyrrolidine-1-carbonyl)-4-methoxy-5-((triisopropylsilyl)oxy)phenyl)carbamate (I8)

I7 (210 g, 1.0 eq.) THF (76 mL), MeOH (76 mL) AcOH (533 mL) and H₂O (151 mL) were added to a reactor and stirred for 20 h. The mixture was diluted with EtOAc (30 V) and H₂O (20 V) and the mixture vigorously stirred. The organic phase was washed with sat. NaHCO₃ solution (20 V), then brine (20 V) and dried over Na₂SO₄ and concentrated in vacuo. Flash column chromatography (8:1-2:1 petroleum ether/EtOAc) afforded I8 as a white solid (150 g, 87%).

(iii) tert-Butyl (11S,11aS)-11-hydroxy-7-methoxy-2-methylene-5-oxo-8-((triisopropylsilyl)oxy)-2,3,11,11a-tetrahydro-1H-benzo[e]pyrrolo[1,2-a][1,4]diazepine-10(5H)-carboxylate (I9)

(COCl)₂ (28.5 g, 1.0 eq.) was added to CH₂Cl₂ (900 mL) in a reactor under N₂ and the mixture was cooled to −80° C. A solution of 18 (120 g, 1.0 eq.) in CH₂Cl₂ (600 mL) was added dropwise over 30 min, then Et₃N (113.5 g, 5.0 eq.) was added dropwise over 30 min. The mixture was warmed to rt and stirred for 5 h the quenched by the addition of 5% aqueous citric acid (10 V). The organic phase was washed successively with sat. NaHCO₃ (5 V) and H₂O (5 V), dried over Na₂SO₄ and concentrated in vacuo. The crude product was stirred in heptane (10 V) at 90° C., then cooled to 0-5° C. The resulting white precipitate was isolated by filtration and dried in a vacuum oven at 50° C. to afford 19 (105 g, 88%).

(iv) tert-Butyl (11S,11aS)-11-((tert-butyldimethylsilyl)oxy)-7-methoxy-2-methylene-5-oxo-8-((triisopropylsilyl)oxy)-2,3,11,11a-tetrahydro-1H-benzo[e]pyrrolo[1,2-a][1,4]diazepine-10(5H)-carboxylate (I10)

I9 (150 g, 1.0 eq.) and CH₂Cl₂ (1.5 L, 10 V) were charged to a reactor and the mixture cooled to 0-5° C. Lutidine (120.6 g, 4.0 eq.), then TBSOTf (223.2 g, 3.0 eq.) were added and the mixture was stirred for 10 min at 0-10° C., then 4 h at rt. The reaction was quenched by the addition of 5% aqueous citric acid (5 V) and the organic phase was successively washed with sat. NaHCO₃ (5 V), H₂O (5 V) then dried over Na₂SO₄ and concentrated in vacuo to afford 5 (179 g, 98%) as an orange oil.

(v) tert-Butyl (11S,11aS)-11-((tert-butyldimethylsilyl)oxy)-8-hydroxy-7-methoxy-2-methylene-5-oxo-2,3,11,11a-tetrahydro-1H-benzo[e]pyrrolo[1,2-a][1,4]diazepine-10(5H)-carboxylate (I5)

DMF (1.83 L, 1 V), H₂O (37.4 mL, 0.2 V) and I10 (187 g, 1.0 eq.) were charged to a reactor. LiOAc (19.1 g, 1.0 eq.) was added and the mixture stirred for 20 h at 10-20° C. The reaction mixture was diluted with cold water (10 V) and EtOAc (20 V). The aqueous phase was washed with EtOAc (10 V), the organic phases combined, successively washed with 5% aqueous citric acid (10 V), 5% aqueous NaHCO₃ (10 V) and H₂O (10 V) and dried over Na₂SO₄ and concentrated in vacuo. The resulting crude was dissolved in EtOAc (6 V) at 77° C., heptane (12 V) was added and the mixture cooled to 0-5° C., the white precipitate collected by filtration and dried at 50° C. in a vacuum oven to afford 6 (101 g, 71%).

Example 1: 3-((((11S,11aS)-10-(((4-((S)-2-((S)-2-(3-(2,5-dioxo-2,5-dihydro-1H-pyrrol-1-yl)propanamido)-3-methylbutanamido)propanamido)benzyl)oxy)carbonyl)-11-hydroxy-7-methoxy-2-methylene-5-oxo-2,3,5,10,11,11a-hexahydro-1H-benzo[e]pyrrolo[1,2-a][1,4]diazepin-8-yl)oxy)methyl)-5-((((S)-7-methoxy-2-methylene-5-oxo-2,3,5,11a-tetrahydro-1H-benzo[e]pyrrolo[1,2-a][1,4]diazepin-8-yl)oxy)methyl)benzoic acid (19)

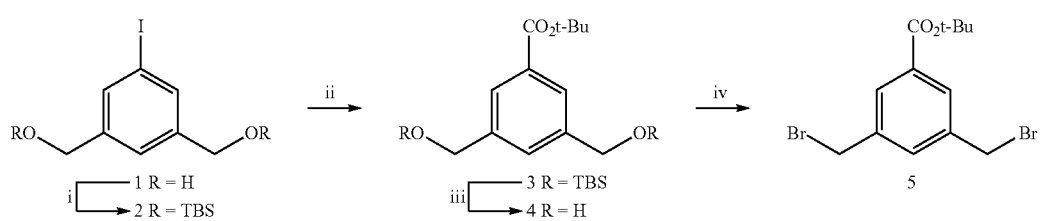

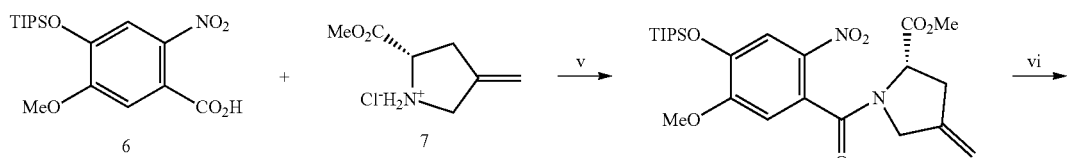

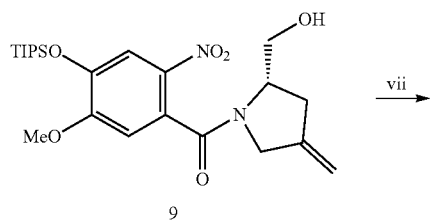
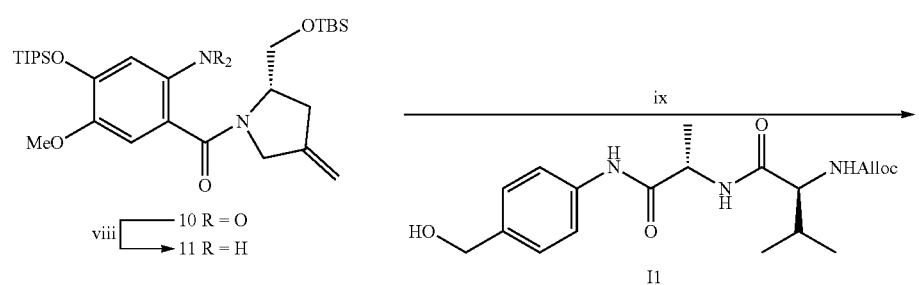
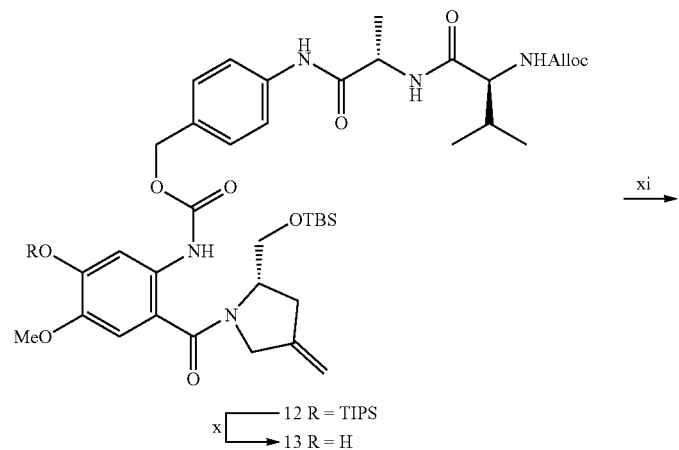
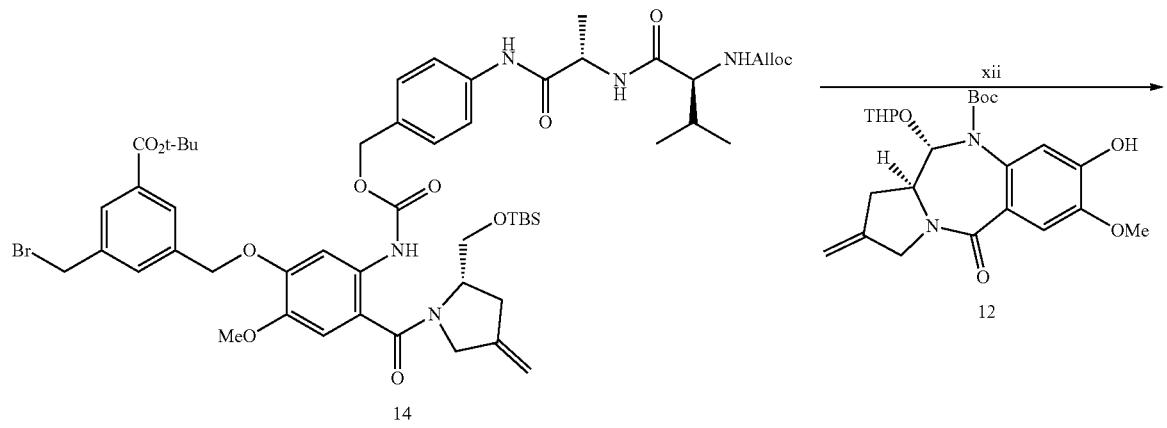

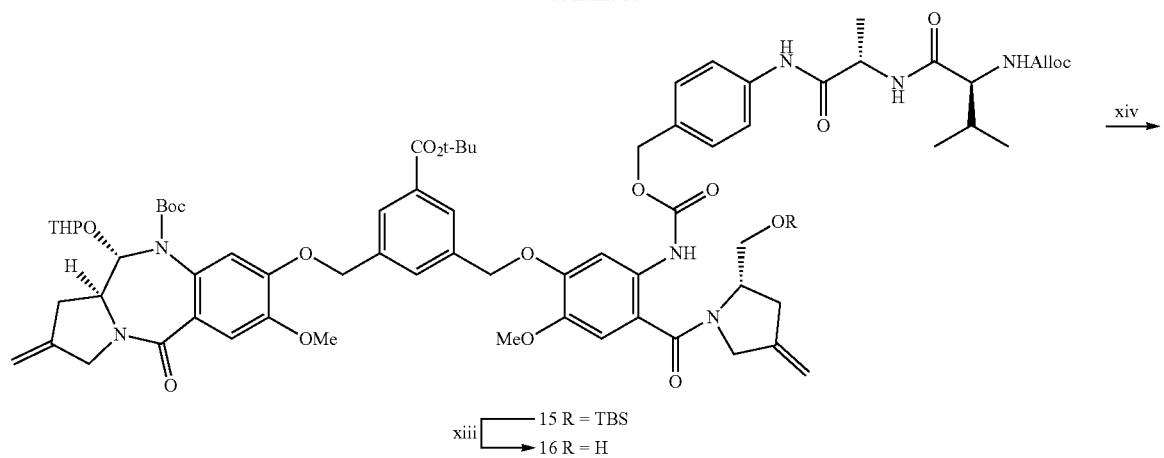
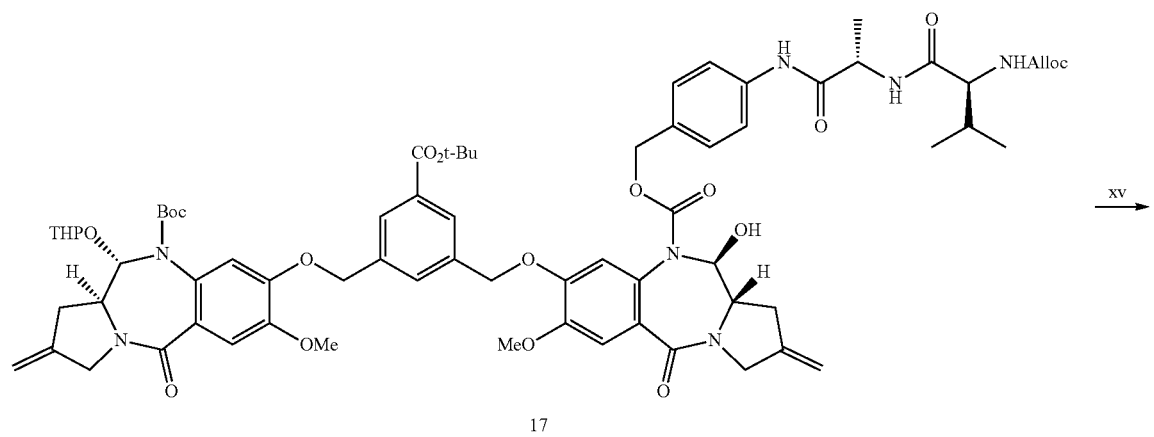
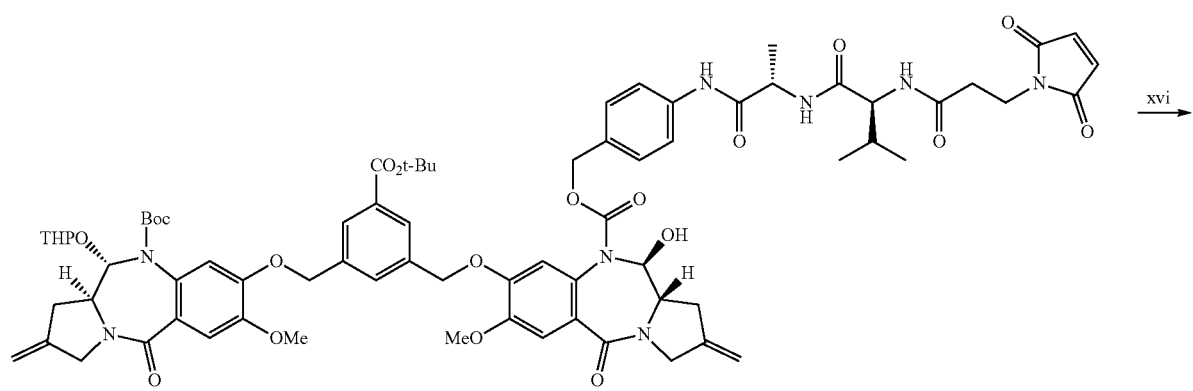

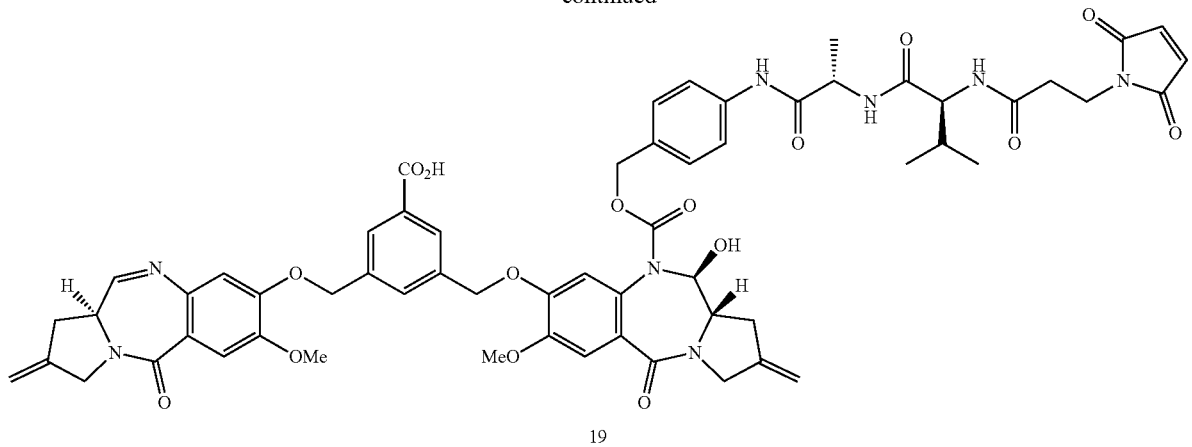

19

20

(i) (((5-iodo-1,3-phenylene)bis(methylene))bis(oxy))bis(tert-butyldimethylsilane) (2)

A round-bottomed flask was charged with a magnetic stirrer bar, DMF (100 mL), diol 1 (10.0 g, 37.87 mmol, 1.0 eq.), TBSCl (17.1 g, 113.6 mmol, 3.0 eq.) imidazole (15.5 g, 227.2 mmol, 6.0 eq.) and the mixture stirred for 20 min, whereupon LCMS indicated the reaction was complete. The reaction mixture was filtered, diluted with EtOAc, washed with water, the organic phase dried over MgSO$_4$ and concentrated in vacuo. Isolera (0-8% EtOAc in hexane) afforded the desired product as a colourless oil (17.9 g, 96%). LCMS-A: 2.29 min (ES+) no ionisation.

(ii) tert-butyl 3,5-bis(((tert-butyldimethylsilyl)oxy)methyl)benzoate (3)

An oven-dried 3-necked round-bottomed flask was charged with a magnetic stirrer bar anhydrous toluene (7.5 mL) and the flask purged with Ar and the flask cooled to −10° C. BuLi (5.6 mL of a 2.5 M solution in hexanes, 14.00 mmol, 2.0 eq.), then slowly BuMgCl (3.5 mL of a 2.0 M solution in THF, 7.000 mmol, 1.0 eq.) were added and stirred for 30 min. 2 (8.21 g, 16.67 mmol, 2.4 eq.) in anhydrous toluene (15 mL) was added slowly and stirred for 2 h at −10° C. Boc$_2$O (4.55 g, 20.84 mmol, 3.0 eq.) in anhydrous toluene (7.5 mL) was added slowly at −10° C. and stirred for 1 h, then poured into cold 10% citric acid. The aqueous phase was extracted with EtOAc, the organics combined, dried over MgSO$_4$ and concentrated in vacuo. Isolera purification (0-20% EtOAc in hexane afforded the product as a colourless oil (7.39 g, 95%). LCMS-A: 1.48 min (ES+) no ionisation.

(iii) tert-butyl 3,5-bis(hydroxymethyl)benzoate (4)

A round-bottomed flask was charged with a magnetic stirrer, 3 (7.39 g, 15.83 mmol, 1.0 eq.) and THF (75 mL). TBAF (31.7 mL of a 1M solution, 31.70 mmol, 2.0 eq.) was added by syringe and stirred for 20 min whereupon LCMS indicated the reaction was complete. The reaction mixture was diluted with EtOAc, washed with H$_2$O, dried over MgSO$_4$ and concentrated in vacuo to afford the product as a white crystalline solid (3.29 g, 87%). LCMS-A: 1.24 min (ES+) no ionisation.

(iv) tert-butyl 3,5-bis(bromomethyl)benzoate (5)

A round-bottomed flask was charged with a magnetic stirrer, 4 (3.29 g, 15.83 mmol, 1.0 eq.), CH$_2$Cl$_2$ (200 mL) and cooled to −78° C. PPh$_3$ (17.4 g, 66.34 mmol, 4.2 eq.) was added, then CBr$_4$ (23.1 g, 69.65 mmol, 4.4 eq.) was added portionwise and the reaction allowed to warm to rt. The reaction was filtered through SiO$_2$ (CH$_2$Cl$_2$/hexane) and purified by isolera (0-20% EtOAc in hexane) to afford the product as a white solid (1.43 g, 26%). LCMS-A: 1.81 min (ES+) no ionisation.

(v) Methyl (S)-1-(5-methoxy-2-nitro-4-((triisopropylsilyl)oxy)benzoyl)-4-methylenepyrrolidine-2-carboxylate (8)

A round-bottomed flask was charged with a magnetic stirrer, THF (15 mL), 6 (1.89 g, 5.118 mmol, 1.0 eq.), HOBt (761 mg, 5.630 mmol, 1.1 eq.), DIC (872 µL, 5.630 mmol, 1.1 eq.) and i-Pr$_2$NEt (1.96 mL, 11.26 mmol, 2.2 eq.) and the mixture was stirred for 10 min. 7 (1.00 g, 5.630 mmol, 1.1 eq.) was added portionwise and the reaction mixture was stirred for 1 h. The reaction was diluted with CH$_2$Cl$_2$, washed with 0.2N HCl solution, the organics dried over MgSO$_4$ and concentrated in vacuo. Flash column chromatography (20-30% EtOAc in hexane) afforded the desired product as a yellow oil (1.19 g, 47%). LCMS-A: 2.00 min (ES+) m/z 493 [M+H]$^+$, 515 [M+Na]$^+$

(vi) (S)-(2-(hydroxymethyl)-4-methylenepyrrolidin-1-yl)(5-methoxy-2-nitro-4-((triisopropylsilyl)oxy)phenyl)methanone (9)

A round-bottomed flask was charged with a magnetic stirrer, THF (15 mL), 8 (1.17 g, 2.383 mmol, 1.0 eq.) and the stirring mixture was cooled to 0° C. Cautiously, LiBH$_4$ (156 mg, 7.149 mmol, 3.0 eq.) was added and the mixture was stirred for 1 h at 0° C. and a further 1.5 h at rt. The reaction was quenched by the addition of ice-cold H$_2$O and the pH adjusted to ca. 6 with 1N HCl. The aqueous mixture was extracted with CH$_2$Cl$_2$, the organics combined, dried over MgSO$_4$ and concentrated in vacuo to afford the desired product as a yellow foam (1.06 g, 96%) which was used without further purification. LCMS-A: 1.92 min (ES+) m/z 465 [M+H]$^+$, 487 [M+Na]$^+$ (vii) (S)-(2-(((tert-butyldimethylsilyl)oxy)methyl)-4-methylenepyrrolidin-1-yl)(5-methoxy-2-nitro-4-((triisopropylsilyl)oxy)phenyl)methanone (10)

A round-bottomed flask was charged with a magnetic stirrer, $CH_2Cl_2$ (10 mL), 9 (1.06 g, 2.281 mmol, 1.0 eq.), imidazole (467 mg, 6.858 mmol, 3.0 eq.) TBSCl (517 mg, 3.429 mmol, 1.5 eq.) and stirred for 1 h, whereupon LCMS indicated the reaction was complete. The reaction mixture was filtered, the filtrate washed with $H_2O$, brine, dried over $MgSO_4$ and concentrated in vacuo. Flash column chromatography (20-30% EtOAc in hexane) afforded the desired product as a yellow oil (1.27 g, 96%). LCMS-A: 2.30 min (ES+) m/z 579 [M+H]$^+$, 601 [M+Na]$^+$ (viii) (S)-(2-amino-5-methoxy-4-((triisopropylsilyl)oxy)phenyl)(2-(((tert-butyldimethylsilyl)oxy)methyl)-4-methylenepyrrolidin-1-yl)methanone (11)

A three-necked round-bottomed flask was charged with a magnetic stirrer, 10 (10.0 g, 17.27 mmol, 1.0 eq.), EtOH (170 mL), Zn (23.6 g, 345.4 mmol, 20 eq.) and cooled to 0° C. 5% $HCO_2H$ in EtOH (340 mL) was added dropwise by dropping funnel and stirred for 30 min, whereupon, LCMS indicated reaction was complete. The reaction mixture was diluted with EtOAc (200 mL) and filtered through Celite. Sat. $NaHCO_3$ solution was added to the filtrate until the pH of the aqueous phase was basic. The phases were separated, the aqueous phase was washed with EtOAc (2×100 mL), the organic phases combined, washed with brine, dried over $MgSO_4$ and concentrated in vacuo to afford a yellow oil which was used without further purification (8.99 g, 95%). LCMS-A: 2.23 min (ES+) m/z 549 [M+H]$^+$, 571 [M+Na]$^+$ (ix) 4-((S)-2-((S)-2-(((allyloxy)carbonyl)amino)-3-methylbutanamido)propanamido)benzyl (2-((S)-2-(((tert-butyldimethylsilyl)oxy)methyl)-4-methylenepyrrolidine-1-carbonyl)-4-methoxy-5-((triisopropylsilyl)oxy)phenyl)carbamate (12)

A round-bottomed flask was charged with a magnetic stirrer, 11 (8.99 g, 16.38 mmol, 1.0 eq.), THF (90 mL), $Et_3N$ (5.4 mL, 35.90 mmol, 2.2 eq.), the flask purged with Ar and the mixture cooled to −10° C. Triphosgene (1.75 g, 5.897 mmol, 0.36 eq.) was added in one portion over a flow of Ar. After 5 min, LCMS indicated isocyanate formation complete (by way of MeOH quench and observation of methyl carbamate). I1 (9.27 g, 24.57 mmol, 1.5 eq.) was added in one portion over a flow of Ar and the reaction mixture was warmed to room temperature and stirred for 24 h. The reaction mixture was filtered, concentrated onto $SiO_2$ in vacuo and purified by flash-column chromatography (0-3% MeOH in $CH_2Cl_2$) to afford the product (10.9 g, 70%). LCMS-A: 2.20 min (ES+) m/z 952 [M+H]$^+$, 974 [M+Na]$^+$ (x) 4-((S)-2-((S)-2-(((allyloxy)carbonyl)amino)-3-methylbutanamido)propanamido)benzyl (2-((S)-2-(((tert-butyldimethylsilyl)oxy)methyl)-4-methylenepyrrolidine-1-carbonyl)-5-hydroxy-4-methoxyphenyl)carbamate (13)

A round-bottomed flask was charged with a magnetic stirrer, silyl ether 12 (10.9 g, 11.47 mmol, 1.0 eq.) DMF (85 mL), $H_2O$ (1.7 mL) and LiOAc (1.17 g, 11.47 mmol, 1.0 eq.). The reaction mixture was stirred for 16 h, whereupon LCMS indicated the reaction was complete. The reaction mixture was diluted with EtOAc (150 mL) and washed successively with $H_2O$ (50 mL) and brine (50 mL). The organic phase was dried over $MgSO_4$ and purified by Isolera chromatography (0-4% MeOH in $CH_2Cl_2$) to afford the product as a yellow foam (6.65 g, 73%). LCMS-A: 1.78 min (ES+) m/z 796 [M+H]$^+$, 818 [M+Na]$^+$ (xi) tert-butyl 3-((5-((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)-4-methylenepyrrolidine-1-carbonyl)-2-methoxyphenoxy)methyl)-5-(bromomethyl)benzoate (14)

A round-bottomed flask was charged with a magnetic stirrer, phenol 13 (1.09 g, 1.364 mmol, 1 eq.), bis bromo 5 (1.43 g, 4.093 mmol, 3.0 eq.), DMF (10 mL) and $K_2CO_3$ (207 mg, 1.500 mmol, 1.1 eq.) and the reaction stirred for 2.5 h at 35° C., whereupon LCMS indicated the reaction was complete. The reaction mixture was diluted with $H_2O$ and washed with $CH_2Cl_2$, dried over $MgSO_4$ and concentrated in vacuo. Isolera purification (10-50% EtOAc in hexane) afforded the product as an off-white foam (946 mg, 64%). LCMS-A: 2.06 min (ES+) m/z 1100.20 [M+Na]$^+$ (xii) (11S,11 aS)-8-((3-((5-((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)-4-methylenepyrrolidine-1-carbonyl)-2-methoxyphenoxy)methyl)-5-(tert-butoxycarbonyl)benzyl)oxy)-7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (15)

A round-bottomed flask was charged with a magnetic stirrer, 14 (946 mg, 0.8766 mmol, 1.0 eq.), 12 (444 mg, 0.9643 mmol, 1.1 eq.), DMF (12 mL) and $K_2CO_3$ (133 mg, 0.9643 mmol, 1.1 eq.) were stirred for 3.5 h at 35° C. whereupon LCMS indicated the reaction was complete. The reaction mixture was diluted with $H_2O$, washed with EtOAc and the organic phase was dried over $MgSO_4$ and concentrated in vacuo. Isolera purification (40-100% EtOAc in hexane afforded the product as a white foam (1.04 g, 82%). LCMS-A: 2.11 min (ES+) m/z 1458.20 [M+H]$^+$, 1480.35 [M+Na]$^+$ (xiii) tert-butyl (11S,11 aS)-8-((3-((5-((((4-((S)-2-((S)-2-(((allyloxy)carbonyl)amino)-3-methylbutanamido)propanamido)benzyl)oxy)carbonyl)amino)-4-((S)-2-(hydroxymethyl)-4-methylenepyrrolidine-1-carbonyl)-2-methoxyphenoxy)methyl)-5-(tert-butoxycarbonyl)benzyl)oxy)-7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (16)

A round-bottomed flask was charged with a magnetic stirrer, 15 (1.04 g, 0.7129 mmol, 1.0 eq.), THF (40 mL) AcOH (82 μL, 1.430 mmol, 2.0 eq.) and TBAF (2.1 mL of a 1M solution, 2.100 mmol, 3.0 eq.) and the reaction stirred for 1 h whereupon LCMS indicated the reaction was complete. The reaction mixture was diluted with $CHCl_3$ and washed with sat. $NaHCO_3$, the organic phase dried over $MgSO_4$ and concentrated in vacuo. Isolera purification (0-4% MeOH in $CH_2Cl_2$) afforded the product as a white foam (961 mg, 100%). LCMS-A: 1.86 min (ES+) m/z 1344.70 [M+H]+, 1366.85 [M+Na]+

(xiv) 4-((S)-2-((S)-2-(((allyloxy)carbonyl)amino)-3-methylbutanamido)propanamido)benzyl (11S,11aS)-8-((3-(tert-butoxycarbonyl)-5-((((11S,11aS)-10-(tert-butoxycarbonyl)-7-methoxy-2-methylene-5-oxo-11-((tetrahydro-2H-pyran-2-yl)oxy)-2,3,5,10,11,11a-hexahydro-1H-benzo[e]pyrrolo[1,2-a][1,4]diazepin-8-yl)oxy)methyl)benzyl)oxy)-11-hydroxy-7-methoxy-2-methylene-5-oxo-2,3,11,11a-tetrahydro-1H-benzo[e]pyrrolo[1,2-a][1,4]diazepine-10(5H)-carboxylate (17)

A round-bottomed flask was charged with a magnetic stirrer, 16 (961 mg, 0.7150 mmol, 1.0 eq.) DMSO (7 mL) and IBX (489 mg, 0.7865, 1.1 eq.) and the reaction mixture stirred at 35° C. for 16 h. IBX (50 mg, 80.35 µmol, 0.11 eq.) was added and the reaction mixture stirred for 48 h, whereupon the reaction mixture was poured into water and washed with 10% MeOH in CH$_2$Cl$_2$, the organic layers combined, dried over MgSO$_4$ and concentrated in vacuo. Isolera purification (0-4% MeOH in CH$_2$Cl$_2$) afforded the product as a white foam (492 mg, 51%). Mixed fractions were purified again by isolera (0-2.5% MeOH in CH$_2$Cl$_2$) affording the product as a white solid (302 mg, 31%). Both clean fractions were combined to afford the product as a white foam (794 mg, 83%). LCMS-A: 1.83 min (ES+) m/z 1364.55 [M+Na]+

(xv) tert-butyl (11S,11aS)-8-((3-(tert-butoxycarbonyl)-5-((((11S,11aS)-10-(((4-((S)-2-((S)-2-(3-(2,5-dioxo-2,5-dihydro-1H-pyrrol-1-yl)propanamido)-3-methylbutanamido)propanamido)benzyl)oxy)carbonyl)-11-hydroxy-7-methoxy-2-methylene-5-oxo-2,3,5,10,11,11a-hexahydro-1H-benzo[e]pyrrolo[1,2-a][1,4]diazepin-8-yl)oxy)methyl)benzyl)oxy)-7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (18)

Around-bottomed flask was charged with a magnetic stirrer, 17 (794 mg, 0.5914 mmol, 1.0 eq.), CH$_2$Cl$_2$ (50 mL), pyrrolidine (121 µL, 1.479 mmol, 2.5 eq.) and the flask purged with Ar. Pd(PPh$_3$)$_4$ (34 mg, 29.58 µmol, 0.050 eq.) was added over a flow of Ar and the reaction mixture stirred for 10 min, whereupon LCMS indicated the reaction was complete. The reaction mixture was thoroughly concentrated in vacuo overnight to remove pyrrolidine traces. The resulting residue was dissolved in CH$_2$Cl$_2$ (10 mL) and maleimide propionic acid (78 mg, 0.4612, 1.1 eq.), EDCl.HCl (880 mg, 0.4589 mmol, 1.1 eq.) and i-Pr$_2$NEt (218 µL, 1.252 mmol, 3.0 eq.) were added and the mixture stirred for 5 h, whereupon LCMS indicated the reaction was incomplete. A further 0.1 eq of EDCl.HCl, 0.1 eq. of maleimide propionic acid and 0.3 eq. of i-Pr$_2$NEt were added and the mixture stirred for 16 h, whereupon LCMS indicated the reaction was incomplete. A further 0.2 eq of EDCl.HCl, 0.2 eq. of maleimide propionic acid and 0.6 eq. of i-Pr$_2$NEt were added and the mixture stirred for 24 h, diluted with CH$_2$Cl$_2$ (20 mL), washed with H$_2$O (10 mL) the organic phase dried over MgSO$_4$ and concentrated in vacuo. Isolera chromatography (2-6% MeOH in CH$_2$Cl$_2$) afforded the desired product (205 mg, 35%). LCMS-A: 1.77 min (ES+) m/z 1410 [M+H]+, 1431 [M+Na]+

(xvi) 3-((((11S,11aS)-10-(((4-((S)-2-((S)-2-(3-(2,5-dioxo-2,5-dihydro-1H-pyrrol-1-yl)propanamido)-3-methylbutanamido)propanamido)benzyl)oxy)carbonyl)-11-hydroxy-7-methoxy-2-methylene-5-oxo-2,3,5,10,11,11a-hexahydro-1H-benzo[e]pyrrolo[1,2-a][1,4]diazepin-8-yl)oxy)methyl)-5-((((S)-7-methoxy-2-methylene-5-oxo-2,3,5,11a-tetrahydro-1H-benzo[e]pyrrolo[1,2-a][1,4]diazepin-8-yl)oxy)methyl)benzoic acid (19)

A round-bottomed flask was charged with a magnetic stirrer, 18 (205 mg, 0.1454 mmol, 1.0 eq.) and cooled to ca. −5° C. 95:5 v/v TFA/H$_2$O was cooled to ca. −20° C. and added to the reaction flask and stirred for 75 min, whereupon LCMS indicated the reaction was complete. The pH of the reaction mixture was adjusted to ca. 7 by the cautious addition of sat. NaHCO$_3$, whereupon a precipitate formed. The aqueous mixture was extracted with 10% MeOH in CH$_2$Cl$_2$, dried over Na$_2$SO$_4$ and concentrated in vacuo. Preparative HPLC (15-70% A in B) afforded the product as a white solid (52 mg, 31%, QC=94%). A=0.05% formic acid in acetonitrile. B=0.05% formic acid in water LCMS-B: 7.13 min (ES+) m/z 1151 [M+H]+.

Example 2: 4-((S)-2-((S)-2-(3-(2,5-dioxo-2,5-dihydro-1H-pyrrol-1-yl)propanamido)-3-methylbutanamido)propanamido)benzyl (11S,11aS)-11-hydroxy-7-methoxy-8-((3-((((S)-7-methoxy-2-methylene-5-oxo-2,3,5,11a-tetrahydro-1H-benzo[e]pyrrolo[1,2-a][1,4]diazepin-8-yl)oxy)methyl)-5-(methoxycarbonyl)benzyl)oxy)-2-methylene-5-oxo-2,3,11,11a-tetrahydro-1H-benzo[e]pyrrolo[1,2-a][1,4]diazepine-10(5H)-carboxylate (27)

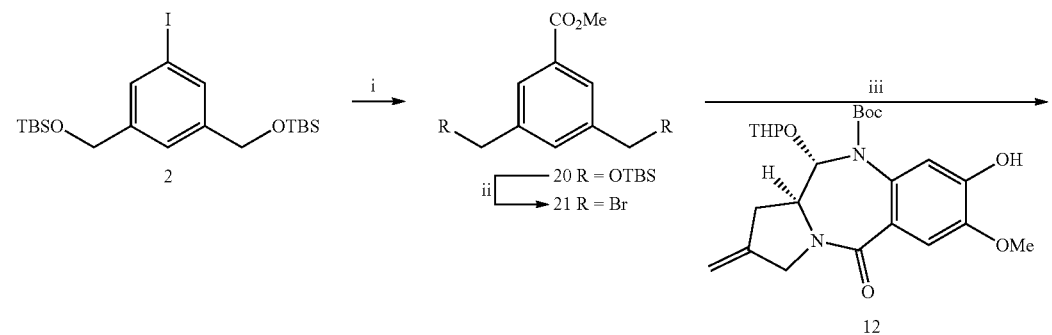

-continued
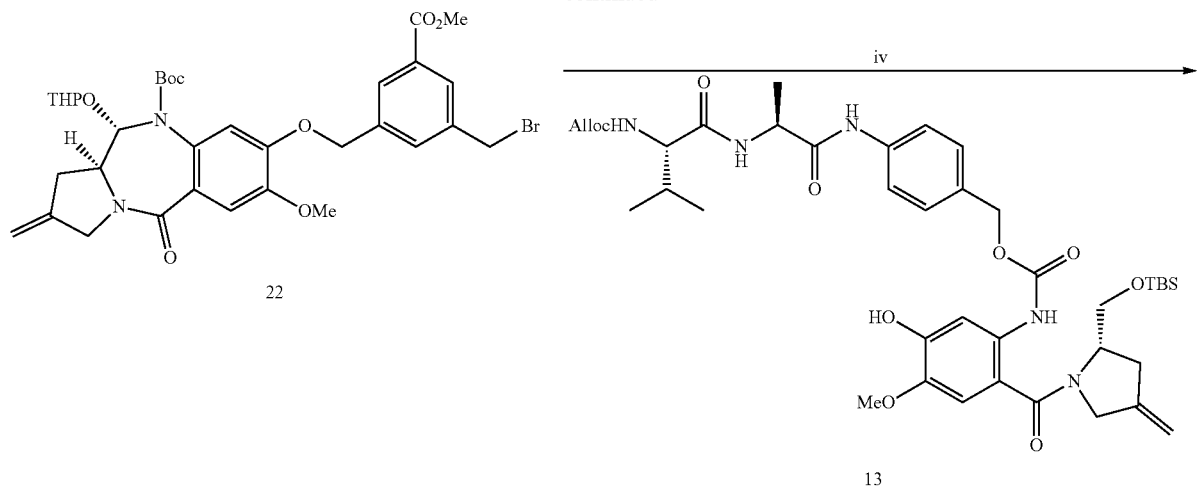
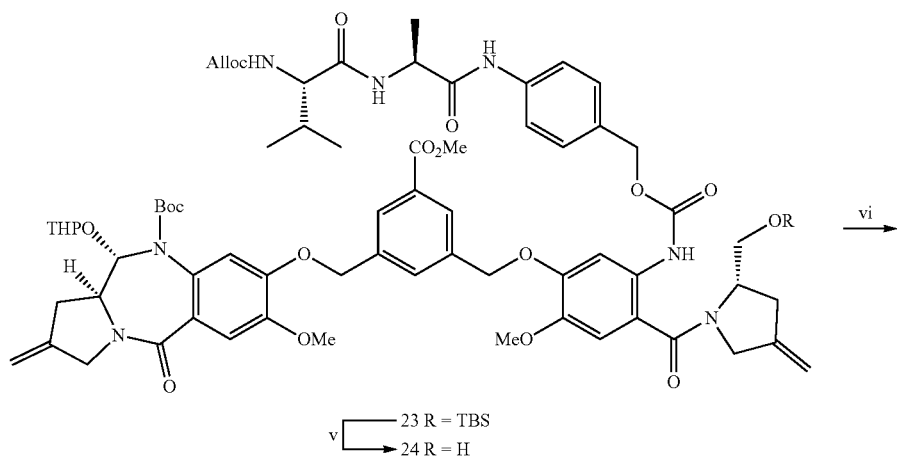
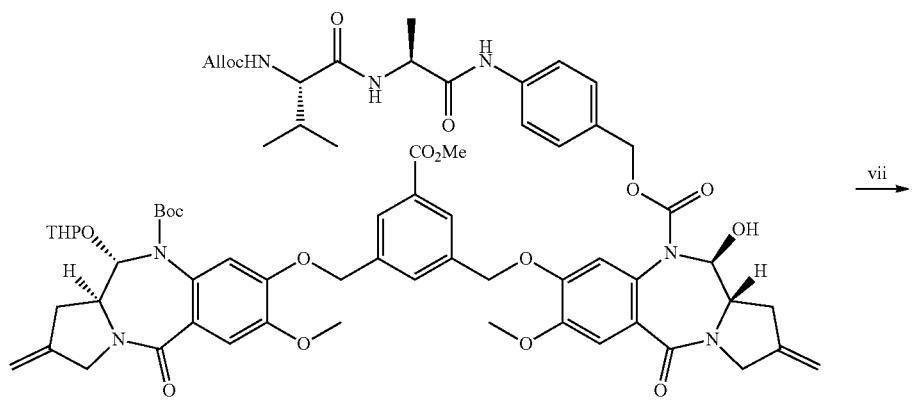

-continued

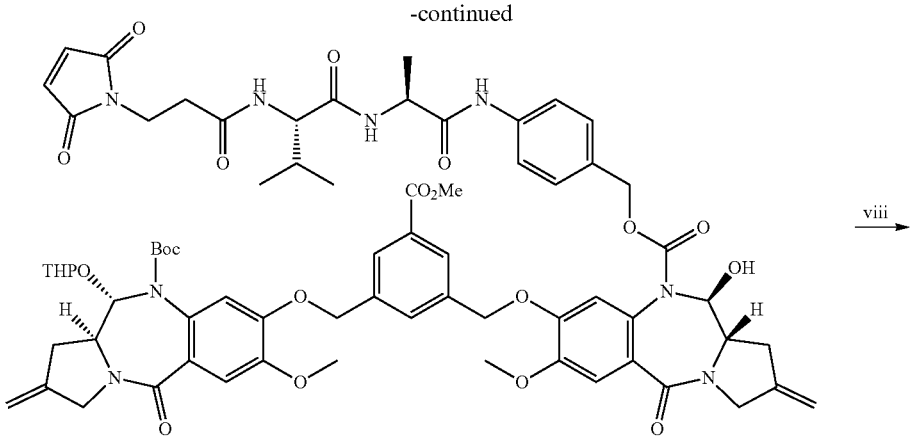

26

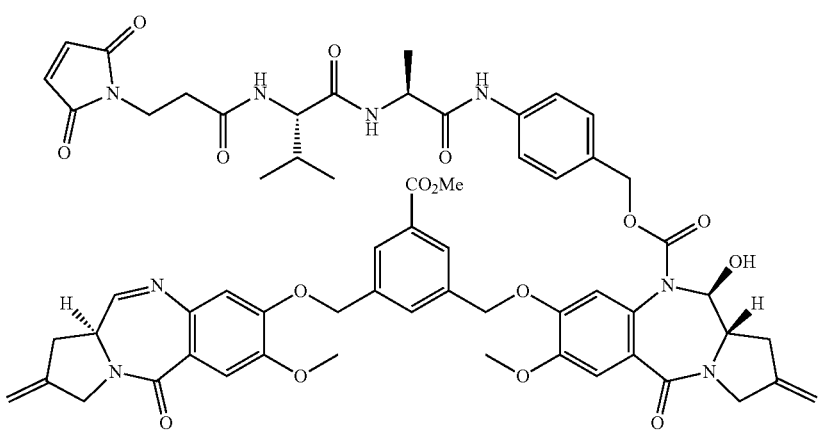

27

(i) Methyl 3,5-bis(((tert-butyldimethylsilyl)oxy)methyl)benzoate (20)

An oven-dried 3-necked round-bottomed flask was charged with a magnetic stirrer bar anhydrous toluene (15 mL) and the flask purged with Ar and the flask cooled to −10° C. BuLi (9.9 mL of a 2.5 M solution in hexanes, 24.86 mmol, 2.0 eq.), then slowly BuMgCl (6.2 mL of a 2.0 M solution in THF, 12.40 mmol, 1.0 eq.) were added and stirred for 30 min. 2 (14.7 g, 29.84 mmol, 2.4 eq.) in anhydrous toluene (30 mL) was added slowly and stirred for 2 h at −10° C. ClCO$_2$Me (2.9 mL, 37.29 mmol, 3.0 eq.) in anhydrous toluene (15 mL) was added slowly at −50° C. and stirred for 2 h, then poured into cold 10% citric acid. The aqueous phase was extracted with EtOAc, the organics combined, washed with NaHCO$_3$, dried over MgSO$_4$ and concentrated in vacuo. Isolera purification (0-20% EtOAc in hexane afforded the product as a pale-yellow oil (11.5 g, 91%). LCMS-A: 2.18 min (ES+) m/z 425 [M+H]$^+$ (ii) Methyl 3,5-bis(bromomethyl)benzoate (21)

A round-bottomed flask was charged with a magnetic stirrer, AcOH (15 mL), 20 (1.00 g, 2.354 mmol, 1.0 eq.) and HBr (33% in AcOH) (10 mL) and the mixture was stirred for 2 h at 50° C. The reaction mixture was cooled to rt, poured into ice-cold water, the resulting precipitate collected by filtration, dissolved in CH$_2$Cl$_2$, dried over MgSO$_4$ and concentrated in vacuo. Isolera (0-50% CH$_2$Cl$_2$ in hexane) afforded the desired product as an off-white solid (460 mg, 61%). LCMS-A: 1.59 min (ES+) No ionisation (iii) tert-Butyl (11S,11aS)-8-((3-(bromomethyl)-5-(methoxycarbonyl)benzyl)oxy)-7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (22)

A round-bottomed flask was charged with a magnetic stirrer, DMF (20 mL), 12 (256 mg, 0.5559 mmol, 1.0 eq.) 21 (716 mg, 2.224 mmol, 4.0 eq.) and K$_2$CO$_3$ (84.5 mg, 0.6115 mmol, 1.1 eq.). The mixture was stirred for 1 h 45 min, whereupon LCMS indicated the reaction was complete. DMF was removed in vacuo, the resulting residue dissolved in CH$_2$Cl$_2$ and washed with sat. NH$_4$Cl solution. The organic phase was collected, dried over MgSO$_4$ and purified by isolera (10-60% EtOAc in heptane) to afford the desired product as a white solid (234 mg, 60%). LCMS-A: 1.77 min (ES+) m/z 701 [M+H]$^+$, 723 [M+Na]$^+$ (iv) tert-Butyl (11S,11aS)-8-((3-((5-(((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)-4-methylenepyrrolidine-1-carbonyl)-2-methoxyphenoxy)methyl)-5-(methoxycarbonyl)benzyl)oxy)-7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (23)

A round-bottomed flask was charged with a magnetic stirrer, DMF (2 mL), 22 (234 mg, 0.3335 mmol, 1.0 eq.), 13 (292 mg, 0.3669 mmol, 1.1 eq.) and $K_2CO_3$ (51 mg, 0.3690 mmol, 1.1 eq.). The mixture was stirred for 4 h whereupon LCMS indicated the reaction was complete. DMF was removed in vacuo, the resulting residue dissolved in $CH_2Cl_2$ and washed with sat. $NH_4Cl$ solution. The organic phase was collected, dried over $MgSO_4$ and purified by isolera (0-3% MeOH in $CH_2Cl_2$) to afford the desired product as a white solid (450 mg, 95%). LCMS-A: 2.00 min (ES+) m/z 1416 [M+H]$^+$, 1438 [M+Na]$^+$ (v) tert-Butyl (11S,11aS)-8-((3-((5-(((((4-((S)-2-((S)-2-(((allyloxy)carbonyl)amino)-3-methylbutanamido)propanamido)benzyl)oxy)carbonyl)amino)-4-((S)-2-(hydroxymethyl)-4-methylenepyrrolidine-1-carbonyl)-2-methoxyphenoxy)methyl)-5-(methoxycarbonyl)benzyl)oxy)-7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (24)

A round-bottomed flask was charged with a magnetic stirrer, THF (18 mL), 23 (450 mg, 0.3176 mmol, 1.0 eq.), AcOH (36.3 µL, 0.6352 mmol, 2.0 eq.) and TBAF (953 µL of 1M solution in THF, 0.9530 mmol, 3.0 eq.). The mixture was stirred for 7 h at rt, then a few drops of TBAF were added and stirred at rt for a further 3 h, whereupon LCMS indicated reaction was complete. The reaction mixture was diluted with EtOAc and washed with $H_2O$, then brine, dried over $MgSO_4$ and concentrated in vacuo. Isolera (0-4% MeOH in $CH_2Cl_2$) afforded the desired product with $Bu_4N+$ salts as an inseparable mixture. The resulting material was used without further purification. LCMS-A: 1.73 min (ES+) m/z 1302 [M+H]$^+$, 1324 [M+Na]$^+$ (vi) 4-((S)-2-((S)-2-(((allyloxy)carbonyl)amino)-3-methylbutanamido)propanamido)benzyl (11S,11aS)-8-((3-(((((11S,11aS)-10-(tert-butoxycarbonyl)-7-methoxy-2-methylene-5-oxo-11-((tetrahydro-2H-pyran-2-yl)oxy)-2,3,5,10,11,11a-hexahydro-1H-benzo[e]pyrrolo[1,2-a][1,4]diazepin-8-yl)oxy)methyl)-5-(methoxycarbonyl)benzyl)oxy)-11-hydroxy-7-methoxy-2-methylene-5-oxo-2,3,11,11a-tetrahydro-1H-benzo[e]pyrrolo[1,2-a][1,4]diazepine-10(5H)-carboxylate (25)

A round-bottomed flask was charged with a magnetic stirrer, DMSO (3 mL), 24 (ca. 0.3176 mmol, 1.0 eq.) and IBX (45% wt.) (237 mg, 0.3811 mmol, 1.2 eq.). The mixture was stirred at rt for 16 h, then a knifepoint of IBX was added and was stirred for 35° C. for 24 h. The reaction mixture was diluted with $H_2O$ and extracted with $CHCl_3$. The organics were combined, dried over $MgSO_4$ and concentrated in vacuo. Isolera (0-4% MeOH in $CH_2Cl_2$) afforded the desired product as a white solid (333 mg, 81% (2 steps)). LCMS-A: 1.71 min (ES+) m/z 1300 [M+H]$^+$, 1323 [M+Na]$^+$ (vii) tert-butyl (11S,11aS)-8-((3-(((((11S,11aS)-10-(((4-((S)-2-((S)-2-(3-(2,5-dioxo-2,5-dihydro-1H-pyrrol-1-yl)propanamido)-3-methylbutanamido)propanamido)benzyl)oxy)carbonyl)-11-hydroxy-7-methoxy-2-methylene-5-oxo-2,3,5,10,11,11a-hexahydro-1H-benzo[e]pyrrolo[1,2-a][1,4]diazepin-8-yl)oxy)methyl)-5-(methoxycarbonyl)benzyl)oxy)-7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (26)

A round-bottomed flask was charged with a magnetic stirrer, $CH_2Cl_2$ (19 mL), 25 (333 mg, 0.2561 mmol, 1.0 eq.), pyrrolidine (42.1 µL, 0.5122 mmol, 2.0 eq.) and Pd(PPh$_3$)$_4$ (7.4 mg, 6.403 µmol, 0.025 eq.). The reaction mixture was stirred for 20 min, whereupon LCMS indicated the reaction was complete. The reaction mixture was thoroughly concentrated in vacuo overnight to remove pyrrolidine traces. The resulting residue was dissolved in $CH_2Cl_2$ (3.5 mL) and maleimide propionic acid NHS ester (82 mg, 0.3080 mmol, 1.2 eq.) and i-Pr$_2$NEt (53.5 µL, 0.3073 mmol, 1.2 eq.) were added and the mixture stirred for 2 h, whereupon LCMS indicated the reaction was complete. The reaction mixture was concentrated in vacuo and purified by isolera (0-4% MeOH in $CH_2Cl_2$) to afford the desired product as a white solid (150 mg, 43%). LCMS-A: 1.65 min (ES+) m/z 1368 [M+H]$^+$, 1389 [M+Na]$^+$ (viii) 4-((S)-2-((S)-2-(3-(2,5-dioxo-2,5-dihydro-1H-pyrrol-1-yl)propanamido)-3-methylbutanamido)propanamido)benzyl (11S,11aS)-11-hydroxy-7-methoxy-8-((3-(((((S)-7-methoxy-2-methylene-5-oxo-2,3,5,11a-tetrahydro-1H-benzo[e]pyrrolo[1,2-a][1,4]diazepin-8-yl)oxy)methyl)-5-(methoxycarbonyl)benzyl)oxy)-2-methylene-5-oxo-2,3,11,11a-tetrahydro-1H-benzo[e]pyrrolo[1,2-a][1,4]diazepine-10(5H)-carboxylate (27)

A round-bottomed flask was charged with a magnetic stirrer, 26 (150 mg, 0.1097 mmol, 1.0 eq.) and cooled to 0° C. 95% TFA in $H_2O$ was cooled to −20° C. and added to the reaction flask in one portion and the mixture stirred for 30 min, whereupon LCMS indicated the reaction was complete. The reaction mixture was poured into ice cold sat. NaHCO$_3$ solution and solid NaHCO$_3$ was added until the pH was approximately neutral. The aqueous mixture was extracted with 10% MeOH in $CH_2Cl_2$, the organics combined, dried over $MgSO_4$ and concentrated in vacuo. Purification by isolera (0-5% MeOH in $CH_2Cl_2$) afforded the desired product as a white solid (52.8 mg, 41% yield, 98.1% QC). LCMS-A: 7.95 min (ES+) m/z 1165 [M+H]$^+$.

Example 3: 4-((S)-2-((S)-2-(3-(2,5-dioxo-2,5-di-hydro-1H-pyrrol-1-yl)propanamido)-3-methylbutanamido)propanamido)benzyl(11S,11aS)-11-hydroxy-7-methoxy-8-((3-((((S)-7-methoxy-2-methyl-5-oxo-5,11a-dihydro-1H-benzo[e]pyrrolo[1,2-a][1,4]diazepin-8-yl)oxy)methyl)-5-(methoxycarbonyl)benzyl)oxy)-2-methyl-5-oxo-11,11a-dihydro-1H-benzo[e]pyrrolo[1,2-a][1,4]diazepine-10(5H)-carboxylate(33) and 3-((((11S,11aS)-10-(((4-((S)-2-((S)-2-(3-(2,5-dioxo-2,5-dihydro-1H-pyrrol-1-yl)propanamido)-3-methylbutanamido)propanamido)benzyl)oxy)carbonyl)-11-hydroxy-7-methoxy-2-methyl-5-oxo-5,10,11,11a-tetrahydro-1H-benzo[e]pyrrolo[1,2-a][1,4]diazepin-8-yl)oxy)methyl)-5-((((S)-7-methoxy-2-methyl-5-oxo-5,11a-dihydro-1H-benzo[e]pyrrolo[1,2-a][1,4]diazepin-8-yl)oxy)methyl)benzoic acid (34)

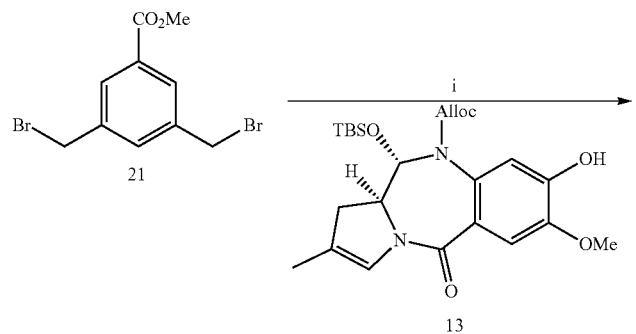

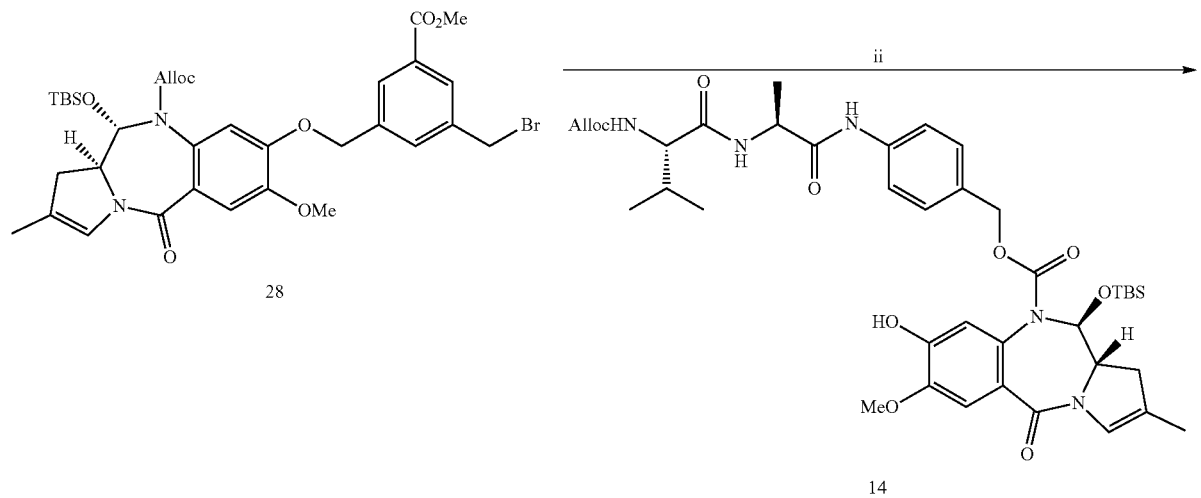

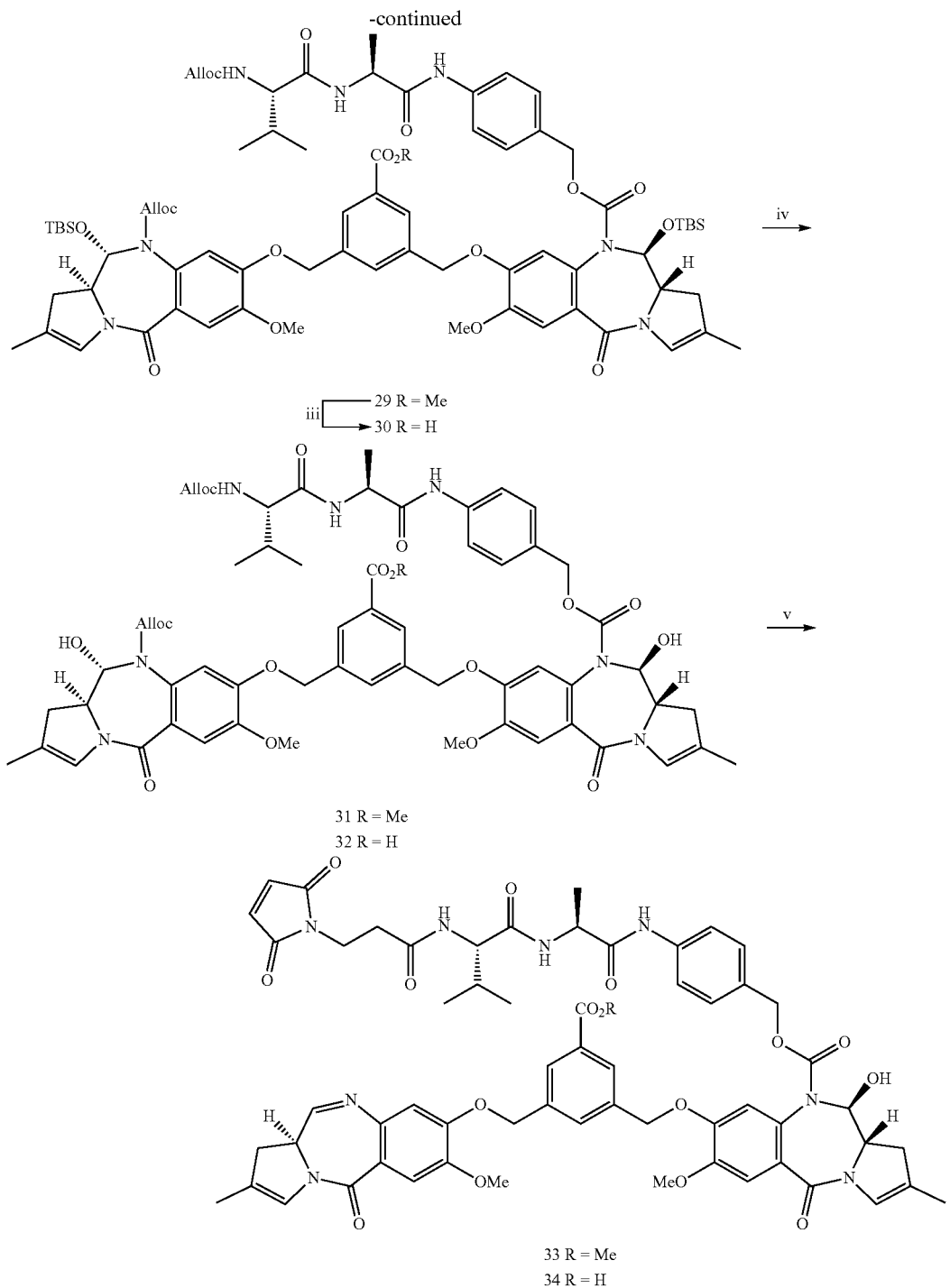

(i) Allyl (11S,11aS)-8-((3-(bromomethyl)-5-(methoxycarbonyl)benzyl)oxy)-11-((tert-butyldimethylsilyl)oxy)-7-methoxy-2-methyl-5-oxo-11,11a-dihydro-1H-benzo[e]pyrrolo[1,2-a][1,4]diazepine-10(5H)-carboxylate (28)

A round-bottomed flask was charged with a magnetic stirrer, DMF (15 mL), 13 (184 mg, 0.3883 mmol, 1.0 eq.) 21 (500 mg, 1.553 mmol, 4.0 eq), $K_2CO_3$ (59 mg, 0.4271 mmol, 1.1 eq.) and TBAI (3.6 mg, 9.708 µmol, 0.025 eq.) and the mixture stirred at 65° C. for 16 h. DMF was removed in vacuo, the resulting residue dissolved in EtOAc and washed with 1N HCl solution. The organic phase was dried over $MgSO_4$ and concentrated in vacuo. Flash column chromatography (0-30% EtOAc in hexane) afforded the desired product (183 mg, 69%). LCMS-A: 2.06 min (ES+) m/z 714 [M+H]$^+$, 737 [M+Na]$^+$ (ii) Allyl (11S,11aS)-8-((3-((((11S,11aS)-10-(((4-((S)-2-((S)-2-(((allyloxy)carbonyl)amino)-3-methylbutanamido)propanamido)benzyl)oxy)carbonyl)-11-((tert-butyldimethylsilyl)oxy)-7-methoxy-2-methyl-5-oxo-5,10,11,11a-tetrahydro-1H-benzo[e]pyrrolo[1,2-a][1,4]diazepin-8-yl)oxy)methyl)-5-(methoxycarbonyl)benzyl)oxy)-11-((tert-butyldimethylsilyl)oxy)-7-methoxy-2-methyl-5-oxo-11,11a-dihydro-1H-benzo[e]pyrrolo[1,2-a][1,4]diazepine-10(5H)-carboxylate (29)

A round-bottomed flask was charged with a magnetic stirrer, DMF (1 mL) 28 (128 mg, 0.1788 mmol, 1.0 eq.), 14 (353 mg, 0.4446 mmol, 2.5 eq.), $K_2CO_3$ (27 mg, 0.1967 mmol, 1.1 eq.) and TBAI (1.7 mg, 4.470 µmol, 0.025 eq.) and the mixture was stirred for 20 h at 65° C. DMF was removed in vacuo, the resulting residue dissolved in EtOAc and washed with $H_2O$, then brine. The organic phase was dried over $MgSO_4$ and concentrated in vacuo. Flash column chromatography (0-3% MeOH in $CH_2Cl_2$) afforded the desired product (117 mg, 46%). LCMSA: 2.20 min (ES+) m/z 1428 [M+H]$^+$, 1450 [M+Na]$^+$ (iii) 3-((((11S,11aS)-10-((allyloxy)carbonyl)-11-((tert-butyldimethylsilyl)oxy)-7-methoxy-2-methyl-5-oxo-5,10,11,11a-tetrahydro-1H-benzo[e]pyrrolo[1,2-a][1,4]diazepin-8-yl)oxy)methyl)-5-((((11S,11aS)-10-(((4-((S)-2-((S)-2-(((allyloxy)carbonyl)amino)-3-methylbutanamido)propanamido)benzyl)oxy)carbonyl)-11-((tert-butyldimethylsilyl)oxy)-7-methoxy-2-methyl-5-oxo-5,10,11,11a-tetrahydro-1H-benzo[e]pyrrolo[1,2-a][1,4]diazepin-8-yl)oxy)methyl)benzoic acid (30)

A microwave vial was charged with a magnetic stirrer, $CHCl_3$ (1 mL) 29 (100 mg, 0.06999 mmol, 1.0 eq.) $SnMe_3OH$ (127 mg, 0.6999 mmol, 10 eq.) and irradiated at 100° C. for 10 h.
The reaction mixture was filtered through Celite® and the filtrate concentrated in vacuo. The resulting residue was dissolved in THF (1 mL) and $H_2O$ (1 mL), $K_2CO_3$ (20 mg, 0.1400 mmol, 2.0 eq.) and allyl chloroformate (14 µL, 0.1400 mmol, 2.0 eq.) were added. The mixture was stirred for 2 h, whereupon LCMS indicated the reaction was complete. The reaction mixture was diluted (EtOAc), washed with 1N HCl solution, dried over $MgSO_4$ and concentrated in vacuo. Flash column chromatography (70-100% EtOAc in hexane, 0.1% AcOH) afforded the desired product (67 mg, 68%). LCMS-A: 2.13 min (ES+) m/z 1414 [M+H]$^+$, 1436 [M+Na]$^+$ (iv-a) Allyl (11S,11aS)-8-((3-((((11S,11aS)-10-(((4-((S)-2-((S)-2-(((allyloxy)carbonyl)amino)-3-methylbutanamido)propanamido)benzyl)oxy)carbonyl)-11-hydroxy-7-methoxy-2-methyl-5-oxo-5,10,11,11a-tetrahydro-1H-benzo[e]pyrrolo[1,2-a][1,4]diazepin-8-yl)oxy)methyl)-5-(methoxycarbonyl)benzyl)oxy)-11-hydroxy-7-methoxy-2-methyl-5-oxo-11,11a-dihydro-1H-benzo[e]pyrrolo[1,2-a][1,4]diazepine-10(5H)-carboxylate (31)

A round-bottomed flask was charged with a magnetic stirrer, THF (10 mL), 29 (200 mg, 0.1400 mmol, 1.0 eq.), AcOH (32 µL, 0.5600 mmol, 4.0 eq.) and TBAF (560 µL of a 1M solution, 0.5600 mmol, 4.0 eq.) were added and the reaction was stirred for 16 h with gradual warming to rt, whereupon LCMS indicated the reaction was complete. The reaction mixture was diluted with $CH_2Cl_2$, washed with sat. $NH_4Cl$, dried over $MgSO_4$ and concentrated in vacuo. Flash column chromatography (3% MeOH in $CHCl_3$) afforded the desired product (140 mg, 83%). LCMS-A: 1.62 min (ES+) m/z 1200 [M+H]$^+$, 1222 [M+Na]$^+$ (iv-b) 3-((((11S,11aS)-10-((allyloxy)carbonyl)-11-hydroxy-7-methoxy-2-methyl-5-oxo-5,10,11,11a-tetrahydro-1H-benzo[e]pyrrolo[1,2-a][1,4]diazepin-8-yl)oxy)methyl)-5-((((11S,11aS)-10-(((4-((S)-2-((S)-2-(((allyloxy)carbonyl)amino)-3-methylbutanamido)propanamido)benzyl)oxy)carbonyl)-11-hydroxy-7-methoxy-2-methyl-5-oxo-5,10,11,11a-tetrahydro-1H-benzo[e]pyrrolo[1,2-a][1,4]diazepin-8-yl)oxy)methyl)benzoic acid (32)

A round-bottomed flask was charged with a magnetic stirrer, THF (10 mL), 30 (135 mg, 0.09542 mmol, 1.0 eq.), cooled to 0° C. and stirred for 10 minutes. AcOH (21.9 µL, 0.3817 mmol, 4.0 eq.) and TBAF (429 µL of a 1M solution, 0.4290 mmol, 4.0 eq.) were added and the reaction was stirred for 16 h with gradual warming to rt, whereupon LCMS indicated the reaction was complete. The reaction mixture was diluted with $CH_2Cl_2$, washed with sat. $NH_4Cl$, dried over $MgSO_4$ and concentrated in vacuo. Flash column chromatography (0-5% MeOH in $CH_2Cl_2$) afforded the product contaminated with $Bu_4N$ salts. The resulting product was used without further purification and the yield was assumed to be 100%. LCMS-A: 1.63 min (ES+) m/z 1186 [M+H]$^+$, 1208 [M+Na]$^+$ (v-a) 4-((S)-2-((S)-2-(3-(2,5-dioxo-2,5-dihydro-1H-pyrrol-1-yl)propanamido)-3-methylbutanamido)propanamido)benzyl (11S,11aS)-11-hydroxy-7-methoxy-8-((3-((((S)-7-methoxy-2-methyl-5-oxo-5,11a-dihydro-1H-benzo[e]pyrrolo[1,2-a][1,4]diazepin-8-yl)oxy)methyl)-5-(methoxycarbonyl)benzyl)oxy)-2-methyl-5-oxo-11,11a-dihydro-1H-benzo[e]pyrrolo[1,2-a][1,4]diazepine-10(5H)-carboxylate (33)

A round-bottomed flask was charged with a magnetic stirrer, $CH_2Cl_2$ (10 mL), 31 (120 mg, 99.98 µmol, 1.0 eq.), pyrrolidine (21 µL, 250 µmol, 2.5 eq.) and $Pd(PPh)_4$ (5.8 mg, 4.999 µmol, 0.050 eq.). The mixture was stirred under Ar for 30 min, whereupon LCMS indicated the reaction was complete. The reaction mixture was thoroughly concentrated in vacuo overnight to remove pyrrolidine traces. The resulting residue was dissolved in $CH_2Cl_2$ (3.5 mL) and maleimide propionic acid (14.9 mg, 88.31 µmol, 1.0 eq.) and EDCl.HCl (13.7 mg, 88.31 µmol, 1.0 eq.) were added and the mixture stirred for 2 h, whereupon LCMS indicated the reaction was complete. The reaction mixture was concentrated in vacuo and purified by flash column chromatography (3-5% MeOH in $CH_2Cl_2$) then preparative HPLC (15-90% A in B) to afford the desired product as a yellow solid (10 mg, 9.7% yield). A=0.05% formic acid in acetonitrile. B=0.05% formic acid in water. LCMS-B: 6.78 min (ES+) m/z 1165 [M+H]$^+$, 1187 [M+Na]$^+$ (v-b) 3-((((11S,11aS)-10-(((4-((S)-2-((S)-2-(3-(2,5-dioxo-2,5-dihydro-1H-pyrrol-1-yl)propanamido)-3-methylbutanamido)propanamido)benzyl)oxy)carbonyl)-11-hydroxy-7-methoxy-2-methyl-5-oxo-5,10,11,11a-tetrahydro-1H-benzo[e]pyrrolo[1,2-a][1,4]diazepin-8-yl)oxy)methyl)-5-((((S)-7-methoxy-2-methyl-5-oxo-5,11a-dihydro-1H-benzo[e]pyrrolo[1,2-a][1,4]diazepin-8-yl)oxy)methyl)benzoic acid (34)

A round-bottomed flask was charged with a magnetic stirrer, $CH_2Cl_2$ (8 mL) 32 (crude from previous step ca.

95.42 μmol, 1.0 eq.) pyrrolidine (19.6 μL, 238.6 μmol, 2.5 eq.), Pd(PPh)$_4$ (5.5 mg, 4.771 μmol, 0.050 eq.) and the mixture stirred for 30 min under Ar, whereupon LCMS indicated the reaction was complete. The reaction mixture was diluted with CHCl$_3$, washed with sat. NH$_4$Cl, the organics combined, dried over MgSO$_4$ and concentrated in vacuo. The resulting residue was dissolved in THE (7 mL) and NaHCO$_3$ (1 mL of a 0.1M solution) and maleimide propionic acid NHS ester (28 mg, 105 μmol, 1.1 eq.) were added. The mixture was stirred for 20 h, diluted with CHCl$_3$, washed with sat. NH$_4$C solution and concentrated in vacuo. Preparative HPLC (15-70% A in B) afforded the desired product as a yellow solid (6.4 mg, 5.8% yield, 84.6% QC). A=0.05% formic acid in acetonitrile. B=0.05% formic acid in water. LCMS-B: 6.52 min (ES+) m/z 1151 [M+H]$^+$.

Example 4: 4-((S)-2-((S)-2-(3-(2,5-dioxo-2,5-dihydro-1H-pyrrol-1-yl)propanamido)-3-methylbutanamido)propanamido)benzyl(11S,11aS)-11-hydroxy-7-methoxy-8-((6-((((S)-7-methoxy-2-methylene-5-oxo-2,3,5,11a-tetrahydro-1H-benzo[e]pyrrolo[1,2-a][1,4]diazepin-8-yl)oxy)methyl)-4-(methoxycarbonyl)pyridin-2-yl)methoxy)-2-methylene-5-oxo-2,3,11,11a-tetrahydro-1H-benzo[e]pyrrolo[1,2-a][1,4]diazepine-10(5H)-carboxylate(44) and 2-((((11S,11aS)-10-(((4-((S)-2-((S)-2-(3-(2,5-dioxo-2,5-dihydro-1H-pyrrol-1-yl)propanamido)-3-methylbutanamido)propanamido)benzyl)oxy)carbonyl)-11-hydroxy-7-methoxy-2-methylene-5-oxo-2,3,5,10,11,11a-hexahydro-1H-benzo[e]pyrrolo[1,2-a][1,4]diazepin-8-yl)oxy)methyl)-6-((((S)-7-methoxy-2-methylene-5-oxo-2,3,5,11a-tetrahydro-1H-benzo[e]pyrrolo[1,2-a][1,4]diazepin-8-yl)oxy)methyl)isonicotinic acid (45)

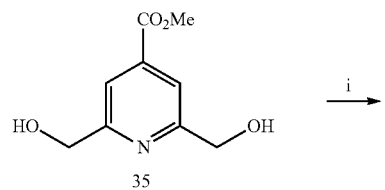

35

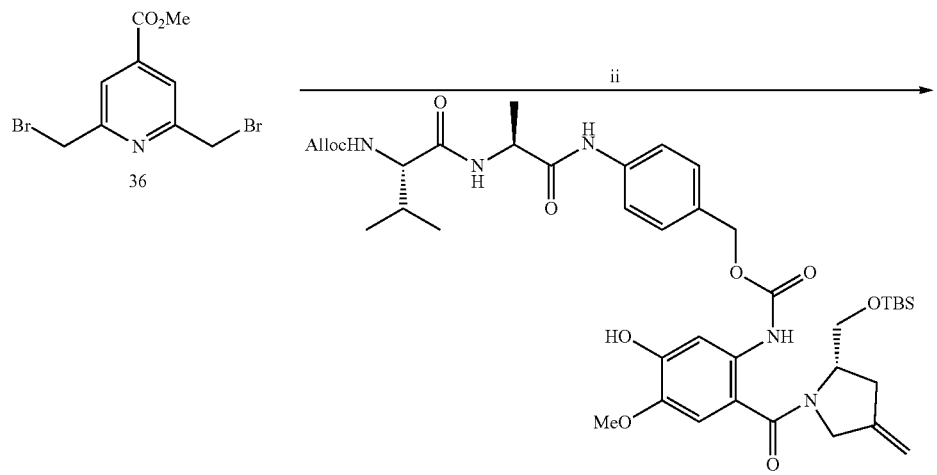

36

13

-continued
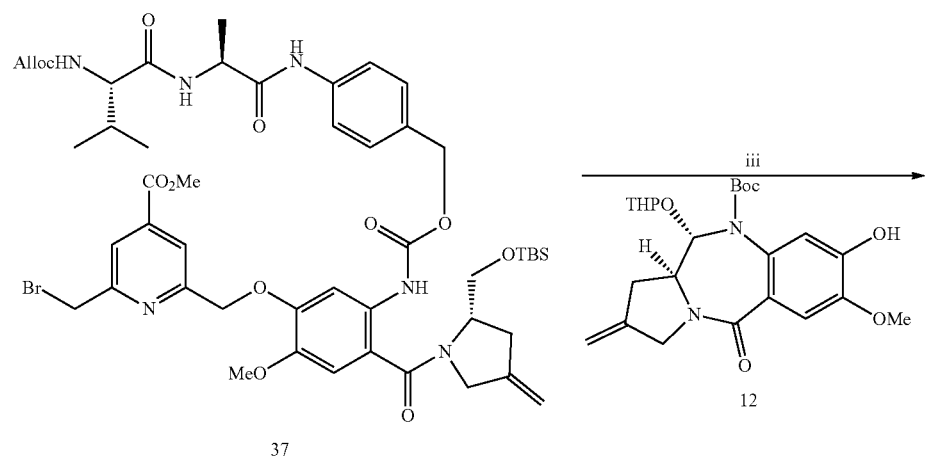
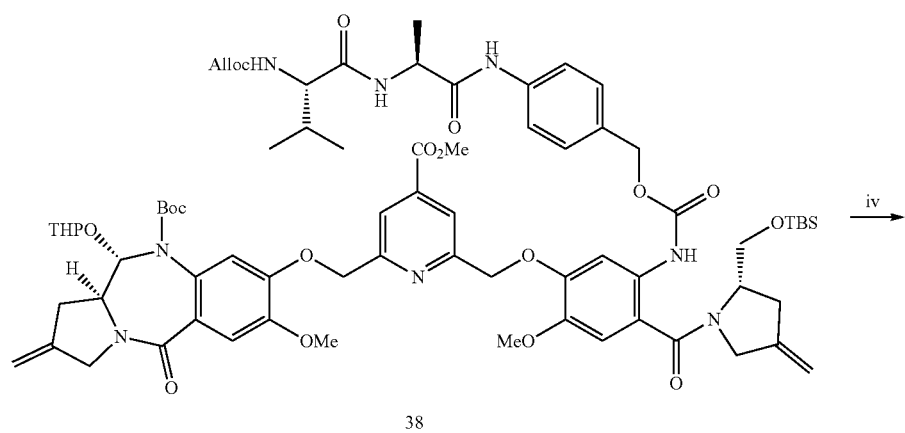
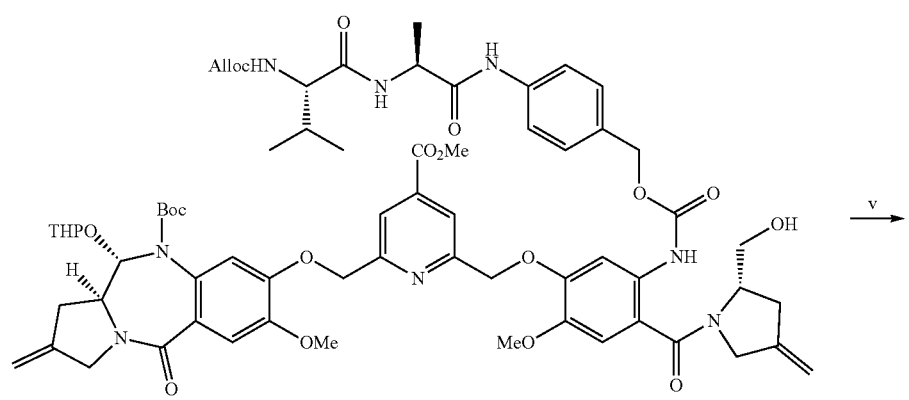

-continued
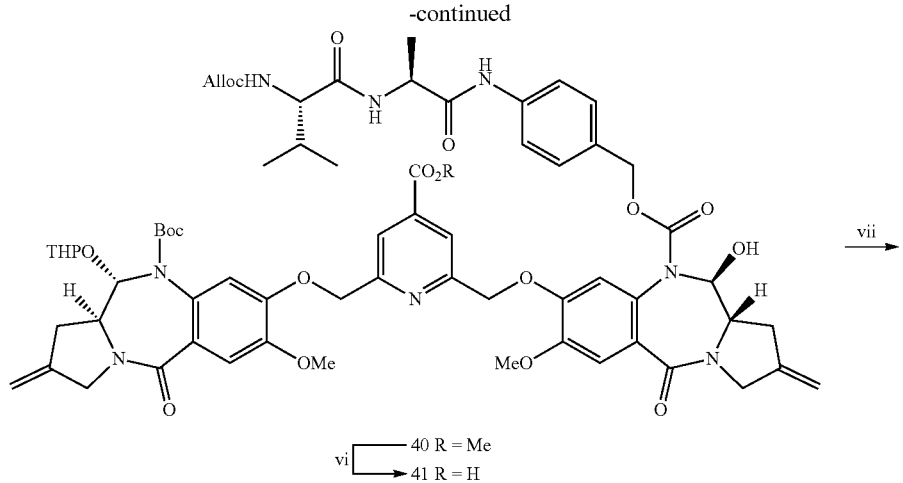
40 R = Me
vi ↓
41 R = H
vii →
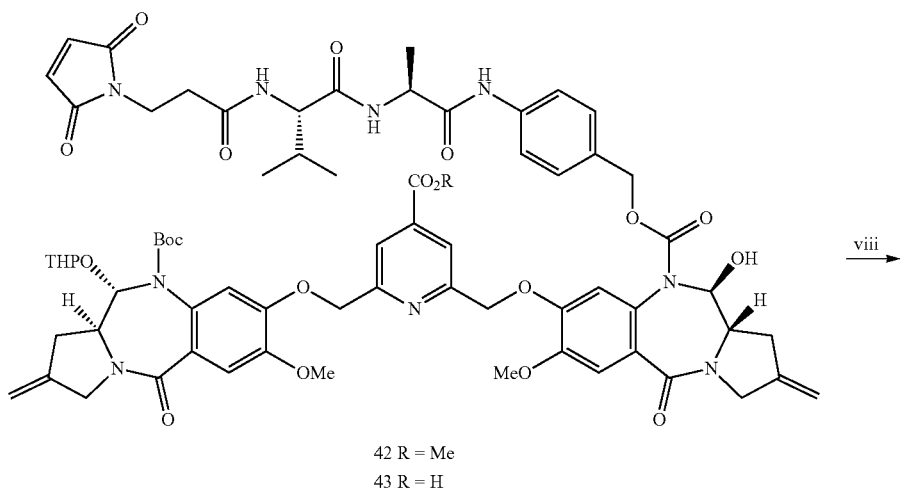
42 R = Me
43 R = H
viii →
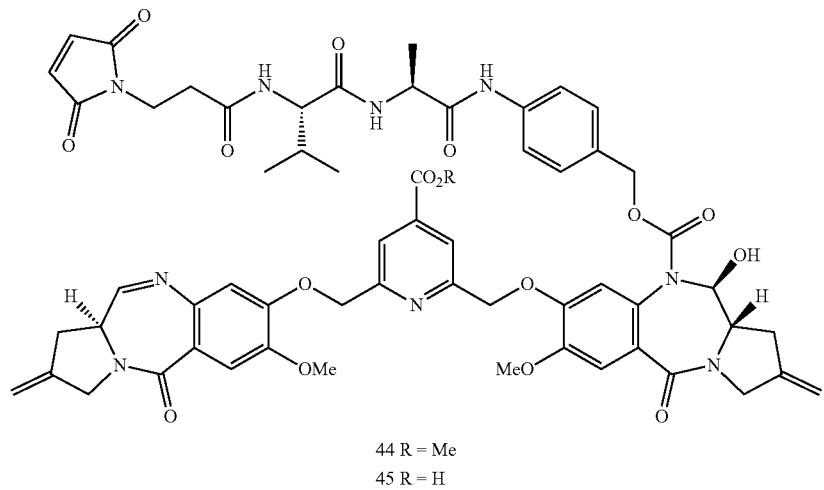
44 R = Me
45 R = H (i) Methyl 2,6-bis(bromomethyl)isonicotinate (36)

A round-bottomed flask was charged with a magnetic stirrer bar, acetonitrile (46 mL), 35 (924 mg, 4.686 mmol, 1.0 eq.) and the mixture cooled to 0° C. PPh$_3$ (3.96 g, 14.06 mmol, 3.0 eq.) then slowly CBr$_4$ (4.66 g, 14.06 mmol, 3.0 eq.) were added and the mixture stirred or 30 min. The reaction mixture was concentrated in vacuo and purified by isolera (0-100% EtOAc in hexane) to afford the desired product (1.01 g, 67%). LCMS-A: 1.46 min (ES+) m/z 321 [M+H]$^+$ (ii) Methyl 2-((5-((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)-4-methylenepyrrolidine-1-carbonyl)-2-methoxyphenoxy)methyl)-6-(bromomethyl)isonicotinate (37)

A round-bottomed flask was charged with a magnetic stirrer bar, DMF (10 mL), 13 (814 mg, 1.022 mmol, 1.0 eq.), 36 (1.32 g, 4.087 mmol, 4.0 eq.) and K$_2$CO$_3$ (155 mg, 1.124 mmol, 1.1 eq.) and stirred for 40 min at 35° C., whereupon LCMS indicated the reaction was complete. DMF was removed in vacuo and the resulting residue was dissolved in EtOAc, washed with H$_2$O, brine and dried over MgSO$_4$. Isolera (50-100% EtOAc in hexane) afforded the desired product as a pale yellow foam (750 mg, 71%). LCMS-A: 1.90 min (ES+) m/z 1037 [M+H]$^+$ (iii) tert-Butyl (11S,11aS)-8-((6-((5-((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)-4-methylenepyrrolidine-1-carbonyl)-2-methoxyphenoxy)methyl)-4-(methoxycarbonyl)pyridin-2-yl)methoxy)-7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (38)

A round-bottomed flask was charged with a magnetic stirrer bar, DMF (6 mL), 37 (750 mg, 0.7225 mmol, 1.0 eq.), 12 (333 mg, 0.7225 mmol, 1.0 eq.) and K$_2$CO$_3$ (100 mg, 0.7235 mmol, 1.0 eq.) and stirred for 80 min at 35° C., whereupon LCMS indicated the reaction was complete. DMF was removed in vacuo and the resulting residue was dissolved in EtOAc, washed with H$_2$O and dried over MgSO$_4$. In vacuo concentration afforded the desired product as a pale-yellow foam (979 mg, 96%). LCMS-A: 1.99 min (ES+) m/z 1417 [M+H]$^+$ (iv) tert-Butyl (11S,11aS)-8-((6-((5-((((4-((S)-2-((S)-2-(((allyloxy)carbonyl)amino)-3-methylbutanamido)propanamido)benzyl)oxy)carbonyl)amino)-4-((S)-2-(hydroxymethyl)-4-methylenepyrrolidine-1-carbonyl)-2-methoxyphenoxy)methyl)-4-(methoxycarbonyl)pyridin-2-yl)methoxy)-7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (39)

A round-bottomed flask was charged with a magnetic stirrer bar, THF (9 mL) 38 (879 mg, 0.6200 mmol, 1.0 eq.) TBAF (1.24 mL of a 1M solution in THF, 1.240 mmol, 2.0 eq.) and the mixture stirred for 80 min whereupon LCMS indicated the reaction was complete. The reaction mixture was concentrated in vacuo and purified by isolera (0-4% MeOH in CH$_2$Cl$_2$) to afford the desired product (746 mg, 83%). LCMS-A: 1.71 min (ES+) m/z 1303 [M+H]$^+$, 1325 [M+Na]$^+$ (v) 4-((S)-2-((S)-2-(((allyloxy)carbonyl)amino)-3-methylbutanamido)propanamido)benzyl (11S,11aS)-8-((6-((((11S,11aS)-10-(tert-butoxycarbonyl)-7-methoxy-2-methylene-5-oxo-11-((tetrahydro-2H-pyran-2-yl)oxy)-2,3,5,10,11,11a-hexahydro-1H-benzo[e]pyrrolo[1,2-a][1,4]diazepin-8-yl)oxy)methyl)-4-(methoxycarbonyl)pyridin-2-yl)methoxy)-11-hydroxy-7-methoxy-2-methylene-5-oxo-2,3,11,11a-tetrahydro-1H-benzo[e]pyrrolo[1,2-a][1,4]diazepine-10(5H)-carboxylate (40)

A round-bottomed flask was charged with a magnetic stirrer bar, acetonitrile (13 mL), 39 (64 mg, 0.4956 mmol, 1.0 eq.), Stahl aerobic oxidation TEMPO solution (248 μL of a 0.2M solution in acetonitrile, 0.04960 mmol, 0.10 eq.), Cu(MeCN)$_4$OTf (18.7 mg, 0.04956 mmol, 0.10 eq.) and the mixture stirred under a balloon of air for 3 d. The reaction mixture was concentrated in vacuo and purified by isolera (0-4% MeOH in CH$_2$Cl$_2$) to afford the desired product as a white solid (523 mg, 81%). LCMS-A: 1.69 min (ES+) m/z 1301 [M+H]$^+$, 1323 [M+Na]$^+$ (vi) 2-((((11S,11aS)-10-(((4-((S)-2-((S)-2-(((allyloxy)carbonyl)amino)-3-methylbutanamido)propanamido)benzyl)oxy)carbonyl)-11-hydroxy-7-methoxy-2-methylene-5-oxo-2,3,5,10,11,11a-hexahydro-1H-benzo[e]pyrrolo[1,2-a][1,4]diazepin-8-yl)oxy)methyl)-6-((((11S,11aS)-10-(tert-butoxycarbonyl)-7-methoxy-2-methylene-5-oxo-11-((tetrahydro-2H-pyran-2-yl)oxy)-2,3,5,10,11,11a-hexahydro-1H-benzo[e]pyrrolo[1,2-a][1,4]diazepin-8-yl)oxy)methyl)isonicotinic acid (41)

A microwave vial was charged with a magnetic stirrer bar, (CH$_2$Cl)$_2$ (0.5 mL) 40 (100 mg, 64.62 μmol, 1.0 eq.), SnMe$_3$OH (35.1 mg, 193.9 μmol, 3.0 eq.) and the vial sealed. The mixture was heated to 80° C. for 4 h, cooled to rt, poured into H$_2$O, extracted with 10% MeOH in CH$_2$Cl$_2$, the organics combined, dried over Na$_2$SO$_4$ and concentrated in vacuo. Isolera (5-15% MeOH in CH$_2$Cl$_2$) afforded the desired product (53 mg, 64%). LCMS-A: min (ES+) m/z 1287 [M+H]$^+$, 1309 [M+Na]$^+$.

(vii-a) tert-Butyl (11S,11aS)-8-((6-((((11S,11aS)-10-(((4-((S)-2-((S)-2-(3-(2,5-dioxo-2,5-dihydro-1H-pyrrol-1-yl)propanamido)-3-methylbutanamido)propanamido)benzyl)oxy)carbonyl)-11-hydroxy-7-methoxy-2-methylene-5-oxo-2,3,5,10,11,11a-hexahydro-1H-benzo[e]pyrrolo[1,2-a][1,4]diazepin-8-yl)oxy)methyl)-4-(methoxycarbonyl)pyridin-2-yl)methoxy)-7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (42)

A round-bottomed flask was charged with a magnetic stirrer bar, 40 (100 mg, 76.84 μmol, 1.0 eq.) CH$_2$Cl$_2$ (6 mL), pyrrolidine (12.6 μL, 153.7 μmol, 2.0 eq.) and Pd(PPh$_3$)$_4$ (2.2 mg, 1.921 μmol, 0.025 eq.). The mixture was stirred under Ar for 25 min, whereupon LCMS indicated the reaction was complete. The reaction mixture was thoroughly concentrated in vacuo overnight to remove pyrrolidine traces. The resulting residue was dissolved in CH$_2$Cl$_2$ (1 mL) and maleimide propionic acid NHS ester (24.5 mg, 92.21 μmol, 1.2 eq.) and i-Pr$_2$NEt (16.1 μL, 92.21 μmol, 1.2 eq.) were added and the mixture stirred for 3.5 h, whereupon LCMS indicated the reaction was complete. The reaction mixture was concentrated in vacuo and purified by isolera (0-4% MeOH in CH$_2$Cl$_2$) to afford the desired product as a white solid (89.5 mg, 85%). LCMS-A: 1.62 min (ES+) m/z 1368 [M+H]$^+$, 1390 [M+Na]$^+$ (vii-b) 2-(((((11S,11aS)-10-(tert-butoxycarbonyl)-7-methoxy-2-methylene-5-oxo-11-((tetrahydro-2H-pyran-2-yl)oxy)-2,3,5,10,11,11a-hexahydro-1H-benzo[e]pyrrolo[1,2-a][1,4]diazepin-8-yl)oxy) methyl)-6-((((11S,11 aS)-10-(((4-((S)-2-((S)-2-(3-(2,5-dioxo-2,5-dihydro-1H-pyrrol-1-yl)propanamido)-3-methylbutanamido)propanamido)benzyl)oxy) carbonyl)-11-hydroxy-7-methoxy-2-methylene-5-oxo-2,3,5,10,11,11a-hexahydro-1H-benzo[e]pyrrolo[1,2-a][1,4]diazepin-8-yl)oxy)methyl)isonicotinic acid (43)

A round-bottomed flask was charged with a magnetic stirrer bar, CH$_2$Cl$_2$ (3 mL), 41 (53 mg, 41.17 μmol, 1.0 eq.), pyrrolidine (10.1 μmol, 122.8 mmol, 3.0 eq.) Pd(PPh$_3$)$_4$ (1.2 mg, 1.024 μmol, 0.025 eq.) and the mixture stirred under Ar for 30 min whereupon LCMS indicated the reaction was complete. The reaction mixture was diluted with CH$_2$Cl$_2$, washed with NH$_4$Cl, dried over Na$_2$SO$_4$ and concentrated in vacuo. The reaction mixture was thoroughly concentrated in vacuo overnight to remove pyrrolidine traces. The resulting residue was dissolved in THF (3 mL) and maleimide propionic acid NHS ester (13.1 mg, 49.13 μmol, 1.2 eq.) and NaHCO$_3$ (0.43 mL of a 100 mM solution) were added and the mixture stirred for 5 h, whereupon LCMS indicated the reaction was complete. The reaction mixture was diluted with EtOAc, washed with NH$_4$Cl, dried over MgSO$_4$ and concentrated in vacuo. Isolera (2-10% MeOH in CH$_2$Cl$_2$) afforded the desired product (39.9 mg, 72% yield). LCMS-A: 1.58 min (ES+) m/z 1354 [M+H]$^+$, 1376 [M+Na]$^+$ (viii-a) 4-((S)-2-((S)-2-(3-(2,5-dioxo-2,5-dihydro-1H-pyrrol-1-yl)propanamido)-3-methylbutanamido) propanamido)benzyl (11S,11aS)-11-hydroxy-7-methoxy-8-((6-((((S)-7-methoxy-2-methylene-5-oxo-2,3,5,11a-tetrahydro-1H-benzo[e]pyrrolo[1,2-a][1,4]diazepin-8-yl)oxy)methyl)-4-(methoxycarbonyl)pyridin-2-yl)methoxy)-2-methylene-5-oxo-2,3,11,11a-tetrahydro-1H-benzo[e]pyrrolo[1,2-a][1,4]diazepine-10(5H)-carboxylate (44)

A round-bottomed flask was charged with a magnetic stirrer bar, 42 (90 mg, 65.77 μmol, 1.0 eq.) and cooled to 0° C. 95% TFA in H$_2$O (3.5 mL) was cooled to −20° C. and added in one portion. The reaction mixture was stirred for 30 min, whereupon LCMS indicated the reaction was complete. The reaction mixture was poured into H$_2$O (10 mL), the pH adjusted to ca. 5 with NaHCO$_3$ and the aqueous mixture extracted with 10% MeOH in CH$_2$Cl$_2$, the organics dried over Na$_2$SO$_4$ and concentrated in vacuo. Isolera purification (0-8% MeOH in CH$_2$Cl$_2$) then preparative HPLC (15-70% A in B) afforded the desired product as a white solid (7 mg, 9.2% yield, 98.4% QC). A=0.05% formic acid in acetonitrile. B=0.05% formic acid in water. LCMS-B: 7.61 min (ES+) m/z 11.66 [M+H]$^+$ (viii-b) 2-(((((11S,11aS)-10-(((4-((S)-2-((S)-2-(3-(2,5-dioxo-2,5-dihydro-1H-pyrrol-1-yl)propanamido)-3-methylbutanamido)propanamido)benzyl)oxy)carbonyl)-11-hydroxy-7-methoxy-2-methylene-5-oxo-2,3,5,10,11,11a-hexahydro-1H-benzo[e]pyrrolo[1,2-a][1,4]diazepin-8-yl)oxy)methyl)-6-((((S)-7-methoxy-2-methylene-5-oxo-2,3,5,11a-tetrahydro-1H-benzo[e]pyrrolo[1,2-a][1,4]diazepin-8-yl)oxy)methyl) isonicotinic acid (45)

A round-bottomed flask was charged with a magnetic stirrer bar, 43 (37 mg, 27.32 μmol, 1.0 eq.) and cooled to 0° C. 95% TFA in H$_2$O (2 mL) was cooled to −20° C. and added in one portion. The reaction mixture was stirred for 30 min, whereupon LCMS indicated the reaction was complete. The reaction mixture was poured into H$_2$O (10 mL) and pH adjusted to ca. 5 with NaHCO$_3$. The solution was loaded onto an SPE cartridge (SCX-2, 10 g), washed with H$_2$O (2×10 mL) then blown dry with air. The organics were eluted from the column with MeOH and concentrated in vacuo. Preparative HPLC (15-70% A in B) afforded the desired product as an off-white solid (5 mg, 16% yield, 92.5% QC). A=0.05% formic acid in acetonitrile. B=0.05% formic acid in water. LCMS-B: 6.93 min (ES+) m/z 1152.

Example 5—Conjugations

Antibody-Drug Conjugate with Compound 19, ConjA

A 50 mM solution of DL-dithiothreitol (DTT) in phosphate-buffered saline pH 7.4 (PBS) was added (40 molar equivalent/antibody, 12 micromoles, 240 μL) to a 7.5 mL solution of antibody Trastuzumab (45 mg, 300 nanomoles) in reduction buffer containing PBS and 1 mM ethylenediaminetetraacetic acid (EDTA) and a final antibody concentration of 4.0 mg/mL.

The reduction mixture was allowed to react at room temperature for 17 hours (or until full reduction is observed by UHPLC) in an orbital shaker with gentle (60 rpm) shaking. The reduced antibody was buffer exchanged, via spin filter centrifugation, into a reoxidation buffer containing PBS and 1 mM EDTA to remove all the excess reducing agent. A 50 mM solution of dehydroascorbic acid (DHAA, 15 molar equivalent/antibody, 4.5 micromoles, 90 μL) in DMSO was added and the reoxidation mixture was allowed to react for 2-3 hours at room temperature with gentle (50 rpm) shaking at an antibody concentration of 1.5 mg/mL (or more DHAA added and reaction left for longer until full reoxidation of the cysteine thiols to reform the inter-chain cysteine disulfides is observed by UHPLC). The reoxidation mixture was then sterile-filtered and diluted in a conjugation buffer containing PBS and 1 mM EDTA for a final antibody concentration of 2.0 mg/mL. Compound 19 was added as a DMSO solution (10 molar equivalent/antibody, 0.9 micromole, in 1.0 mL DMSO) to 10.0 mL of this reoxidised antibody solution (13.5 mg, 90 nanomoles) for a 10% (v/v) final DMSO concentration. The solution left to react at room temperature for 2 hours at room temperature with gentle shaking. Then the conjugation was quenched by addition of N-acetyl cysteine (4.5 micromoles, 45 μL at 100 mM), then purified by spin filtration using a 15 mL Amicon Ultracell 50 kDa MWCO spin filter, sterile-filtered and analysed.

UHPLC analysis on a Shimadzu Prominence system using a Thermo Scientific MAbPac 50 mm×2.1 mm column eluting with a gradient of water and acetonitrile on a reduced sample of ConjA at 280 nm and 330 nm (Compound 19 specific) shows unconjugated light chains and a mixture of unconjugated heavy chains and heavy chains attached to a single molecule of Compound 19, consistent with a drug-per-antibody ratio (DAR) of 1.89 molecules of Compound 19 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjA at 280 nm shows a monomer purity of 96%. UHPLC SEC analysis gives a concentration of final ConjA at 1.39 mg/mL in 8.0 mL, obtained mass of ConjA is 11.15 mg (74% yield).

Antibody-Drug Conjugate with Compound 27, ConjB

A 50 mM solution of DL-dithiothreitol (DTT) in phosphate-buffered saline pH 7.4 (PBS) was added (40 molar equivalent/antibody, 27 μmol, 536 μL) to a 25 mL solution of antibody Trastuzumab (100 mg, 0.67 micromoles) in reduction buffer containing PBS and 1 mM ethylenediaminetetraacetic acid (EDTA) and a final antibody concentration of 4.0 mg/mL.

The reduction mixture was allowed to react at room temperature for 17 hours (or until full reduction is observed by UHPLC) in an orbital shaker with gentle (60 rpm) shaking. After cooling down to room temperature, the reduced antibody was buffer exchanged, via Tangential Flow Filtration unit (TFF) using mPES, MidiKros® 30 kDa fiber filter with 115 $cm^2$ surface area, into a reoxidation buffer containing PBS pH 7.4 and 1 mM EDTA to remove all the excess reducing agent. The reduced antibody was centrifuged for 3 min at 4000 rpm and then filtered using 0.22 μM membrane filter. A 50 mM solution of dehydroascorbic acid (DHAA, 20 molar equivalent/antibody, 12 micromoles, 240 μL) in DMSO was added and the reoxidation mixture was allowed to react for 2-3 hours at room temperature with gentle (50 rpm) shaking at an antibody concentration of ~1.7 mg/mL (or more DHAA added and reaction left for longer until full reoxidation of the cysteine thiols to reform the inter-chain cysteine disulfides is observed by UHPLC). The reoxidation mixture was then sterile-filtered and diluted in a conjugation buffer containing PBS and 1 mM EDTA for a final antibody concentration of 1.7 mg/mL. Compound 27 was added as a DMSO solution (12 molar equivalent/antibody, 1.2 micromole, in 1.5 mL DMSO) to 15.0 mL of this reoxidised antibody solution (15.3 mg, 0.1 μmoles) for a 10% (v/v) final DMSO concentration. The solution left to react at room temperature for 2 hours at room temperature with gentle shaking. Then the conjugation was quenched by addition of N-acetyl cysteine (6.0 micromoles, 60 μL at 100 mM), then purified by spin filtration using a 15 mL Amicon Ultracell 50 kDa MWCO spin filter, sterile-filtered and analysed.

UHPLC analysis on a Shimadzu Prominence system using a Thermo Scientific MAbPac 50 mm×2.1 mm column eluting with a gradient of water and acetonitrile on a reduced sample of ConjB at 280 nm and 330 nm (Compound 27 specific) shows unconjugated light chains and a mixture of unconjugated heavy chains and heavy chains attached to a single molecule of Compound 27, consistent with a drug-per-antibody ratio (DAR) of 1.69 molecules of Compound 27 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjB at 280 nm shows a monomer purity of 99%. UHPLC SEC analysis gives a concentration of final ConjB at 2.31 mg/mL in 5.8 mL, obtained mass of ConjB is 13.4 mg (67% yield).

Antibody-Drug Conjugate with Compound 33, ConjC

A 50 mM solution of DL-dithiothreitol (DTT) in phosphate-buffered saline pH 7.4 (PBS) was added (125 molar equivalent/antibody, 25 micromoles, 500 μL) to a 7.5 mL solution of antibody (30 mg, 200 nanomoles) in reduction buffer containing PBS and 1 mM ethylenediaminetetraacetic acid (EDTA) and a final antibody concentration of 4.0 mg/mL.

The reduction mixture was allowed to react at room temperature for 3-4 hours (or until full reduction is observed by UHPLC) in an orbital shaker with gentle (60 rpm) shaking. The reduced antibody was buffer exchanged, via spin filter centrifugation, into a reoxidation buffer containing PBS and 1 mM EDTA to remove all the excess reducing agent. A 50 mM solution of dehydroascorbic acid (DHAA, 20 molar equivalent/antibody, 4 micromoles, 80 μL) in DMSO was added and the reoxidation mixture was allowed to react for 16 hours at room temperature with gentle (50 rpm) shaking at an antibody concentration of 2.5 mg/mL (or more DHAA added and reaction left for longer until full reoxidation of the cysteine thiols to reform the inter-chain cysteine disulfides is observed by UHPLC). The reoxidation mixture was then sterile-filtered and diluted in a conjugation buffer containing PBS and 1 mM EDTA for a final antibody concentration of 2.0 mg/mL. Compound 33 was added as a DMSO solution (10 molar equivalent/antibody, 1 micromole, in 0.75 mL DMSO) to 6.75 mL of this reoxidised antibody solution (15 mg, 100 nanomoles) for a 10% (v/v) final DMSO concentration. The solution was mixed for 4 hours at room temperature (0.5-1.0 mL propylene glycol added after 2 hours to aid solubility), then the conjugation was quenched by addition of N-acetyl cysteine (5 micromoles, 50 μL at 100 mM), then purified by spin filtration using a 15 mL Amicon Ultracell 50 kDa MWCO spin filter, sterile-filtered and analysed.

UHPLC analysis on a Shimadzu Prominence system using a Thermo Scientific MAbPac 50 mm×2.1 mm column eluting with a gradient of water and acetonitrile on a reduced sample of ConjC at 280 nm and 330 nm (Compound 33 specific) shows unconjugated light chains and a mixture of unconjugated heavy chains and heavy chains attached to a single molecule of Compound 33, consistent with a drug-per-antibody ratio (DAR) of 1.63 molecules of Compound 33 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjC at 280 nm shows a monomer purity of 99%. UHPLC SEC analysis gives a concentration of final ConjC at 1.89 mg/mL in 7.0 mL, obtained mass of ConjC is 13.2 mg (88% yield).

Antibody-Drug Conjugate with Compound 34, ConjD

A 50 mM solution of DL-dithiothreitol (DTT) in phosphate-buffered saline pH 7.4 (PBS) was added (40 molar equivalent/antibody, 28 micromoles, 560 μL) to a 26.25 mL solution of antibody Trastuzumab (105 mg, 700 nanomoles) in reduction buffer containing PBS and 1 mM ethylenediaminetetraacetic acid (EDTA) and a final antibody concentration of 4.0 mg/mL.

The reduction mixture was allowed to react at room temperature for 20 hours (or until full reduction is observed by UHPLC) in an orbital shaker with gentle (60 rpm) shaking. The reduced antibody was buffer exchanged, via tangential flow filtration (TFF) using a Spectrum Labs KrosFlo Research IIi system with a 30 kDa MWCO, 115 cm$^2$ surface area hollow fibre filter module at 50 mL/min in PBS with a transmembrane pressure (TMP) of 0.5-1.0 bar, into a reoxidation buffer containing PBS and 1 mM EDTA to remove all the excess reducing agent, recovery 97 mg (667 nanomoles). A 50 mM solution of dehydroascorbic acid (DHAA, 20 molar equivalent/antibody, 12.9 micromoles, 259 μL) in DMSO was added and the reoxidation mixture was allowed to react for 17 hours at room temperature with gentle (50 rpm) shaking at an antibody concentration of 1.5 mg/mL (or more DHAA added and reaction left for longer until full reoxidation of the cysteine thiols to reform the inter-chain cysteine disulfides is observed by UHPLC). The reoxidation mixture was then sterile-filtered and diluted in a conjugation buffer containing PBS and 1 mM EDTA for a final antibody concentration of 1.0 mg/mL. Compound 34 was added as a DMSO solution (15 molar equivalent/antibody, 1.4 micromoles, in 1.4 mL DMSO) to 12.6 mL of this reoxidised antibody solution (14 mg, 93 nanomoles) for a 10% (v/v) final DMSO concentration. The solution was mixed for 2 hours at room temperature, stored at +4° C. for 16 hours then the conjugation was quenched by addition of N-acetyl cysteine (3.7 micromoles, 37 μL at 100 mM). Reaction mixture was purified by spin filtration using a 15 mL Amicon Ultracell 50 kDa MWCO spin filter, further purified by TFF (800 mL permeated), sterile-filtered and analysed. UHPLC analysis on a Shimadzu Prominence system using a Phenomenex Aeris 3.6u XB-C18 150 mm×2.1 mm column eluting with a gradient of water and acetonitrile on a reduced sample of ConjD at 280 nm and 330 nm (Compound 34 specific) shows unconjugated light chains and a mixture of unconjugated heavy chains and heavy chains attached to a single molecule of Compound 34, consistent with a drug-per-antibody ratio (DAR) of 1.81 molecules of Compound 34 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjD at 280 nm shows a monomer purity of 97%. UHPLC SEC analysis gives a concentration of final ConjD at 0.49 mg/mL in 5.5 mL, obtained mass of ConjD is 2.59 mg (19% yield).

Antibody-Drug Conjugate with Compound 44, ConjE

A 50 mM solution of DL-dithiothreitol (DTT) in phosphate-buffered saline pH 7.4 (PBS) was added Trastuzumab (40 molar equivalent/antibody, 27 μmol, 536 μL) to a 25 mL solution of antibody (100 mg, 0.67 micromoles) in reduction buffer containing PBS and 1 mM ethylenediaminetetraacetic acid (EDTA) and a final antibody concentration of 4.0 mg/mL.

The reduction mixture was allowed to react at room temperature for 17 hours (or until full reduction is observed by UHPLC) in an orbital shaker with gentle (60 rpm) shaking. After cooling down to room temperature, the reduced antibody was buffer exchanged, via Tangential Flow Filtration unit (TFF) using mPES, MidiKros® 30 kDa fiber filter with 115 cm$^2$ surface area, into a reoxidation buffer containing PBS pH 7.4 and 1 mM EDTA to remove all the excess reducing agent. The reduced antibody was centrifuged for 3 min at 4000 rpm and then filtered using 0.22 μM membrane filter. A 50 mM solution of dehydroascorbic acid (DHAA, 20 molar equivalent/antibody, 12 micromoles, 240 μL) in DMSO was added and the reoxidation mixture was allowed to react for 2-3 hours at room temperature with gentle (50 rpm) shaking at an antibody concentration of ~1.7 mg/mL (or more DHAA added and reaction left for longer until full reoxidation of the cysteine thiols to reform the inter-chain cysteine disulfides is observed by UHPLC). The reoxidation mixture was then sterile-filtered and diluted in a conjugation buffer containing PBS and 1 mM EDTA for a final antibody concentration of 1.7 mg/mL. Compound 44 was added as a DMSO solution (10 molar equivalent/antibody, 1.0 micromole, in 1.5 mL DMSO) to 15.0 mL of this reoxidised antibody solution (15.3 mg, 0.1 μmoles) for a 10% (v/v) final DMSO concentration. The solution left to react at room temperature for 2 hours at room temperature with gentle shaking. Then the conjugation was quenched by addition of N-acetyl cysteine (5.0 micromoles, 50 μL at 100 mM), then purified by spin filtration using a 15 mL Amicon Ultracell 50 kDa MWCO spin filter, sterile-filtered and analysed.

UHPLC analysis on a Shimadzu Prominence system using a Thermo Scientific MAbPac 50 mm×2.1 mm column eluting with a gradient of water and acetonitrile on a reduced sample of ConjE at 280 nm and 330 nm (Compound 44 specific) shows unconjugated light chains and a mixture of unconjugated heavy chains and heavy chains attached to a single molecule of Compound 44, consistent with a drug-per-antibody ratio (DAR) of 1.85 molecules of Compound 44 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjE at 280 nm shows a monomer purity of 99%. UHPLC SEC analysis gives a concentration of final ConjE at 2.06 mg/mL in 6.8 mL, obtained mass of ConjE is 14 mg (70% yield).

Antibody-Drug Conjugate with Compound 45, ConjF

A 50 mM solution of DL-dithiothreitol (DTT) in phosphate-buffered saline pH 7.4 (PBS) was added (40 molar equivalent/antibody, 27 μmol, 536 μL) to a 25 mL solution of antibody Trastuzumab (100 mg, 0.67 micromoles) in reduction buffer containing PBS and 1 mM ethylenediaminetetraacetic acid (EDTA) and a final antibody concentration of 4.0 mg/mL.

The reduction mixture was allowed to react at room temperature for 17 hours (or until full reduction is observed by UHPLC) in an orbital shaker with gentle (60 rpm) shaking. After cooling down to room temperature, the reduced antibody was buffer exchanged, via Tangential Flow Filtration unit (TFF) using mPES, MidiKros® 30 kDa fiber filter with 115 cm$^2$ surface area, into a reoxidation buffer containing PBS pH 7.4 and 1 mM EDTA to remove all the excess reducing agent. The reduced antibody was centrifuged for 3 min at 4000 rpm and then filtered using 0.22 μM membrane filter. A 50 mM solution of dehydroascorbic acid (DHAA, 20 molar equivalent/antibody, 12 micromoles, 240 μL) in DMSO was added and the reoxidation mixture was allowed to react for 2-3 hours at room temperature with gentle (50 rpm) shaking at an antibody concentration of ~1.7 mg/mL (or more DHAA added and reaction left for longer until full reoxidation of the cysteine thiols to reform the inter-chain cysteine disulfides is observed by UHPLC). The reoxidation mixture was then sterile-filtered and diluted in a conjugation buffer containing PBS and 1 mM EDTA for a final antibody concentration of 1.7 mg/mL. Compound 45 was added as a DMSO solution (10 molar equivalent/antibody, 1.0 micromole, in 1.5 mL DMSO) to 15.0 mL of this reoxidised antibody solution (15.3 mg, 0.1 µmoles) for a 10% (v/v) final DMSO concentration. The solution left to react at room temperature for 2 hours at room temperature with gentle shaking. Then the conjugation was quenched by addition of N-acetyl cysteine (5.0 micromoles, 50 µL at 100 mM), then purified by spin filtration using a 15 mL Amicon Ultracell 50 kDa MWCO spin filter, sterile-filtered and analysed.

UHPLC analysis on a Shimadzu Prominence system using a Thermo Scientific MAbPac 50 mm×2.1 mm column eluting with a gradient of water and acetonitrile on a reduced sample of ConjF at 280 nm and 330 nm (Compound 45 specific) shows unconjugated light chains and a mixture of unconjugated heavy chains and heavy chains attached to a single molecule of Compound 45, consistent with a drug-per-antibody ratio (DAR) of 1.72 molecules of Compound 45 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjF at 280 nm shows a monomer purity of 99%. UHPLC SEC analysis gives a concentration of final ConjF at 2.02 mg/mL in 6.7 mL, obtained mass of ConjF is 13.5 mg (68% yield).

Antibody-Drug Conjugate with Compound 19, ConjA*

R347 antibody (30 mg) was loaded onto solid support and reduced, reoxidised, conjugated to Compound 19, purified, released from the resin and formulated onto 25 mM Histidine, 200 mM Sucrose, Tween-20 0.02%, pH 6.0 according to patent #US 2014/036111 A1.

UHPLC analysis on a Shimadzu Prominence system using a Thermo Scientific MAbPac 50 mm×2.1 mm mm column eluting with a gradient of water and acetonitrile on a reduced sample of Conjugate at 214 nm and 330 nm (Compound 19 specific) shows unconjugated light chains and a mixture of unconjugated heavy chains and heavy chains attached to a single molecule of Compound 19, consistent with a drug-per-antibody ratio (DAR) of 1.9 molecules of Compound 19 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ADC at 280 nm shows a monomer purity of 97%. Nanodrop UV-Vis analysis gave a concentration of final ADC at 2.0 mg/mL in 107 mL, obtained mass of ADC is 214 mg (71% yield).

Example 6—In Vitro Cytotoxicity Assay

Medium from sub-confluent (80-90% confluency) cell culture in a T75 flask was aspirated and the flask rinsed with PBS (about 20 ml) and emptied. Trypsin-EDTA (5 ml) was added, the flask returned to the 37 C gassed incubator for up to about 5 minutes, then rapped sharply to dislodge and dissociate cells from the plastic. The cell suspension was transferred to a sterile 50 ml screw-top centrifuge tube, diluted with growth medium to a final volume of 15 ml, then centrifuged (400 g for 5 min). The supernatant was aspirated and the pellet re-suspended in 10 ml culture medium. Repeated pipetting may be necessary to produce monodisperse cell suspensions. The cell concentration and viability are measured by trypan blue staining, and counting using the LUNA-II™ Automated Cell Counter. Cells were diluted to $2 \times 10^5$/ml, dispensed (50 µl/well) into 96-well flat-bottom plates and incubated overnight before use.

A stock solution (1 ml) of antibody drug conjugate (ADC) (20 µg/ml) was made by dilution of filter-sterilised ADC into cell culture medium. A set of 8×10-fold dilutions of stock ADC were made in a 24-well plate by serial transfer of 100 µl into 900 µl of cell culture medium. ADC dilution was dispensed (50 µl/well) into 4 replicate wells of the 96-well plate, containing 50 µl cell suspension seeded the previous day. Control wells received 50 µl cell culture medium. The 96-well plate containing cells and ADCs was incubated at 37 C in a $CO_2$-gassed incubator for the exposure time.

At the end of the incubation period, cell viability was measured by MTS assay. MTS (Promega) was dispensed (20 µl per well) into each well and incubated for 4 hours at 37 C in the $CO_2$-gassed incubator. Well absorbance was measured at 490 nm. Percentage cell survival was calculated from the mean absorbance in the 4 ADC-treated wells compared to the mean absorbance in the 4 control untreated wells (100%). $IC_{50}$ was determined from the dose-response data using GraphPad Prism using the non-linear curve fit algorithm: sigmoidal dose response, X is log(concentration). ADC incubation times were 4 and 7 days for MDA MB 468 and NCI N87 respectively. Cell growth medium for MDA MB 468 was RPMI 1640 with glutamax, 10% (v/v) HyClone™ Fetal Bovine Serum and for NCI N87 was RPMI 1640 with glutamax, 10% (v/v) HyClone™ Fetal Bovine Serum.

| $EC_{50}$ (µg/ml) | NCI-N87 | MDA-MB-468 |
|---|---|---|
| ConjA | 0.00661 | ~27500 |
| ConjB | 0.000670 | 10.4 |
| ConjC | 0.00135 | 0.829 |
| ConjD | 0.00783 | ~1.35 |
| ConjE | 0.0124 | ~1.69 |
| ConjF | 0.000968 | 2.62 |

Example 7—In Vivo Assay

Mice

Female severe combined immune-deficient mice (Fox Chase SCID, C.B-17/lcr-Prkdcscid, Charles River) were eight to twelve weeks old on Day 1 of the study. The animals were fed ad libitum water (reverse osmosis, 1 ppm Cl), and NIH 31 Modified and Irradiated Lab Diet® consisting of 18.0% crude protein, 5.0% crude fat, and 5.0% crude fibre. The mice were housed on irradiated Enricho'cobs™ Laboratory Animal Bedding in static micro-isolators on a 12-hour light cycle at 20-22° C. (68-72° F.) and 40-60% humidity. CR Discovery Services specifically complies with the recommendations of the Guide for Care and Use of Laboratory Animals with respect to restraint, husbandry, surgical procedures, feed and fluid regulation, and veterinary care. The animal care and use program at CR Discovery Services is accredited by the Association for Assessment and Accreditation of Laboratory Animal Care International (AAALAC), which assures compliance with accepted standards for the care and use of laboratory animals.

Tumor Cell Culture

Human NCI-N87 gastric carcinoma lymphoma cells were cultured in RPMI-1640 medium supplemented with 10% fetal bovine serum, 2 mM glutamine, 100 units/mL penicillin, 100 μg/mL streptomycin sulfate and 25 μg/mL gentamicin. The cells were grown in tissue culture flasks in a humidified incubator at 37° C., in an atmosphere of 5% $C_{o2}$ and 95% air.

In Vivo Implantation and Tumor Growth

The NCI-N87 cells used for implantation were harvested during log phase growth and resuspended in phosphate buffered saline (PBS) containing 50% Matrigel™ (BD Biosciences). On the day of tumor implant, each test mouse was injected subcutaneously in the right flank with $1 \times 10^7$ cells (0.1 mL cell suspension), and tumor growth was monitored as the average size approached the target range of 100 to 150 mm³. Eleven days later, designated as Day 1 of the study, mice were sorted according to calculated tumor size into groups each consisting of ten animals and equivalent group mean tumor volumes. Tumors were measured in two dimensions using calipers, and volume was calculated using the formula:

$$\text{Tumour Volume (mm}^3) = 0.5(w^2 \times l)$$

where w=width and l=length, in mm, of the tumour. Tumour weight may be estimated with the assumption that 1 mg is equivalent to 1 mm³ of tumour volume Treatment On Day 1 of the study, female SCID mice bearing established NCI-N87 xenografts were sorted into groups (n=10), and dosing was initiated as shown below. All agents were administered intravenously (i.v.) via tail vein injection once on Day 1 (qd×1). The dosing volume was 0.2 mL per 20 grams of body weight (10 mL/kg), and was scaled to the body weight of each individual animal. A vehicle-treated group served as the control group for efficacy analysis. Tumors were measured using calipers twice per week, and each animal was euthanized when its tumor reached the endpoint volume of 800 mm³ or at the end of the study (Day 85), whichever came first.

Treatment outcome was determined from percent tumor growth delay (% TGD), defined as the percent increase in median TTE for treated versus control mice, with differences between groups deemed statistically significant at P≤0.05 using logrank survival analysis. Treatment may cause partial regression (PR) or complete regression (CR) of the tumor in an animal. In a PR response, the tumor volume was 50% or less of its Day 1 volume for three consecutive measurements during the course of the study, and equal to or greater than 13.5 mm³ for one or more of these three measurements. In a CR response, the tumor volume was less than 13.5 mm³ for three consecutive measurements during the course of the study.

Treatment tolerability was assessed by body weight measurements and frequent observation for signs of treatment-related side effects. Treatment tolerability was assessed by body weight measurements and frequent observation for signs of treatment-related side effects.

All regimens were acceptably tolerated. The median TTE for vehicle-treated controls was 33.5 days, establishing a maximum possible TGD of 51.5 days (154%) for the 85-day study.

All ADC treatments produced TGD outcomes that were significantly different from the vehicle-treated controls (P<0.001).

|       | Dose    | % TGD | PR | CR | TFS |
|-------|---------|-------|----|----|-----|
| ConjA | 1 mg/kg | 154   | 0  | 0  | 0   |
| ConjB | 1 mg/kg | 154   | 9  | 0  | 0   |
| ConjC | 1 mg/kg | 154   | 7  | 1  | 1   |
| ConjE | 1 mg/kg | 117   | 0  | 0  | 0   |
| ConjF | 1 mg/kg | 154   | 8  | 0  | 0   |

Example 8—Synthesis of Drug Payloads

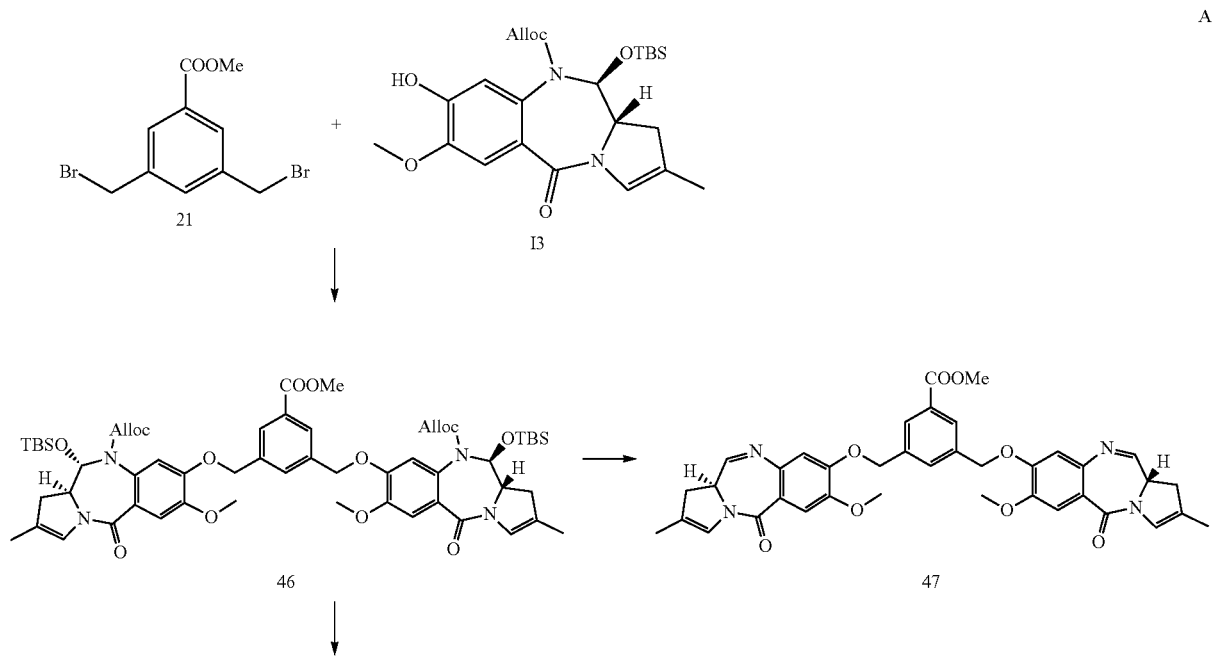

A

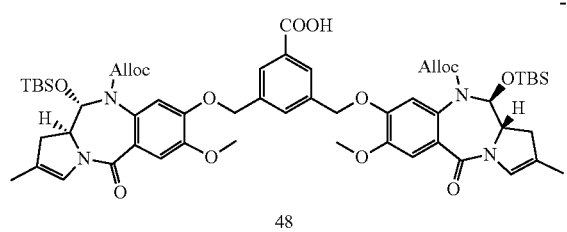

48

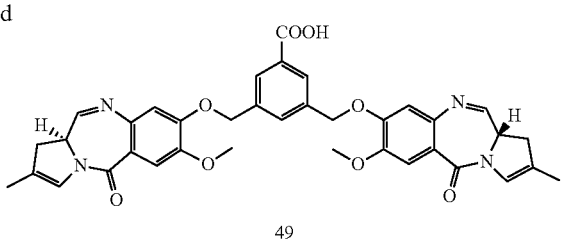

49

(i) Diallyl 8,8'-(((5-(methoxycarbonyl)-1,3-phenylene)bis(methylene))bis(oxy))(11S,11aS,11'S,11a'S)-bis(11-((tert-butyldimethylsilyl)oxy)-7-methoxy-2-methyl-5-oxo-11,11a-dihydro-1H-benzo[e]pyrrolo[1,2-a][1,4]diazepine-10(5H)-carboxylate) (46)

Phenol I3 (240 mg, 0.5 mmol, 2 eq.) and dibromo-m-xylene 21 (81 mg, 0.253 mmol, 1 eq.) were solubilised in dry DMF (20 mL) before TBAI (11 mg, 0.03 mmol, 0.1 eq.) and $K_2CO_3$ (70 mg, 0.5 mmol, 2 eq) were added. The mixture was heated to 60° C. for an hour at which point the reaction was completed. DMF was removed under vacuum and the crude product was purified by Biotage chromatography to give pure product 46 (273 mg, 97% yield). LCMS-A: r.t.=2.24 min, [M+H]$^+$=1109.

(ii) Methyl 3,5-bis((((S)-7-methoxy-2-methyl-5-oxo-5,11a-dihydro-1H-benzo[e]pyrrolo[1,2-a][1,4]diazepin-8-yl)oxy)methyl)benzoate (47)

In a glovebox, ester 46 (60 mg, 0.054 mmol, 1 eq.) was solubilised in $CH_2Cl_2$ (5 mL) before PdP(Ph$_3$)$_4$ (3.5 mg, 0.003 mmol, 0.05 eq.) and pyrrolidine (11 μL, 0.135 mmol, 2.5 eq.) were added and the mixture left to stir until complete. The organics were diluted with more $CH_2Cl_2$ and washed with sat $NH_4Cl_{(aq)}$, water and brine before being dried with MgSO$_4$, filtered and the volatiles removed in vacuo. The crude material was purified by Biotage chromatography to give pure product 47 (17.8 mg, 48% yield). LCMS-A: r.t.=1.42 min, [M+H]$^+$=677; LCMS$^2$: r.t.=6.35 min, [M+H]$^+$=677.

(iii) 3,5-bis((((11S,11aS)-10-((allyloxy)carbonyl)-11-((tert-butyldimethylsilyl)oxy)-7-methoxy-2-methyl-5-oxo-5,10,11,11a-tetrahydro-1H-benzo[e]pyrrolo[1,2-a][1,4]diazepin-8-yl)oxy)methyl)benzoic acid (48)

Ester 46 (185 mg, 0.17 mmol, 1 eq.) was solubilised in a 1:1:1 mixture of THF/H$_2$O/MeOH (10 mL) and the mixture was stirred for 15h and after work up, product 48 (59 mg, 32% yield) was isolated. LCMS-A: r.t.=2.15 min, [M+H]$^+$=1095.

(iv) 3,5-bis((((S)-7-methoxy-2-methyl-5-oxo-5,11a-dihydro-1H-benzo[e]pyrrolo[1,2-a][1,4]diazepin-8-yl)oxy)methyl)benzoic acid (49)

In a glovebox, ester 48 (59 mg, 0.054 mmol, 1 eq.) was solubilised in $CH_2Cl_2$ (5 mL) before PdP(Ph$_3$)$_4$ (3.5 mg, 0.003 mmol, 0.05 eq.) and pyrrolidine (11 μL, 0.135 mmol, 2.5 eq.) were added and the mixture left to stir until complete. The organics were diluted with more $CH_2Cl_2$ and washed with sat $NH_4Cl_{(aq)}$, water and brine before being dried with MgSO$_4$, filtered and the volatiles removed in vacuo. The crude material was purified by Biotage chromatography to give pure product 49 (17.08 mg, 48% yield). LCMS-A: r.t.=1.35 min, [M+H]$^+$=663; LCMS-B: r.t.=5.70 min, [M+H]$^+$=663.

B

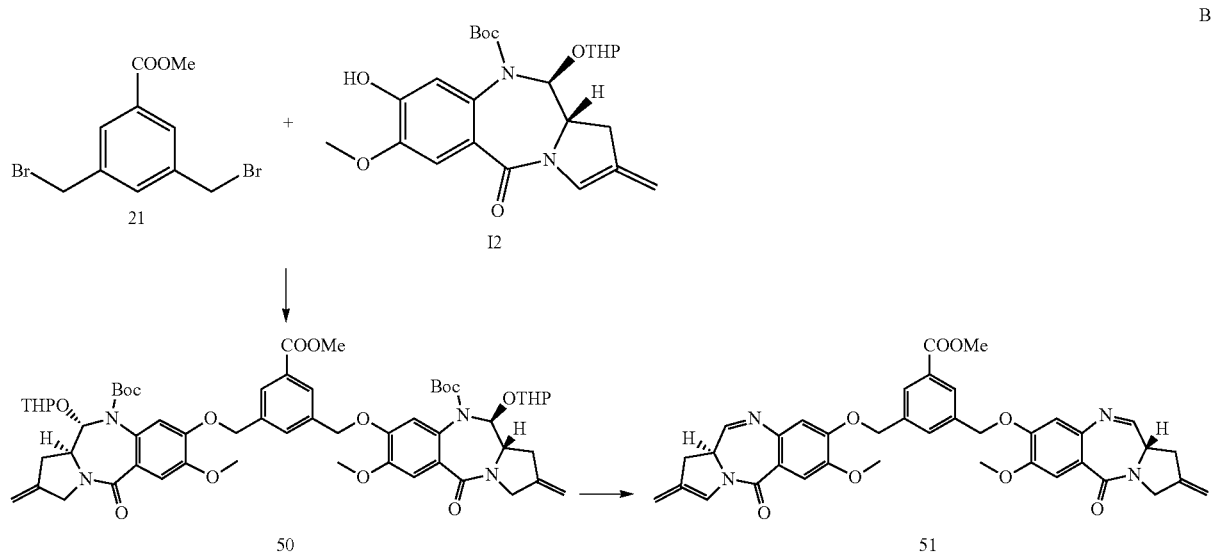

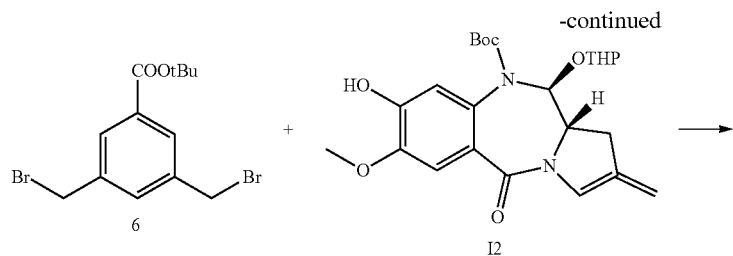

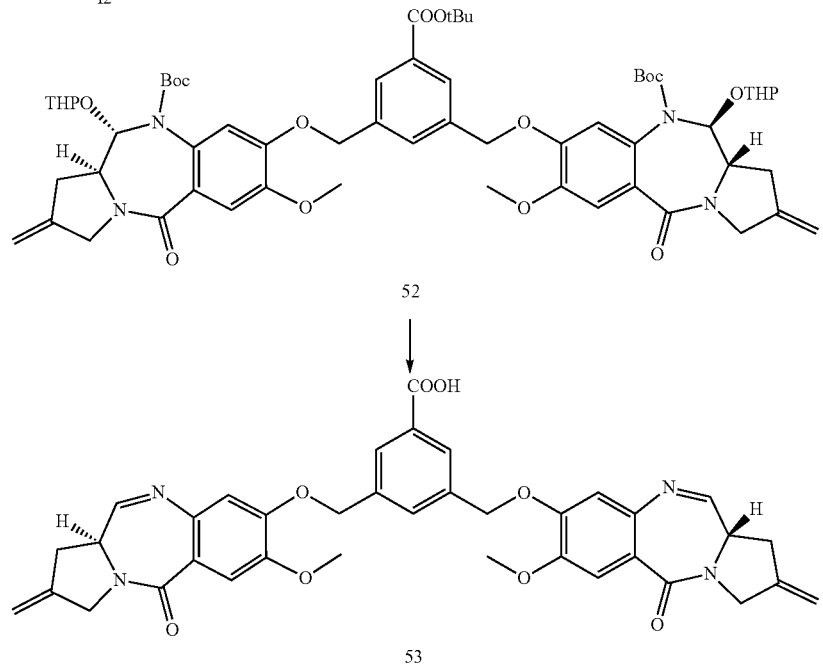

(i) Di-tert-butyl 8,8'-(((5-(methoxycarbonyl)-1,3-phenylene)bis(methylene))bis(oxy))(11S,11aS,11'S,11a'S)-bis(7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate) (50)

Phenol I2 (100 mg, 0.2171 mmol, 2.0 eq.), bromide 21 (35 mg, 0.1086 mmol, 1.0 eq.), TBAI (1 mg, 0.002715 mmol, 0.025 eq.) and $K_2CO_3$ (31.5 mg, 22.81 mmol, 2.1 eq.) were dissolved in DMF (1.5 mL) and the mixture stirred at 35° C. for 16 h, whereupon LCMS indicated the reaction complete. The reaction mixture was concentrated in vacuo and purified by isolera chromatography (50-80% EtOAc in hexane) to afford 50 as an oil (98.3 mg, 84%).

LCMS-A: r.t.=1.93, $[M+H]^+$=1103

(ii) Methyl 3,5-bis((((S)-7-methoxy-2-methylene-5-oxo-2,3,5,11a-tetrahydro-1H-benzo[e]pyrrolo[1,2-a][1,4]diazepin-8-yl)oxy)methyl)benzoate (51)

50 (86.6 mg, 80.09 µmol, 1.0 eq) was dissolved in 95% aq. TFA (0.5 mL) at 0° C. and the mixture stirred for 40 min, whereupon LCMS indicated the reaction was complete. Ice cold water was added to the reaction mixture and solid $NaHCO_3$ was added until the pH was slightly basic. The aqueous was extracted with $CHCl_3$, the combined organics dried over $MgSO_4$ and concentrated in vacuo. HPLC (20-60% B in A*) afforded 51 as a yellow solid (6.2 mg, 11%). *A=0.1% $HCO_2H$ in $H_2O$. B=0.1% $HCO_2H$ in MeCN. LCMS-B: r.t.=6.37 min, $[M+H]^+$=677.

(iii) Di-tert-butyl 8,8'-(((5-(tert-butoxycarbonyl)-1,3-phenylene)bis(methylene))bis(oxy))(11S,11aS,11'S,11a'S)-bis(7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate) (52)

Phenol I2 (100 mg, 0.2171 mmol, 2.0 eq.), bromide 6 (39.5 mg, 0.1086 mmol, 1.0 eq.), TBAI (1 mg, 0.002715 mmol, 0.025 eq.) and $K_2CO_3$ (31.5 mg, 22.81 mmol, 2.1 eq.) were dissolved in DMF (1.5 mL) and the mixture stirred at 35° C. for 16 h, whereupon LCMS indicated the reaction was complete. The reaction mixture was concentrated in vacuo and purified by isolera chromatography (50-80% EtOAc in hexane) to afford 52 as an oil (120 mg, 98%).

LCMS-A: r.t.=2.03, $[M+H]^+$=1145

(iv) 3,5-bis((((S)-7-Methoxy-2-methylene-5-oxo-2,3,5,11a-tetrahydro-1H-benzo[e]pyrrolo[1,2-a][1,4]diazepin-8-yl)oxy)methyl)benzoic acid (53)

52 (106 mg, 94.36 µmol, 1.0 eq) was dissolved in 95% aq. TFA (0.5 mL) at 0° C. and the mixture stirred for 40 min. Ice cold water was added to the reaction mixture and solid $NaHCO_3$ was added until the pH was neutral. The aqueous was extracted with $CHCl_3$. The pH of the aqueous phase was adjusted to ca. pH 3 and extracted with $CHCl_3$. The combined organics were dried over $MgSO_4$ and concentrated in vacuo. HPLC (20-60% B in A*) afforded 53 as a yellow solid (3.8 mg, 6.1%). *A=0.1% $HCO_2H$ in $H_2O$. B=0.1% $HCO_2H$ in MeCN. LCMS-B: r.t.=5.68, $[M+H]^+$=663

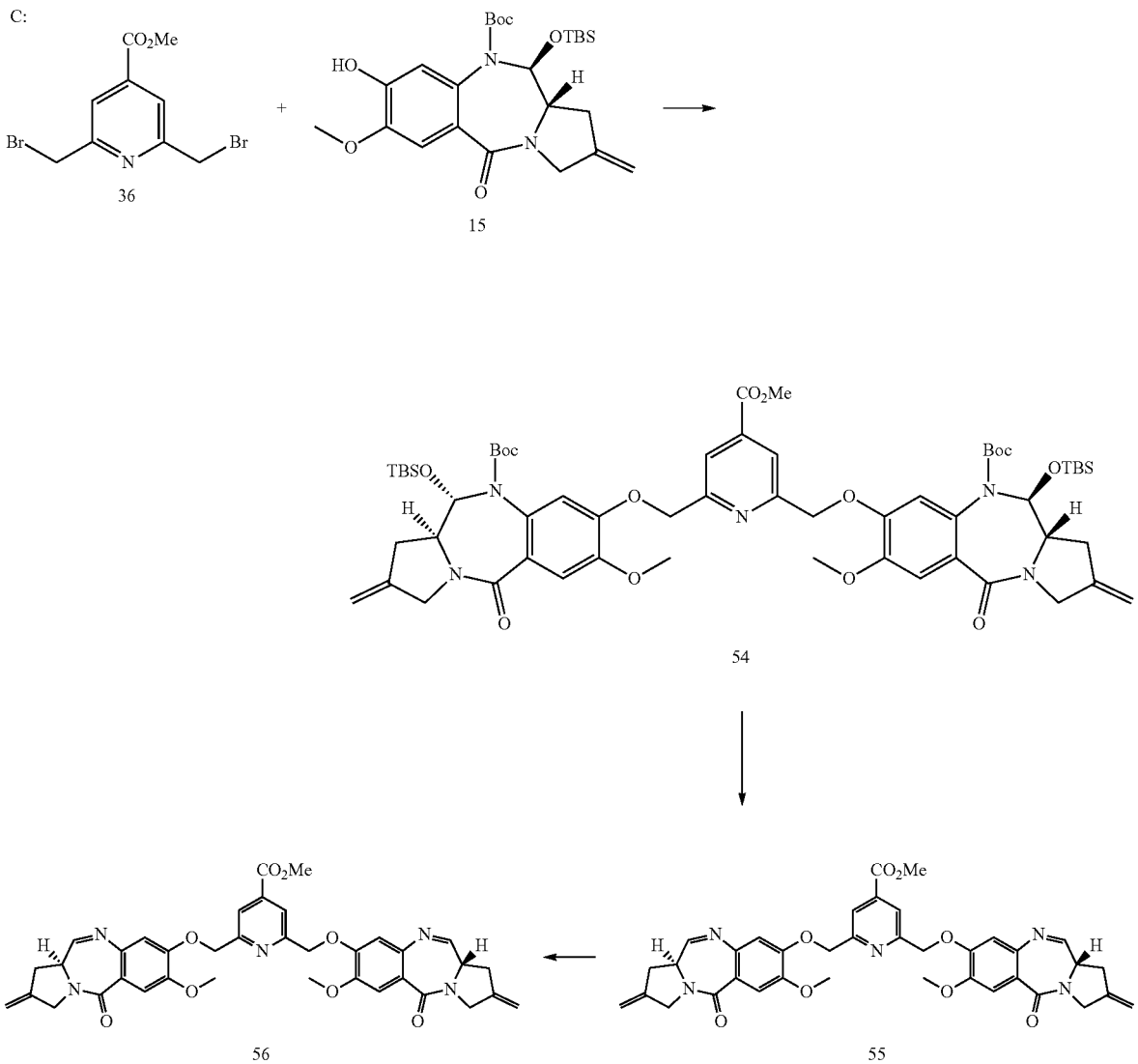

(i) Di-tert-butyl 8,8'-(((4-(methoxycarbonyl)pyridine-2,6-diyl)bis(methylene))bis(oxy))(11S,11aS,11'S,11a'S)-bis(11-((tert-butyldimethylsilyl)oxy)-7-methoxy-2-methylene-5-oxo-2,3,11,11a-tetrahydro-1H-benzo[e]pyrrolo[1,2-a][1,4]diazepine-10(5H)-carboxylate) (54)

Phenol I5 (668 mg, 1.362 mmol, 2.2 eq.), bromide 36 (200 mg, 0.0.6192 mmol, 1.0 eq.) and K₂CO₃ (188 mg, 1.362 mmol, 2.2 eq.) were dissolved in DMF (3 mL) and the mixture stirred at rt for 3 h, then 2 h at 40° C., whereupon LCMS indicated the reaction was complete. The reaction mixture was concentrated in vacuo and purified by isolera chromatography (0-5% MeOH in CH₂Cl₂) to afford 54 as a white solid (610 mg, 86%). LCMS-A: r.t.=2.17, [M+Na]⁺=1164

(ii) Methyl 2,6-bis((((S)-7-methoxy-2-methylene-5-oxo-2,3,5,11a-tetrahydro-1H-benzo[e]pyrrolo[1,2-a][1,4]diazepin-8-yl)oxy)methyl)isonicotinate (55)

54 (200 mg, 0.1751 mmol, 1.0 eq) was dissolved in 95% aq. TFA (14 mL) at 0° C. and the mixture stirred for 30 min. Ice cold water was added to the reaction mixture and solid NaHCO₃ was added until the pH was neutral to slightly basic. The aqueous was extracted with CHCl₃, dried over MgSO₄ and concentrated. Isolera chromatography (0-4% MeOH in CH₂Cl₂) afforded 55 (61.4 mg, 52%). LCMS-A: r.t.=5.43 min, [M+H]⁺=678

(iii) 2,6-Bis((((S)-7-methoxy-2-methylene-5-oxo-2,3,5,11a-tetrahydro-1H-benzo[e]pyrrolo[1,2-a][1,4]diazepin-8-yl)oxy)methyl)isonicotinic acid (56)

55 (55 mg, 81.16 µmol, 1.0 eq.) and SnMe₃OH (58.7 mg, 324.6 µmol, 4.0 eq.) were dissolved in (CH₂C)₂ (0.6 mL) and the mixture warmed to 80° C. and stirred for 2.5 h, whereupon LCMS indicated the reaction was complete. The reaction mixture was diluted with CH₂Cl₂, filtered through celite and concentrated in vacuo. HPLC (5-70% B in A*) afforded 56 (20 mg, 37%). *A=0.1% HCO₂H in H₂O. B=0.1% HCO₂H in MeCN.

LCMS-B: r.t.=5.50 min, [M+H]⁺=664

D:

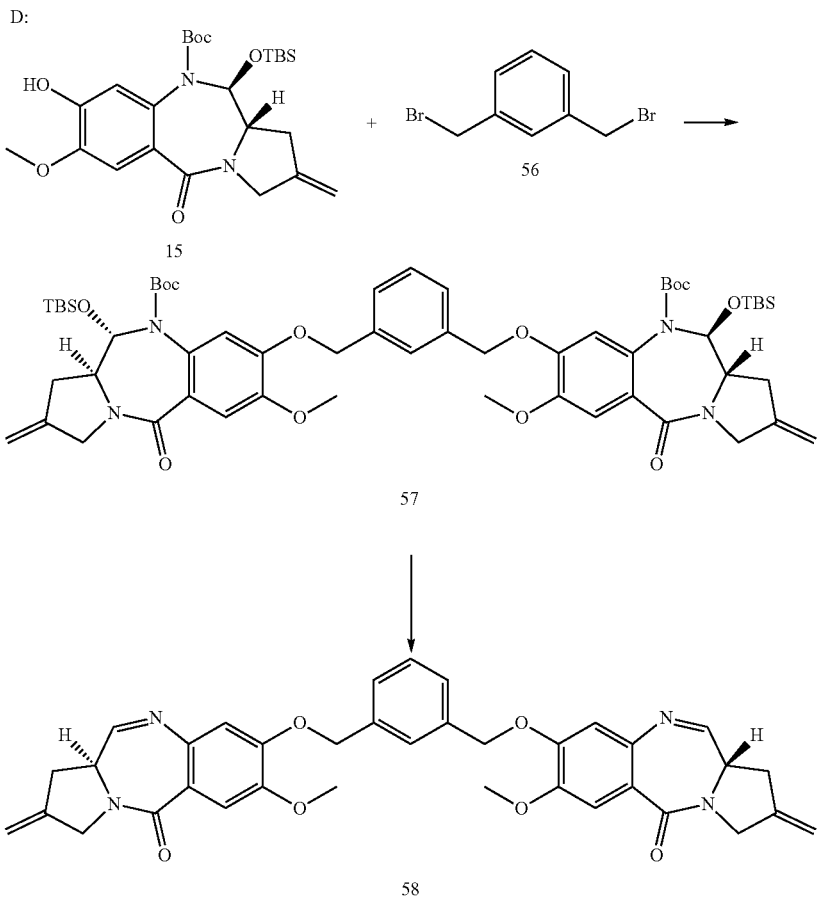

(i) Di-tert-butyl 8,8'-((1,3-phenylenebis(methylene))bis(oxy))(11S,11aS,11'S,11a'S)-bis(11-((tert-butyldimethylsilyl)oxy)-7-methoxy-2-methylene-5-oxo-2,3,11,11a-tetrahydro-1H-benzo[e]pyrrolo[1,2-a][1,4]diazepine-10(5H)-carboxylate) (57)

Phenol I5 (400 mg, 0.8152 mmol, 2.1 eq.), bromide 56 (103 mg, 0.3902 mmol, 1.0 eq.) and $K_2CO_3$ (115 mg, 0.8321 mmol, 2.1 eq.) were dissolved in MEK (5 mL) and the mixture stirred at 40° C. for 2 h, then 2 h at 90° C., whereupon LCMS indicated the reaction was incomplete. KI (knifept.) was added and the mixture stirred at 90° C. for 2 h, whereupon LCMS indicated the reaction was complete. The reaction mixture was concentrated in vacuo and purified by isolera chromatography (10-25% EtOAc in isohexane) to afford 57 as an off-white foam (391 mg, 92%). LCMS-A: r.t.=2.47 min, [M+H]$^+$=1084

(ii) (11aS,11a'S)-8,8'-((1,3-phenylenebis(methylene))bis(oxy))bis(7-methoxy-2-methylene-1,2,3,11a-tetrahydro-5H-benzo[e]pyrrolo[1,2-a][1,4]diazepin-5-one) (58)

57 (98 mg, 0.09045 mmol, 1.0 eq) was dissolved in 95% aq. TFA (2 mL) at 0° C. and the mixture stirred for 30 min. Ice cold water was added to the reaction mixture and solid $NaHCO_3$ was added until the pH was neutral to slightly basic. The aqueous was extracted with $CHCl_3$, dried over $MgSO_4$ and concentrated. Isolera chromatography (0-4% MeOH in $CH_2Cl_2$) afforded 58 (27.9 mg, 50%) as a pale-yellow solid. LCMS-B: r.t.=7.55 min, [M+H]$^+$=619.

K562 Assay

The potency of each of the PBD molecules were measured via in vitro cytotox assays in the carcinoma cell line K562.

Solid PBD material was dissolved in DMSO to a 2 mM stock solution, from which eight serial dilutions were made at a 1:10 ratio in DMSO and stored at −20° C. until use.

Adherent K562 cells were washed with D-PBS and detached with Trypsin-EDTA, cell density and viability were then determined in duplicate by Trypan blue exclusion assay using an automated cell counter (LUNA-II™). Cell suspension was diluted to 1×10$^5$ cells/ml in growth media (RPMI 1640 with Glutamax+10% (v/v) HyClone™ Fetal Bovine Serum) and vortexed before dispensing 2 mL per well into sterile 3 mL polypropylene plates. Warhead dilutions were then dispensed into the appropriate wells at 10 µl/well and mixed by repeat pipetting. For control wells 10 µl of DMSO was dispensed onto 2 mL cell suspension, and thoroughly mixed. 100 µl of each sample was then aliquoted into 2 replicate wells of a sterile flat 96-well microplate and incubated in a 37° C. $CO_2$-gassed (5%) incubator. At the end of the incubation period time (4 days), cell viability was measured by CellTiter 96® Aqueous One (MTS) assay, which was dispensed at 20 µl/well and incubated for 4 hours at 37° C., 5% $CO_2$. Plates were then read on an EnVision® Multi-label Plate Reader (Perkin Elmer) using absorbance at 490 nm.

Cell survival percentage was calculated from the mean absorbance of the 2 replicate wells for each sample, compared to the mean absorbance in the two control wells treated with DMSO only (100%). The $IC_{50}$ was determined by fitting each data set to sigmoidal dose-response curves with a variable slope using the non-linear curve fit algorithm on the GraphPad Prism software (San Diego, Calif.).

All the experiments in this report were carried out and tested in three independent experiments. Data are reported as the mean of the three independent replicates.

NCI-N87 Assay

The potency of each of the PBD molecules were measured via in vitro cytotoxicity assays in the carcinoma cell line NCI-N87.

Solid PBD material was dissolved in DMSO to a 2 mM stock solution, from which eight serial dilutions were made at a 1:10 ratio in DMSO and stored at −20° C. until use.

Adherent NCI-N87 cells were washed with D-PBS and detached with Trypsin-EDTA, cell density and viability were then determined in duplicate by Trypan blue exclusion assay using an automated cell counter (LUNA-II™). Cell suspension was diluted to $1\times10^5$ cells/ml in growth media (RPMI 1640 with Glutamax+10% (v/v) HyClone™ Fetal Bovine Serum) and vortexed before dispensing 2 mL per well into sterile 3 mL polypropylene plates. Warhead dilutions were then dispensed into the appropriate wells at 10 μl/well and mixed by repeat pipetting. For control wells 10 μl of DMSO was dispensed onto 2 mL cell suspension, and thoroughly mixed. 100 μl of each sample was then aliquoted into 2 replicate wells of a sterile flat 96-well microplate and incubated in a 37° C. $CO_2$-gassed (5%) incubator. At the end of the incubation period time (7 days), cell viability was measured by CellTiter 96® Aqueous One (MTS) assay, which was dispensed at 20 μl/well and incubated for 4 hours at 37° C., 5% $CO_2$.

Plates were then read on an EnVision® Multi-label Plate Reader (Perkin Elmer) using absorbance at 490 nm.

Cell survival percentage was calculated from the mean absorbance of the 2 replicate wells for each sample, compared to the mean absorbance in the two control wells treated with DMSO only (100%). The $IC_{50}$ was determined by fitting each data set to sigmoidal dose-response curves with a variable slope using the non-linear curve fit algorithm on the GraphPad Prism software (San Diego, Calif.).

All the experiments in this report were carried out and tested in three independent experiments. Data are reported as the mean of the three independent replicates.

|    | K562 (nM) | NCI-N87 (nM) |
| --- | --- | --- |
| 47 | 0.162 |  |
| 49 | 1.84 |  |
| 51 |  | 0.06848 |
| 53 |  | 4.309 |
| 55 |  | 0.0168 |
| 56 |  | 20.7 |
| 58 |  | 0.0172 |

These results show the acid payload to have a much lower activity in vitro than the ester, and that the addition of the ester group slightly reduces the activity of the payload.

Example 9—Toxicity of Conjugates

A single dose nonGLP toxicity study was carried out on ConjA*.

Male Sprague Dawley rats (Envigo, Inc) were dosed once by slow bolus intravenous injection via the tail vein with ADC. The vehicle for dilution used was 25 mM Histidine-HCl, 7% sucrose, 0.02% Polysorbate 80, pH 6.0. Parameters evaluated during the study included mortality, physical examinations, cageside observations, body weights, body weight changes, clinical pathology (clinical chemistry, hematology, and coagulation), and gross pathology findings. All animals were terminated on Study Day (SD) 29.

ConjA*

| Group | Dose (mg/kg) | N |
| --- | --- | --- |
| 1 | 1.2 | 4 |
| 2 | 2 | 4 |

Administration of either dose did not not result in any early mortalities. Test article-associated changes in the hematology data were indicative of myelotoxicity and included decreases in all cell lineages (red blood cells, reticulocytes, platelets, neutrophils, lymphocytes, monocytes and eosinophils in most dose groups. The values generally increased at subsequent intervals, indicating reversibility.

In the coagulation data, increased fibrinogen on Day 29, in association with decreased albumin and A/G ratio, and increased globulin, was consistent with an acute systemic inflammatory response.

In group 2, there was an increased mean ALT on Day 8 that correlated with increased liver weights and mild multifocal hepatocellular hypertrophy in that group. The activities of these enzymes were comparable to, or lower than, the control group at the subsequent collections on Days 15 and 29. ALP increases of a lesser magnitude were observed in group 1 on Day 8 only. Total cholesterol and triglycerides were also elevated in both groups on Days 15 and/or 29, consistent with altered lipid metabolism and likely associated with the liver enzymes and anatomic pathology findings. Microscopic changes included randomly oriented mild multifocal hepatocellular hypertrophy in all Group 2 animals. This hepatic change correlated to increased liver weights and increased liver enzymes.

No significant changes in the bone marrow were seen in either group, which contrasts with the typical profile associated with pyrrolobenzodiazepine dimers.

Abbreviations

Ac acetyl
Acm acetamidomethyl
Alloc allyloxycarbonyl
Boc di-tert-butyldicarbonate
t-Bu tert-butyl
Bzl benzyl, where Bzl-OMe is methoxybenzyl and Bzl-Me is methylbenzene
Cbz or Z benzyloxy-carbonyl, where Z—Cl and Z—Br are chloro- and bromobenzyloxy carbonyl respectively
DMF N,N-dimethylformamide
Dnp dinitrophenyl
DTT dithiothreitol
Fmoc 9H-fluoren-9-ylmethoxycarbonyl
imp N-10 imine protecting group: 3-(2-methoxyethoxy) propanoate-Val-Ala-PAB
MC-OSu maleimidocaproyl-O—N-succinimide
Moc methoxycarbonyl
MP maleimidopropanamide Mtr 4-methoxy-2,3,6-trimethtylbenzenesulfonyl
PAB para-aminobenzyloxycarbonyl
PEG ethyleneoxy
PNZ p-nitrobenzylcarbamate
Psec 2-(phenylsulfonyl)ethoxycarbonyl
TBDMS tert-butyldimethylsilyl
TBDPS tert-butyldiphenylsilyl
Teoc 2-(trimethylsilyl)ethoxycarbonyl
Tos tosyl
Troc 2,2,2-trichlorethoxycarbonylchloride
Trt trityl
Xan xanthyl Numbered Statements of the Invention
1. A compound with the formula I:

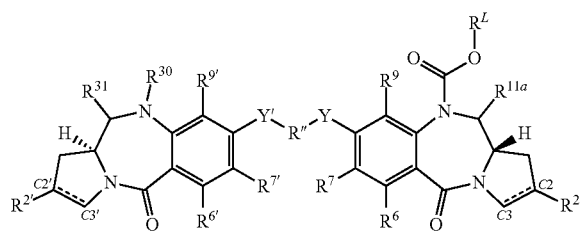

I and salts and solvates thereof, wherein:
R" is a group of formula II:

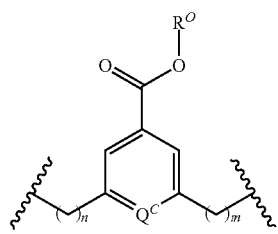

II where each of n and m are independently selected from 1, 2 and 3;
$R^O$ is selected from the group consisting of H, methyl, ethyl, iso-propyl and benzyl;
$Q^C$ is selected from N and CH;
Y and Y' are selected from O, S, or NH;
when there is a double bond present between C2 and C3, $R^2$ is selected from the group consisting of:
(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;
(ib) $C_{1-5}$ saturated aliphatic alkyl;
(ic) $C_{3-6}$ saturated cycloalkyl;

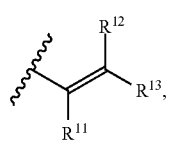

(id)

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

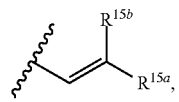

(ie)

wherein one of $R^{15a}$ and $R^{15b}$ is H and the other is selected from: phenyl, which phenyl is optionally substituted by a group selected from halo, methyl, methoxy; pyridyl; and thiophenyl; and

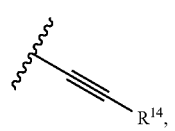

(if)

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;
when there is a single bond present between $C_2$ and $C_3$, $R^2$ is H or

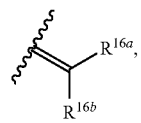

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;
when there is a double bond present between C2' and C3', $R^{2'}$ is selected from the group consisting of:
(iia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;
(iib) $C_{1-5}$ saturated aliphatic alkyl;
(iic) $C_{3-6}$ saturated cycloalkyl;

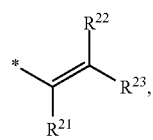

(iid)

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{2'}$ group is no more than 5;

(iie)

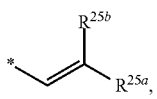

wherein one of $R^{25a}$ and $R^{25b}$ is H and the other is selected from: phenyl, which phenyl is optionally substituted by a group selected from halo, methyl, methoxy; pyridyl; and thiophenyl; and (iif)

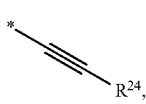

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2' and C3', $R^{2'}$ is H or

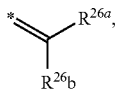

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;

$R^6$ and $R^9$ are independently selected from H, R, OH, OR, SH, SR, $NH_2$, NHR, NRR', nitro, $Me_3Sn$ and halo;

where R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, $NH_2$, NHR, NHRR', nitro, $Me_3Sn$ and halo;

$R^{6'}$, $R^{7'}$, $R^{9'}$ are selected from the same groups as $R^6$, $R^7$ and $R^9$ respectively;

$R^{11a}$ is selected from OH, $OR^A$, where $R^A$ is $C_{1-4}$ alkyl, and $SO_zM$, where z is 2 or 3 and M is a monovalent pharmaceutically acceptable cation;

and either (a) $R^{30}$ is H, and $R^{31}$ is OH, $OR^A$, where $R^A$ is $C_{1-4}$alkyl;

(b) $R^{30}$ and $R^{31}$ form a nitrogen-carbon double bond between the nitrogen and carbon atoms to which they are bound; or (c) $R^{30}$ is H and $R^{31}$ is $SO_zM$, where z is 2 or 3 and M is a monovalent pharmaceutically acceptable cation, wherein if $R^{11a}$ and $R^{31}$ are $SO_zM$, M may represent a divalent pharmaceutically acceptable cation $R^L$ is a linker for connection to a cell binding agent, which is selected from:

(iiia)

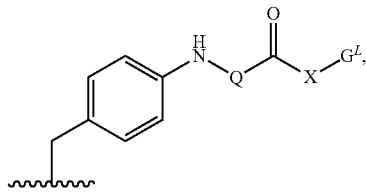

IIIa wherein
Q is:

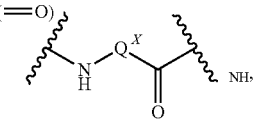

where $Q^X$ is such that Q is an amino-acid residue, a dipeptide residue or a tripeptide residue;
X is:

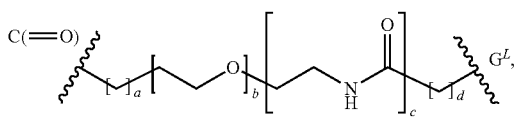

where a=0 to 5, b=0 to 16, c=0 or 1, d=0 to 5;
$G^L$ is a linker for connecting to a Ligand Unit; and (iiib)

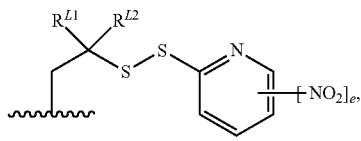

IIIb where $R^{L1}$ and $R^{L2}$ are independently selected from H and methyl, or together with the carbon atom to which they are bound form a cyclopropylene or cyclobutylene group; and e is 0 or 1.

2. A compound according to statement 1, wherein Y and Y' are O.

3. A compound according to either statement 1 or statement 2, wherein n is 1.

4. A compound according to either statement 1 or statement 2, wherein n is 2.

5. A compound according to either statement 1 or statement 2, wherein n is 3.

6. A compound according to any one of statements 1 to 5, wherein m is 1.

7. A compound according to any one of statements 1 to 5, wherein m is 2.

8. A compound according to any one of statements 1 to 5, wherein m is 3.

9. A compound according to any one of statements 1 to 8, wherein $Q^C$ is N.

10. A compound according to any one of statements 1 to 8, wherein $Q^C$ is CH.

11. A compound according to any one of statements 1 to 10, wherein $R^O$ is H.

12. A compound according to any one of statements 1 to 10, wherein $R^O$ is methyl.

13. A compound according to any one of statements 1 to 10, wherein $R^O$ is ethyl.

14. A compound according to any one of statements 1 to 10, wherein $R^O$ is iso-propyl.

15. A compound according to any one of statements 1 to 10, wherein $R^O$ is benzyl.

16. A compound according to either statement 1 or statement 2, wherein R" is of formula IIa:

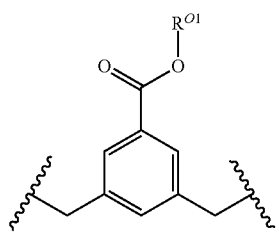

IIa where $R^{O1}$ is selected from the group consisting of H and methyl.

17. A compound according to any one of statements 1 to 16, wherein $R^9$ and $R^{9'}$ are H.

18. A compound according to any one of statements 1 to 17, wherein $R^6$ and $R^{6'}$ are independently selected from H and halo.

19. A compound according to statement 18, wherein $R^6$ and $R^{6'}$ are H.

20. A compound according to any one of statements 1 to 19, wherein $R^7$ and $R^{7'}$ are independently selected from H, OH and OR.

21. A compound according to statement 20, wherein $R^7$ and $R^{7'}$ are independently a $C_{1-4}$ alkoxy group.

22. A compound according to statement 21, wherein $R^7$ and $R^{7'}$ are methoxy.

23. A compound according to any one of statements 1 to 22, wherein there is a double bond between C2 and C3, and $R^2$ is a $C_{5-7}$ aryl group.

24. A compound according to statement 23, wherein $R^2$ is phenyl.

25. A compound according to any one of statements 1 to 22, wherein there is a double bond between C2 and C3, and $R^2$ is a $C_{8-10}$ aryl group.

26. A compound according to any one of statements 23 to 25, wherein $R^2$ bears one to three substituent groups.

27. A compound according to any one of statements 23 to 26, wherein the substituents are selected from methoxy, ethoxy, fluoro, chloro, cyano, bis-oxy-methylene, methyl-piperazinyl, morpholino and methyl-thiophenyl.

28. A compound according to any one of statements 1 to 22, wherein there is a double bond between C2 and C3, and $R^2$ is a $C_{1-5}$ saturated aliphatic alkyl group.

29. A compound according to statement 28, wherein $R^2$ is methyl, ethyl or propyl.

30. A compound according to any one of statements 1 to 22, wherein there is a double bond between C2 and C3, and $R^2$ is a $C_{3-6}$ saturated cycloalkyl group.

31. A compound according to statement 30, wherein $R^2$ is cyclopropyl.

32. A compound according to any one of statements 1 to 22, wherein there is a double bond between C2 and C3, and $R^2$ is a group of formula:

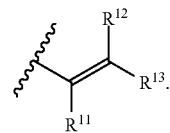

33. A compound according to statement 32, wherein the total number of carbon atoms in the $R^2$ group is no more than 4.

34. A compound according to statement 32, wherein the total number of carbon atoms in the $R^2$ group is no more than 3.

35. A compound according to any one of statements 32 to 34, wherein one of $R^{11}$, $R^{12}$ and $R^{13}$ is H, with the other two groups being selected from H, $C_{1-3}$ saturated alkyl, $C_{2-3}$ alkenyl, $C_{2-3}$ alkynyl and cyclopropyl.

36. A compound according to any one of statements 32 to 34, wherein two of $R^{11}$, $R^{12}$ and $R^{13}$ are H, with the other group being selected from H, $C_{1-3}$ saturated alkyl, $C_{2-3}$ alkenyl, $C_{2-3}$ alkynyl and cyclopropyl.

37. A compound according to any one of statements 1 to 22, wherein there is a double bond between $C_2$ and $C_3$, and $R^2$ is a group of formula:

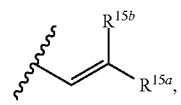

38. A compound according to statement 37, wherein $R^2$ is the group:

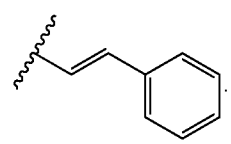 [SMILES: */C=C/c1ccccc1]

39. A compound according to any one of statements 1 to 22, wherein there is a double bond between C2 and C3, and $R^2$ is a group of formula:

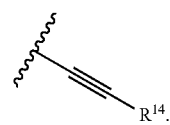

40. A compound according to statement 39, wherein $R^{14}$ is selected from H, methyl, ethyl, ethenyl and ethynyl.

41. A compound according to statement 40, wherein $R^{14}$ is selected from H and methyl.

42. A compound according to any one of statements 1 to 22, wherein there is a single bond between C2 and C3, $R^2$ is H.

43. A compound according to any one of statements 1 to 22, wherein there is a single bond between C2 and C3, $R^2$ is

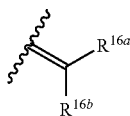

and $R^{16a}$ and $R^{16b}$ are both H.

44. A compound according to any one of statements 1 to 22, wherein there is a single bond between C2 and C3, $R^2$ is

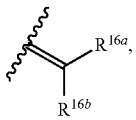

and $R^{16a}$ and $R^{16b}$ are both methyl.

45. A compound according to any one of statements 1 to 22, wherein there is a single bond between C2 and C3, $R^2$ is

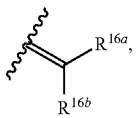

one of $R^{16a}$ and $R^{16b}$ is H, and the other is selected from $C_{1-4}$ saturated alkyl, $C_{2-3}$alkenyl, which alkyl and alkenyl groups are optionally substituted.

46. A compound according to any one of statements 1 to 45, wherein there is a double bond between C2' and C3', and $R^{2'}$ is a $C_{5-7}$ aryl group.

47. A compound according to statement 46, wherein $R^{2'}$ is phenyl.

48. A compound according to any one of statements 1 to 45, wherein there is a double bond between C2' and C3', and $R^{2'}$ is a $C_{8-10}$ aryl group.

49. A compound according to any one of statements 46 to 48, wherein $R^{2'}$ bears one to three substituent groups.

50. A compound according to any one of statements 46 to 49, wherein the substituents are selected from methoxy, ethoxy, fluoro, chloro, cyano, bis-oxy-methylene, methyl-piperazinyl, morpholino and methyl-thiophenyl.

51. A compound according to any one of statements 1 to 45, wherein there is a double bond between C2' and C3', and $R^{2'}$ is a $C_{1-5}$ saturated aliphatic alkyl group.

52. A compound according to statement 51, wherein $R^{2'}$ is methyl, ethyl or propyl.

53. A compound according to any one of statements 1 to 45, wherein there is a double bond between C2' and C3', and $R^{2'}$ is a $C_{3-6}$ saturated cycloalkyl group.

54. A compound according to statement 53, wherein $R^{2'}$ is cyclopropyl.

55. A compound according to any one of statements 1 to 45, wherein there is a double bond between C2' and C3', and $R^{2'}$ is a group of formula:

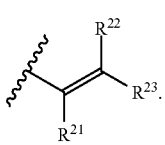

56. A compound according to statement 55, wherein the total number of carbon atoms in the $R^{2'}$ group is no more than 4.

57. A compound according to statement 56, wherein the total number of carbon atoms in the $R^{2'}$ group is no more than 3.

58. A compound according to any one of statements 55 to 57, wherein one of $R^{21}$, $R^{22}$ and $R^{23}$ is H, with the other two groups being selected from H, $C_{1-3}$ saturated alkyl, $C_{2-3}$ alkenyl, $C_{2-3}$ alkynyl and cyclopropyl.

59. A compound according to any one of statements 55 to 57, wherein two of $R^{21}$, $R^{22}$ and $R^{23}$ are H, with the other group being selected from H, $C_{1-3}$ saturated alkyl, $C_{2-3}$ alkenyl, $C_{2-3}$ alkynyl and cyclopropyl.

60. A compound according to any one of statements 1 to 45, wherein there is a double bond between C2' and C3', and $R^{2'}$ is a group of formula:

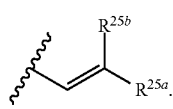

61. A compound according to statement 60, wherein $R^{2'}$ is the group:

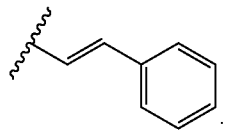 [SMILES: */C=C/c1ccccc1]

62. A compound according to any one of statements 1 to 45, wherein there is a double bond between C2' and C3', and $R^{2'}$ is a group of formula:

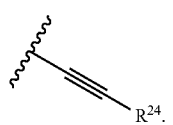

63. A compound according to statement 62, wherein $R^{24}$ is selected from H, methyl, ethyl, ethenyl and ethynyl.

64. A compound according to statement 63, wherein $R^{24}$ is selected from H and methyl.

65. A compound according to any one of statements 1 to 45, wherein there is a single bond between C2' and C3', $R^{2'}$ is H.

66. A compound according to any one of statements 1 to 45, wherein there is a single bond between C2' and C3', $R^{2'}$ is

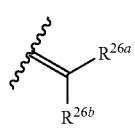

and $R^{26a}$ and $R^{26b}$ are both H.

67. A compound according to any one of statements 1 to 45, wherein there is a single bond between C2' and C3', $R^2$ is

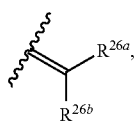

and $R^{26a}$ and $R^{26b}$ are both methyl.

68. A compound according to any one of statements 1 to 45, wherein there is a single bond between C2' and C3', $R^{2'}$ is

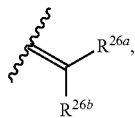

one of $R^{26a}$ and $R^{26b}$ is H, and the other is selected from $C_{1-4}$ saturated alkyl, $C_{2-3}$ alkenyl, which alkyl and alkenyl groups are optionally substituted.

69. A compound according to any one of statements 1 to 68, wherein $R^{11a}$ is OH.
70. A compound according to any one of statements 1 to 68, wherein $R^{11a}$ is $OR^A$.
71. A compound according to statement 70, wherein $R^A$ is methyl.
72. A compound according to any one of statements 1 to 68, wherein $R^{11a}$ is $SO_zM$.
73. A compound according to statement 72, wherein M is $Na^+$ and z is 3.
74. A compound according to any one of statements 1 to 73, wherein $R^{30}$ is H, and $R^{31}$ is OH.
75. A compound according to any one of statements 1 to 73, wherein $R^{30}$ is H, and $R^{31}$ is $OR^A$.
76. A compound according to statement 75, wherein $R^A$ is methyl.
77. A compound according to any one of statements 1 to 73, wherein $R^{30}$ and $R^{31}$ form a nitrogen-carbon double bond between the nitrogen and carbon atoms to which they are bound.
78. A compound according to any one of statements 1 to 73, wherein $R^{30}$ is H and $R^{31}$ is $SO_zM$.
79. A compound according to statement 78, wherein M is $Na^+$ and z is 3.
80. A compound according to statement 1 of formula Ia:

where $R^{2a}$ and $R^{2a'}$ are the same and are selected from:

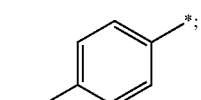
(a)

(b)

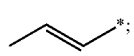
(c)

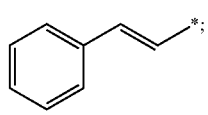
(d)

(e)

(f)

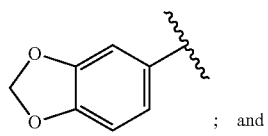
; and
(g)

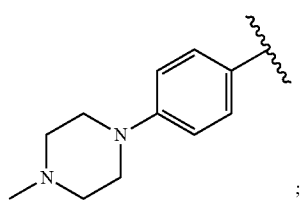
;
(h)

$R^{7a}$ and $R^{7a'}$ are the same and are selected from methoxy and benzyloxy.

Ia

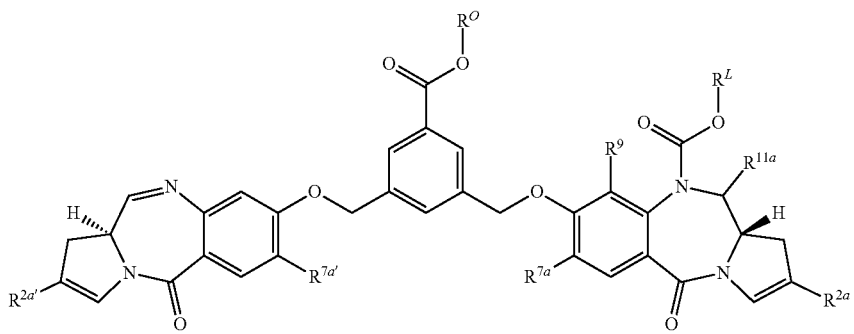

81. A compound according to statement 1 of formula Ib:

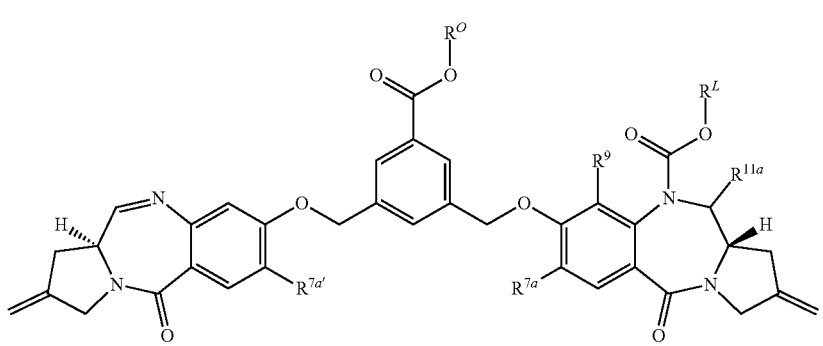

Ib wherein $R^{7a}$ and $R^{7a'}$ are the same and are selected from methoxy and benzyloxy.

82. A compound according to statement 1 of formula Ic:

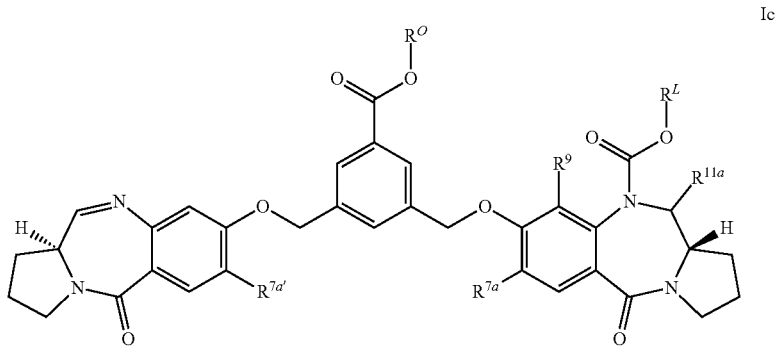

Ic wherein $R^{7a}$ and $R^{7a'}$ are the same and are selected from methoxy and benzyloxy.

83. A compound according to any one of statements 1 to 82, wherein $R^L$ is of formula IIIa, and Q is an amino acid residue selected from Phe, Lys, Val, Ala, Cit, Leu, Ie, Arg, and Trp.

84. A compound according to any one of statements 1 to 82, wherein $R^L$ is of formula IIIa, and Q is a dipeptide residue selected from:
$^{CO}$-Phe-Lys-$^{NH}$
$^{CO}$-Val-Ala-$^{NH}$
$^{CO}$-Val-Lys-$^{NH}$
$^{CO}$-Ala-Lys-$^{NH}$,
$^{CO}$-Val-Cit-$^{NH}$,
$^{CO}$-Phe-Cit-$^{NH}$,
$^{CO}$-Leu-Cit-$^{NH}$
$^{CO}$-Ile-Cit-$^{NH}$
$^{CO}$-Phe-Arg-$^{NH}$, and
$^{CO}$-Trp-Cit-$^{NH}$;

85. A compound according to statement 84, wherein Q is selected from $^{CO}$-Phe-Lys-$^{NH}$, $^{CO}$-Val-Cit-$^{NH}$ and $^{CO}$-Val-Aa-$^{NH}$.

86. A compound according to any one of statements 1 to 82, wherein $R^L$ is of formula IIIa, and Q is a tripeptide residue.

87. A compound according to any one of statements 1 to 86, wherein $R^L$ is of formula IIIa and a is 0 to 3.

88. A compound according to statement 87, wherein a is 0.

89. A compound according to any one of statements 1 to 88, wherein $R^L$ is of formula IIIa and b is 0 to 12.

90. A compound according to statement 89, wherein b is 0 to 8.

91. A compound according to any one of statements 1 to 90, wherein $R^L$ is of formula IIIa and d is 0 to 3.

92. A compound according to statement 91, wherein d is 2.

93. A compound according to any one of statements 1 to 86, wherein $R^L$ is of formula IIIa and, a is 0, cis 1 and d is 2, and b is from 0 to 8.

94. A compound according to statement 93 wherein b is 0, 4 or 8.

95. A compound according to any one of statements 1 to 94, wherein $R^L$ is of formula IIIa and $G^L$ is selected from

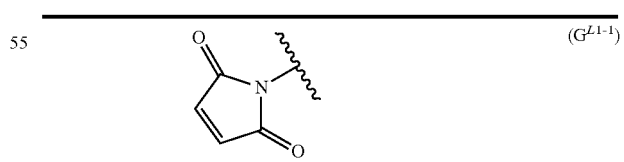

($G^{L1-1}$)

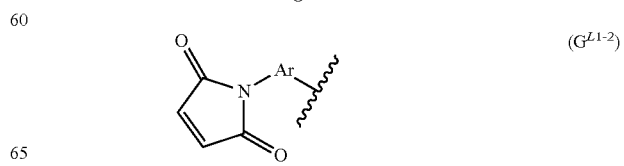

($G^{L1-2}$)

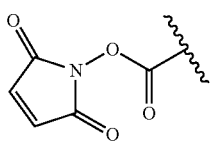 [SMILES: *C(=O)ON1C(=O)C=CC1=O] (G$^{L2}$)

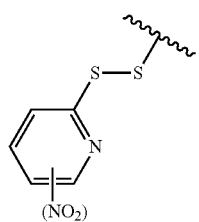 (G$^{L3-1}$)

where the NO$_2$ group is optional

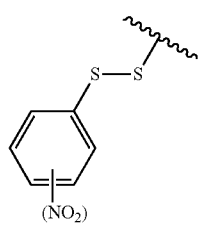 (G$^{L3-2}$)

where the NO$_2$ group is optional

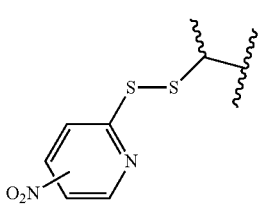 (G$^{L3-3}$)

where the NO$_2$ group is optional

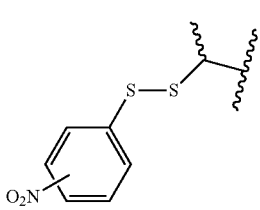 (G$^{L3-4}$)

where the NO$_2$ group is optional

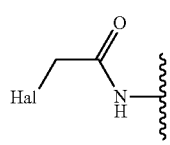 (G$^{L4}$)

Where Hal = I, Br, Cl

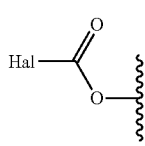 (G$^{L5}$)

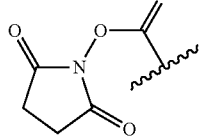 (G$^{L6}$)

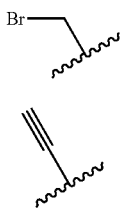 (G$^{L7}$)

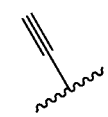 (G$^{L8}$)

 (G$^{L9}$)

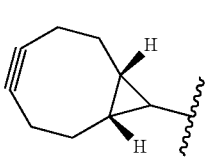 [SMILES: *C1[C@H]2CCC#CCC[C@@H]12] (G$^{L10}$)

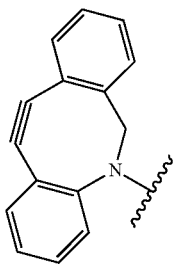 [SMILES: *N1Cc2ccccc2C#Cc2ccccc21] (G$^{L11}$)

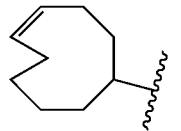 (G$^{L12}$)

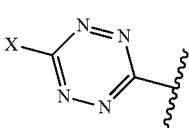 (G$^{L13}$)

where Ar represents a C$_{5-6}$ arylene group, e.g. phenylene, and represents C$_{1-4}$ alkyl.

96. A compound according to statement 95, wherein Ar is a phenylene group.

97. A compound according to either statement 95 or statement 96, wherein G$^L$ is selected from G$^{L1-1}$ and G$^{L1-2}$.

98. A compound according to statement 97, wherein G$^L$ is G$^{L1-1}$.

99. A compound according to any one of statements 1 to 82, wherein R$^L$ is of formula IIIb, and both R$^L$ and R$^{L2}$ are H.

100. A compound according to any one of statements 1 to 82, wherein R$^L$ is of formula IIIb, R$^{L1}$ is H and R$^{L2}$ is methyl.

101. A compound according to any one of statements 1 to 82, wherein R$^L$ is of formula IIIb, and both R$^L$ and R$^{L2}$ are methyl.

102. A compound according to any one of statements 1 to 82, wherein $R^L$ is of formula IIIb, and, $R^L$ and $R^{L2}$ together with the carbon atom to which they are bound form a cyclopropylene group.

103. A compound according to any one of statements 1 to 82, wherein $R^L$ is of formula IIIb, and, $R^L$ and $R^{L2}$ together with the carbon atom to which they are bound form a cyclobutylene group.

104. A compound according to any one of statements 1 to 82 and 99 to 103, wherein $R^L$ is of formula IIIb, and e is 0.

105. A compound according to any one of statements 1 to 82 and 99 to 103, wherein $R^L$ is of formula IIIb, and e is 1.

106. A compound according to statement 105, wherein the nitro group is in the para position.

107. The use of a compound according to any one of statements 1 to 106 in the manufacture of a medicament for treating a proliferative disease.

108. A compound according to any one of statements 1 to 106 for use in the treatment of a proliferative disease.

109. A conjugate comprising a compound of formula I according to any one of statements 1 to 106, or a pharmaceutically acceptable salt or solvate thereof, linked to a Ligand unit.

110. A conjugate of formula IV:

L-(D$^L$)$_p$      (IV)

or a pharmaceutically acceptable salt or solvate thereof, wherein L is a Ligand unit, D$^L$ is of formula III:

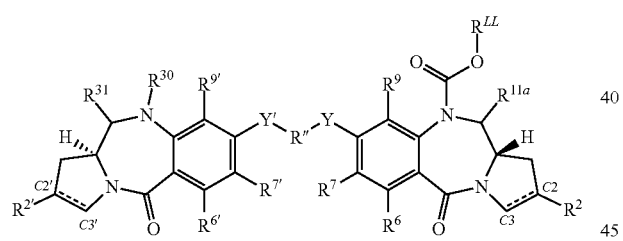

III wherein $R^2$, $R^6$, $R^7$, $R^9$, $R^{11a}$, Y, R", Y', $R^2$, $R^{6'}$, $R^{7'}$, $R^{9'}$, $R^{30}$ and $R^{31}$ are as defined in any one of statements 1 to 79;

$R^{LL}$ is a linker for connection to a cell binding agent, which is selected from:

(iiia)

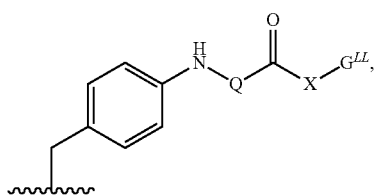

IIIa' where Q and X are as defined in any one of statements 1 and 83 to 86 and G$^{LL}$ is a linker connected to a Ligand Unit; and (iiib)

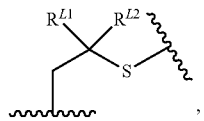

IIIb' where $R^{L1}$ and $R^{L2}$ are as defined in any one of statements 1 and 99 to 103;

wherein p is an integer of from 1 to 20.

111. A conjugate according to statement 110, wherein G$^{LL}$ is selected from:

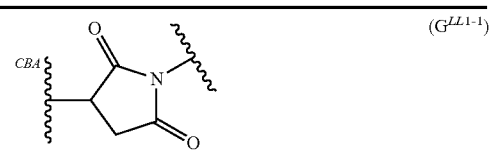

(G$^{LL1-1}$)

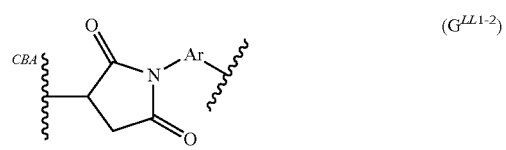

(G$^{LL1-2}$)

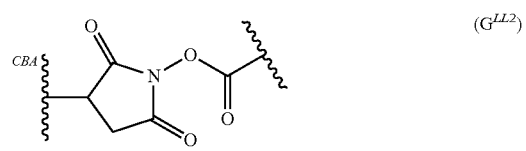

(G$^{LL2}$)

(G$^{LL3-1}$)

(G$^{LL3-2}$)

(G$^{LL4}$)

(G$^{LL5}$)

(G$^{LL6}$)

(G$^{LL7}$)

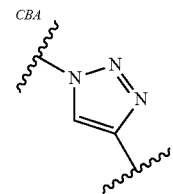 [SMILES: *c1cn(*)nn1]

(G^{LL8-1})

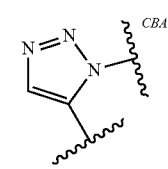

(G^{LL8-2})

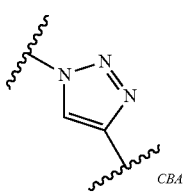 [SMILES: *c1cn(*)nn1]

(G^{LL9-1})

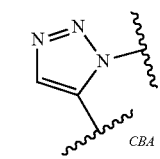

(G^{LL9-2})

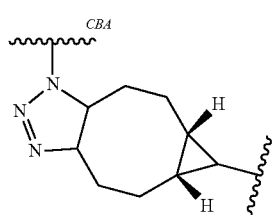 [SMILES: *C1[C@H]2CCC3C(CC[C@@H]12)N=NN3*]

G^{L10}

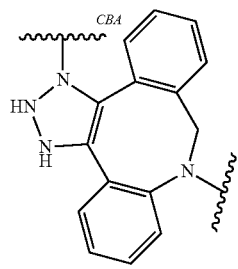 [SMILES: *N1NNC2=C1c1ccccc1CN(*)c1ccccc12]

G^{L11}

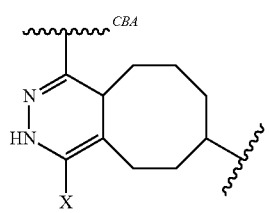

G^{L12}

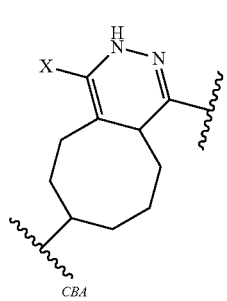

G^{L13} where Ar represents a $C_{5-6}$ arylene group, e.g. phenylene and X represents $C_{1-4}$ alkyl.

112. A conjugate according to statement 111, wherein Ar is a phenylene group.

113. A compound according to either statement 111 or statement 112, wherein $G^{LL}$ is selected from $G^{LL1-1}$ and $G^{LL1-2}$.

114. A compound according to statement 112, wherein $G^{LL}$ is $G^{LL1-1}$.

115. A conjugate according to statement 110, wherein $D^L$ is of formula IIIa:

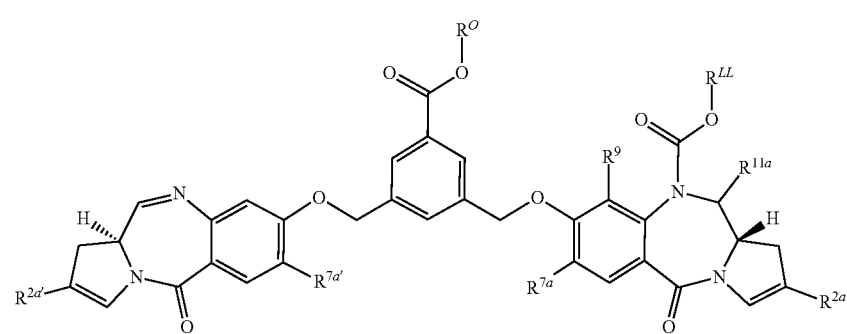

IIIa where $R^{2a}$ and $R^{2a'}$ are the same and are selected from:

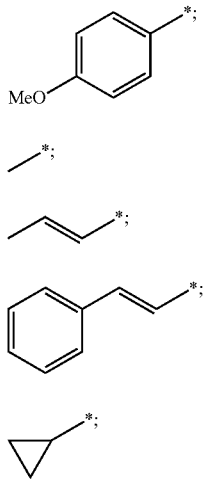

(a)
(b)
(c)
(d)
(e)

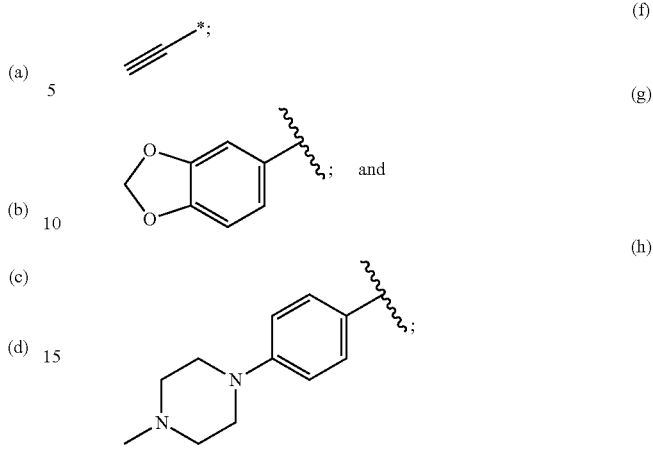

(f)
(g)
and
(h)

$R^{7a}$ and $R^{7a'}$ are the same and are selected from methoxy and benzyloxy.

116. A conjugate according to statement 110, wherein $D^L$ is of formula IIIb:

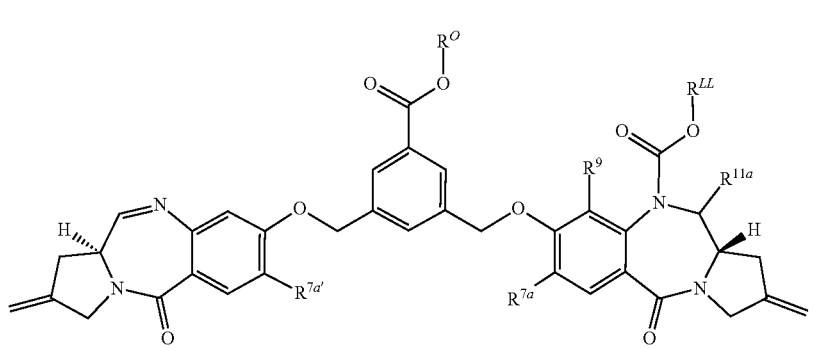

IIIb where $R^{7a}$ and $R^{7a'}$ are the same and are selected from methoxy and benzyloxy.

117. A conjugate according to statement 110, wherein $D^L$ is of formula IIIc:

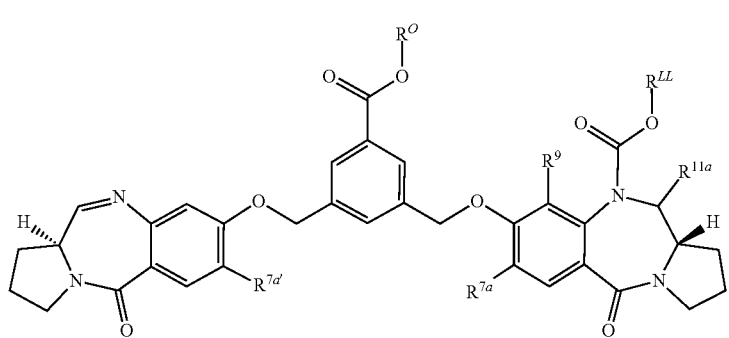

IIIc where $R^{7a}$ and $R^{7a'}$ are the same and are selected from methoxy and benzyloxy.

118. A conjugate according to any one of statements 109 to 117, wherein the Ligand Unit is an antibody or an active fragment thereof.

119. The conjugate according to statement 118, wherein the antibody or antibody fragment is an antibody or antibody fragment for a tumour-associated antigen.

120. The conjugate according to statement 119, wherein the antibody or antibody fragment is an antibody which binds to one or more tumor-associated antigens or cell-surface receptors selected from (1)-(88):
(1) BMPR1B;
(2) E16;
(3) STEAP1;
(4) 0772P;
(5) MPF;
(6) Napi3b;
(7) Sema 5b;
(8) PSCA hlg;
(9) ETBR;
(10) MSG783;
(11) STEAP2;
(12) TrpM4;
(13) CRIPTO;
(14) CD21;
(15) CD79b;
(16) FcRH2;
(17) HER2;
(18) NCA;
(19) MDP;
(20) IL20R-alpha;
(21) Brevican;
(22) EphB2R;
(23) ASLG659;
(24) PSCA;
(25) GEDA;
(26) BAFF-R;
(27) CD22;
(28) CD79a;
(29) CXCR5;
(30) HLA-DOB;
(31) P2X5;
(32) CD72;
(33) LY64;
(34) FcRH1;
(35) IRTA2;
(36) TENB2;
(37) PSMA—FOLH1;
(38) SST;
(38.1) SSTR2;
(38.2) SSTR5;
(38.3) SSTR1;
(38.4) SSTR3;
(38.5) SSTR4;
(39) ITGAV;
(40) ITGB6;
(41) CEACAM5;
(42) MET;
(43) MUC1;
(44) CA9;
(45) EGFRvIII;
(46) CD33;
(47) CD19;
(48) IL2RA;
(49) AXL;
(50) CD30—TNFRSF8;
(51) BCMA—TNFRSF17;
(52) CT Ags—CTA;
(53) CD174 (Lewis Y)—FUT3;
(54) CLEC14A;
(55) GRP78—HSPA5;
(56) CD70;
(57) Stem Cell specific antigens;
(58) ASG-5;
(59) ENPP3;
(60) PRR4;
(61) GCC—GUCY2C;
(62) Liv-1—SLC39A6;
(63) 5T4;
(64) CD56—NCMA1;
(65) CanAg;
(66) FOLR1;
(67) GPNMB;
(68) TIM-1—HAVCR1;
(69) RG-1/Prostate tumor target Mindin—Mindin/RG-1;
(70) B7-H4—VTCN1;
(71) PTK7;
(72) CD37;
(73) CD138—SDC1;
(74) CD74;
(75) Claudins—CLs;
(76) EGFR;
(77) Her3;
(78) RON—MST1R;
(79) EPHA2;
(80) CD20-MS4A1;
(81) Tenascin C—TNC;
(82) FAP;
(83) DKK-1;
(84) CD52;
(85) CS1—SLAMF7;
(86) Endoglin—ENG;
(87) Annexin A1—ANXA1;
(88) V-CAM (CD106)—VCAM1.

121. The conjugate of any one of statements 118 to 120 wherein the antibody or antibody fragment is a cysteine-engineered antibody.

122. The conjugate according to any one of statements 110 to 121 wherein p is an integer from 1 to 8.

123. The conjugate according to statement 122, wherein p is 1, 2, 3, or 4.

124. A composition comprising a mixture of conjugates according to any one of statements 110 to 123, wherein the average p in the mixture of conjugate compounds is about 1 to about 8.

125. The conjugate according to any one of statements 109 to 123, for use in therapy.

126. A pharmaceutical composition comprising the conjugate of any one of statements 109 to 123 and a pharmaceutically acceptable diluent, carrier or excipient.

127. The conjugate according to any one of statements 109 to 123 or the pharmaceutical composition according to statement 126, for use in the treatment of a proliferative disease in a subject.

128. The conjugate for use according to statement 127, wherein the disease treated is cancer.

129. Use of a conjugate according to any one of statements 109 to 123 or the pharmaceutical composition according to statement 126 in a method of medical treatment.

130. A method of medical treatment comprising administering to a patient the pharmaceutical composition of statement 126.

131. The method of statement 130 wherein the method of medical treatment is for treating cancer.
132. The method of statement 131, wherein the patient is administered a chemotherapeutic agent, in combination with the conjugate.
133. Use of a conjugate according to any one of statements 109 to 123 in a method of manufacture of a medicament for the treatment of a proliferative disease.
134. A method of treating a mammal having a proliferative disease, comprising administering an effective amount of a conjugate according to any one of statements 109 to 123 or the pharmaceutical composition according to statement 126.
135. A compound with the formula REL:

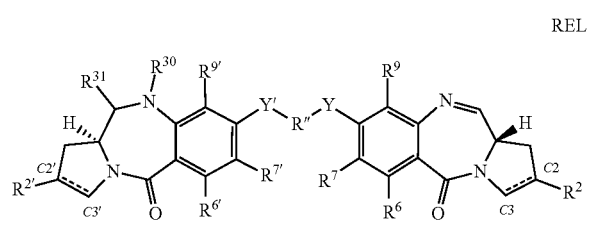

REL and salts and solvates thereof, wherein $R^2$, R, $R^7$, $R^9$, Y, R", Y', $R^{2'}$, $R^{6'}$, $R^{7'}$, $R^{9'}$, $R^{30}$ and $R^{31}$ are as defined in any one of statements 1 to 79.

The invention claimed is:
1. A compound of formula I:

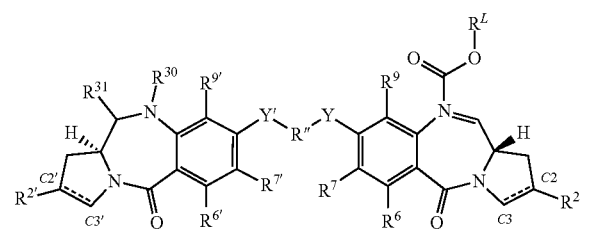

I or a pharmaceutically acceptable salt thereof, wherein:
R" is a group of formula II:

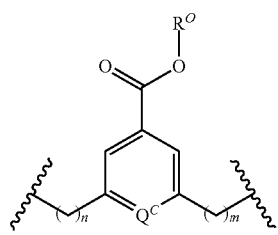

II where each of n and m are independently selected from 1, 2 and 3;
$R^O$ is selected from the group consisting of H, methyl, ethyl, iso-propyl and benzyl;
$Q^C$ is selected from N and CH;
Y and Y' are selected from O, S, or NH;
when there is a double bond present between C2 and C3, $R^2$ is selected from the group consisting of:
(ia) $C_{6-10}$ carboaryl group or $C_{5-10}$ heteroaryl group, wherein said $C_{6-10}$ carboaryl or $C_{5-10}$ heteroaryl group is optionally substituted by one or more substituents selected from the group consisting of: halo, nitro, cyano, —OR, carboxy, —C(=O)OR, $C_{1-7}$ alkyl, $C_{3-7}$ heterocyclyl and bis-oxy-$C_{1-3}$ alkylene, wherein R is selected from a $C_{1-7}$ alkyl group, a $C_{3-20}$ heterocyclyl group, a $C_{6-10}$ carboaryl group or a $C_{5-10}$ heteroaryl group;
(ib) $C_{1-5}$ alkyl;
(ic) $C_{3-6}$ cycloalkyl;

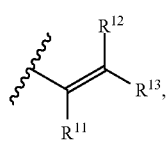

(id)

wherein each of $R^{11}$, $R^{12}$ and $R^{13}$ are independently selected from H, $C_{1-3}$ alkyl, $C_{2-3}$ alkenyl, $C_{2-3}$ alkynyl and cyclopropyl, where the total number of carbon atoms in the $R^2$ group is no more than 5;

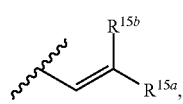

(ie)

wherein one of $R^{15a}$ and $R^{15b}$ is H and the other is selected from: phenyl, which phenyl is optionally substituted by a group selected from halo, methyl, methoxy; pyridyl; and thiophenyl; and

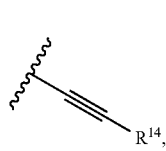

(if)

where $R^{14}$ is selected from: H; $C_{1-3}$ alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;
when there is a single bond present between C2 and C3, $R^2$ is H or

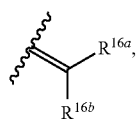

where $R^{16a}$ and $R^{16b}$ are independently selected from H, F, $C_{1-4}$ alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;
when there is a double bond present between C2' and C3', $R^{2'}$ is selected from the group consisting of:

(iia) $C_{6-10}$ carboaryl group or $C_{5-10}$ heteroaryl group, wherein said $C_{6-10}$carboaryl or $C_{5-10}$ heteroaryl group is optionally substituted by one or more substituents selected from the group consisting of: halo, nitro, cyano, —OR, carboxy, —C(=O)OR, $C_{1-7}$ alkyl, $C_{3-7}$ heterocyclyl and bis-oxy-$C_{1-3}$ alkylene, wherein R is selected from a $C_{1-7}$ alkyl group, a $C_{3-20}$ heterocyclyl group, a $C_{6-10}$ aryl group or a $C_{5-10}$ heteroaryl group;

(iib) $C_{1-5}$ alkyl;

(iic) $C_{3-6}$ cycloalkyl;

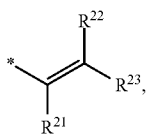
(iid)

wherein each of $R^{21}$, $R^{22}$ and $R^{23}$ are independently selected from H, $C_{1-3}$ alkyl, $C_{2-3}$ alkenyl, $C_{2-3}$ alkynyl and cyclopropyl, where the total number of carbon atoms in the $R^{2'}$ group is no more than 5;

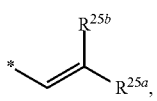
(iie)

wherein one of $R^{25a}$ and $R^{25b}$ is H and the other is selected from: phenyl, which phenyl is optionally substituted by a group selected from halo, methyl, methoxy; pyridyl; and thiophenyl; and

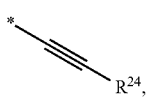
(iif)

where $R^{24}$ is selected from: H; $C_{1-3}$ alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2' and C3', $R^{2'}$ is H or

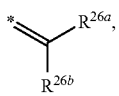

where $R^{26a}$ and $R^{26b}$ are independently selected from H, F, $C_{1-4}$ alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;

$R^6$ and $R^9$ are independently selected from H, R, OH, OR, SH, SR, NH$_2$, NHR, NRR', nitro, Me$_3$Sn and halo;

where R and R' are independently selected from $C_{1-12}$ alkyl, $C_{3-20}$ heterocyclyl and $C_{6-20}$ aryl groups;

$R^7$ is selected from H, R, OH, OR, SH, SR, NH$_2$, NHR, NHRR', nitro, Me$_3$Sn and halo;

$R^{6'}$, $R^{7'}$, $R^{9'}$ are selected from the same groups as $R^6$, $R^7$ and $R^9$ respectively;

$R^{11a}$ is selected from OH, OR$^A$, where R$^A$ is $C_{1-4}$ alkyl, and SO$_z$M, where z is 2 or 3 and M is a monovalent pharmaceutically acceptable cation;

and either (a) $R^{30}$ is H, and $R^{31}$ is OH, OR$^A$, where R$^A$ is $C_{1-4}$ alkyl;

(b) $R^{30}$ and $R^{31}$ form a nitrogen-carbon double bond between the nitrogen and carbon atoms to which they are bound; or (c) $R^{30}$ is H and $R^{31}$ is SO$_z$M, where z is 2 or 3 and M is a monovalent pharmaceutically acceptable cation, wherein if $R^{11a}$ and $R^{31}$ are SO$_z$M, M may represent a divalent pharmaceutically acceptable cation $R^L$ is a linker for connection to an antibody Or an antigen-binding fragment of an antibody, which is selected from:

(iiia)
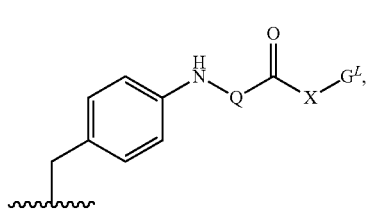
IIIa wherein
Q is:

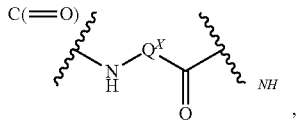

where $Q^X$ is such that Q is an amino-acid residue, a dipeptide residue or a tripeptide residue;

X is:

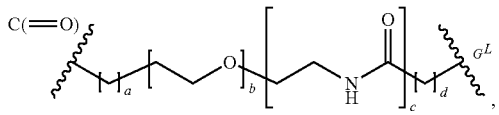

where a=0 to 5, b=0 to 16, c=0 or 1, d=0 to 5;

$G^L$ is a linker for connecting to an antibody or an antigen-binding fragment of an antibody; and (iiib)
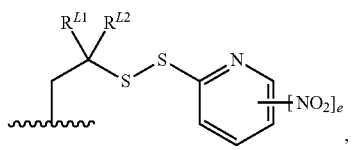
IIIb where $R^{L1}$ and $R^{L2}$ are independently selected from H and methyl, or together with the carbon atom to which they are bound form a cyclopropylene or cyclobutylene group;

and e is 0 or 1;
wherein the heterocyclyl group in $C_{3-7}$ heterocyclyl contains 1 to 4 ring heteroatoms selected from N, O and S;
wherein the heterocyclyl group in $C_{3-20}$ heterocyclyl contains 1 to 10 ring heteroatoms selected from N, O and S; and
wherein the heteroaryl group in $C_{5-10}$ heteroaryl contains 1 to 4 ring heteroatoms selected from N, O and S.

2. A compound according to claim 1, wherein:
a) Y and Y' are O,
b) $R^O$ is H or methyl;
c) R" is of formula IIa:

IIa where $R^{O1}$ is selected from the group consisting of H and methyl;
d) $R^6$, $R^9$, $R^{6'}$ and $R^{9'}$ are H, and $R^7$ and $R^{7'}$ are methoxy;
e) $R^{11a}$ is OH;
f) $R^{30}$ and $R^{31}$ form a nitrogen-carbon double bond between the nitrogen and carbon atoms to which they are bound.

3. A compound according to claim 1 of:
(i) formula Ia:

Ia where $R^{2a}$ and $R^{2a'}$ are the same and are selected from:

(a)

MeO (b)

(c)

-continued (d)

(e)

(f)

(g)

; and

-continued (h)

(ii) formula Ib:

Ib

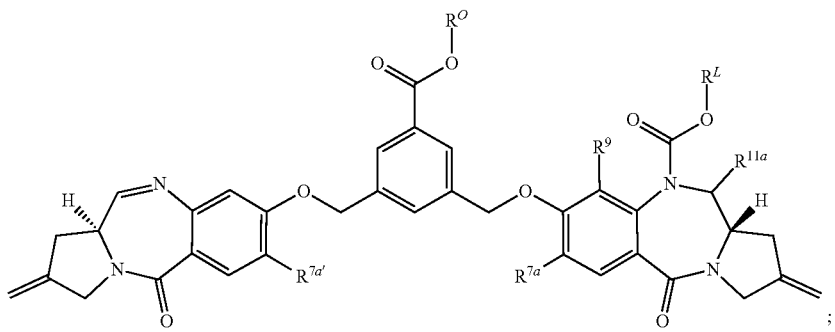

(iii) formula Ic:

Ic

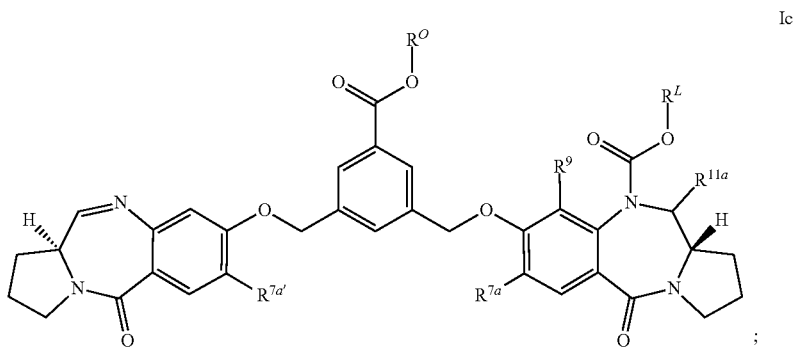

wherein $R^{7a}$ and $R^{7a'}$ are the same and are selected from methoxy and benzyloxy.

4. A compound according to claim 2 wherein $R^L$ is of formula IIIa, and Q is a dipeptide residue selected from:
$^{CO}$-Phe-Lys-$^{NH}$,
$^{CO}$-Val-Ala-$^{NH}$,
$^{CO}$-Val-Lys-$^{NH}$,
$^{CO}$-Ala-Lys-$^{NH}$,
$^{CO}$-Val-Cit-$^{NH}$,
$^{CO}$-Phe-Cit-$^{NH}$,
$^{CO}$-Leu-Cit-$^{NH}$,
$^{CO}$-Ile-Cit-$^{NH}$,
$^{CO}$-Phe-Arg-$^{NH}$, and
$^{CO}$-Trp-Cit-$^{NH}$.

5. A compound according to claim 1, wherein $R^L$ is of formula IIIa and, a is 0, c is 1 and d is 2, and b is from 0 to 8.

6. A compound according to claim 1, wherein $R^L$ is of formula IIIa and $G^L$ is selected from

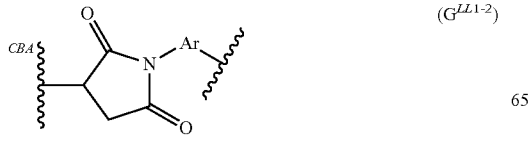
(G$^{LL1-1}$)

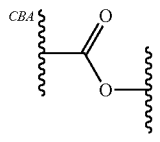
(G$^{LL1-2}$)

-continued

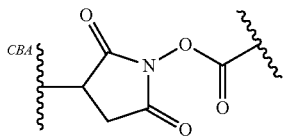 [SMILES: *C(=O)ON1C(=O)CC(*)C1=O]
(G$^{LL2}$)

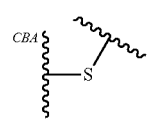 [SMILES: *S*]
(G$^{LL3-1}$)

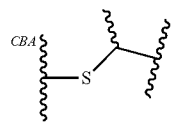 [SMILES: *SC(*)C]
(G$^{LL3-2}$)

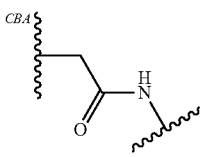
(G$^{LL-4}$)

(G$^{LL5}$)

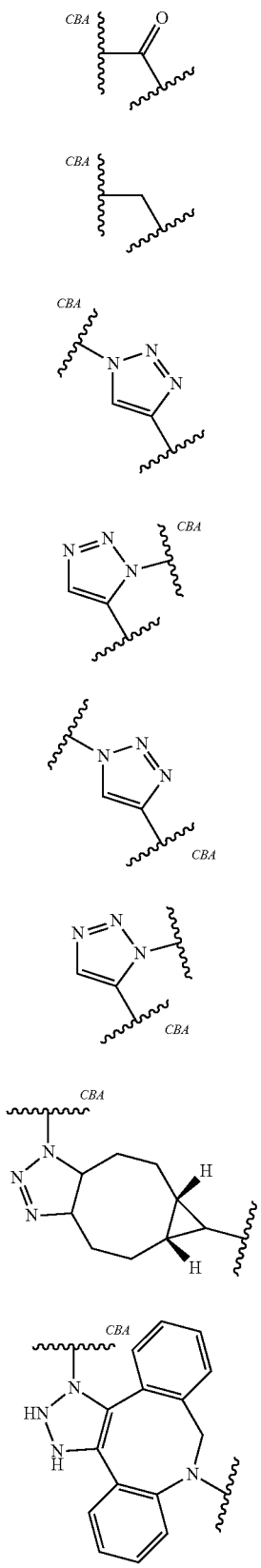

(G^{LL6})
(G^{LL7})
(G^{LL8-1})
(G^{LL8-2})
(G^{LL9-1})
(G^{LL9-2})
(G^{L10})
(G^{L11})

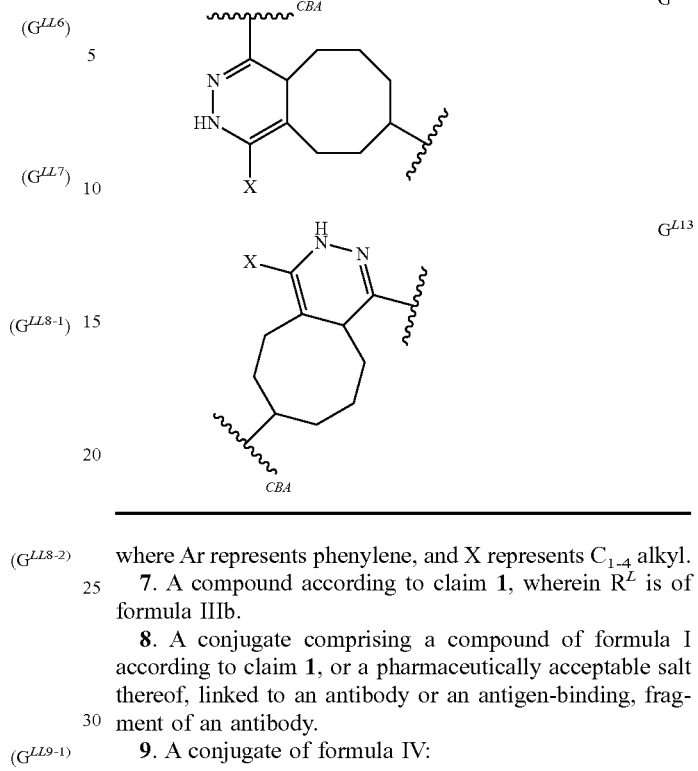

(G^{L12})
(G^{L13})

where Ar represents phenylene, and X represents $C_{1-4}$ alkyl.

7. A compound according to claim 1, wherein $R^L$ is of formula IIIb.

8. A conjugate comprising a compound of formula I according to claim 1, or a pharmaceutically acceptable salt thereof, linked to an antibody or an antigen-binding, fragment of an antibody.

9. A conjugate of formula IV:

L-(D$^L$)$_p$  (IV)

or a pharmaceutically acceptable salt thereof, wherein L is an antibody or an antigen-binding fragment of an antibody, $D^L$ is of formula III:

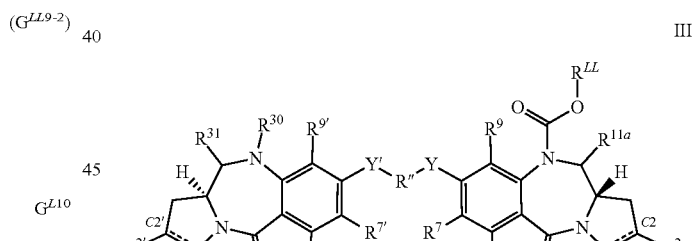

wherein:
R″ is a group of formula II:

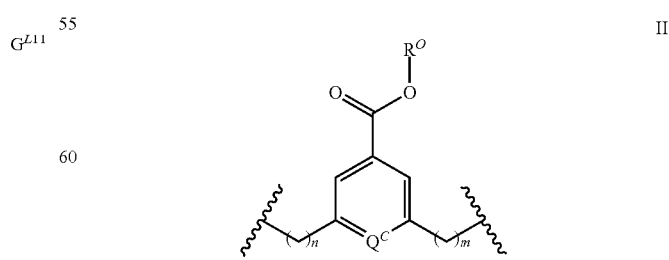

where each of n and m are independently selected from 1, 2 and 3;

$R^O$ is selected from the group consisting of H, methyl, ethyl, iso-propyl and benzyl;

$Q^C$ is selected from N and CH:

Y and Y' are selected from O, S, or NH;

when there is a double bond present between C2 and C3, $R^2$ is selected from the group consisting of:
(ia) $C_{6-10}$ carboaryl group or $C_{5-10}$ heteroaryl group, wherein said $C_{6-10}$ carboaryl or $C_{5-10}$ heteroaryl group is optionally substituted by one or more substituents selected from the group consisting of: halo, nitro, cyano, —OR, carboxy, —C(=O)OR, $C_{1-7}$ alkyl, $C_{3-7}$ heterocyclyl and bis-oxy-$C_{1-3}$ alkylene, wherein R is selected from a $C_{1-7}$ alkyl group, a $C_{3-20}$ heterocyclyl group or a $C_{6-10}$ carboaryl or $C_{5-10}$ heteroaryl group;
(ib) $C_{1-5}$ alkyl;
(ic) $C_{3-6}$ cycloalkyl;

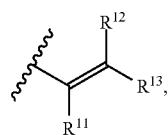

(id)

wherein each of $R^{11}$, $R^{12}$ and $R^{13}$ are independently selected from H, $C_{1-3}$ alkyl, $C_{2-3}$ alkenyl, $C_{2-3}$ alkynyl and cyclopropyl, where the total number of carbon atoms in the $R^2$ group is no more than 5;

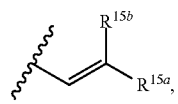

(ie)

wherein one of $R^{15a}$ and $R^{15b}$ is H and the other is selected from: phenyl, which phenyl is optionally substituted by a group selected from halo, methyl, methoxy; pyridyl; and thiophenyl; and

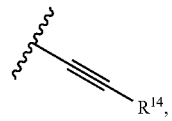

(if)

where $R^{14}$ is selected from: H; $C_{1-3}$ alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl:

when there is a single bond present between C2 and C3, $R^2$ is H or

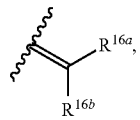

where $R^{16a}$ and $R^{16b}$ are independently selected from H, F, $C_{1-4}$ alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

when there is a double bond present between C2' and C3', $R^{2'}$ is selected from the group consisting of:
(iia) $C_{6-10}$ carboaryl group or a $C_{5-10}$ heteroaryl group, wherein said $C_{6-10}$ carboaryl group or $C_{5-10}$ heteroaryl group is optionally substituted by one or more substituents selected from the group consisting of: halo, nitro, cyano, —OR, carboxy, —C(=O)OR, $C_{1-7}$ alkyl, $C_{3-7}$ heterocyclyl and bis-oxy-$C_{1-3}$ alkylene, wherein R is selected from a $C_{1-7}$ alkyl group, a $C_{3-20}$ heterocyclyl group or a $C_{6-10}$ carboaryl or $C_{5-10}$ heteroaryl group;
(iib) $C_{1-5}$ alkyl;
(iic) $C_{3-6}$ cycloalkyl;

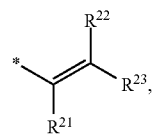

(iid)

wherein each of $R^{21}$, $R^{22}$ and $R^{23}$ are independently selected from H, $C_{1-3}$ alkyl, $C_{2-3}$ alkenyl, $C_{2-3}$ alkynyl and cyclopropyl, where the total number of carbon atoms in the $R^{2'}$ group is no more than 5;

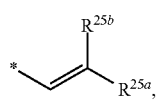

(iie)

wherein one of $R^{25a}$ and $R^{25b}$ is H and the other is selected from: phenyl, which phenyl is optionally substituted by a group selected from halo, methyl, methoxy: pyridyl; and thiophenyl; and

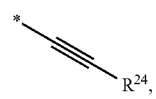

(iif)

where $R^{24}$ is selected from: H; $C_{1-3}$ alkyl: $C_{2-3}$ alkenyl: $C_{2-3}$ alkynyl: cyclopropyl: phenyl, which phenyl is optionally substituted by a group selected from halo, methyl, methoxy; pyridyl; and thiophenyl;

when there is a single bond present between C2' and C3', $R^{2'}$ is H or

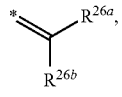

where $R^{26a}$ and $R^{26b}$ are independently selected from H, F, $C_{1-4}$ alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester; $R^6$ and $R^9$ are independently selected from H, R, OH, OR, SH, SR, $NH_2$, NHR, NRR', nitro, $Me_3Sn$ and halo;

where R and R' are independently selected from $C_{1-12}$ alkyl, $C_{3-20}$ heterocyclyl and $C_{6-20}$ aryl groups;

$R^7$ is selected from H, R, OH, OR, SH, SR, $NH_2$, NHR, NHRR', nitro, $Me_3Sn$ and halo;

$R^{6'}$, $R^{7'}$, $R^{9'}$ are selected from the same groups as $R^6$, $R^7$ and $R^9$ respectively;

$R^{11a}$ is selected from OH, $OR^A$, where $R^A$ is $C_{1-4}$ alkyl, and $SO_zM$, where z is 2 or 3 and M is a monovalent pharmaceutically acceptable cation;

and either (a) $R^{30}$ is H, and $R^{31}$ is OH, $OR^A$, where $R^A$ is $C_{1-4}$ alkyl;

(b) $R^{30}$ and $R^{31}$ form a nitrogen-carbon double bond between the nitrogen and carbon atoms to which they are bound; or (c) $R^{30}$ is H and $R^{31}$ is $SO_zM$, where z is 2 or 3 and M is a monovalent pharmaceutically acceptable cation, wherein if $R^{11a}$ and $R^{31}$ are $SO_zM$, M may represent a divalent pharmaceutically acceptable cation;

$R^{LL}$ is a linker for connection to an antibody or an antigen-binding fragment of an antibody, which is selected from:

(iiia)

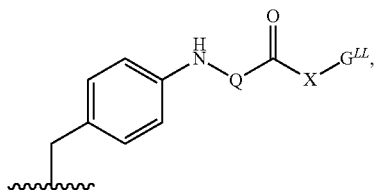

IIIa' where Q is:

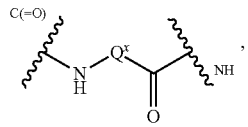

where $Q^X$ is such that Q is an amino-acid residue, a dipeptide residue or a tripeptide residue;

X is:

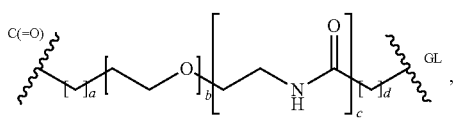

where a=0 to 5, b=0 to 16, c=0 or 1, d=0 to 5; and $G^{LL}$ is a linker connected to an antibody or an antigen-binding fragment of an antibody; and (iiib)

IIIb'

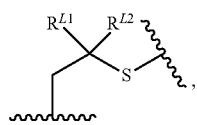

where $R^{L1}$ and $R^{L2}$ are independently selected from H and methyl, or together with the carbon atom to which they are bound form a cyclopropylene or cyclobutylene group;

and e is 0 or 1;

wherein the heterocyclyl group in $C_{3-7}$ heterocyclyl contains 1 to 4 ring heteroatoms selected from N, O and S;

wherein the heterocyclyl group in $C_{3-20}$ heterocyclyl contains 1 to 10 ring heteroatoms selected from N, O and S; and wherein the heteroaryl group in $C_{5-10}$ heteroaryl contains 1 to 4 ring heteroatoms selected from N, O and S;

wherein p is an integer of from 1 to 20.

10. A conjugate according to claim 9, wherein $G^{LL}$ is selected from:

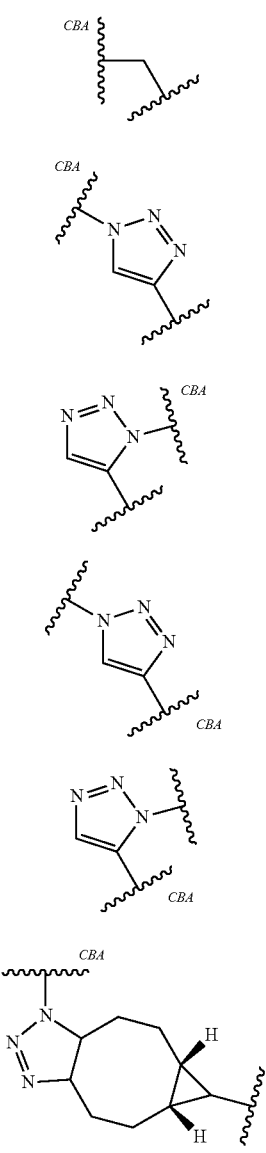
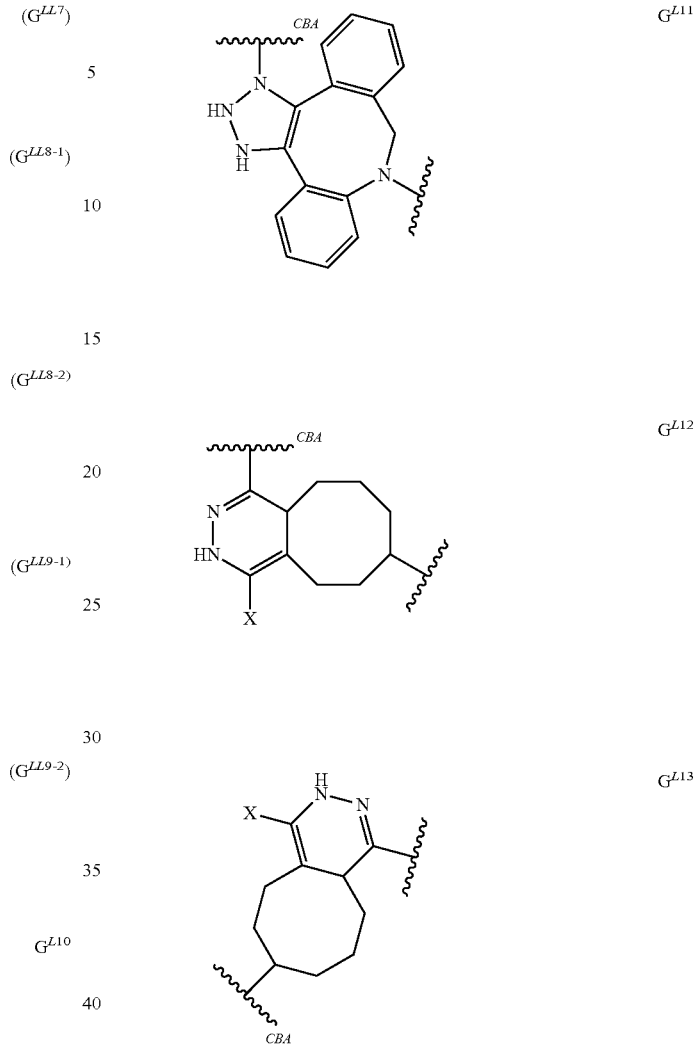
where Ar represents phenylene and X represents $C_{1-4}$ alkyl.
11. A conjugate according to claim 9, wherein $D^L$ is of:
(i) formula IIIa:
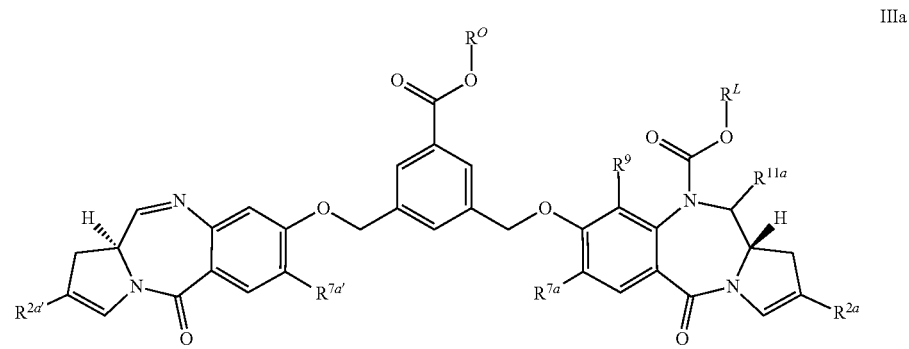

151
where $R^{2a}$ and $R^{2a'}$ are the same and are selected from:
(a)
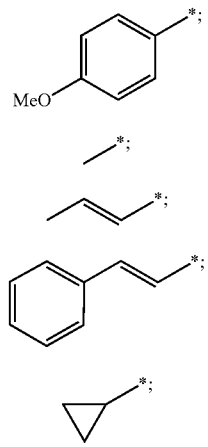
(b)
(c)
(d)
(e)
152
-continued
(f)
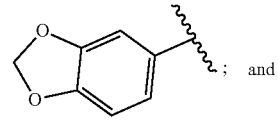
(g)
and
(h)
(ii) formula IIIb:
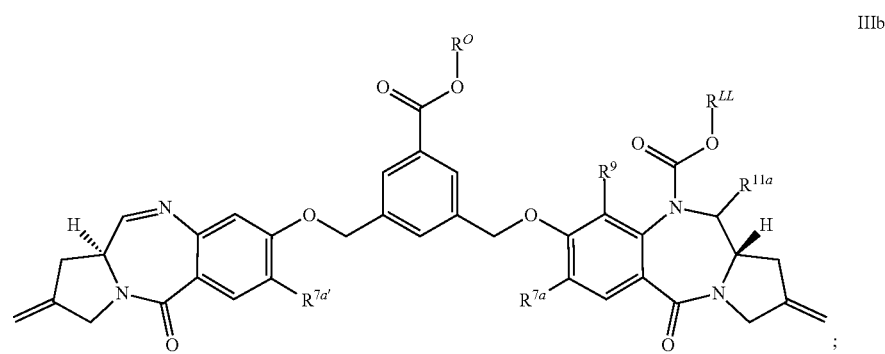
IIIb
(iii) formula IIIc:
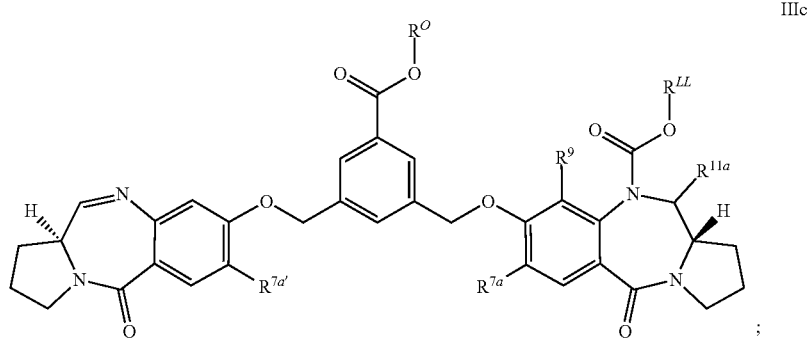
IIIc where $R^{7a}$ and $R^{7a'}$ are the same and are selected from methoxy and benzyloxy.

12. The conjugate according to claim 9, wherein the antibody or antibody fragment is an antibody which binds to one or more tumor-associated antigens or cell-surface receptors selected from (1)-(88):
(1) BMPR1B;
(2) E16;
(3) STEAP1;
(4) 0772P;
(5) MPF;
(6) Napi3b;
(7) Sema 5b;
(8) PSCA hlg;
(9) ETBR;
(10) MSG783;
(11) STEAP2;
(12) TrpM4;
(13) CRIPTO;
(14) CD21;
(15) CD79b;
(16) FcRH2;
(17) HER2;
(18) NCA;
(19) MDP;
(20) IL20R-alpha;
(21) Brevican;
(22) EphB2R;
(23) ASLG659;
(24) PSCA;
(25) GEDA;
(26) BAFF-R;
(27) CD22;
(28) CD79a;
(29) CXCR5;
(30) HLA-DOB;
(31) P2X5;
(32) CD72;
(33) LY64;
(34) FcRH1;
(35) IRTA2;
(36) TENB2;
(37) PSMA—FOLH1;
(38) SST;
(38.1) SSTR2;
(38.2) SSTR5;
(38.3) SSTR1;
(38.4) SSTR3;
(38.5) SSTR4;
(39) ITGAV;
(40) ITGB6;
(41) CEACAM5;
(42) MET;
(43) MUCI;
(44) CA9;
(45) EGFRvIII;
(46) CD33;
(47) CD19;
(48) IL2RA;
(49) AXL;
(50) CD30—TNFRSF8;
(51) BCMA—TNFRSF17;
(52) CT Ags—CTA;
(53) CD174 (Lewis Y)—FUT3;
(54) CLEC14A;
(55) GRP78—HSPA5;
(56) CD70;
(57) Stem Cell specific antigens;
(58) ASG-5;
(59) ENPP3;
(60) PRR4;
(61) GCC—GUCY2C;
(62) Liv-1—SLC39A6;
(63) 5T4;
(64) CD56—NCMA1;
(65) CanAg;
(66) FOLR1;
(67) GPNMB;
(68) TIM-1—HAVCR1;
(69) RG-1/Prostate tumor target Mindin—Mindin/RG-1;
(70) B7-H4—VTCN1;
(71) PTK7;
(72) CD37;
(73) CD138—SDC1;
(74) CD74;
(75) Claudins—CLs;
(76) EGFR;
(77) Her3;
(78) RON—MST1R;
(79) EPHA2;
(80) CD20—MS4A1;
(81) Tenascin C—TNC;
(82) FAP;
(83) DKK-1;
(84) CD52;
(85) CS1—SLAMF7;
(86) Endoglin—ENG;
(87) Annexin A1—ANXA1;
(88) V-CAM (CD106)—VCAM1.

13. A composition comprising a mixture of conjugates according to claim 9, wherein the average p in the mixture of conjugate compounds is about 1 to about 8.

14. A pharmaceutical composition comprising the conjugate of claim 8 and a pharmaceutically acceptable diluent, carrier or excipient.

15. A method of treating a mammal having gastric carcinoma, gastrointestinal cancer or leukaemia, comprising administering an effective amount of a conjugate of claim 8 or a pharmaceutical composition of claim 14.

16. A compound of formula REL:

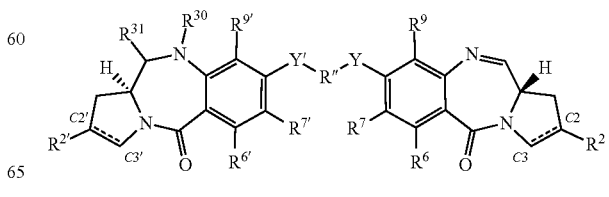

REL or a pharmaceutically acceptable salt thereof, wherein:
R" is a group of formula II:

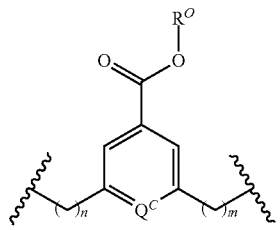

where each of n and m are independently selected from 1, 2 and 3;
$R^O$ is selected from the group consisting of H, methyl, ethyl, iso-propyl and benzyl;
$Q^C$ is selected from N and CH,
Y and Y' are selected from O, S, or NH;
when there is a double bond present between C2 and C3, $R^2$ is selected from the group consisting of:
(ia) $C_{6-10}$ carboaryl group or $C_{5-10}$ heteroaryl group, wherein said $C_{6-10}$ carboaryl group or $C_{5-10}$ heteroaryl group is optionally substituted by one or more substituents selected from the group consisting of: halo, nitro, cyano, —OR, carboxy, —C(=O)OR, $C_{1-7}$ alkyl, $C_{3-7}$ heterocyclyl and bis-oxy-$C_{1-3}$ alkylene, wherein R is selected from a $C_{1-7}$ alkyl group, a $C_{3-20}$ heterocyclyl group or a $C_{6-10}$ carboaryl or a $C_{5-10}$ heteroaryl group;
(ib) $C_{1-5}$ alkyl;
(ic) $C_{3-6}$ cycloalkyl;

(id)
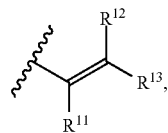

wherein each of $R^{11}$, $R^{12}$ and $R^{13}$ are independently selected from H, $C_{1-3}$ alkyl, $C_{2-3}$ alkenyl, $C_{2-3}$ alkynyl and cyclopropyl, where the total number of carbon atoms in the $R^2$ group is no more than 5;

(ie)
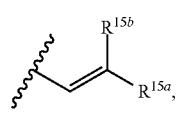

wherein one of $R^{15a}$ and $R^{15b}$ is H and the other is selected from: phenyl, which phenyl is optionally substituted by a group selected from halo, methyl, methoxy; pyridyl; and thiophenyl; and (if)
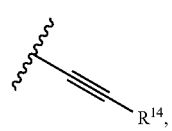

where $R^{14}$ is selected from: H; $C_{1-3}$ alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;
when there is a single bond present between C2 and C3, $R^2$ is H or

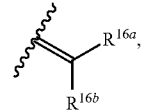

where $R^{16a}$ and $R^{16b}$ are independently selected from H, F, $C_{1-4}$ alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;
when there is a double bond present between C2' and C3', $R^{2'}$ is selected from the group consisting of:
(iia) $C_{6-10}$ carboaryl group or $C_{5-10}$ heteroaryl group, wherein said $C_{6-10}$ carboaryl group or $C_{5-10}$ heteroaryl group is optionally substituted by one or more substituents selected from the group consisting of: halo, nitro, cyano, —OR, carboxy, —C(=O)OR, $C_{1-7}$ alkyl, $C_{3-7}$ heterocyclyl and bis-oxy-$C_{1-3}$ alkylene, wherein R is selected from a $C_{1-7}$ alkyl group, a $C_{3-20}$ heterocyclyl group or a $C_{6-10}$ carboaryl or a $C_{5-10}$ heteroaryl group;
(iib) $C_{1-5}$ alkyl;
(iic) $C_{3-6}$ cycloalkyl;

(iid)
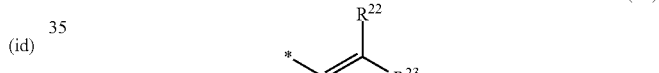

wherein each of $R^{21}$, $R^{22}$ and $R^{23}$ are independently selected from H, $C_{1-3}$ alkyl, $C_{2-3}$ alkenyl, $C_{2-3}$ alkynyl and cyclopropyl, where the total number of carbon atoms in the $R^{2'}$ group is no more than 5;

(ie)
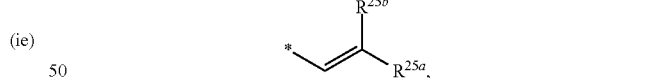

wherein one of $R^{25a}$ and $R^{25b}$ is H and the other is selected from: phenyl, which phenyl is optionally substituted by a group selected from halo, methyl, methoxy; pyridyl; and thiophenyl; and (iif)

where $R^{24}$ is selected from: H; $C_{1-3}$ alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2' and C3', $R^{2'}$ is H or

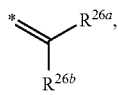

where $R^{26a}$ and $R^{26b}$ are independently selected from H, F, $C_{1-4}$ alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester; $R^6$ and $R^9$ are independently selected from H, R, OH, OR, SH, SR, $NH_2$, NHR, NRR', nitro, $Me_3Sn$ and halo;

where R and R' are independently selected from $C_{1-12}$ alkyl, $C_{3-20}$ heterocyclyl and $C_{6-20}$ aryl groups;

$R^7$ is selected from H, R, OH, OR, SH, SR, $NH_2$, NHR, NHRR', nitro, $Me_3Sn$ and halo;

$R^{6'}$, $R^{7'}$, $R^{9'}$ are selected from the same groups as $R^6$, $R^7$ and $R^9$ respectively;

$R^{11a}$ is selected from OH, $OR^A$, where $R^A$ is $C_{1-4}$ alkyl, and $SO_zM$, where z is 2 or 3 and M is a monovalent pharmaceutically acceptable cation;

and either (a) $R^{30}$ is H, and $R^{31}$ is OH, $OR^A$, where $R^A$ is $C_{1-4}$ alkyl;

(b) $R^{30}$ and $R^{31}$ form a nitrogen-carbon double bond between the nitrogen and carbon atoms to which they are bound; or (c) $R^{30}$ is H and $R^{31}$ is $SO_zM$, where z is 2 or 3 and M is a monovalent pharmaceutically acceptable cation, wherein if $R^{11a}$ and $R^{31}$ are $SO_zM$, M may represent a divalent pharmaceutically acceptable cation;

wherein the heterocyclyl group in $C_{3-7}$ heterocyclyl contains 1 to 4 ring heteroatoms selected from N, O and S;

wherein the heterocyclyl group in $C_{3-20}$ heterocyclyl contains 1 to 10 ring heteroatoms selected from N, O and S; and wherein the heteroaryl group in $C_{5-10}$ heteroaryl contains 1 to 4 ring heteroatoms selected from N, O and S.

\* \* \* \* \*

UNITED STATES PATENT AND TRADEMARK OFFICE
CERTIFICATE OF CORRECTION

Page 1 of 3

PATENT NO. : 11,524,969 B2
APPLICATION NO. : 17/046498
DATED : December 13, 2022
INVENTOR(S) : Philip Wilson Howard and Niall John Dickinson It is certified that error appears in the above-identified patent and that said Letters Patent is hereby corrected as shown below:

In the Claims

Column 141, Claim 6, Line 55 should read:

| | |
|---|---|
| ($G^{L1-1}$) | 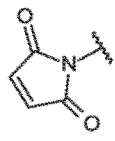 |
| ($G^{L1-2}$) | 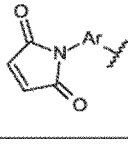 |
| ($G^{L2}$) | 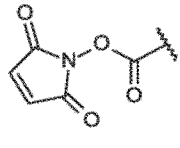 |
| ($G^{L3-1}$) | 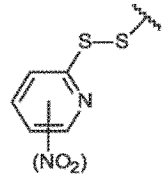<br>where the NO2 group is optional |
| ($G^{L3-2}$) | 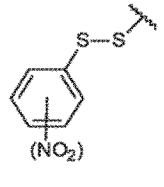<br>where the NO2 group is optional |

Signed and Sealed this
Sixth Day of June, 2023

Katherine Kelly Vidal
*Director of the United States Patent and Trademark Office*

| | | |
|---|---|---|
| (G$^{L3-3}$) | 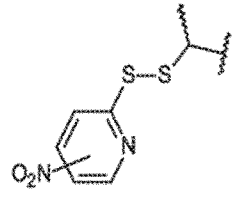 | |
| | where the NO$_2$ group is optional | |
| (G$^{L3-4}$) | 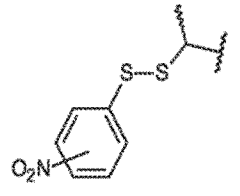 | |
| | where the NO2 group is optional | |
| (G$^{L4}$) | 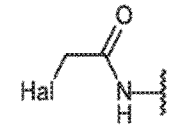 | |
| | Where Hal = I, Br, Cl | |
| (G$^{L5}$) | 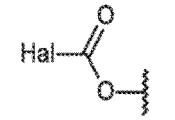 | |
| (G$^{L6}$) | 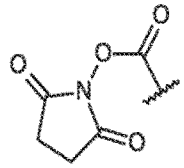 | |
| (G$^{L7}$) |  | |
| (G$^{L8}$) |  | |
| (G$^{L9}$) |  | |
| (GL$^{10}$) | 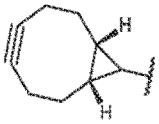 | |

| (G^{L11}) | 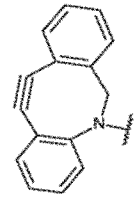 |
| (G^{L12}) |  |
| (G^{L13}) | 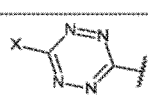 |
where Ar represents phenylene, and X represents $C_{1-4}$ alkyl.
Column 145, Claim 9, Line 3 should read:
QC is selected from N and CH;